(12) United States Patent
Rider

US007566694B2

(10) Patent No.: US 7,566,694 B2
(45) Date of Patent: *Jul. 28, 2009

(54) ANTI-PATHOGEN TREATMENTS

(75) Inventor: Todd H. Rider, Littleton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 47 days.

This patent is subject to a terminal disclaimer.

(21) Appl. No.: 11/503,416

(22) Filed: Aug. 11, 2006

(65) Prior Publication Data

US 2007/0031965 A1 Feb. 8, 2007

Related U.S. Application Data

(62) Division of application No. 10/361,208, filed on Feb. 7, 2003, now Pat. No. 7,125,839.

(60) Provisional application No. 60/355,359, filed on Feb. 7, 2002, provisional application No. 60/355,022, filed on Feb. 7, 2002, provisional application No. 60/432,386, filed on Dec. 10, 2002.

(51) Int. Cl.
*A61K 38/00* (2006.01)
*A61K 38/43* (2006.01)
*C07K 14/00* (2006.01)
*C07K 1/00* (2006.01)
*C07K 1/107* (2006.01)
*C12P 21/00* (2006.01)

(52) U.S. Cl. .................... 514/2; 530/300; 530/350; 530/402; 424/94.1; 435/69.1; 435/69.7

(58) Field of Classification Search ..................... None
See application file for complete search history.

(56) References Cited

U.S. PATENT DOCUMENTS

| | | | |
|---|---|---|---|
| 5,561,222 A | | 10/1996 | Keene et al. |
| 5,965,131 A | * | 10/1999 | Griffiths et al. .......... 424/133.1 |
| 5,976,800 A | | 11/1999 | Lau et al. |
| 5,989,886 A | | 11/1999 | Boeke et al. |
| 5,990,388 A | | 11/1999 | Roth et al. |
| 6,037,461 A | | 3/2000 | Alnermri |
| 6,074,636 A | | 6/2000 | Nichols |
| 6,221,355 B1 | | 4/2001 | Dowdy |
| 6,319,500 B1 | | 11/2001 | Goldenberg |
| 6,326,466 B1 | | 12/2001 | Bottaro et al. |
| 6,416,785 B1 | | 7/2002 | Riesenberg et al. |
| 6,495,516 B1 | * | 12/2002 | Little, II .................. 514/2 |
| 6,660,264 B1 | * | 12/2003 | Pasechnik et al. ......... 424/93.6 |
| 2003/0054000 A1 | | 3/2003 | Dowdy |

OTHER PUBLICATIONS

Lauber et al., "The Adapter Protein Apoptotic Protease-activating Factor-1 (Apaf-1) Is Proteolytically Processed during Apoptosis," Journal of Biological Chemistry, vol. 276 No. 32, pp. 29772-29781 (Aug. 2001).*
Finlay et al., "Exploitation of Mammalian host cell functions by bacterial pathogens," Science, vol. 276 No. 5313, pp. 718-725 (May 1997).*
Allgood, Victoria E. and Eastman, Eric M., "Chimeric Receptors as Gene Switches," *Curr. Opin. in Biotech.*, 8(4):474-479 (1997).
Aqeilan, Rami et al., "Interleukin 2-Bax:A Novel Prototype of Human Chimeric Proteins for Targeted Therapy," *FEBS Letters*, 457:271-276 (1999).
Azar, Y. and Loberboum-Galeski, H., "GnRH-Bik/Bax/Bak Chimeric Proteins Target and Kill Adenocarcinoma Cells; The General Use of Pro-Apoptotic Proteins of the Bcl-2 Family as Novel Killing Components of Targeting Chimeric Proteins," *Apoptosis*, 5:531-542 (2000).
Boeke, Jef D. and Hahn, Beatrice, "Destroying Retroviruses from Within," *Trends in Microbiology*, 4(11):421-426 (1996).
Finlay, B. Brett and Cossart, Pascale, "Exploitation of Mammalian Host Cell Functions by Bacterial Pathogens," *Science*, 276:718-725 (1997).
Bukrinsky, Michael I. and Haffar, Omar K., "HIV-1 Nuclear Import: In Search of a Leader," *Frontiers in Bioscience*, 4:d772-781 (1999).
Chen, Qi et al., "Structure-Based Discovery of Ligands Targeted to the RNA Double Helix," *Biochemistry* 36:11402-11407 (1997).
Fan, Liangfen et al., "Improved Artificial Death Switches Based on Caspases and FADD," *Human Gene Therapy* 10:2273-2285 (1999).
Friedler, Assaf et al., "Backbone Cyclic Peptide, Which Mimics the Nuclear Localization Signal of Human Immunodeficiency Virus Type 1 Matrix Protein, Inhibits Nuclear Import and Virus Production in Nondividing Cells, " *Biochemistry* 37:5616-5622 (1998).
Gao, Lian-Young and Kwaik, Yousef Abu, "Hijacking of Apoptotic Pathways by Bacterial Pathogens," *Microbes and Infection*, 2:1705-1719 (2000).
Gao, Lian-Young and Kwaik, Yousef Abu, "The Modulation of Host Cell Apoptosis by Intracellular Bacterial Pathogens," *Trends in Microbiology* 8(7):306-313 (2000).
Greenberg, Steven J. et al., "Pleiotropic Expression of Heterologous Cytokine/Receptor Genes in HTLV-1 Associated Diseases: Candidate TRS for Chimeric Gene Therapy," *Leukemia*, 11(Supp. 3):79-81 (1997).
Knodler, Leigh A. et al., "Pathogenic Trickery: Deception of Host Cell Processes," *Nature Reviews Molecular Cell Biology*, 2(8):578-588 (2001).

(Continued)

*Primary Examiner*—Zachariah Lucas
(74) *Attorney, Agent, or Firm*—Hamilton, Brook, Smith & Reynolds, P.C.

(57) ABSTRACT

Chimeric molecules that contain at least one pathogen-detection domain and at least one effector domain, and their methods of use in preventing or treating a pathogen infection in a cell or organism are described. The pathogen-detection domain and effector domain of the chimeric molecules are domains not typically found in nature to be associated together. Agents are also described herein having at least one pathogen-interacting molecular structure and at least one effector-mediating molecular structure, the agent being one that is non-naturally-occurring in a cell. The methods of prevention and treatment described herein are effective for a broad spectrum of pathogens and exhibit little or no toxic side-effects. Assays for the detection of a pathogen, pathogen component, or product produced or induced by a pathogen, are also provided.

6 Claims, 86 Drawing Sheets

OTHER PUBLICATIONS

MacCorkle, Rebecca A. et al., "Synthetic Activation of Caspases: Artificial Death Switches," *Proc. Natl. Acad. Sci. USA*, 95:3655-3660 (1998).

Müller, Anne and Rudel, Thomas, "Modification of Host Cell Apoptosis by Viral and Bacterial Pathogens," *Int. J. Med Microbiol.* 291:197-207 (2001).

Popov, Serguei et al., "Critical Role of Reverse Transcriptase in the Inhibitory Mechanism of CNI-H0294 on HIV-1 Nuclear Translocation," *Proc. Natl. Acad. Sci. USA*, 93:11859-11864 (1996).

Schwarze, Steven R. et al., "In Vivo Protein Transduction: Delivery of a Biologically Active Protein into the Mouse," *Science*, 285:1569-1572 (1999).

Shariat, Shahrokh F. et al., "Adenovirus-mediated Transfer of Inducible Caspases: A Novel "Death Switch" Gene Therapeutic Approach to Prostate Cancer," *Cancer Research*, 61(6):2562-2571 (2001).

Thomis, Daniel C. et al., "A Fas-based Suicide Switch in Human T Cells for the Treatment of Graft-Versus-Host Disease," *Blood*, 97(5):1249-1257 (2001).

Vocero-Akbani, Adita M. et al., "Killing HIV-Infected Cells by Transduction with an HIV Protease-Activated Caspase-3 Protein," *Nature Medicine*, 5(1):29-33 (1999).

Sakamoto, Kathleen M., et al., "Protacs: Chimeric molecules that target proteins to the Skp 1-Cullin-F box complex for ubiquitination and degradation," *Proc. Natl. Acad. Sci. USA* 98:8554-8559 (2001).

Wainwright, Mark, "Photodynamic antimicrobial chemotherapy (PACT)," *J. Antimicrobial Chemotherapy 42*:13-28 (1988).

Devanathan, S., et al., "Readily available fluorescein isothiocyanate-conjugated antibodies can be easily converted into targeted phototoxic agents for antibacterial, antiviral, and anticancer therapy," *Proc. Natl. Acad. Sci. USA 87*:2980-2984 (1990).

Qian, Xiao-Yan, et al., "New approach for inhibiting REV function and HIV-1 production using the influenza virus NS1 protein," *Proc. Natl. Acad. Sci. USA 93*:8873-8877 (1996).

Nagata, Shigekazu, "Apoptosis By Death Factor," *Cell 88*:355-365 (1997).

Nuñez, Gabriel, et al., "Caspases:the Proteases of the Apoptotic Pathway," *Oncogene 17*: 3237-3245 (1998).

Hu, Shimin, et al., "Caspase-14 Is a Novel Developmentally Regulated Protease," *J. Bio. Chem.*, 273(45):29648-29653(1998).

Ashorn, P., et al., "Elimination of Infectious Human Immunodeficiency Virus from Human T-Cell Cultures by Synergistic Action of CD4-Pseudomonas Exotoxin and Reverse Transcriptase Inhibitors," *Proceedings of the National Academy of Sciences, USA*, 87(22):8889-8893 (1990).

Tse E. and Rabbitts, T.H., "Intracellular Antibody-Caspase-Mediated Cell Killing: An Approach for Application in Cancer Therapy," *Proceedings of the National Academy of Sciences, USA*, 97(22):12266-12271 (2000).

Bertin J., et al., "Death Effector Domain-Containing Herpesvirus and Poxvirus Proteins Inhibit Both Fas- and TNFR1- Induced Apoptosis," *Proceedings of the National Academy of Sciences, USA* , 94:1172-1176 (1997).

Inohara, N., et al., "CLARP, a Death Effector Domain-Containing Protein Interacts with Capase-8 and Regulates Apoptosis," *Proceedings of the National Academy of Sciences, USA*, 94:10717-10722 (1997).

Kaufmann, M., et al., "Identification of a Basic Surface Area of the FADD Death Effector Domain Critical for Apoptotic Signaling," *FEBS Letters*, 527:250-254 (2002).

Thornberry, N.A. and Lazebnik, Y., "Caspases: Enemies Within," *Science*, 281:1312-1316 (1998).

Wolf, B.B. and Green, D.R., "Suicidal Tendencies: Apoptotic Cell Death by Caspase Family Proteinases," *The Journal of Biological Chemistry*, 274:20049-20052 (1999).

\* cited by examiner

Examples of Links Between Cellular Methods of Detecting and Responding to Pathogens

| | | Some nonspecific methods of detecting pathogens | | | |
|---|---|---|---|---|---|
| | | dsRNA | Interferon | Apoptosis signals | LPS |
| Some responses to pathogens | Apoptosis/ internal degradation | | | Some natural links | |
| | Interferon responses | Some natural links | Some natural links | | Some natural links |
| | Stress responses | | | | Some natural links |
| | dsRNase | | | | |
| | Endosome inhibitor | | | | |
| | Nucl. localiz. signal inhib. | | | | |
| | Enhance immune response | | Some natural links | | Some natural links |

Many viruses, bacteria, fungi, and protozoa are able to block natural links

New links may be created between various detection methods and responses

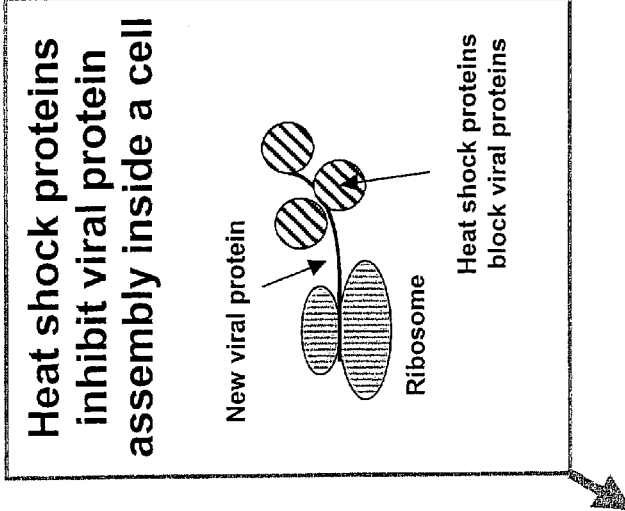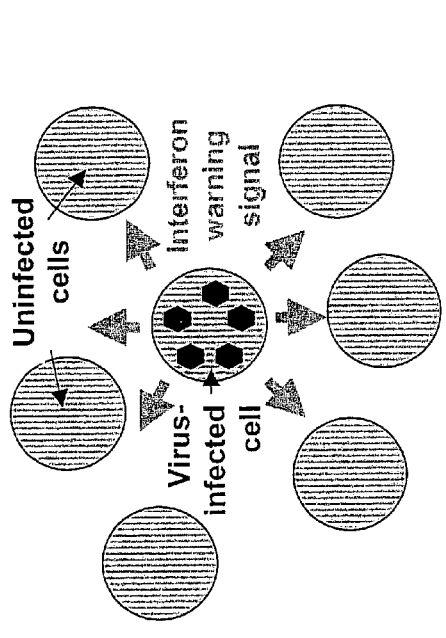
Fig. 25

IFN-Induced HSP Expression Vectors
Added IFN-inducible promoter ($P_{ISRE}$) and poly-A tail (SV40 pA)
Inserted genes into multiple cloning sequence (MCS):
- Hsp70 heat shock protein
- Hsp90 heat shock protein
- Hdj-1 heat shock protein
- Luciferase (control)
- Can add other anti-pathogen genes
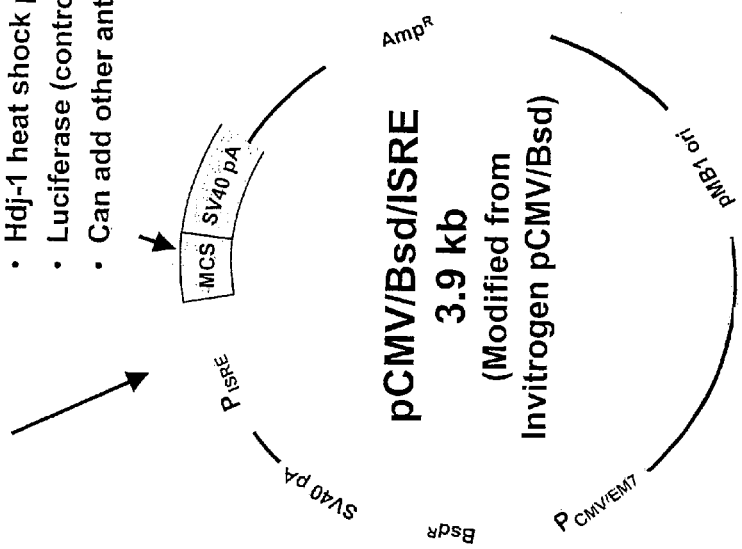
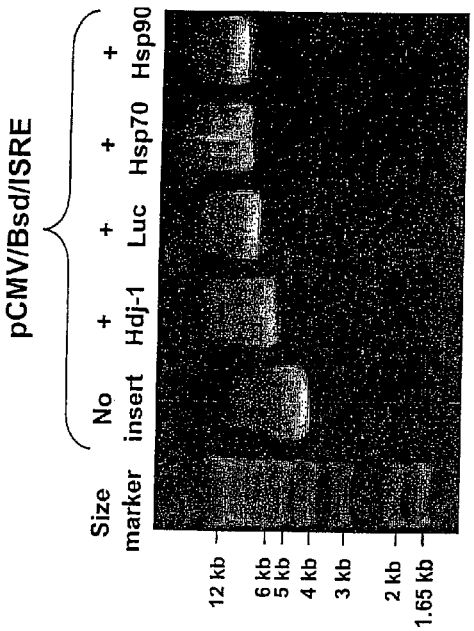
Fig. 35

Further Chimeric Caspases

Most Efficient Response to Pathogens with Least Toxicity in Uninfected Cells

Pathogen detection domain from:

- RNase L
  - Amino acids 1-335
  - Binds to 2',5'-oligoadenylate, which is produced within cells only in response to viral dsRNA

- PKR with Vaccinia E3L dsRNA binding motifs
  - Amino acids 1-181 of PKR with a.a. 54-74 and 145-165 replaced by a.a. 162-182 of E3L
  - High affinity for viral dsRNA

- LPS binding domain from BPI protein
  - Amino acids 1-199
  - Binds to most intracellular bacteria

Apoptosis effector domain from:

- APAF-1
  - Amino acids 1-97
  - Binds to Caspase 9

- Caspase 8
  - Full length  *or*
  - Amino acids 216-496

- Caspase 9
  - Full length  *or*
  - Amino acids 92-416

Fig. 48

Other IFN-Induced Anti-Pathogen Genes

Insert defense genes:

- RNase III (human)
- RNase III (*E. coli*)
- HPV-16 E5 protein
- *Salmonella* SpiC protein
- Importin $\alpha$1 (amino acids 1-99 deleted)
- Importin $\alpha$4 (amino acids 1-94 deleted)
- Importin $\alpha$6 (amino acids 1-103 deleted)
- dsRNA-activated caspase
- Other anti-pathogen genes

PCR 31: Truncated Importin α4

MluI    Kozak
ACGCGT-GCCACC-ATG-GGA-TAC 3' (SEQ ID NO: 163)

48°C

..BssHII-Kozak-HA-α4-HindIII...   pCMV/Bsd/ISRE/α4 Vector

3' TT-TGT-TTT--CTT-AAA-TTA-AAA-ATT-CGCCGGCG 5' (SEQ ID NO: 164)

50°C    NotI

→

MluI-Kozak-HA-α4-NotI    PCR Product 31

Fig. 55

PCR 32: Truncated Importin α6

BamHI    Kozak

5' GGATCC-GCCACC-ATG-GGA-TA 3' (SEQ ID NO: 171)

48°C

...BssHII-Kozak-HA-α6-HindIII...    pCMV/Bsd/ISRE/α6 Vector

3' C-CTA-CCT-AAA-GTT-GAA-ATT-TGCGCA 5' (SEQ ID NO: 172)

50°C    MluI

↓

BamHI-Kozak-HA-α6-MluI    PCR Product 32

Fig. 57

RNase III (E. coli)
Inserted Into pCMV/Bsd/ISRE Vector

SalI  Kozak    HA tag    Second 5' primer

5' GTCGAC-GCCACC-ATG-GGA-TAC-CCA-TAC-GAT-GTT-CCA-GAT-TAC-G 3' (SEQ ID NO: 173)

50°C        Gly-Gly

5' C-GAT-GTT-CCA-GAT-TAC-GCT-GGA-GGT-ATG-AAC-CCC-ATC-GTA-ATT 3' (SEQ ID NO: 174)

50°C 1  2  3  4  5  6  7 ....221 222 223 224 225 226

M  N  P  I  V  I  N ....K  K  L  E  L  E  Stop  (SEQ ID NO: 175)

5' ATG-AAC-CCC-ATC-GTA-ATT-AAT...AAA-AAA-CTG-GAG-CTG-GAA-TGA 3' (SEQ ID NO: 176)
3' TAC-TTG-GGG-TAG-CAT-TAA-TTA...TTT--TTT--GAC-CTC-GAC-CTT--ACT 5' (SEQ ID NO: 177)

First 5' primer

3' TT--GAC-CTC-GAC-CTT--ACT-TGCGCA 5'

(SEQ ID NO: 178)

3' primer  50°C        MluI pCMV/Bsd/ISRE Vector

Cut ↓ React 10

...Bsd gene-EcoRI-SmaI-BamHI-ISRE-KpnI-BssHII-AccI-PstI-SphI-HindIII-MluI-SpeI-PolyA-KasI-AmpR gene...
                    XmaI                                               SalI                                        NarI Cut ↓ NEB3

Ligate ➔

...Bsd gene-EcoRI-SmaI-BamHI-ISRE-KpnI-BssHII-AccI-Kozak-HA-RNaseIII-MluI-SpeI-PolyA-KasI-AmpR gene...
                    XmaI                                       SalI                                          NarI pCMV/Bsd/ISRE/RNase III Vector

Fig. 58

PCR 33: RNase III (*E. coli*)

BamHI  Kozak
5' GGATCC-GCCACC-ATG-GGA-TA 3'  (SEQ ID NO: 179)
48°C

...AccI-Kozak-HA-RNaseIII-MluI...    pCMV/Bsd/ISRE/RNase III Vector
SalI

3' C-GAC-CTT–ACT-TGCGCA 5'  (SEQ ID NO: 180)
50°C  MluI

BamHI-Kozak-HA-RNaseIII-MluI    PCR Product 33

PCR 34: HPV-16 E5

BamHI    Kozak        48°C
5' GGATCC-GCCACC-ATG-ACA-AAT 3' (SEQ ID NO: 186)

...BssHII-Kozak-E5-HindIII...    pCMV/Bsd/ISRE/SpiC Vector

3' GT-GCG-AAA-AAT-TAA-TGT-ATT-TGCGCA 5' (SEQ ID NO: 187)

50°C    MluI

BamHI-Kozak-E5-MluI        PCR Product 34

PCR 35: SpiC

BamHI　　Kozak

5' GGATCC-GCCACC-ATG-GGA-TA 3' (SEQ ID NO: 194)

48°C

...AccI-Kozak-HA-SpiC-MluI...　　pCMV/Bsd/ISRE/SpiC Vector
SalI

3' A-CCC-CAT-ATT-TGCGCA 5' (SEQ ID NO: 195)

48°C　　MluI

↓

BamHI-Kozak-HA-SpiC-MluI　　　PCR Product 35

Fig. 63

PCR 37: Hsp70

BamHI  Kozak

5' GGATCC-GCCACC-ATG-GCC-AA 3' (SEQ ID NO: 201)

50°C

Hsp70

```
    1   2   3   4   5   6   7     656 657 658 659 660 661 662
    M   A   K   A   A   A   V  ...  T   I   E   E   V   D  Stop   (SEQ ID NO: 202)
5'  ATG-GCC-AAA-GCC-GCG-GCA-GTC...ACC-ATT-GAG-GAG-GTA-GAT-TAG  3' (SEQ ID NO: 203)
3'  TAC-CGG-TTT-CGG-CGC-CGT-CAG...TGG-TAA-CTC-CTC-CAT-CTA-ATC  5' (SEQ ID NO: 204)
```

50°C

3' TC-CAT-CTA-ATC-TGCGCA 5' (SEQ ID NO: 205)

MluI

↓

BamHI-Kozak-Hsp70-MluI    PCR Product 37

PCR 38: Hsp90

MluI   Kozak

5' ACGCGT-GCCACC-ATG-CCT-GAG 3'  (SEQ ID NO: 206)

50°C

Hsp90

```
     1   2   3   4   5   6   7  ...719 720 721 722 723 724 725
     M   P   E   E   V   H   H  ... R   M   E   E   V   D  Stop   (SEQ ID NO: 207)
5' ATG-CCT-GAG-GAA-GTG-CAC-CAT...CGC-ATG-GAA-GAA-GTC-GAT-TAG 3'  (SEQ ID NO: 208)
3' TAC-GGA-CTC-CTT-CAC-GTG-GTA...GCG-TAC-CTT-CTT-CAG-CTA-ATC 5'  (SEQ ID NO: 209)
```

50°C

3' TAC-CTT-CTT-CAG-CTA-ATC-CGCCGGCG 5'  (SEQ ID NO: 210)

NotI

PCR Product 38

MluI-Kozak-Hsp90-NotI

Insert Aequorin with 5' Delivery Tag Into Invitrogen pET100/D-TOPO Vector

```
          G   Y   G   R   K   K   R   R   Q   R   (SEQ ID NO: 214)
5' CACC-GGC-TAT-GGC-CGC-AAG-AAA-CGT-CGC-CAG-CGT-CG 3' (SEQ ID NO: 215)
                                  50°C
First 5' TAT primer
```
```
                    R   R   Q   R   R   R   R   G  (SEQ ID NO: 216)       48°C
                5' CGT-CGC-CAG-CGT-CGC-CGC-CGT-GGC-ATG-ACC-AGC-GAA-CAA-TA 3'
                                                               (SEQ ID NO: 217)
Second 5' TAT primer
```
⎫ TAT tag

```
          G   Y   A   R   A   A   A   R   Q   A   (SEQ ID NO: 218)
5' CACC-GGC-TAT-GCG-CGC-GCA-GCG-GCT-CGC-CAG-GCG-C 3' (SEQ ID NO: 219)
                                 48°C
First 5' PTD-4 primer
```
```
                    A   R   Q   A   R   A   A   G  (SEQ ID NO: 220)       48°C
                5' GCT-CGC-CAG-GCG-CGC-GCA-GCG-GCA-GGC-ATG-ACC-AGC-GAA-CAA-TA 3'
                                                                  (SEQ ID NO: 221)
Second 5' PTD-4 primer
```
⎫ PTD-4 tag

```
          G   R   R   G   R   R   R   G   (SEQ ID NO: 222)
5' CACC-GGC-CGC-CGG-GGT-CGG-CGT-CGC-GGG-C 3' (SEQ ID NO: 223)
                            48°C
First 5' Arg primer
```
```
                    G   R   G   R   R   R   G  (SEQ ID NO: 224)       48°C
                5' GGA-CGT-CGC-GGG-CGG-CGC-CGC-ATG-ACC-AGC-GAA-CAA-TA 3'
                                                            (SEQ ID NO: 225)
Second 5' Arg primer
```
⎫ Arg tag 5' primer--no tag    5' CACC-GGC-ATG-ACC-AGC-GAA-CAA-TA 3'  ⎤ No tag
                                              (SEQ ID NO: 226)

Aequorin

```
     M   T   S   E   Q   Y    ......  Y   G   G   A   V   P   stop (SEQ ID NO: 227)
5'  ATG-ACC-AGC-GAA-CAA-TAC......TAC-GGT-GGA-GCT-GTC-CCC-TAA 3' (SEQ ID NO: 228)
3'  TAC-TGG-TCG-CTT-GTT--ATG......ATG-CCA-CCT-CGA-CAG-GGG-ATT 5' (SEQ ID NO: 229)
                            50°C
```

3' A-CCT-CGA-CAG-GGG-ATT 5' (SEQ ID NO: 230)   3' primer

Fig. 69

Insert EGFP with 5' Delivery Tag
Into Invitrogen pET100/D-TOPO Vector

```
       G   Y   G   R   K   K   R   R   Q   R (SEQ ID NO: 231)
5' CACC-GGC-TAT-GGC-CGC-AAG-AAA-CGT-CGC-CAG-CGT-CG 3' (SEQ ID NO: 232)     Second 5' TAT primer
                          50°C                           R   R   Q   R   R   R       G (SEQ ID NO: 233)  48°C
                                  First 5' TAT primer  5' CGT-CGC-CAG-CGT-CGC-CGT-CGC-ATG-GTG-AGC-AAG-GGC 3'
                                                                                          (SEQ ID NO: 234)
```

```
       G   Y   A   R   A   A   A   R   Q   A (SEQ ID NO: 235)
5' CACC-GGC-TAT-GCG-CGC-GCA-GCG-GCT-CGC-CAG-GCG-C 3' (SEQ ID NO: 236)  Second 5' PTD-4 primer
                           48°C                          A   R   Q   A   R   A       G (SEQ ID NO: 237) 48°C
                                First 5' PTD-4 primer  5' GCT-CGC-CAG-GCG-CGC-GCA-GCG-CGC-ATG-GTG-AGC-AAG-GGC 3'
                                                                                           (SEQ ID NO: 238)
```

```
       G   R   R   G   R   R   R   G   R   R       G (SEQ ID NO: 239)
5' CACC-GGC-CGC-CGC-GGT-CGC-CGG-CGT-GGA-CGT-CGC-GGG-C 3' (SEQ ID NO: 240)  Second 5' Arg primer
                           48°C                           G   R   R   G   R   R       G (SEQ ID NO: 241) 48°C
                                First 5' Arg primer  5' GGA-CGT-CGC-GGG-CGG-CGC-GGG-CGG-CGC-ATG-GTG-AGC-AAG-GGC 3'
                                                                                          (SEQ ID NO: 242)
```

```
                                G
                         5' primer--no tag    5' CACC-GGC-ATG-GTG-AGC-AAG-GGC 3'
                                                         (SEQ ID NO: 243)
```

} TAT tag

} PTD-4 tag

} Arg tag

} No tag

EGFP

```
   M   V   S   K   G   E   ......   M   D   E   L   Y   K   stop (SEQ ID NO: 244)
5' ATG-GTG-AGC-AAG-GGC-GAG......ATG-GAC-GAG-CTG-TAC-AAG-TAA 3' (SEQ ID NO: 245)
3' TAC-CAC-TCG-TTC-CCG-CTC......TAC-CTG-CTC-GAC-ATG-TTC--ATT 5' (SEQ ID NO: 246)
                         48°C
                                 3' TG-CTC-GAC-ATG-TTC-ATT  5' (SEQ ID NO: 247)   3' primer
```

Fig. 70

Insert Coding Sequence from PCR 7 or 8 with 5' Delivery Tag Into Invitrogen pET100/D-TOPO Vector

```
        G    Y    G    R    K    K    R    R    Q    R (SEQ ID NO: 248)                Second 5' TAT primer
5' CACC-GGC-TAT-GGC-CGT-AAG-AAA-CGT-CGC-CAG-CGT-CG 3' (SEQ ID NO: 249)
                                                                                                50°C
        First 5' TAT primer    5'  CGT-CGC-CGC-CAG-CGT-CGC-CGT-GGC-ATG-GCT-GGT-GAT-CTT-TC 3'
                                    R    R    R    Q    R    R    G  (SEQ ID NO: 250)
                                                                                                                    } TAT tag
                                                                                                                    (SEQ ID NO: 251)

G    Y    A    R    A    A    A    R    Q    A (SEQ ID NO: 252)                Second 5' PTD-4 primer
5' CACC-GGC-TAT-GCG-CGC-GCA-GCG-GCT-CGC-CAG-GCG-C 3' (SEQ ID NO: 253)
                                                48°C
                                         A    R    Q    A    R    A    G (SEQ ID NO: 254)
        First 5' PTD-4 primer  5'  GCT-CGC-CAG-GCG-CGC-GCA-GGC-ATG-GCT-GGT-GAT-CTT-TC 3'
                                                                                                                    } PTD-4 tag
                                                                                                                    (SEQ ID NO: 255)

G    R    R    R    R    R    G    R    R    R    G (SEQ ID NO: 256)           Second 5' Arg primer
5' CACC-GGC-CGC-CGC-CGG-CGT-GGA-CGT-CGC-GGG-C 3' (SEQ ID NO: 257)
                                    48°C
                                    G    R    R    /G    R    R    R    G (SEQ ID NO: 258)
        First 5' Arg primer    5'  GGA-CGT-CGC-GGG-CGG-CGC-CGC-CGG-ATG-GCT-GGT-GAT-CTT-TC 3'
                                                                                                50°C
                                                                                                                    } Arg tag
                                                                                                                    (SEQ ID NO: 259)

5' primer--no tag      5'  CACC-GGC-ATG-GCT-GGT-GAT-CTT-TC 3'
                                                                        50°C
                                                                                                                    } No tag
                                                                        (SEQ ID NO: 260)

3' primer   3'  TT-GAG-ATA-AAA-ATA-GTG-ATT 5'
                                    48°C
                                                        (SEQ ID NO: 261)
```

Fig. 71

Insert Coding Sequence from PCR 9 or 10 with 5' Delivery Tag Into Invitrogen pET100/D-TOPO Vector

```
       G   Y   G   R   K   K   R   R   Q   R (SEQ ID NO: 262)
5' CACC-GGC-TAT-GGC-CGC-AAG-AAA-CGT-CGC-CAG-CGT-CG 3' (SEQ ID NO: 263)
                     50°C
   First 5' TAT primer
```
⎫
⎬ TAT tag
⎭

```
                     Second 5' TAT primer
               R   R   Q   R   R   R   G (SEQ ID NO: 264)
                          50°C
   5' CGT-CGC-CAG-CGT-CGC-CGT-CGG-ATG-GCT-GGT-GAT-CTT-TC 3'
                                              (SEQ ID NO: 265)
```

```
       G   Y   A   R   A   A   A   R   Q   A (SEQ ID NO: 266)
5' CACC-GGC-TAT-GCG-CGC-GCC-GCA-GCG-GCT-CGC-CAG-GCG-C 3' (SEQ ID NO: 267)
                     48°C
   First 5' PTD-4 primer
```
⎫
⎬ PTD-4 tag
⎭

```
                     Second 5' PTD-4 primer
           R   Q   A   R   A      G (SEQ ID NO: 268)
                          50°C
   5' GCT-CGC-CAG-GCG-CGC-GCC-GCA-GGC-ATG-GCT-GGT-GAT-CTT-TC 3'
                                              (SEQ ID NO: 269)
```

```
       G   R   R   G   R   R   R   G (SEQ ID NO: 270)
5' CACC-GGC-CGC-CGG-GGT-CGG-CGT-GGA-CGT-CGC-CGC-GGG-C 3' (SEQ ID NO: 271)
                     48°C
   First 5' Arg primer
```
⎫
⎬ Arg tag
⎭

```
                     Second 5' Arg primer
           G   R   R   G   R   R   R   G (SEQ ID NO: 272)
                          50°C
   5' GGA-CGT-CGC-GGG-CGC-GGG-CGG-CGC-ATG-GCT-GGT-GAT-CTT-TC 3'
                                              (SEQ ID NO: 273)
```

```
                                G
   5' primer--no tag   5' CACC-GGC-ATG-GCT-GGT-GAT-CTT-TC 3'
                              50°C                (SEQ ID NO: 274)
```
⎱ No tag

```
                          48°C
   3' primer   3' AG-AGT-CTG-TGG-TTC-ATT 5'
                                (SEQ ID NO: 275)
```

Fig. 72

Insert Coding Sequence from PCR 25 with 5' Delivery Tag Into Invitrogen pET100/D-TOPO Vector

```
          G    Y    G    R    K    K    R    R    Q    R  (SEQ ID NO: 276)
5' CACC-GGC-TAT-GGC-CGC-AAG-AAA-CGT-CGC-CAG-CGT-CG 3' (SEQ ID NO: 277)         Second 5' TAT primer    ⎫
                                                       50°C                                            ⎬ TAT tag
              First 5' TAT primer   5' CGT-CGC-CAG-CGT-CGC-CGT-GGC-CGT-GGC-AGC-AGG-AGG-GAT-C 3'        ⎭
                                        R    R    Q    R    R    R    G (SEQ ID NO: 278)
                                                                      (SEQ ID NO: 279)

G    Y    A    R    A    A    A    R    Q    A  (SEQ ID NO: 280)
5' CACC-GGC-TAT-GCG-CGC-GCA-GCG-GCT-CGC-CAG-GCG-C 3' (SEQ ID NO: 281)          Second 5' PTD-4 primer   ⎫
                                                       48°C                                             ⎬ PTD-4 tag
              First 5' PTD-4 primer  5' GCT-CGC-CAG-GCG-CGC-GCG-GCA-GGC-GCC-ATG-GAG-AGC-AGG-GAT-C 3'   ⎭
                                        A    R    Q    A    R    A    A    G (SEQ ID NO: 282)
                                                                             (SEQ ID NO: 283)

G    R    R    G    R    R    G    R    R    R  (SEQ ID NO: 284)
5' CACC-GGC-CGC-CGG-GGT-CGG-CGT-GGA-CGT-CGC-GGG-C 3' (SEQ ID NO: 285)          Second 5' Arg primer    ⎫
                                                       48°C                                            ⎬ Arg tag
              First 5' Arg primer    5' GGA-CGT-CGC-GGG-CGG-CGG-CGC-GGC-ATG-GAG-AGC-AGG-GAT-C 3'       ⎭
                                        G    R    R    G    R    R    R    G (SEQ ID NO: 286)
                                                                             (SEQ ID NO: 287)

G
          5' primer--no tag    5' CACC-GGC-ATG-GAG-AGC-AGG-GAT-C 3'    ⎤ No tag
                                                       50°C            ⎦
                                                    (SEQ ID NO: 288)

3' primer    3' CAA-CAG-AGA-AGA-AGG-ATT 5'
                                                    50°C
                                                  (SEQ ID NO: 289)
```

Fig. 73

Insert Coding Sequence from PCR 27 with 5' Delivery Tag Into Invitrogen pET100/D-TOPO Vector

```
     G    Y    G    R    K    K    R    R    Q    R  (SEQ ID NO: 304)
5' CACC-GGC-TAT-GGC-CGC-AAG-AAA-CGT-CGC-CAG-CGT-CG 3' (SEQ ID NO: 305)
                          50°C
```
First 5' TAT primer

```
                                              R    Q    R    R    R    R    G  (SEQ ID NO: 306)
                           Second 5' TAT primer    5' CGT-CGC-CAG-CGT-CGC-CGC-CGT-GGC-ATG-GCT-GGT-GAT-CTT-TC 3'
                                                                             50°C
                                                                     (SEQ ID NO: 307)
```
} TAT tag

```
     G    Y    A    R    A    A    A    A    R    Q    A  (SEQ ID NO: 308)
5' CACC-GGC-TAT-GCG-CGC-GCG-GCA-GCG-GCT-CGC-CAG-GCG-C 3' (SEQ ID NO: 309)
                          48°C
```
First 5' PTD-4 primer

```
                                              A    R    Q    A    R    A    G  (SEQ ID NO: 310)
                          Second 5' PTD-4 primer   5' GCT-CGC-CAG-GCG-CGC-GCA-GGC-CGC-ATG-GCT-GGT-GAT-CTT-TC 3'
                                                                             50°C
                                                                     (SEQ ID NO: 311)
```
} PTD-4 tag

```
     G    R    R    G    R    R    R    G    R    R    R    G  (SEQ ID NO: 312)
5' CACC-GGC-CGC-CGG-GGT-CGG-CGT-CGC-CGA-CGT-CGC-CGC-GGG-C 3' (SEQ ID NO: 313)
                          48°C
```
First 5' Arg primer

```
                                              G    R    G    R    R    R    G  (SEQ ID NO: 314)
                          Second 5' Arg primer   5' GGA-CGT-CGC-GGG-CGG-CGC-GGC-ATG-GCT-GGT-GAT-CTT-TC 3'
                                                                             50°C
                                                                     (SEQ ID NO: 315)
```
} Arg tag 5' primer--no tag    5' CACC-GGC-ATG-GCT-GGT-GAT-CTT-TC 3'  } No tag
                                       50°C
                                 (SEQ ID NO: 316)

3' primer    3' CAA-CAG-AGA-AGA-AGG-ATT 5'
                        50°C
                  (SEQ ID NO: 317)

Fig. 75

Insert Coding Sequence from PCR 28 with 5' Delivery Tag Into Invitrogen pET100/D-TOPO Vector

```
      G    Y    G    R    K    K    R    R    Q    R  (SEQ ID NO: 318)           ⎫
5' CACC-GGC-TAT-GGC-CGC-AAG-AAA-CGT-CGC-CAG-CGT-CG 3' (SEQ ID NO: 319)   Second 5' TAT primer   ⎬ TAT tag
                                  50°C                                                         ⎭
                         R    R    Q    R    R    R    R  G (SEQ ID NO: 320)
First 5' TAT primer  5' CGT-CGC-CAG-CGT-CGC-CGT-CGT-GGC-ATG-GAG-AGC-AGG-GAT-C 3'
                                            50°C                (SEQ ID NO: 321)

G    Y    A    R    A    A    A    R    Q    A  (SEQ ID NO: 322)           ⎫
5' CACC-GGC-TAT-GCG-CGC-GCA-GCG-GCT-CGC-CAG-GCG-C 3' (SEQ ID NO: 323)   Second 5' PTD-4 primer ⎬ PTD-4 tag
                                  48°C                                                         ⎭
                         A    R    Q    A    A    R    A   G (SEQ ID NO: 324)
First 5' PTD-4 primer 5' GCT-CGC-CAG-GCG-CGC-GCA-GGC-GCA-GGC-ATG-GAG-AGC-AGG-GAT-C 3'
                                            50°C                (SEQ ID NO: 325)

G    R    R    G    R    R    G    R    R    R  (SEQ ID NO: 326)           ⎫
5' CACC-GGC-CGC-CGG-GGT-CGG-CGT-GGA-CGT-CGC-GGG-C 3' (SEQ ID NO: 327)   Second 5' Arg primer   ⎬ Arg tag
                                  48°C                                                         ⎭
                         G    R    R    G    R    R    R   G (SEQ ID NO: 328)
First 5' Arg primer  5' GGA-CGT-CGC-GGG-CGG-CGG-CGT-GGA-CGT-CGC-GGG-CGG-CGG-CGT-GGA-CGT-CGC-GGG-C 3'
                                                                (SEQ ID NO: 329)
                                            50°C
                                                                                                } No tag
5' primer--no tag   5' CACC-GGC-CGC-ATG-GAG-AGC-AGG-GAT-C 3'
                                     50°C                   (SEQ ID NO: 330)

3' primer   3' TT-GAG-ATA-AAA-ATA-GTG-ATT 5'
                                              48°C          (SEQ ID NO: 331)
```

Fig. 76

Insert Coding Sequence from PCR 29 with 5' Delivery Tag Into Invitrogen pET100/D-TOPO Vector

```
        G    Y    G    R    K    K    R    R    Q    R  (SEQ ID NO: 332)       Second 5' TAT primer  ⎫
5' CACC-GGC-TAT-GGC-CGC-AAG-AAA-CGT-CGC-CAG-CGT-CG 3' (SEQ ID NO: 333)                                ⎬ TAT tag
                                  50°C                                                                ⎭
                                        R    R    Q    R    R    R     G (SEQ ID NO: 334)
                                                              50°C
   First 5' TAT primer    5' CGT-CGC-CAG-CGT-CGC-CGT-GGC-GTC-AAC-CCT-GGC-GTC 3'
                                                                          (SEQ ID NO: 335)

G    Y    A    R    A    A    A    A    R    Q    A  (SEQ ID NO: 336)   Second 5' PTD-4 primer ⎫
5' CACC-GGC-TAT-GCG-CGC-GCA-GCG-GCT-CGC-CAG-GCG-C 3' (SEQ ID NO: 337)                                   ⎬ PTD-4 tag
                                        48°C                                                            ⎭
                                        A    R    Q    A    R    A    A     G (SEQ ID NO: 338)
                                                              50°C
   First 5' PTD-4 primer  5' GCT-CGC-CAG-GCG-CGC-GCA-GGC-GTC-AAC-CCT-GGC-GTC 3'
                                                                          (SEQ ID NO: 339)

G    R    R    G    R    R    R    R    R     G  (SEQ ID NO: 340)       Second 5' Arg primer  ⎫
5' CACC-GGC-CGC-CGG-GGT-CGG-CGT-CGA-CGT-CGC-GGG-C 3' (SEQ ID NO: 341)                                  ⎬ Arg tag
                                        48°C                                                           ⎭
                                        G    R    G    R    R     R    G (SEQ ID NO: 342)
                                                              50°C
   First 5' Arg primer   5' GGA-CGT-CGC-GGG-CGG-CGG-CGT-AAC-CCT-GGC-GTC 3'
                                                                          (SEQ ID NO: 343)

5' primer--no tag   5' CACC-GGC-GTC-AAC-CCT-GGC-GTC 3'                 ⎤ No tag
                                        50°C          (SEQ ID NO: 344)    ⎦

48°C
                       3' primer  3' TT-GAG-ATA-AAA-ATA-GTG-ATT 5'
                                                      (SEQ ID NO: 345)
```

Fig. 77

Insert Coding Sequence from PCR 30 with 5' Delivery Tag Into Invitrogen pET100/D-TOPO Vector

```
     G    Y    G    R    K    K    R    R    Q    R (SEQ ID NO: 346)
5' CACC-GGC-TAT-GGC-CGC-AAG-AAA-CGT-CGC-CAG-CGT-CG 3' (SEQ ID NO: 347)              Second 5' TAT primer  ⎫
                                                                                                          ⎬ TAT tag
               R    R    Q    R    R    R    R    G (SEQ ID NO: 348)       50°C                           ⎭
First 5' TAT primer   5' CGT-CGC-CAG-CGT-CGC-CGT-CGC-GGT-GCC-GCC-AGG-AAA-CTA-CTT-TC 3'
                                                                                   (SEQ ID NO: 349)

G    Y    A    R    A    A    A    R    Q    A (SEQ ID NO: 350)
5' CACC-GGC-TAT-GCG-CGC-GCA-GCG-GCT-CGC-CAG-GCG-C 3' (SEQ ID NO: 351)               Second 5' PTD-4 primer ⎫
                                                                                                          ⎬ PTD-4 tag
               A    R    Q    A    A    R    A    G (SEQ ID NO: 352)       50°C                           ⎭
First 5' PTD-4 primer  5' GCT-CGC-CAG-GCG-GCA-GCG-CGC-GCA-GGC-GCC-AGG-AAA-CTA-CTT-TC 3'
                                                                                    (SEQ ID NO: 353)

G    R    R    G    R    R    R    G    R    R (SEQ ID NO: 354)
5' CACC-GGC-CGC-CGG-GGT-CGG-CGT-CGG-CGT-CGC-GGG-C 3' (SEQ ID NO: 355)               Second 5' Arg primer  ⎫
                                                                                                          ⎬ Arg tag
               G    R    R    G    R    R    R    G (SEQ ID NO: 356)       50°C                          ⎭
First 5' Arg primer  5' GGA-CGT-CGC-GGG-CGG-CGC-GGC-GCC-AGG-AAA-CTA-CTT-TC 3'
                                                                            (SEQ ID NO: 357)

5' primer--no tag   5' CACC-GGC-GCC-AGG-AAA-CTA-CTT-TC 3'  ⎱ No tag
                                                (SEQ ID NO: 358)

50°C
3' primer    3' CCC-TGG-AAA-TTG-AAA-ATC 5'
                                       (SEQ ID NO: 359)
```

Fig. 78

Insert Coding Sequence from PCR 31 with 5' Delivery Tag Into Invitrogen pET100/D-TOPO Vector

```
            G   Y   G   R   K   K   R   R   Q   R (SEQ ID NO: 360)
5' CACC-GGC-TAT-GGC-CGC-AAG-AAA-CGT-CGC-CAG-CGT-CG 3' (SEQ ID NO: 361)      Second 5' TAT primer ⎫
                                                                                                 ⎬ TAT tag
First 5' TAT primer                           50°C                                               ⎭
                        R   R   Q   R   R   R   G (SEQ ID NO: 362)
                5' CGT-CGC-CAG-CGT-CGC-CGT-CGG-GCA-GCA-AGA-AAA-CTG-TTA-TCC 3'
                                                 50°C
                                         (SEQ ID NO: 363)

G   Y   A   R   A   A   A   A   R   Q   A (SEQ ID NO: 364)
5' CACC-GGC-TAT-GCG-CGC-GCA-GCG-GCT-CGC-CAG-GCG-C 3' (SEQ ID NO: 365)        Second 5' PTD-4 primer ⎫
                                                                                                   ⎬ PTD-4 tag
First 5' PTD-4 primer                 48°C                                                         ⎭
                            A   R   Q   A   R   A   A   G (SEQ ID NO: 366)
                5' GCT-CGC-CAG-GCG-CGC-GCG-GCA-GGC-GCA-AGA-AAA-CTG-TTA-TCC 3'
                                                 50°C
                                         (SEQ ID NO: 367)

G   R   R   G   R   R   R   G (SEQ ID NO: 368)
5' CACC-GGC-CGC-CGG-GGT-CGG-CGT-CGG-GGG-C 3' (SEQ ID NO: 369)                Second 5' Arg primer ⎫
                                                                                                 ⎬ Arg tag
First 5' Arg primer               48°C                                                           ⎭
                            G   R   R   G   R   R   R   G (SEQ ID NO: 370)
                5' GGA-CGT-CGC-GGG-CGG-CGC-GGC-GGC-GCA-AGA-AAA-CTG-TTA-TCC 3'
                                                 50°C
                                         (SEQ ID NO: 371)
                                                                G
5' primer--no tag   5' CACC-GGC-GCA-AGA-AAA-CTG-TTA-TCC 3' ⎤ No tag
                                 50°C                      ⎦ (SEQ ID NO: 372)

3' primer   3' TT-TGT-TTT-CTT-AAA-TTA-AAA-ATT 5'
                                        (SEQ ID NO: 373)
```

Fig. 79

Insert Coding Sequence from PCR 32 with 5' Delivery Tag Into Invitrogen pET100/D-TOPO Vector

```
     G   Y   G   R   K   K   R   R   Q   R (SEQ ID NO: 374)
5' CACC-GGC-TAT-GGC-CGC-AAG-AAA-CGT-CGC-CAG-CGT-CG 3' (SEQ ID NO: 375)    Second 5' TAT primer  ⎫
                                                50°C                                           ⎬ TAT tag
                        R   R   Q   R   R   R   R   G (SEQ ID NO: 376)                         ⎭
   First 5' TAT primer  5' CGT-CGC-CAG-CGT-CGC-CGT-CGC-CGT-GGC-TTT-AGA-AAG-CTG-CTT-TCT-A 3'
                                                50°C
                                                (SEQ ID NO: 377)

G   Y   A   R   A   A   A   A   R   Q   A (SEQ ID NO: 378)
5' CACC-GGC-TAT-GCG-CGC-GCA-GCG-GCT-GCG-CAG-GCG-C 3' (SEQ ID NO: 379)       Second 5' PTD-4 primer  ⎫
                                          48°C                                                     ⎬ PTD-4 tag
                        A   R   Q   A   R   A   A   G (SEQ ID NO: 380)                             ⎭
   First 5' PTD-4 primer  5' GCT-CGC-CAG-GCG-CGC-GCA-GCG-GCA-GGC-TTT-AGA-AAG-CTG-CTT-TCT-A 3'
                                                50°C
                                                (SEQ ID NO: 381)

G   R   R   G   R   R   R   G   R   R   G (SEQ ID NO: 382)
5' CACC-GGC-CGC-CGC-CGG-GGT-CGC-CGG-CGT-GGA-CGT-GGG-C 3' (SEQ ID NO: 383)    Second 5' Arg primer  ⎫
                                          48°C                                                     ⎬ Arg tag
                        G   R   R   G   R   R   R   G (SEQ ID NO: 384)                             ⎭
   First 5' Arg primer  5' GGA-CGT-CGC-GGG-CGG-CGC-GGC-GGG-GGC-TTT-AGA-AAG-CTG-CTT-TCT-A 3'
                                                50°C
                                                (SEQ ID NO: 385)

5' primer--no tag   5' CACC-GGC-TTT-AGA-AAG-CTG-CTT-TCT-A 3' ⎱ No tag
                                                (SEQ ID NO: 386)

G
                                 50°C
                3' primer  3' C-CTA-CCT-AAA-GTT-GAA-ATT 5'
                                                (SEQ ID NO: 387)
```

Fig. 80

Insert Coding Sequence from PCR 33 with 5' Delivery Tag Into Invitrogen pET100/D-TOPO Vector

```
     G    Y    G    R    K    K    R    R    Q    R (SEQ ID NO: 388)
5' CACC-GGC-TAT-GGC-CGC-AAG-AAA-CGT-CGC-CAG-CGT-CG 3' (SEQ ID NO: 389)       Second 5' TAT primer  ⎫
         First 5' TAT primer                    50°C                                                ⎬ TAT tag
                                  R    R    Q    R    R    R    G (SEQ ID NO: 390)                  ⎭
                          5' CGT-CGC-CAG-CGT-CGC-CGT-GGC-ATG-AAC-CCC-ATC-GTA-ATT 3'
                                                        50°C
                                                   (SEQ ID NO: 391)

G    Y    A    R    A    A    A    A    R    Q    A (SEQ ID NO: 392)
5' CACC-GGC-TAT-GCG-CGC-GCA-GCG-GCT-CGC-CAG-GCG-C 3' (SEQ ID NO: 393)       Second 5' PTD-4 primer  ⎫
         First 5' PTD-4 primer                  48°C                                                ⎬ PTD-4 tag
                              A    R    Q    A    R    A    A    G (SEQ ID NO: 394)                 ⎭
                          5' GCT-CGC-CAG-GCG-CGC-GCA-GCG-GCA-GGC-ATG-AAC-CCC-ATC-GTA-ATT 3'
                                                        50°C
                                                   (SEQ ID NO: 395)

G    R    R    G    R    R    G    R    R    G (SEQ ID NO: 396)
5' CACC-GGC-CGC-CGG-GGT-CGG-CGT-CGG-GGA-CGT-CGC-CGC-GGG-C 3' (SEQ ID NO: 397)   Second 5' Arg primer ⎫
         First 5' Arg primer                    48°C                                                 ⎬ Arg tag
                              G    R    R    G    R    R    G (SEQ ID NO: 398)                       ⎭
                          5' GGA-CGT-CGC-GGG-CGG-CGG-CGT-GGC-ATG-AAC-CCC-ATC-GTA-ATT 3'
                                                        50°C
                                                   (SEQ ID NO: 399)

5' primer--no tag    5' CACC-GGC-ATG-AAC-CCC-ATC-GTA-ATT 3'  ⎫ No tag
                                        50°C                   ⎭
                                   (SEQ ID NO: 400)

3' primer       3' TT-GAC-CTC-GAC-CTT-ACT 5'
                                        50°C
                                   (SEQ ID NO: 401)
```

Fig. 81

Insert Coding Sequence from PCR 34 with 5' Delivery Tag Into Invitrogen pET100/D-TOPO Vector

```
      G    Y    G    R    K    K    R    R    Q    R  (SEQ ID NO: 402)
5' CACC-GGC-TAT-GGC-CGC-AAG-AAA-CGT-CGC-CAG-CGT-CG 3' (SEQ ID NO: 403)                Second 5' TAT primer  ⎫
                             50°C                                                                            ⎬ TAT tag
                     R    R    Q    R    R    R    R    G  (SEQ ID NO: 404)                                 ⎭
First 5' TAT primer   5' CGT-CGC-CAG-CGT-CGC-CGT-CGC-GGC-ATG-ACA-AAT-CTT-GAT-ACT-G 3'   50°C
                                                                                  (SEQ ID NO: 405)

G    Y    A    R    A    A    A    R    Q    A  (SEQ ID NO: 406)
5' CACC-GGC-TAT-GCG-CGC-GCA-GCG-GCT-CGC-CAG-GCG-C 3' (SEQ ID NO: 407)                Second 5' PTD-4 primer  ⎫
                             48°C                                                                            ⎬ PTD-4 tag
                     A    R    Q    A    A    R    A    G  (SEQ ID NO: 408)                                 ⎭
First 5' PTD-4 primer  5' GCT-CGC-CAG-GCG-CGC-CGC-GCA-GGC-ATG-ACA-AAT-CTT-GAT-ACT-G 3'   50°C
                                                                                    (SEQ ID NO: 409)

G    R    R    G    R    R    R    G    R    R    G  (SEQ ID NO: 410)
5' CACC-GGC-CGC-CGC-GGG-CGT-CGA-CGT-CGC-GGG-C 3' (SEQ ID NO: 411)                    Second 5' Arg primer  ⎫
                             48°C                                                                          ⎬ Arg tag
                     G    R    G    R    R    G    R    R    G  (SEQ ID NO: 412)                          ⎭
First 5' Arg primer   5' GGA-CGT-CGC-GGG-CGG-CGG-CGC-GGG-CGC-ATG-ACA-AAT-CTT-GAT-ACT-G 3'   50°C
                                                                                      (SEQ ID NO: 413)

5' primer--no tag    5' CACC-GGC-CGC-ATG-ACA-AAT-CTT-GAT-ACT-G 3' ⎤ No tag
                                                (SEQ ID NO: 414)   ⎦
                               50°C 3' primer    3' GT-GCG-AAA-AAT-TAA-TGT-ATT 5'
                                (SEQ ID NO: 415)
```

Fig. 82

Insert Coding Sequence from PCR 35 with 5' Delivery Tag Into Invitrogen pET100/D-TOPO Vector

```
     G    Y    G    R    K    K    R    R    Q    R (SEQ ID NO: 416)
5' CACC-GGC-TAT-GGC-CGC-AAG-AAA-CGT-CGC-CAG-CGT-CG 3' (SEQ ID NO: 417)
                      50°C
```
First 5' TAT primer

```
                                          R    R    Q    R    R    R    R    G (SEQ ID NO: 418)    Second 5' TAT primer    } TAT tag
                                       5' CGT-CGC-CAG-CGT-CGC-CGT-CGC-CGT-GGC-ATG-CTG-GCA-GTT-TTA-AAA 3'
                                                                48°C
                                                                                   (SEQ ID NO: 419)
```

```
     G    Y    A    R    A    A    A    A    R    Q    A (SEQ ID NO: 420)
5' CACC-GGC-TAT-GCG-CGC-GCA-GCG-GCT-CGC-CAG-GCG-C 3' (SEQ ID NO: 421)
                      48°C
```
First 5' PTD-4 primer

```
                                          A    R    Q    A    R    A    A    G (SEQ ID NO: 422)    Second 5' PTD-4 primer   } PTD-4 tag
                                       5' GCT-CGC-CAG-GCG-CGC-GCA-GCC-GCA-GGC-ATG-CTG-GCA-GTT-TTA-AAA 3'
                                                                48°C
                                                                                   (SEQ ID NO: 423)
```

```
     G    R    R    G    R    R    R    R    G    R    R    G (SEQ ID NO: 424)
5' CACC-GGC-CGC-CGC-GGC-CGG-CGT-CGG-CGT-CGC-CGC-GGG-C 3' (SEQ ID NO: 425)
                      48°C
```
First 5' Arg primer

```
                                          G    R    R    G    R    R    R    R    G (SEQ ID NO: 426)    Second 5' Arg primer    } Arg tag
                                       5' GGA-CGT-CGC-GGG-CGG-CGC-CGG-CGT-CGC-ATG-CTG-GCA-GTT-TTA-AAA 3'
                                                                48°C
                                                                                   (SEQ ID NO: 427)
```

```
5' primer--no tag   5' CACC-GGC-ATG-CTG-GCA-GTT-TTA-AAA 3'  } No tag
                                             (SEQ ID NO: 428)

3' primer     3' TA-AGC-CCA-CCC-CAT-ATT 5'
                                 50°C
                                          (SEQ ID NO: 429)
```

Fig. 83

Insert Coding Sequence from PCR 36 with 5' Delivery Tag Into Invitrogen pET100/D-TOPO Vector

```
           G    Y    G    R    K    K    R    R    Q    R  (SEQ ID NO: 430)
5' CACC-GGC-TAT-GGC-CGC-AAG-AAA-CGT-CGC-CAG-CGT-CG 3' (SEQ ID NO: 431)      Second 5' TAT primer  ⎫
                                                     50°C                                         ⎬ TAT
             R    R    Q    R    R    R    G (SEQ ID NO: 432)                                     ⎪ tag
 First 5' TAT primer   5' CGT-CGC-CAG-CGT-CGC-CGT-GGT-ATG-GGT-AAA-GAT-TAC-TAC 3'                   ⎭
                                                     48°C
                                                             (SEQ ID NO: 433)

G    Y    A    R    A    A    A    R    Q    A  (SEQ ID NO: 434)
5' CACC-GGC-TAT-GCG-CGC-GCA-GCG-GCT-CGC-CAG-GCG-C 3' (SEQ ID NO: 435)        Second 5' PTD-4 primer ⎫
                                                     48°C                                          ⎬ PTD-4
             A    R    Q    A    R    A    A    G (SEQ ID NO: 436)                                 ⎪ tag
 First 5' PTD-4 primer  5' GCT-CGC-CAG-GCG-CGC-GCG-GCA-GGC-ATG-GGT-AAA-GAT-TAC-TAC 3'               ⎭
                                                     48°C
                                                             (SEQ ID NO: 437)

G    R    R    G    R    R    R    G    R    R    G (SEQ ID NO: 438)
5' CACC-GGC-CGC-CGC-GGG-CGT-CGG-CGT-GGA-CGT-CGC-GGG-C 3' (SEQ ID NO: 439)    Second 5' Arg primer  ⎫
                                                     48°C                                         ⎬ Arg
             G    R    R    G    R    R    G (SEQ ID NO: 440)                                     ⎪ tag
 First 5' Arg primer   5' GGA-CGT-CGC-GGG-CGG-CGG-CGC-ATG-GGT-AAA-GAT-TAC-TAC 3'                   ⎭
                                                     48°C
                                                             (SEQ ID NO: 441)

5' primer--no tag   5' CACC-GGC-ATG-GGT-AAA-GAT-TAC-TAC 3' ⎤ No tag
                                                           ⎦ (SEQ ID NO: 442)
                                   G
                                  48°C 3' primer    3' GTC-CAA-GAA-GGT-TAT-ATC 5'
                                     50°C
                                                    (SEQ ID NO: 443)
```

Fig. 84

Insert Coding Sequence from PCR 37 with 5' Delivery Tag Into Invitrogen pET100/D-TOPO Vector

```
         G    Y    G    R    K    K    R    R    Q    R  (SEQ ID NO: 444)
5' CACC-GGC-TAT-GGC-CGC-AAG-AAA-CGT-CGC-CAG-CGT-CG 3' (SEQ ID NO: 445)    ⎫
                                                                          ⎬ TAT tag
First 5' TAT primer           50°C           Second 5' TAT primer         ⎭

R    R    Q    R    R    R    R    G  (SEQ ID NO: 446)
                         5' CGT-CGC-CAG-CGT-CGC-CGC-CGT-GGC-CGT-GGC-ATG-GCC-AAA-GCC-GCG 3'
                                                                          (SEQ ID NO: 447)

G    Y    A    R    A    A    A    R    Q    A  (SEQ ID NO: 448)
5' CACC-GGC-TAT-GCG-CGC-GCA-GCG-GCT-CGC-CAG-GCG-C 3' (SEQ ID NO: 449)     ⎫
                                                                          ⎬ PTD-4 tag
First 5' PTD-4 primer         48°C           Second 5' PTD-4 primer       ⎭

A    R    Q    A    A    R    A    A    G  (SEQ ID NO: 450)
                         5' GCT-CGC-CAG-GCG-GCA-CGC-GCA-GCG-GCC-AAA-GCC-GCG 3'
                                                                          (SEQ ID NO: 451)

G    R    R    G    R    R    G    R    R    G  (SEQ ID NO: 452)
5' CACC-GGC-CGC-CGC-GGT-CGG-CGT-GGA-CGT-CGC-GGG-C 3' (SEQ ID NO: 453)     ⎫
                                                                          ⎬ Arg tag
First 5' Arg primer           48°C           Second 5' Arg primer         ⎭

G    R    R    G    R    R    G  (SEQ ID NO: 454)
                         5' GGA-CGT-CGC-GGG-CGG-CGC-GGG-CGC-ATG-GCC-AAA-GCC-GCG 3'
                                                                          (SEQ ID NO: 455)

5' primer--no tag   5' CACC-GGC-ATG-GCC-AAA-GCC-GCG 3'  ⎤ No tag
                                        (SEQ ID NO: 456) ⎦
                              50°C 3' primer   3' TAA-CTC-CTC-CAT-CTA-ATC 5'
                                        (SEQ ID NO: 457)
```

Fig. 85

Insert Coding Sequence from PCR 38 with 5' Delivery Tag Into Invitrogen pET100/D-TOPO Vector

```
      G   Y   G   R   K   K   R   R   Q                    R (SEQ ID NO: 458)           Second 5' TAT primer    ⎫
5' CACC-GGC-TAT-GGC-CGC-AAG-AAA-CGT-CGC-CAG-CGT-CG 3' (SEQ ID NO: 459)                                          ⎬ TAT
                                                 50°C                                                            ⎪  tag
                    R   R   Q    R   R   R   Q   R   G (SEQ ID NO: 460)                                         ⎪
        First 5' TAT primer    5' CGT-CGC-CAG-CGT-CGC-CGC-CGT-GGC-CGT-GAG-GAA-GTG-C 3'                          ⎪
                                                                  (SEQ ID NO: 461)                              ⎭
                                                                                       50°C G   Y   A   R   A   A   A   A   R   Q                  A (SEQ ID NO: 462)           Second 5' PTD-4 primer  ⎫
5' CACC-GGC-TAT-GCG-CGC-GCA-GCG-CCT-CGC-CAG-GCG-C 3' (SEQ ID NO: 463)                                              ⎬ PTD-4
                                                   48°C                                                            ⎪  tag
                    A   R   Q   A    R   A   A   G (SEQ ID NO: 464)                                               ⎪
        First 5' PTD-4 primer  5' GCT-CGC-CAG-CGC-CGC-GCA-GCG-CGC-ATG-CCT-GAG-GAA-GTG-C 3'                        ⎪
                                                                    (SEQ ID NO: 465)                              ⎭
                                                                                        50°C G   R   R   G   R   R   R   G   R    R                     G (SEQ ID NO: 466)        Second 5' Arg primer   ⎫
5' CACC-GGC-CGC-CGG-GGT-CGC-CGT-CGG-CGT-GGA-CGT-CGC-GGG-C 3' (SEQ ID NO: 467)                                      ⎬ Arg
                                                    48°C                                                           ⎪ tag
                    G   R   G   R   R    R   R   G (SEQ ID NO: 468)                                               ⎪
        First 5' Arg primer   5' GGA-CGT-CGC-GGG-CGG-CGC-CGG-CGC-ATG-CCT-GAG-GAA-GTG-C 3'                         ⎪
                                                                       (SEQ ID NO: 469)                            ⎭
                                                                                        50°C 5' primer--no tag    5' CACC-GGC-ATG-CCT-GAG-GAA-GTG-C 3'                                       ⎤ No tag
                                                          (SEQ ID NO: 470)                      ⎦
                                                        50°C 3' primer    3' TAC-CTT-CTT-CAG-CTA-ATC 5'
                                              (SEQ ID NO: 471)
```

Fig. 86

SEQUENCE LISTING

<160> NUMBER OF SEQ ID NOS: 473

<210> SEQ ID NO 1
<211> LENGTH: 6
<212> TYPE: PRT
<213> ORGANISM: Artificial Sequence
<220> FEATURE:
<223> OTHER INFORMATION: polypeptide linker

<400> SEQUENCE: 1

Ser Gly Gly Gly Ser Gly
 1               5

<210> SEQ ID NO 2
<211> LENGTH: 12
<212> TYPE: PRT
<213> ORGANISM: Unknown
<220> FEATURE:
<223> OTHER INFORMATION: partial PKR N and C terminal sequence
<220> FEATURE:
<221> NAME/KEY: NON_CONS
<222> LOCATION: 6-7

<400> SEQUENCE: 2

Met Ala Gly Asp Leu Ser Glu Thr Ser Val Lys Ser
 1               5                  10

<210> SEQ ID NO 3
<211> LENGTH: 36
<212> TYPE: DNA
<213> ORGANISM: Unknown
<220> FEATURE:
<223> OTHER INFORMATION: partial PKR 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 3
atggctggtg atctttcaga aacctcagtg aaatct                               36

<210> SEQ ID NO 4
<211> LENGTH: 36
<212> TYPE: DNA
<213> ORGANISM: Unknown
<220> FEATURE:
<223> OTHER INFORMATION: partial PKR 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 4
agatttcact gaggtttctg aaagatcacc agccat                               36

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
ggatccgcca ccatggctgg tgatctttc                                       29

<210> SEQ ID NO 6

```
<211> LENGTH: 35
<212> TYPE: DNA
<213> ORGANISM: Artificial Sequence
<220> FEATURE:
<223> OTHER INFORMATION: primer

<400> SEQUENCE: 6
cctgatccac cgccagaaga tttcactgag gtttc                              35

<210> SEQ ID NO 7
<211> LENGTH: 14
<212> TYPE: PRT
<213> ORGANISM: Unknown
<220> FEATURE:
<223> OTHER INFORMATION: partial caspase 3 N and C terminal sequence
<220> FEATURE:
<221> NAME/KEY: NON_CONS
<222> LOCATION: 7-8

<400> SEQUENCE: 7

Met Glu Asn Thr Glu Asn Ser Lys Glu Leu Tyr Phe Tyr His
 1               5                  10

<210> SEQ ID NO 8
<211> LENGTH: 42
<212> TYPE: DNA
<213> ORGANISM: Unknown
<220> FEATURE:
<223> OTHER INFORMATION: partial caspase 3  5' and 3' sequence
<220> FEATURE:
<221> NAME/KEY: misc_difference
<222> LOCATION: 21-22
<223> OTHER INFORMATION: non-consecutive nucleotides

<400> SEQUENCE: 8
atggagaaca ctgaaaactc aaaagaactc tattttatc ac                       42

<210> SEQ ID NO 9
<211> LENGTH: 42
<212> TYPE: DNA
<213> ORGANISM: Unknown
<220> FEATURE:
<223> OTHER INFORMATION: partial caspase 3  5' and 3' complement
      sequence
<220> FEATURE:
<221> NAME/KEY: misc_difference
<222> LOCATION: 21-22

<400> SEQUENCE: 9
gtgataaaaa tagagttctt ttgagttttc agtgttctcc at                      42

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
tggcggtgga tcaggaatgg agaacactga aaactc                             36

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
```

```
acgcgtttag tgataaaaat agagttctt                                         29
```

```
<210> SEQ ID NO 12
<211> LENGTH: 22
<212> TYPE: PRT
<213> ORGANISM: Artificial Sequence
<220> FEATURE:
<223> OTHER INFORMATION: partial PKR(1-174) + linker + caspase 3
      sequence
<220> FEATURE:
<221> NAME/KEY: NON_CONS
<222> LOCATION: 4-5, 18-19

<400> SEQUENCE: 12

Met Ala Gly Asp Ser Val Lys Ser Ser Gly Gly Gly Ser Gly Met Glu
1               5                   10                  15

Asn Thr Tyr Phe Tyr His
            20
```

```
<210> SEQ ID NO 13
<211> LENGTH: 87
<212> TYPE: DNA
<213> ORGANISM: Artificial Sequence
<220> FEATURE:
<223> OTHER INFORMATION: partial PKR(1-174) + linker + caspase 3
      sequence
<220> FEATURE:
<221> NAME/KEY: misc_difference
<222> LOCATION: 24-25, 66-67
<223> OTHER INFORMATION: non-consecutive nucleotides

<400> SEQUENCE: 13
ggatccgcca ccatggctgg tgattcagtg aaatcttctg gcggtggatc aggaatggag    60
aacacttatt tttatcacta aacgcgt                                        87
```

```
<210> SEQ ID NO 14
<211> LENGTH: 87
<212> TYPE: DNA
<213> ORGANISM: Artificial Sequence
<220> FEATURE:
<223> OTHER INFORMATION: partial PKR(1-174) + linker + caspase 3
      complement
      sequence
<220> FEATURE:
<221> NAME/KEY: misc_difference
<222> LOCATION: 21-22, 63-64
<223> OTHER INFORMATION: non-consecutive nucleotides

<400> SEQUENCE: 14
acgcgtttag tgataaaaat aagtgttctc cattcctgat ccaccgccag aagatttcac    60
tgaatcacca gccatggtgg cggatcc                                        87
```

```
<210> SEQ ID NO 15
<211> LENGTH: 19
<212> TYPE: PRT
<213> ORGANISM: Unknown
<220> FEATURE:
<223> OTHER INFORMATION: PKR partial N and C terminal sequence
<220> FEATURE:
<221> NAME/KEY: NON_CONS
<222> LOCATION: 6-7

<400> SEQUENCE: 15

Met Ala Gly Asp Leu Ser Glu Thr Ser Val Lys Ser Asp Tyr Leu Ser
1               5                   10                  15

Ser Gly Ser
```

```
<210> SEQ ID NO 16
<211> LENGTH: 57
<212> TYPE: DNA
<213> ORGANISM: unknown
<220> FEATURE:
<223> OTHER INFORMATION: partial PKR 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 16
atggctggtg atctttcaga aacctcagtg aaatctgact acctgtcctc tggttct          57

<210> SEQ ID NO 17
<211> LENGTH: 57
<212> TYPE: DNA
<213> ORGANISM: Unknown
<220> FEATURE:
<223> OTHER INFORMATION: partial PKR 5' and 3' complement sequence
<220> FEATURE:
<221> NAME/KEY: misc_difference
<222> LOCATION: 39-40
<223> OTHER INFORMATION: non-consecutive nucleotides

<400> SEQUENCE: 17
agaaccagag gacaggtagt cagatttcac tgaggtttct gaaagatcac cagccat          57

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
ggatccgcca ccatggctgg tgatctttc                                          29

<210> SEQ ID NO 19
<211> LENGTH: 16
<212> TYPE: DNA
<213> ORGANISM: Artificial Sequence
<220> FEATURE:
<223> OTHER INFORMATION: primer

<400> SEQUENCE: 19
agaaccagag gacagg                                                        16

<210> SEQ ID NO 20
<211> LENGTH: 14
<212> TYPE: PRT
<213> ORGANISM: Unknown
<220> FEATURE:
<223> OTHER INFORMATION: partial caspase 3 N and C terminal sequence
<220> FEATURE:
<221> NAME/KEY: NON_CONS
<222> LOCATION: 7-8

<400> SEQUENCE: 20

Met Glu Asn Thr Glu Asn Ser Lys Glu Leu Tyr Phe Tyr His
 1               5                  10

<210> SEQ ID NO 21
<211> LENGTH: 42
<212> TYPE: DNA
<213> ORGANISM: Unknown
<220> FEATURE:
```

```
<223> OTHER INFORMATION: partial caspase 3 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 21
atggagaaca ctgaaaactc aaaagaactc tattttatc ac                    42

<210> SEQ ID NO 22
<211> LENGTH: 42
<212> TYPE: DNA
<213> ORGANISM: Unknown
<220> FEATURE:
<223> OTHER INFORMATION: partial caspase 3 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 22
gtgataaaaa tagagttctt ttgagttttc agtgttctcc at                   42

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
cctgtcctct ggttctatgg agaacactga aaactc                          36

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
acgcgtttag tgataaaaat agagttctt                                  29

<210> SEQ ID NO 25
<211> LENGTH: 23
<212> TYPE: PRT
<213> ORGANISM: Artificial Sequence
<220> FEATURE:
<223> OTHER INFORMATION: partial PKR(1-181) + caspase 3 sequence
<220> FEATURE:
<221> NAME/KEY: NON_CONS
<222> LOCATION: 4-5, 19-20

<400> SEQUENCE: 25

Met Ala Gly Asp Ser Val Lys Ser Asp Tyr Leu Ser Ser Gly Ser Met
 1               5                  10                  15

Glu Asn Thr Tyr Phe Tyr His
            20

<210> SEQ ID NO 26
<211> LENGTH: 90
<212> TYPE: DNA
<213> ORGANISM: Artificial Sequence
<220> FEATURE:
<223> OTHER INFORMATION: partial PKR(1-181) + caspase 3 sequence
<220> FEATURE:
<221> NAME/KEY: misc_difference
<222> LOCATION: 24-25, 69-70
```

```
<223> OTHER INFORMATION: non-consecutive nucleotides

<400> SEQUENCE: 26
ggatccgcca ccatggctgg tgattcagtg aaatctgact acctgtcctc tggttctatg      60
gagaacactt atttttatca ctaaacgcgt                                       90

<210> SEQ ID NO 27
<211> LENGTH: 90
<212> TYPE: DNA
<213> ORGANISM: Artificial Sequence
<220> FEATURE:
<223> OTHER INFORMATION: partial PKR(1-181) + caspase 3 complement
      sequence
<220> FEATURE:
<221> NAME/KEY: misc_difference
<222> LOCATION: 21-22, 66-67
<223> OTHER INFORMATION: non-consecutive nucleotides

<400> SEQUENCE: 27
acgcgtttag tgataaaaat aagtgttctc catagaacca gaggacaggt agtcagattt      60
cactgaatca ccagccatgg tggcggatcc                                       90

<210> SEQ ID NO 28
<211> LENGTH: 19
<212> TYPE: PRT
<213> ORGANISM: unknown
<220> FEATURE:
<223> OTHER INFORMATION: partial PKR N and C terminal sequence
<220> FEATURE:
<221> NAME/KEY: NON_CONS
<222> LOCATION: 6-7

<400> SEQUENCE: 28

Met Ala Gly Asp Leu Ser Glu Thr Ser Val Lys Ser Asp Tyr Leu Ser
 1               5                  10                  15

Ser Gly Ser

<210> SEQ ID NO 29
<211> LENGTH: 57
<212> TYPE: DNA
<213> ORGANISM: Unknown
<220> FEATURE:
<223> OTHER INFORMATION: partial PKR 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 29
atggctggtg atctttcaga aacctcagtg aaatctgact acctgtcctc tggttct         57

<210> SEQ ID NO 30
<211> LENGTH: 57
<212> TYPE: DNA
<213> ORGANISM: Unknown
<220> FEATURE:
<223> OTHER INFORMATION: partial PKR 5' and 3' complement sequence
<220> FEATURE:
<221> NAME/KEY: misc_difference
<222> LOCATION: 39-40
<223> OTHER INFORMATION: non-consecutive nucleotides

<400> SEQUENCE: 30
agaaccagag gacaggtagt cagatttcac tgaggtttct gaaagatcac cagccat         57

<210> SEQ ID NO 31
```

```
<211> LENGTH: 29
<212> TYPE: DNA
<213> ORGANISM: Artificial Sequence
<220> FEATURE:
<223> OTHER INFORMATION: primer

<400> SEQUENCE: 31
ggatccgcca ccatggctgg tgatctttc                                           29

<210> SEQ ID NO 32
<211> LENGTH: 16
<212> TYPE: DNA
<213> ORGANISM: Artificial Sequence
<220> FEATURE:
<223> OTHER INFORMATION: primer

<400> SEQUENCE: 32
agaaccagag gacagg                                                         16

<210> SEQ ID NO 33
<211> LENGTH: 14
<212> TYPE: PRT
<213> ORGANISM: unknown
<220> FEATURE:
<223> OTHER INFORMATION: partial FADD N and C terminal sequence
<220> FEATURE:
<221> NAME/KEY: NON_CONS
<222> LOCATION: 7-8

<400> SEQUENCE: 33

Met Asp Pro Phe Leu Val Leu Leu Lys Val Ser Asp Thr Lys
  1               5                  10

<210> SEQ ID NO 34
<211> LENGTH: 42
<212> TYPE: DNA
<213> ORGANISM: unknown
<220> FEATURE:
<223> OTHER INFORMATION: partial FADD 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 34
atggacccgt tcctggtgct gctcaaagtc tcagacacca ag                            42

<210> SEQ ID NO 35
<211> LENGTH: 42
<212> TYPE: DNA
<213> ORGANISM: unknown
<220> FEATURE:
<223> OTHER INFORMATION: partial FADD 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 35
cttggtgtct gagactttga gcagcaccag gaacgggtcc at                            42

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
```

```
cctgtcctct ggttctatgg acccgttcct ggt                                     33

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
acgcgtttac ttggtgtctg agactt                                             26

<210> SEQ ID NO 38
<211> LENGTH: 23
<212> TYPE: PRT
<213> ORGANISM: Artificial Sequence
<220> FEATURE:
<223> OTHER INFORMATION: partial PKR (1-181) + FADD (1-125) sequence
<220> FEATURE:
<221> NAME/KEY: NON_CONS
<222> LOCATION: 4-5, 19-20

<400> SEQUENCE: 38

Met Ala Gly Asp Ser Val Lys Ser Asp Tyr Leu Ser Ser Gly Ser Met
 1               5                  10                  15

Asp Pro Phe Ser Asp Thr Lys
            20

<210> SEQ ID NO 39
<211> LENGTH: 90
<212> TYPE: DNA
<213> ORGANISM: Artificial Sequence
<220> FEATURE:
<223> OTHER INFORMATION: partial PKR (1-181) + FADD (1-125) sequence
<220> FEATURE:
<221> NAME/KEY: misc_difference
<222> LOCATION: 25-25
<223> OTHER INFORMATION: non-consecutive nucleotides

<400> SEQUENCE: 39
ggatccgcca ccatggctgg tgattcagtg aaatctgact acctgtcctc tggttctatg       60
gacccgttct cagacaccaa gtaaacgcgt                                         90

<210> SEQ ID NO 40
<211> LENGTH: 90
<212> TYPE: DNA
<213> ORGANISM: Artificial Sequence
<220> FEATURE:
<223> OTHER INFORMATION: partial PKR (1-181) + FADD (1-125) complement
      sequences
<220> FEATURE:
<221> NAME/KEY: misc_difference
<222> LOCATION: 21-22, 66-67
<223> OTHER INFORMATION: non-consecutive nucleotides

<400> SEQUENCE: 40
acgcgtttac ttggtgtctg agaacgggtc catagaacca gaggacaggt agtcagattt       60
cactgaatca ccagccatgg tggcggatcc                                         90

<210> SEQ ID NO 41
<211> LENGTH: 12
<212> TYPE: PRT
<213> ORGANISM: unknown
<220> FEATURE:
<223> OTHER INFORMATION: partial PKR N and C terminal sequence
<220> FEATURE:
```

```
<221> NAME/KEY: NON_CONS
<222> LOCATION: 6-7

<400> SEQUENCE: 41

Met Ala Gly Asp Leu Ser Glu Thr Ser Val Lys Ser
 1               5                  10

<210> SEQ ID NO 42
<211> LENGTH: 36
<212> TYPE: DNA
<213> ORGANISM: unknown
<220> FEATURE:
<223> OTHER INFORMATION: partial PKR 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 42
atggctggtg atctttcaga aacctcagtg aaatct                              36

<210> SEQ ID NO 43
<211> LENGTH: 36
<212> TYPE: DNA
<213> ORGANISM: unknown
<220> FEATURE:
<223> OTHER INFORMATION: partial PKR 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 43
agatttcact gaggtttctg aaagatcacc agccat                              36

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44
ggatccgcca ccatggctgg tgatctttc                                      29

<210> SEQ ID NO 45
<211> LENGTH: 35
<212> TYPE: DNA
<213> ORGANISM: Artificial Sequence
<220> FEATURE:
<223> OTHER INFORMATION: primer

<400> SEQUENCE: 45
cctgatccac cgccagaaga tttcactgag gtttc                               35

<210> SEQ ID NO 46
<211> LENGTH: 14
<212> TYPE: PRT
<213> ORGANISM: unknown
<220> FEATURE:
<223> OTHER INFORMATION: partial FADD N and C terminal sequence
<220> FEATURE:
<221> NAME/KEY: NON_CONS
<222> LOCATION: 7-8

<400> SEQUENCE: 46

Met Asp Pro Phe Leu Val Leu Leu Lys Val Ser Asp Thr Lys
 1               5                  10
```

```
<210> SEQ ID NO 47
<211> LENGTH: 42
<212> TYPE: DNA
<213> ORGANISM: unknown
<220> FEATURE:
<223> OTHER INFORMATION: partial FADD 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 47
atggacccgt tcctggtgct gctcaaagtc tcagacacca ag                           42

<210> SEQ ID NO 48
<211> LENGTH: 42
<212> TYPE: DNA
<213> ORGANISM: unknown
<220> FEATURE:
<223> OTHER INFORMATION: partial FADD 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 48
cttggtgtct gagactttga gcagcaccag gaacgggtcc at                           42

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
tggcggtgga tcaggaatgg acccgttcct ggt                                     33

<210> SEQ ID NO 50
<211> LENGTH: 26
<212> TYPE: DNA
<213> ORGANISM: Artificial Sequence
<220> FEATURE:
<223> OTHER INFORMATION: primer

<400> SEQUENCE: 50
acgcgtttac ttggtgtctg agactt                                             26

<210> SEQ ID NO 51
<211> LENGTH: 22
<212> TYPE: PRT
<213> ORGANISM: Artificial Sequence
<220> FEATURE:
<223> OTHER INFORMATION: partial PKR (1-174) + linker + FADD (1-125)
      sequence
<220> FEATURE:
<221> NAME/KEY: NON_CONS
<222> LOCATION: 4-5, 18-19

<400> SEQUENCE: 51

Met Ala Gly Asp Ser Val Lys Ser Ser Gly Gly Gly Ser Gly Met Asp
 1               5                  10                  15

Pro Phe Ser Asp Thr Lys
            20

<210> SEQ ID NO 52
```

```
<211> LENGTH: 87
<212> TYPE: DNA
<213> ORGANISM: Artificial Sequence
<220> FEATURE:
<223> OTHER INFORMATION: partial PKR (1-174) + linker + FADD (1-125)
      sequence
<220> FEATURE:
<221> NAME/KEY: misc_difference
<222> LOCATION: 24-25, 66-67
<223> OTHER INFORMATION: non-consecutive nucleotides

<400> SEQUENCE: 52
ggatccgcca ccatggctgg tgattcagtg aaatcttctg gcggtggatc aggaatggac    60
ccgttctcag acaccaagta aacgcgt                                        87

<210> SEQ ID NO 53
<211> LENGTH: 87
<212> TYPE: DNA
<213> ORGANISM: Artificial Sequence
<220> FEATURE:
<223> OTHER INFORMATION: partial PKR (1-174) + linker + FADD (1-125)
      complement sequence
<220> FEATURE:
<221> NAME/KEY: misc_difference
<222> LOCATION: 21-22, 63-64
<223> OTHER INFORMATION: non-consecutive nucleotides

<400> SEQUENCE: 53
acgcgtttac ttggtgtctg agaacgggtc cattcctgat ccaccgccag aagatttcac    60
tgaatcacca gccatggtgg cggatcc                                        87

<210> SEQ ID NO 54
<211> LENGTH: 68
<212> TYPE: DNA
<213> ORGANISM: Artificial Sequence
<220> FEATURE:
<223> OTHER INFORMATION: multiple cloning site

<400> SEQUENCE: 54
ggatcctcta gtcagctgac gcgtgctagc gcggccgcat cgataagctt gtcgacgata    60
tctctaga                                                             68

<210> SEQ ID NO 55
<211> LENGTH: 37
<212> TYPE: DNA
<213> ORGANISM: Artificial Sequence
<220> FEATURE:
<223> OTHER INFORMATION: primer

<400> SEQUENCE: 55
aagcttacgc gtactagtaa cttgtttatt gcagctt                             37

<210> SEQ ID NO 56
<211> LENGTH: 43
<212> TYPE: DNA
<213> ORGANISM: unknown
<220> FEATURE:
<223> OTHER INFORMATION: partial SV40 Poly-A sequence
<220> FEATURE:
<221> NAME/KEY: misc_difference
<222> LOCATION: 21-22
<223> OTHER INFORMATION: non-consecutive nucleotides

<400> SEQUENCE: 56
aacttgttta ttgcagctta ttcaatgtat cttatcatgt ctg                      43
```

```
<210> SEQ ID NO 57
<211> LENGTH: 43
<212> TYPE: DNA
<213> ORGANISM: unknown
<220> FEATURE:
<223> OTHER INFORMATION: partial SV40 Poly-A complement sequence
<220> FEATURE:
<221> NAME/KEY: misc_difference
<222> LOCATION: 22-23
<223> OTHER INFORMATION: non-consecutive nucleotides

<400> SEQUENCE: 57
cagacatgat aagatacatt gaataagctg caataaacaa gtt                 43

<210> SEQ ID NO 58
<211> LENGTH: 24
<212> TYPE: DNA
<213> ORGANISM: Artificial Sequence
<220> FEATURE:
<223> OTHER INFORMATION: primer

<400> SEQUENCE: 58
ggcgccagac atgataagat acat                                      24

<210> SEQ ID NO 59
<211> LENGTH: 17
<212> TYPE: DNA
<213> ORGANISM: Artificial Sequence
<220> FEATURE:
<223> OTHER INFORMATION: primer

<400> SEQUENCE: 59
tcatgtctgg atccaag                                              17

<210> SEQ ID NO 60
<211> LENGTH: 139
<212> TYPE: DNA
<213> ORGANISM: unknown
<220> FEATURE:
<223> OTHER INFORMATION: partial ISRE promoter sequence
<220> FEATURE:
<221> NAME/KEY: misc_difference
<222> LOCATION: 93-94
<223> OTHER INFORMATION: non-consecutive nucleotides
<220> FEATURE:
<221> NAME/KEY: misc_feature
<222> LOCATION: 101, 102, 103, 104, 105, 106, 107, 108, 109, 110, 111,
      112, 113, 114, 115, 116, 117, 118, 119, 120
<223> OTHER INFORMATION: n = A,T,C or G

<400> SEQUENCE: 60
tcatgtctgg atccaagcta gtttcacttt ccctagtttc actttcccta gtttcacttt   60
ccctagtttc actttcccta gtttcacttt ccctatataa nnnnnnnnnn nnnnnnnnnn  120
tggcattccg gtactgttg                                             139

<210> SEQ ID NO 61
<211> LENGTH: 139
<212> TYPE: DNA
<213> ORGANISM: unknown
<220> FEATURE:
<223> OTHER INFORMATION: partial ISRE promoter complement sequence
<220> FEATURE:
<221> NAME/KEY: misc_difference
<222> LOCATION: 45-46
<223> OTHER INFORMATION: non-consecutive nucleotides
<220> FEATURE:
<221> NAME/KEY: misc_feature
<222> LOCATION: 20, 21, 22, 23, 24, 25, 26, 27, 28, 29, 30, 31, 32, 33,
      34, 35, 36, 37, 38, 39
```

```
<223> OTHER INFORMATION: n = A,T,C or G

<400> SEQUENCE: 61
caacagtacc ggaatgccan nnnnnnnnnn nnnnnnnnnt tatataggga aagtgaaact      60
agggaaagtg aaactaggga aagtgaaact agggaaagtg aaactaggga aagtgaaact     120
agcttggatc cagacatga                                                 139

<210> SEQ ID NO 62
<211> LENGTH: 33
<212> TYPE: DNA
<213> ORGANISM: Artificial Sequence
<220> FEATURE:
<223> OTHER INFORMATION: primer

<400> SEQUENCE: 62
gtcgacgcgc gcggtaccaa cagtaccgga atg                                  33

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
gcgcgcgcca ccatgggtaa agattactac                                      30

<210> SEQ ID NO 64
<211> LENGTH: 13
<212> TYPE: PRT
<213> ORGANISM: unknown
<220> FEATURE:
<223> OTHER INFORMATION: partial Hdj-1 sequence
<220> FEATURE:
<221> NAME/KEY: NON_CONS
<222> LOCATION: 7-8

<400> SEQUENCE: 64

Met Gly Lys Asp Tyr Tyr Gln Glu Gln Val Leu Pro Ile
 1               5                  10

<210> SEQ ID NO 65
<211> LENGTH: 42
<212> TYPE: DNA
<213> ORGANISM: unknown
<220> FEATURE:
<223> OTHER INFORMATION: partial Hdj-1 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 65
atgggtaaag attactacca ggagcaggtt cttccaatat ag                        42

<210> SEQ ID NO 66
<211> LENGTH: 42
<212> TYPE: DNA
<213> ORGANISM: unknown
<220> FEATURE:
<223> OTHER INFORMATION: partial Hdj-1 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 66
```
ctatattgga agaacctgct cctggtagta atctttaccc at                    42

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
acgcgtctat attggaagaa cctg                                       24

<210> SEQ ID NO 68
<211> LENGTH: 27
<212> TYPE: DNA
<213> ORGANISM: Artificial Sequence
<220> FEATURE:
<223> OTHER INFORMATION: primer

<400> SEQUENCE: 68
gcgcgcgcca ccatggccaa agccgcg                                    27

<210> SEQ ID NO 69
<211> LENGTH: 13
<212> TYPE: PRT
<213> ORGANISM: unknown
<220> FEATURE:
<223> OTHER INFORMATION: partial Hsp70 sequence
<220> FEATURE:
<221> NAME/KEY: NON_CONS
<222> LOCATION: 7-8

<400> SEQUENCE: 69

Met Ala Lys Ala Ala Ala Val Thr Ile Glu Glu Val Asp
 1               5                  10

<210> SEQ ID NO 70
<211> LENGTH: 42
<212> TYPE: DNA
<213> ORGANISM: unknown
<220> FEATURE:
<223> OTHER INFORMATION: partial Hsp70 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 70
atggccaaag ccgcggcagt caccattgag gaggtagatt ag                   42

<210> SEQ ID NO 71
<211> LENGTH: 42
<212> TYPE: DNA
<213> ORGANISM: unknown
<220> FEATURE:
<223> OTHER INFORMATION: partial Hsp70 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 71
ctaatctacc tcctcaatgg tgactgccgc ggctttggcc at                   42

<210> SEQ ID NO 72
<211> LENGTH: 24
<212> TYPE: DNA

```
<213> ORGANISM: Artificial Sequence
<220> FEATURE:
<223> OTHER INFORMATION: primer

<400> SEQUENCE: 72
acgcgtctaa tctacctcct caat                                              24

<210> SEQ ID NO 73
<211> LENGTH: 28
<212> TYPE: DNA
<213> ORGANISM: Artificial Sequence
<220> FEATURE:
<223> OTHER INFORMATION: primer

<400> SEQUENCE: 73
gcgcgcgcca ccatgcctga ggaagtgc                                          28

<210> SEQ ID NO 74
<211> LENGTH: 13
<212> TYPE: PRT
<213> ORGANISM: unknown
<220> FEATURE:
<223> OTHER INFORMATION: partial Hsp90 sequence
<220> FEATURE:
<221> NAME/KEY: NON_CONS
<222> LOCATION: 7-8

<400> SEQUENCE: 74

Met Pro Glu Glu Val His His Arg Met Glu Glu Val Asp
 1               5                  10

<210> SEQ ID NO 75
<211> LENGTH: 42
<212> TYPE: DNA
<213> ORGANISM: unknown
<220> FEATURE:
<223> OTHER INFORMATION: partial Hsp90 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 75
atgcctgagg aagtgcacca tcgcatggaa gaagtcgatt ag                          42

<210> SEQ ID NO 76
<211> LENGTH: 42
<212> TYPE: DNA
<213> ORGANISM: unknown
<220> FEATURE:
<223> OTHER INFORMATION: partial Hsp90 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 76
ctaatcgact tcttccatgc gatggtgcac ttcctcaggc at                          42

<210> SEQ ID NO 77
<211> LENGTH: 24
<212> TYPE: DNA
<213> ORGANISM: Artificial Sequence
<220> FEATURE:
<223> OTHER INFORMATION: primer

<400> SEQUENCE: 77
acgcgtctaa tcgacttctt ccat                                              24
```

```
<210> SEQ ID NO 78
<211> LENGTH: 29
<212> TYPE: DNA
<213> ORGANISM: Artificial Sequence
<220> FEATURE:
<223> OTHER INFORMATION: primer

<400> SEQUENCE: 78
gcgcgcgcca ccatggaaga cgccaaaaa                                       29

<210> SEQ ID NO 79
<211> LENGTH: 12
<212> TYPE: PRT
<213> ORGANISM: unknown
<220> FEATURE:
<223> OTHER INFORMATION: partial luciferase sequence
<220> FEATURE:
<221> NAME/KEY: NON_CONS
<222> LOCATION: 6-7

<400> SEQUENCE: 79

Met Glu Asp Ala Lys Asn Gly Gly Lys Ser Lys Leu
 1               5                  10

<210> SEQ ID NO 80
<211> LENGTH: 39
<212> TYPE: DNA
<213> ORGANISM: unknown
<220> FEATURE:
<223> OTHER INFORMATION: partial luciferase 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 80
atggaagacg ccaaaaacgg cggaaagtcc aaattgtaa                            39

<210> SEQ ID NO 81
<211> LENGTH: 39
<212> TYPE: DNA
<213> ORGANISM: unknown
<220> FEATURE:
<223> OTHER INFORMATION: partial luciferase 5' and 3' complement
      sequence
<220> FEATURE:
<221> NAME/KEY: misc_difference
<222> LOCATION: 21-22
<223> OTHER INFORMATION: non-consecutive nucleotides

<400> SEQUENCE: 81
ttacaatttg gactttccgc cgttttggc gtcttccat                             39

<210> SEQ ID NO 82
<211> LENGTH: 24
<212> TYPE: DNA
<213> ORGANISM: Artificial Sequence
<220> FEATURE:
<223> OTHER INFORMATION: primer

<400> SEQUENCE: 82
acgcgtttac aatttggact ttcc                                            24

<210> SEQ ID NO 83
<211> LENGTH: 12
<212> TYPE: PRT
<213> ORGANISM: unknown
```

```
<220> FEATURE:
<223> OTHER INFORMATION: partial RNase L N and C terminal sequence
<220> FEATURE:
<221> NAME/KEY: NON_CONS
<222> LOCATION: 6-7

<400> SEQUENCE: 83

Met Glu Ser Arg Asp His His Pro Pro Ala Glu Asp
 1               5                  10

<210> SEQ ID NO 84
<211> LENGTH: 36
<212> TYPE: DNA
<213> ORGANISM: unknown
<220> FEATURE:
<223> OTHER INFORMATION: partial RNase L 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 84
atggagagca gggatcatca ccctcctgct gaagac                                 36

<210> SEQ ID NO 85
<211> LENGTH: 36
<212> TYPE: DNA
<213> ORGANISM: unknown
<220> FEATURE:
<223> OTHER INFORMATION: partial RNase L 5' and 3'  complement sequence
<220> FEATURE:
<221> NAME/KEY: misc_difference
<222> LOCATION: 18-19
<223> OTHER INFORMATION: non-consecutive nucleotides

<400> SEQUENCE: 85
gtcttcagca ggagggtgat gatccctgct ctccat                                 36

<210> SEQ ID NO 86
<211> LENGTH: 28
<212> TYPE: DNA
<213> ORGANISM: Artificial Sequence
<220> FEATURE:
<223> OTHER INFORMATION: primer

<400> SEQUENCE: 86
ggatccgcca ccatggagag cagggatc                                          28

<210> SEQ ID NO 87
<211> LENGTH: 32
<212> TYPE: DNA
<213> ORGANISM: Artificial Sequence
<220> FEATURE:
<223> OTHER INFORMATION: primer

<400> SEQUENCE: 87
cctgatccac cgccagagtc ttcagcagga gg                                     32

<210> SEQ ID NO 88
<211> LENGTH: 12
<212> TYPE: PRT
<213> ORGANISM: unknown
<220> FEATURE:
<223> OTHER INFORMATION: partial Apaf-1 N and C terminal sequence
<220> FEATURE:
<221> NAME/KEY: NON_CONS
<222> LOCATION: 6-7

<400> SEQUENCE: 88
```

Met Asp Ala Lys Ala Arg Pro Val Val Ser Ser Ser
 1               5                  10

<210> SEQ ID NO 89
<211> LENGTH: 36
<212> TYPE: DNA
<213> ORGANISM: unknown
<220> FEATURE:
<223> OTHER INFORMATION: partial Apaf-1 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 89
atggatgcaa aagctcgacc tgttgtctct tcttcc                               36

<210> SEQ ID NO 90
<211> LENGTH: 36
<212> TYPE: DNA
<213> ORGANISM: unknown
<220> FEATURE:
<223> OTHER INFORMATION: partial Apaf-1 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 90
ggaagaagag acaacaggtc gagcttttgc atccat                               36

<210> SEQ ID NO 91
<211> LENGTH: 33
<212> TYPE: DNA
<213> ORGANISM: Artificial Sequence
<220> FEATURE:
<223> OTHER INFORMATION: primer

<400> SEQUENCE: 91
tggcggtgga tcaggaatgg atgcaaaagc tcg                                  33

<210> SEQ ID NO 92
<211> LENGTH: 26
<212> TYPE: DNA
<213> ORGANISM: Artificial Sequence
<220> FEATURE:
<223> OTHER INFORMATION: primer

<400> SEQUENCE: 92
acgcgtttag gaagaagaga caacag                                          26

<210> SEQ ID NO 93
<211> LENGTH: 22
<212> TYPE: PRT
<213> ORGANISM: Artificial Sequence
<220> FEATURE:
<223> OTHER INFORMATION: partial RNase L (1-335) + linker + APAF-1
      (1-97) sequence
<220> FEATURE:
<221> NAME/KEY: NON_CONS
<222> LOCATION: 4-5, 18-19

<400> SEQUENCE: 93

Met Glu Ser Arg Pro Ala Glu Asp Ser Gly Gly Gly Ser Gly Met Asp
 1               5                  10                  15

Ala Lys Val Ser Ser Ser
            20

```
<210> SEQ ID NO 94
<211> LENGTH: 87
<212> TYPE: DNA
<213> ORGANISM: Artificial Sequence
<220> FEATURE:
<223> OTHER INFORMATION: partial RNase L (1-335) + linker + APAF-1
      (1-97)
<220> FEATURE:
<221> NAME/KEY: misc_difference
<222> LOCATION: 24-25, 66-67
<223> OTHER INFORMATION: non-consecutive nucleotides

<400> SEQUENCE: 94
ggatccgcca ccatggagag caggcctgct gaagactctg gcggtggatc aggaatggat    60
gcaaaagtct cttcttccta aacgcgt                                        87

<210> SEQ ID NO 95
<211> LENGTH: 87
<212> TYPE: DNA
<213> ORGANISM: Artificial Sequence
<220> FEATURE:
<223> OTHER INFORMATION: partial RNase L (1-335) + linker + APAF-1
      (1-97)
      complement
<220> FEATURE:
<221> NAME/KEY: misc_difference
<222> LOCATION: 21-22, 63-64
<223> OTHER INFORMATION: non-consecutive nucleotides

<400> SEQUENCE: 95
acgcgtttag gaagaagaga cttttgcatc cattcctgat ccaccgccag agtcttcagc    60
aggcctgctc tccatggtgg cggatcc                                        87

<210> SEQ ID NO 96
<211> LENGTH: 12
<212> TYPE: PRT
<213> ORGANISM: unknown
<220> FEATURE:
<223> OTHER INFORMATION: partial BPI N and C terminal sequence
<220> FEATURE:
<221> NAME/KEY: NON_CONS
<222> LOCATION: 6-7

<400> SEQUENCE: 96

Val Asn Pro Gly Val Val Pro Val Met Thr Lys Ile
 1               5                  10

<210> SEQ ID NO 97
<211> LENGTH: 36
<212> TYPE: DNA
<213> ORGANISM: unknown
<220> FEATURE:
<223> OTHER INFORMATION: partial BPI 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 97
gtcaaccctg gcgtcgtgcc agtaatgacc aaaata                              36

<210> SEQ ID NO 98
<211> LENGTH: 36
<212> TYPE: DNA
<213> ORGANISM: unknown
<220> FEATURE:
<223> OTHER INFORMATION: partial BPI 5' and 3' complement sequence
```

```
<220> FEATURE:
<221> NAME/KEY: misc_difference
<222> LOCATION: 18-19
<223> OTHER INFORMATION: non-consecutive nucleotides

<400> SEQUENCE: 98
tattttggtc attactggca cgacgccagg gttgac                                    36

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ggatccgcca ccatggtcaa ccctggcgtc                                           30

<210> SEQ ID NO 100
<211> LENGTH: 35
<212> TYPE: DNA
<213> ORGANISM: Artificial Sequence
<220> FEATURE:
<223> OTHER INFORMATION: primer

<400> SEQUENCE: 100
cctgatccac cgccagatat tttggtcatt actgg                                     35

<210> SEQ ID NO 101
<211> LENGTH: 12
<212> TYPE: PRT
<213> ORGANISM: unknown
<220> FEATURE:
<223> OTHER INFORMATION: partial Apaf-1 N and C terminal sequence
<220> FEATURE:
<221> NAME/KEY: NON_CONS
<222> LOCATION: 6-7

<400> SEQUENCE: 101

Met Asp Ala Lys Ala Arg Pro Val Val Ser Ser Ser
 1               5                  10

<210> SEQ ID NO 102
<211> LENGTH: 36
<212> TYPE: DNA
<213> ORGANISM: unknown
<220> FEATURE:
<223> OTHER INFORMATION: partial Apaf-1 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 102
atggatgcaa aagctcgacc tgttgtctct tcttcc                                    36

<210> SEQ ID NO 103
<211> LENGTH: 36
<212> TYPE: DNA
<213> ORGANISM: unknown
<220> FEATURE:
<223> OTHER INFORMATION: partial Apaf-1 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 103
```

```
ggaagaagag acaacaggtc gagcttttgc atccat                                    36

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104
tggcggtgga tcaggaatgg atgcaaaagc tcg                                       33

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
acgcgtttag gaagaagaga caacag                                               26

<210> SEQ ID NO 106
<211> LENGTH: 21
<212> TYPE: PRT
<213> ORGANISM: Artificial Sequence
<220> FEATURE:
<223> OTHER INFORMATION: partial BPI (1-199) + linker + APAF-1 (1-97)
      sequence
<220> FEATURE:
<221> NAME/KEY: NON_CONS
<222> LOCATION: 4-5, 18-19

<400> SEQUENCE: 106

Met Val Asn Pro Thr Lys Ile Ser Gly Gly Gly Ser Gly Met Asp Ala
 1               5                  10                  15

Lys Val Ser Ser Ser
            20

<210> SEQ ID NO 107
<211> LENGTH: 87
<212> TYPE: DNA
<213> ORGANISM: Artificial Sequence
<220> FEATURE:
<223> OTHER INFORMATION: partial BPI (1-199) + linker + APAF-1 (1-97)
<220> FEATURE:
<221> NAME/KEY: misc_difference
<222> LOCATION: 24-25, 66-67
<223> OTHER INFORMATION: non-consecutive nucleotides

<400> SEQUENCE: 107
ggatccgcca ccatggtcaa ccctatgacc aaaatatctg gcggtggatc aggaatggat          60
gcaaaagtct cttcttccta aacgcgt                                              87

<210> SEQ ID NO 108
<211> LENGTH: 87
<212> TYPE: DNA
<213> ORGANISM: Artificial Sequence
<220> FEATURE:
<223> OTHER INFORMATION: partial BPI (1-199) + linker + APAF-1 (1-97)
      complement sequence
<220> FEATURE:
<221> NAME/KEY: misc_difference
<222> LOCATION: 21-22, 63-64
<223> OTHER INFORMATION: non-consecutive nucleotides

<400> SEQUENCE: 108
```

```
acgcgtttag gaagaagaga cttttgcatc cattcctgat ccaccgccag atattttggt      60
catagggttg accatggtgg cggatcc                                         87
```

<210> SEQ ID NO 109
<211> LENGTH: 19
<212> TYPE: PRT
<213> ORGANISM: unknown
<220> FEATURE:
<223> OTHER INFORMATION: partial PKR N and C terminal sequence
<220> FEATURE:
<221> NAME/KEY: NON_CONS
<222> LOCATION: 6-7

<400> SEQUENCE: 109

```
Met Ala Gly Asp Leu Ser Glu Thr Ser Val Lys Ser Asp Tyr Leu Ser
 1               5                  10                  15

Ser Gly Ser
```

<210> SEQ ID NO 110
<211> LENGTH: 57
<212> TYPE: DNA
<213> ORGANISM: unknown
<220> FEATURE:
<223> OTHER INFORMATION: partial PKR 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 110

```
atggctggtg atctttcaga aacctcagtg aaatctgact acctgtcctc tggttct         57
```

<210> SEQ ID NO 111
<211> LENGTH: 57
<212> TYPE: DNA
<213> ORGANISM: unknown
<220> FEATURE:
<223> OTHER INFORMATION: partial PKR 5' and 3' complement sequence
<220> FEATURE:
<221> NAME/KEY: misc_difference
<222> LOCATION: 39-40
<223> OTHER INFORMATION: non-consecutive nucleotides

<400> SEQUENCE: 111

```
agaaccagag gacaggtagt cagatttcac tgaggtttct gaaagatcac cagccat         57
```

<210> SEQ ID NO 112
<211> LENGTH: 29
<212> TYPE: DNA
<213> ORGANISM: Artificial Sequence
<220> FEATURE:
<223> OTHER INFORMATION: primer

<400> SEQUENCE: 112

```
ggatccgcca ccatggctgg tgatctttc                                       29
```

<210> SEQ ID NO 113
<211> LENGTH: 16
<212> TYPE: DNA
<213> ORGANISM: Artificial Sequence
<220> FEATURE:
<223> OTHER INFORMATION: primer

<400> SEQUENCE: 113

```
agaaccagag gacagg                                                     16
```

<210> SEQ ID NO 114
<211> LENGTH: 12
<212> TYPE: PRT
<213> ORGANISM: unknown
<220> FEATURE:
<223> OTHER INFORMATION: partial Apaf-1 N and C terminal sequence
<220> FEATURE:
<221> NAME/KEY: NON_CONS
<222> LOCATION: 6-7

<400> SEQUENCE: 114

Met Asp Ala Lys Ala Arg Pro Val Val Ser Ser Ser
 1               5                  10

<210> SEQ ID NO 115
<211> LENGTH: 36
<212> TYPE: DNA
<213> ORGANISM: unknown
<220> FEATURE:
<223> OTHER INFORMATION: partial Apaf-1 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 115
atggatgcaa aagctcgacc tgttgtctct tcttcc                              36

<210> SEQ ID NO 116
<211> LENGTH: 36
<212> TYPE: DNA
<213> ORGANISM: unknown
<220> FEATURE:
<223> OTHER INFORMATION: partial Apaf-1 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 116
ggaagaagag acaacaggtc gagcttttgc atccat                              36

<210> SEQ ID NO 117
<211> LENGTH: 33
<212> TYPE: DNA
<213> ORGANISM: Artificial Sequence
<220> FEATURE:
<223> OTHER INFORMATION: primer

<400> SEQUENCE: 117
cctgtcctct ggttctatgg atgcaaaagc tcg                                 33

<210> SEQ ID NO 118
<211> LENGTH: 26
<212> TYPE: DNA
<213> ORGANISM: Artificial Sequence
<220> FEATURE:
<223> OTHER INFORMATION: primer

<400> SEQUENCE: 118
acgcgtttag gaagaagaga caacag                                         26

<210> SEQ ID NO 119
<211> LENGTH: 23
<212> TYPE: PRT
<213> ORGANISM: Artificial Sequence
<220> FEATURE:
<223> OTHER INFORMATION: partial PKR(1-181)+APAF-1(1-97) sequence
<220> FEATURE:

```
<221> NAME/KEY: NON_CONS
<222> LOCATION: 4-5, 19-20

<400> SEQUENCE: 119

Met Ala Gly Asp Ser Val Lys Ser Asp Tyr Leu Ser Ser Gly Ser Met
1               5                   10                  15
Asp Ala Lys Val Ser Ser Ser
            20

<210> SEQ ID NO 120
<211> LENGTH: 90
<212> TYPE: DNA
<213> ORGANISM: Artificial Sequence
<220> FEATURE:
<223> OTHER INFORMATION: partial PKR (1-181)+APAF-1 (1-97)
<220> FEATURE:
<221> NAME/KEY: misc_difference
<222> LOCATION: 24-25, 69-70
<223> OTHER INFORMATION: non-consecutive nucleotides

<400> SEQUENCE: 120
ggatccgcca ccatggctgg tgattcagtg aaatctgact acctgtcctc tggttctatg      60
gatgcaaaag tctcttcttc ctaaacgcgt                                       90

<210> SEQ ID NO 121
<211> LENGTH: 90
<212> TYPE: DNA
<213> ORGANISM: Artificial Sequence
<220> FEATURE:
<223> OTHER INFORMATION: partial PKR (1-181)+APAF-1(1-97) complement
      sequence
<220> FEATURE:
<221> NAME/KEY: misc_difference
<222> LOCATION: 21-22, 63-64
<223> OTHER INFORMATION: non-consecutive nucleotides

<400> SEQUENCE: 121
acgcgtttag gaagaagaga cttttgcatc catagaacca gaggacaggt agtcagattt      60
cactgaatca ccagccatgg tggcggatcc                                       90

<210> SEQ ID NO 122
<211> LENGTH: 12
<212> TYPE: PRT
<213> ORGANISM: Unknown
<220> FEATURE:
<223> OTHER INFORMATION: partial RNase L N and C terminal sequence
<220> FEATURE:
<221> NAME/KEY: NON_CONS
<222> LOCATION: 6-7

<400> SEQUENCE: 122

Met Glu Ser Arg Asp His His Pro Pro Ala Glu Asp
1               5                   10

<210> SEQ ID NO 123
<211> LENGTH: 36
<212> TYPE: DNA
<213> ORGANISM: Unknown
<220> FEATURE:
<223> OTHER INFORMATION: partial RNase L 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 123
atggagagca gggatcatca ccctcctgct gaagac                                36
```

<210> SEQ ID NO 124
<211> LENGTH: 36
<212> TYPE: DNA
<213> ORGANISM: Unknown
<220> FEATURE:
<223> OTHER INFORMATION: partial RNase L 5' and 3' complement sequence
<220> FEATURE:
<221> NAME/KEY: misc_difference
<222> LOCATION: 18-19
<223> OTHER INFORMATION: non-consecutive nucleotides

<400> SEQUENCE: 124
gtcttcagca ggagggtgat gatccctgct ctccat                                36

<210> SEQ ID NO 125
<211> LENGTH: 28
<212> TYPE: DNA
<213> ORGANISM: Artificial Sequence
<220> FEATURE:
<223> OTHER INFORMATION: primer

<400> SEQUENCE: 125
ggatccgcca ccatggagag cagggatc                                         28

<210> SEQ ID NO 126
<211> LENGTH: 32
<212> TYPE: DNA
<213> ORGANISM: Artificial Sequence
<220> FEATURE:
<223> OTHER INFORMATION: primer

<400> SEQUENCE: 126
cctgatccac cgccagagtc ttcagcagga gg                                    32

<210> SEQ ID NO 127
<211> LENGTH: 14
<212> TYPE: PRT
<213> ORGANISM: Unknown
<220> FEATURE:
<223> OTHER INFORMATION: partial caspase 3 N and C terminal sequence
<220> FEATURE:
<221> NAME/KEY: NON_CONS
<222> LOCATION: 7-8

<400> SEQUENCE: 127

Met Glu Asn Thr Glu Asn Ser Lys Glu Leu Tyr Phe Tyr His
 1               5                  10

<210> SEQ ID NO 128
<211> LENGTH: 42
<212> TYPE: DNA
<213> ORGANISM: Unknown
<220> FEATURE:
<223> OTHER INFORMATION: partial caspase 3 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 128
atggagaaca ctgaaaactc aaaagaactc tattttatc ac                          42

<210> SEQ ID NO 129
<211> LENGTH: 42
<212> TYPE: DNA
<213> ORGANISM: Unknown
<220> FEATURE:

<223> OTHER INFORMATION: partial caspase 3 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 129
gtgataaaaa tagagttctt ttgagttttc agtgttctcc at         42

<210> SEQ ID NO 130
<211> LENGTH: 35
<212> TYPE: DNA
<213> ORGANISM: Artificial Sequence
<220> FEATURE:
<223> OTHER INFORMATION: primer

<400> SEQUENCE: 130
tggcggtgga tcaggaatgg agaacactga aaact                 35

<210> SEQ ID NO 131
<211> LENGTH: 29
<212> TYPE: DNA
<213> ORGANISM: Artificial Sequence
<220> FEATURE:
<223> OTHER INFORMATION: primer

<400> SEQUENCE: 131
acgcgtttag tgataaaaat agagttctt                        29

<210> SEQ ID NO 132
<211> LENGTH: 22
<212> TYPE: PRT
<213> ORGANISM: Artificial Sequence
<220> FEATURE:
<223> OTHER INFORMATION: partial RNase L(1-335)+Linker+Caspase 3
      sequence
<220> FEATURE:
<221> NAME/KEY: NON_CONS
<222> LOCATION: 4-5, 18-19

<400> SEQUENCE: 132

Met Glu Ser Arg Pro Ala Glu Asp Ser Gly Gly Gly Ser Gly Met Glu
 1               5                  10                  15

Asn Thr Tyr Phe Tyr His
            20

<210> SEQ ID NO 133
<211> LENGTH: 87
<212> TYPE: DNA
<213> ORGANISM: Artificial Sequence
<220> FEATURE:
<223> OTHER INFORMATION: partial RNase L(1-335)+Linker+Caspase3
<220> FEATURE:
<221> NAME/KEY: misc_difference
<222> LOCATION: 24-25, 66-67
<223> OTHER INFORMATION: non-consecutive nucleotides

<400> SEQUENCE: 133
ggatccgcca ccatggagag caggcctgct gaagactctg gcggtggatc aggaatggag    60
aacacttatt tttatcacta aacgcgt                                        87

<210> SEQ ID NO 134
<211> LENGTH: 87
<212> TYPE: DNA
<213> ORGANISM: Artificial Sequence
<220> FEATURE:
<223> OTHER INFORMATION: partial RNase L(1-335)+Linker+Caspase3 complement sequence
<220> FEATURE:
<221> NAME/KEY: misc_difference
<222> LOCATION: 21-22, 63-64
<223> OTHER INFORMATION: non-consecutive nucleotides

<400> SEQUENCE: 134
acgcgtttag tgataaaaat aagtgttctc cattcctgat ccaccgccag agtcttcagc    60
aggcctgctc tccatggtgg cggatcc                                       87

<210> SEQ ID NO 135
<211> LENGTH: 12
<212> TYPE: PRT
<213> ORGANISM: Unknown
<220> FEATURE:
<223> OTHER INFORMATION: partial BPI N and C terminal sequence
<220> FEATURE:
<221> NAME/KEY: NON_CONS
<222> LOCATION: 6-7

<400> SEQUENCE: 135

Val Asn Pro Gly Val Val Pro Val Met Thr Lys Ile
 1               5                  10

<210> SEQ ID NO 136
<211> LENGTH: 36
<212> TYPE: DNA
<213> ORGANISM: Unknown
<220> FEATURE:
<223> OTHER INFORMATION: partial BPI 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 136
gtcaaccctg gcgtcgtgcc agtaatgacc aaaata                             36

<210> SEQ ID NO 137
<211> LENGTH: 36
<212> TYPE: DNA
<213> ORGANISM: Unknown
<220> FEATURE:
<223> OTHER INFORMATION: partial BPI 5' and 3' complement sequence
<220> FEATURE:
<221> NAME/KEY: misc_difference
<222> LOCATION: 18-19
<223> OTHER INFORMATION: non-consevutive nucleotides

<400> SEQUENCE: 137
tattttggtc attactggca cgacgccagg gttgac                             36

<210> SEQ ID NO 138
<211> LENGTH: 30
<212> TYPE: DNA
<213> ORGANISM: Artificial Sequence
<220> FEATURE:
<223> OTHER INFORMATION: primer

<400> SEQUENCE: 138
ggatccgcca ccatggtcaa ccctggcgtc                                    30

<210> SEQ ID NO 139
<211> LENGTH: 35
<212> TYPE: DNA
<213> ORGANISM: Artificial Sequence
<220> FEATURE:
<223> OTHER INFORMATION: primer

<400> SEQUENCE: 139
cctgatccac cgccagatat tttggtcatt actgg                              35

<210> SEQ ID NO 140
<211> LENGTH: 14
<212> TYPE: PRT
<213> ORGANISM: Unknown
<220> FEATURE:
<223> OTHER INFORMATION: partial caspase 3 N and C terminal sequence
<220> FEATURE:
<221> NAME/KEY: NON_CONS
<222> LOCATION: 7-8

<400> SEQUENCE: 140

Met Glu Asn Thr Glu Asn Ser Lys Glu Leu Tyr Phe Tyr His
 1               5                  10

<210> SEQ ID NO 141
<211> LENGTH: 42
<212> TYPE: DNA
<213> ORGANISM: Unknown
<220> FEATURE:
<223> OTHER INFORMATION: partial caspase 3 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 141
atggagaaca ctgaaaactc aaaagaactc tattttatc ac                      42

<210> SEQ ID NO 142
<211> LENGTH: 42
<212> TYPE: DNA
<213> ORGANISM: Unknown
<220> FEATURE:
<223> OTHER INFORMATION: partial caspase 3 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 142
gtgataaaaa tagagttctt ttgagttttc agtgttctcc at                     42

<210> SEQ ID NO 143
<211> LENGTH: 35
<212> TYPE: DNA
<213> ORGANISM: Artificial Sequence
<220> FEATURE:
<223> OTHER INFORMATION: primer

<400> SEQUENCE: 143
tggcggtgga tcaggaatgg agaacactga aaact                             35

<210> SEQ ID NO 144
<211> LENGTH: 29
<212> TYPE: DNA
<213> ORGANISM: Artificial Sequence
<220> FEATURE:
<223> OTHER INFORMATION: primer

<400> SEQUENCE: 144
acgcgtttag tgataaaaat agagttctt                                    29

<210> SEQ ID NO 145

```
<211> LENGTH: 22
<212> TYPE: PRT
<213> ORGANISM: Artificial Sequence
<220> FEATURE:
<223> OTHER INFORMATION: partial BPI(1-199)+Linker+Caspase 3 sequence
<220> FEATURE:
<221> NAME/KEY: NON_CONS
<222> LOCATION: 4-5, 18-19

<400> SEQUENCE: 145

Met Val Asn Pro Met Thr Lys Ile Ser Gly Gly Gly Ser Gly Met Glu
 1               5                  10                  15

Asn Thr Tyr Phe Tyr His
            20

<210> SEQ ID NO 146
<211> LENGTH: 87
<212> TYPE: DNA
<213> ORGANISM: Artificial Sequence
<220> FEATURE:
<223> OTHER INFORMATION: partial BPI(1-199)+Linker+Caspase 3
<220> FEATURE:
<221> NAME/KEY: misc_difference
<222> LOCATION: 24-25, 66-67
<223> OTHER INFORMATION: non-consecutive nucleotides

<400> SEQUENCE: 146
ggatccgcca ccatggtcaa ccctatgacc aaaatatctg gcggtggatc aggaatggag      60
aacacttatt tttatcacta aacgcgt                                          87

<210> SEQ ID NO 147
<211> LENGTH: 87
<212> TYPE: DNA
<213> ORGANISM: Artificial Sequence
<220> FEATURE:
<223> OTHER INFORMATION: partial BPI(1-199)+Linker+Caspase 3 complement
      sequence
<220> FEATURE:
<221> NAME/KEY: misc_difference
<222> LOCATION: 21-22, 63-64
<223> OTHER INFORMATION: non-consecutive nucleotides

<400> SEQUENCE: 147
acgcgtttag tgataaaaat aagtgttctc cattcctgat ccaccgccag atattttggt      60
catagggttg accatggtgg cggatcc                                          87

<210> SEQ ID NO 148
<211> LENGTH: 68
<212> TYPE: DNA
<213> ORGANISM: Artificial Sequence
<220> FEATURE:
<223> OTHER INFORMATION: multiple cloning site (MCS)

<400> SEQUENCE: 148
ggatcctcta gtcagctgac gcgtgctagc gcggccgcat cgataagctt gtcgacgata      60
tctctaga                                                               68

<210> SEQ ID NO 149
<211> LENGTH: 40
<212> TYPE: DNA
<213> ORGANISM: Artificial Sequence
<220> FEATURE:
<223> OTHER INFORMATION: primer

<400> SEQUENCE: 149
gtcgacgcca ccatgggata cccatacgat gttccagatt                            40
```

```
<210> SEQ ID NO 150
<211> LENGTH: 40
<212> TYPE: DNA
<213> ORGANISM: Artificial Sequence
<220> FEATURE:
<223> OTHER INFORMATION: primer

<400> SEQUENCE: 150
catacgatgt tccagattac gctgccagga aactactttc                                40

<210> SEQ ID NO 151
<211> LENGTH: 13
<212> TYPE: PRT
<213> ORGANISM: Unknown
<220> FEATURE:
<223> OTHER INFORMATION: partial Importin alpha1 sequence
<220> FEATURE:
<221> NAME/KEY: NON_CONS
<222> LOCATION: 7-8

<400> SEQUENCE: 151

Ala Arg Lys Leu Leu Ser Arg Pro Gly Thr Phe Asn Phe
 1               5                  10

<210> SEQ ID NO 152
<211> LENGTH: 42
<212> TYPE: DNA
<213> ORGANISM: Unknown
<220> FEATURE:
<223> OTHER INFORMATION: partial Importin alpha1
<220> FEATURE:
<221> NAME/KEY: misc_difference
<222> LOCATION: 21-22
<223> OTHER INFORMATION: non-consecutive nucleotides

<400> SEQUENCE: 152
gccaggaaac tactttccag acctgggacc tttaactttt ag                             42

<210> SEQ ID NO 153
<211> LENGTH: 42
<212> TYPE: DNA
<213> ORGANISM: Unknown
<220> FEATURE:
<223> OTHER INFORMATION: partial Importin alpha1 complement
<220> FEATURE:
<221> NAME/KEY: misc_difference
<222> LOCATION: 21-22
<223> OTHER INFORMATION: non-consecutive nucleotides

<400> SEQUENCE: 153
ctaaaagtta aggtcccag gtctggaaag tagtttcctg gc                              42

<210> SEQ ID NO 154
<211> LENGTH: 24
<212> TYPE: DNA
<213> ORGANISM: Artificial Sequence
<220> FEATURE:
<223> OTHER INFORMATION: primer

<400> SEQUENCE: 154
acgcgtctaa aagttaaagg tccc                                                 24

<210> SEQ ID NO 155
<211> LENGTH: 20
<212> TYPE: DNA
<213> ORGANISM: Artificial Sequence
<220> FEATURE:
```

```
<223> OTHER INFORMATION: primer

<400> SEQUENCE: 155
ggatccgcca ccatgggata                                                    20

<210> SEQ ID NO 156
<211> LENGTH: 18
<212> TYPE: DNA
<213> ORGANISM: Artificial Sequence
<220> FEATURE:
<223> OTHER INFORMATION: primer

<400> SEQUENCE: 156
acgcgtctaa aagttaaa                                                      18

<210> SEQ ID NO 157
<211> LENGTH: 40
<212> TYPE: DNA
<213> ORGANISM: Artificial Sequence
<220> FEATURE:
<223> OTHER INFORMATION: primer

<400> SEQUENCE: 157
gcgcgcgcca ccatgggata cccatacgat gttccagatt                              40

<210> SEQ ID NO 158
<211> LENGTH: 41
<212> TYPE: DNA
<213> ORGANISM: Artificial Sequence
<220> FEATURE:
<223> OTHER INFORMATION: primer

<400> SEQUENCE: 158
catacgatgt tccagattac gctgcaagaa aactgttatc c                            41

<210> SEQ ID NO 159
<211> LENGTH: 14
<212> TYPE: PRT
<213> ORGANISM: unknown
<220> FEATURE:
<223> OTHER INFORMATION: partial Importin alpha4 sequence
<220> FEATURE:
<221> NAME/KEY: NON_CONS
<222> LOCATION: 7-8

<400> SEQUENCE: 159

Ala Arg Lys Leu Leu Ser Ser Gln Thr Lys Glu Phe Asn Phe
 1               5                  10

<210> SEQ ID NO 160
<211> LENGTH: 45
<212> TYPE: DNA
<213> ORGANISM: Unknown
<220> FEATURE:
<223> OTHER INFORMATION: partial Importin alpha4
<220> FEATURE:
<221> NAME/KEY: misc_difference
<222> LOCATION: 21-22
<223> OTHER INFORMATION: non-consecutive nucleotides

<400> SEQUENCE: 160
gcaagaaaac tgttatccag tcaaacaaaa gaatttaatt tttaa                        45

<210> SEQ ID NO 161
<211> LENGTH: 45
<212> TYPE: DNA
<213> ORGANISM: Unknown
```

```
<220> FEATURE:
<223> OTHER INFORMATION: partial Importin alpha4 complement
<220> FEATURE:
<221> NAME/KEY: misc_difference
<222> LOCATION: 24-25
<223> OTHER INFORMATION: non-consecutive nucleotides

<400> SEQUENCE: 161
ttaaaaatta aattcttttg tttgactgga taacagtttt cttgc            45

<210> SEQ ID NO 162
<211> LENGTH: 29
<212> TYPE: DNA
<213> ORGANISM: Artificial Sequence
<220> FEATURE:
<223> OTHER INFORMATION: primer

<400> SEQUENCE: 162
aagcttttaa aaattaaatt cttttgttt                              29

<210> SEQ ID NO 163
<211> LENGTH: 21
<212> TYPE: DNA
<213> ORGANISM: Artificial Sequence
<220> FEATURE:
<223> OTHER INFORMATION: primer

<400> SEQUENCE: 163
acgcgtgcca ccatgggata c                                      21

<210> SEQ ID NO 164
<211> LENGTH: 31
<212> TYPE: DNA
<213> ORGANISM: Artificial Sequence
<220> FEATURE:
<223> OTHER INFORMATION: primer

<400> SEQUENCE: 164
gcggccgctt aaaaattaaa ttcttttgtt t                           31

<210> SEQ ID NO 165
<211> LENGTH: 40
<212> TYPE: DNA
<213> ORGANISM: Artificial Sequence
<220> FEATURE:
<223> OTHER INFORMATION: primer

<400> SEQUENCE: 165
gcgcgcgcca ccatgggata cccatacgat gttccagatt                  40

<210> SEQ ID NO 166
<211> LENGTH: 42
<212> TYPE: DNA
<213> ORGANISM: Artificial Sequence
<220> FEATURE:
<223> OTHER INFORMATION: primer

<400> SEQUENCE: 166
catacgatgt tccagattac gcttttagaa agctgctttc ta               42

<210> SEQ ID NO 167
<211> LENGTH: 13
<212> TYPE: PRT
<213> ORGANISM: unknown
<220> FEATURE:
<223> OTHER INFORMATION: partial Importin alpha6 sequence
<220> FEATURE:
```

```
<221> NAME/KEY: NON_CONS
<222> LOCATION: 7-8

<400> SEQUENCE: 167

Phe Arg Lys Leu Leu Ser Lys Met Asp Gly Phe Gln Leu
 1               5                   10

<210> SEQ ID NO 168
<211> LENGTH: 42
<212> TYPE: DNA
<213> ORGANISM: unknown
<220> FEATURE:
<223> OTHER INFORMATION: partial Importin alpha6
<220> FEATURE:
<221> NAME/KEY: misc_difference
<222> LOCATION: 21-22
<223> OTHER INFORMATION: non-consecutive nucleotides

<400> SEQUENCE: 168
tttagaaagc tgctttctaa aatggatgga tttcaacttt aa                    42

<210> SEQ ID NO 169
<211> LENGTH: 42
<212> TYPE: DNA
<213> ORGANISM: Unknown
<220> FEATURE:
<223> OTHER INFORMATION: partial Importin alpha6 complement
<220> FEATURE:
<221> NAME/KEY: misc_difference
<222> LOCATION: 21-22
<223> OTHER INFORMATION: non-consecutive nucleotides

<400> SEQUENCE: 169
ttaaagttga aatccatcca ttttagaaag cagctttcta aa                    42

<210> SEQ ID NO 170
<211> LENGTH: 25
<212> TYPE: DNA
<213> ORGANISM: Artificial Sequence
<220> FEATURE:
<223> OTHER INFORMATION: primer

<400> SEQUENCE: 170
aagcttttaa agttgaaatc catcc                                       25

<210> SEQ ID NO 171
<211> LENGTH: 20
<212> TYPE: DNA
<213> ORGANISM: Artificial Sequence
<220> FEATURE:
<223> OTHER INFORMATION: primer

<400> SEQUENCE: 171
ggatccgcca ccatgggata                                             20

<210> SEQ ID NO 172
<211> LENGTH: 25
<212> TYPE: DNA
<213> ORGANISM: Artificial Sequence
<220> FEATURE:
<223> OTHER INFORMATION: primer

<400> SEQUENCE: 172
acgcgtttaa agttgaaatc catcc                                       25

<210> SEQ ID NO 173
<211> LENGTH: 43
```

```
<212> TYPE: DNA
<213> ORGANISM: Artificial Sequence
<220> FEATURE:
<223> OTHER INFORMATION: primer

<400> SEQUENCE: 173
gtcgacgcca ccatgggata cccatacgat gttccagatt acg                              43

<210> SEQ ID NO 174
<211> LENGTH: 43
<212> TYPE: DNA
<213> ORGANISM: Artificial Sequence
<220> FEATURE:
<223> OTHER INFORMATION: primer

<400> SEQUENCE: 174
cgatgttcca gattacgctg gaggtatgaa ccccatcgta att                              43

<210> SEQ ID NO 175
<211> LENGTH: 13
<212> TYPE: PRT
<213> ORGANISM: Escherichia coli
<220> FEATURE:
<221> NAME/KEY: NON_CONS
<222> LOCATION: 7-8

<400> SEQUENCE: 175

Met Asn Pro Ile Val Ile Asn Lys Lys Leu Glu Leu Glu
 1               5                  10

<210> SEQ ID NO 176
<211> LENGTH: 42
<212> TYPE: DNA
<213> ORGANISM: Escherichi coli
<220> FEATURE:
<221> NAME/KEY: misc_difference
<222> LOCATION: 21-22
<223> OTHER INFORMATION: non-consecutive nucleotides

<400> SEQUENCE: 176
atgaacccca tcgtaattaa taaaaaactg gagctggaat ga                               42

<210> SEQ ID NO 177
<211> LENGTH: 42
<212> TYPE: DNA
<213> ORGANISM: Escherichi coli
<220> FEATURE:
<221> NAME/KEY: misc_difference
<222> LOCATION: 21-22
<223> OTHER INFORMATION: non-consecutive nucleotides

<400> SEQUENCE: 177
tcattccagc tccagttttt tattaattac gatggggttc at                               42

<210> SEQ ID NO 178
<211> LENGTH: 23
<212> TYPE: DNA
<213> ORGANISM: Artificial Sequence
<220> FEATURE:
<223> OTHER INFORMATION: primer

<400> SEQUENCE: 178
acgcgttcat tccagctcca gtt                                                    23

<210> SEQ ID NO 179
<211> LENGTH: 20
<212> TYPE: DNA
```

```
<213> ORGANISM: Artificial Sequence
<220> FEATURE:
<223> OTHER INFORMATION: primer

<400> SEQUENCE: 179
ggatccgcca ccatgggata                                                    20

<210> SEQ ID NO 180
<211> LENGTH: 16
<212> TYPE: DNA
<213> ORGANISM: Artificial Sequence
<220> FEATURE:
<223> OTHER INFORMATION: primer

<400> SEQUENCE: 180
acgcgttcat tccagc                                                        16

<210> SEQ ID NO 181
<211> LENGTH: 31
<212> TYPE: DNA
<213> ORGANISM: Artificial Sequence
<220> FEATURE:
<223> OTHER INFORMATION: primer

<400> SEQUENCE: 181
gcgcgcgcca ccatgacaaa tcttgatact g                                       31

<210> SEQ ID NO 182
<211> LENGTH: 13
<212> TYPE: PRT
<213> ORGANISM: unknown
<220> FEATURE:
<223> OTHER INFORMATION: partial HPV-16 E5
<220> FEATURE:
<221> NAME/KEY: NON_CONS
<222> LOCATION: 7-8

<400> SEQUENCE: 182

Met Thr Asn Leu Asp Thr Ala Ala Arg Phe Leu Ile Thr
 1               5                  10

<210> SEQ ID NO 183
<211> LENGTH: 42
<212> TYPE: DNA
<213> ORGANISM: unknown
<220> FEATURE:
<223> OTHER INFORMATION: partial HPV-16 E5 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 183
atgacaaatc ttgatactgc agcacgcttt ttaattacat aa                           42

<210> SEQ ID NO 184
<211> LENGTH: 42
<212> TYPE: DNA
<213> ORGANISM: unknown
<220> FEATURE:
<223> OTHER INFORMATION: partial HPV-16 E5 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 184
ttatgtaatt aaaaagcgtg ctgcagtatc aagatttgtc at                           42
```

```
<210> SEQ ID NO 185
<211> LENGTH: 26
<212> TYPE: DNA
<213> ORGANISM: Artificial Sequence
<220> FEATURE:
<223> OTHER INFORMATION: primer

<400> SEQUENCE: 185 aagctttat gtaattaaaa agcgtg                                          26

<210> SEQ ID NO 186
<211> LENGTH: 21
<212> TYPE: DNA
<213> ORGANISM: Artificial Sequence
<220> FEATURE:
<223> OTHER INFORMATION: primer

<400> SEQUENCE: 186
ggatccgcca ccatgacaaa t                                              21

<210> SEQ ID NO 187
<211> LENGTH: 26
<212> TYPE: DNA
<213> ORGANISM: Artificial Sequence
<220> FEATURE:
<223> OTHER INFORMATION: primer

<400> SEQUENCE: 187
acgcgtttat gtaattaaaa agcgtg                                         26

<210> SEQ ID NO 188
<211> LENGTH: 43
<212> TYPE: DNA
<213> ORGANISM: Artificial Sequence
<220> FEATURE:
<223> OTHER INFORMATION: primer

<400> SEQUENCE: 188
gtcgacgcca ccatgggata cccatacgat gttccagatt acg                      43

<210> SEQ ID NO 189
<211> LENGTH: 43
<212> TYPE: DNA
<213> ORGANISM: Artificial Sequence
<220> FEATURE:
<223> OTHER INFORMATION: primer

<400> SEQUENCE: 189
cgatgttcca gattacgctg gaggtatgct ggcagtttta aaa                      43

<210> SEQ ID NO 190
<211> LENGTH: 12
<212> TYPE: PRT
<213> ORGANISM: unknown
<220> FEATURE:
<223> OTHER INFORMATION: partial SpiC sequence
<220> FEATURE:
<221> NAME/KEY: NON_CONS
<222> LOCATION: 6-7

<400> SEQUENCE: 190

Met Leu Ala Val Leu Lys Leu Tyr Ser Gly Gly Val
 1               5                  10

<210> SEQ ID NO 191
```

```
<211> LENGTH: 39
<212> TYPE: DNA
<213> ORGANISM: unknown
<220> FEATURE:
<223> OTHER INFORMATION: partial SpiC 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 191
atgctggcag ttttaaaact ttattcgggt ggggtataa                              39

<210> SEQ ID NO 192
<211> LENGTH: 39
<212> TYPE: DNA
<213> ORGANISM: unknown
<220> FEATURE:
<223> OTHER INFORMATION: partial SpiC 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 192
ttatacccca cccgaataaa gttttaaaac tgccagcat                              39

<210> SEQ ID NO 193
<211> LENGTH: 23
<212> TYPE: DNA
<213> ORGANISM: Artificial Sequence
<220> FEATURE:
<223> OTHER INFORMATION: primer

<400> SEQUENCE: 193
acgcgtttat accccacccg aat                                              23

<210> SEQ ID NO 194
<211> LENGTH: 20
<212> TYPE: DNA
<213> ORGANISM: Artificial Sequence
<220> FEATURE:
<223> OTHER INFORMATION: primer

<400> SEQUENCE: 194
ggatccgcca ccatgggata                                                  20

<210> SEQ ID NO 195
<211> LENGTH: 16
<212> TYPE: DNA
<213> ORGANISM: Artificial Sequence
<220> FEATURE:
<223> OTHER INFORMATION: primer

<400> SEQUENCE: 195
acgcgtttat acccca                                                      16

<210> SEQ ID NO 196
<211> LENGTH: 21
<212> TYPE: DNA
<213> ORGANISM: Artificial Sequence
<220> FEATURE:
<223> OTHER INFORMATION: primer

<400> SEQUENCE: 196
ggatccgcca ccatgggtaa a                                                21
```

```
<210> SEQ ID NO 197
<211> LENGTH: 13
<212> TYPE: PRT
<213> ORGANISM: unknown
<220> FEATURE:
<223> OTHER INFORMATION: partial Hdj-1 sequence
<220> FEATURE:
<221> NAME/KEY: NON_CONS
<222> LOCATION: 7-8

<400> SEQUENCE: 197

Met Gly Lys Asp Tyr Tyr Gln Glu Gln Val Leu Pro Ile
 1               5                  10

<210> SEQ ID NO 198
<211> LENGTH: 42
<212> TYPE: DNA
<213> ORGANISM: unknown
<220> FEATURE:
<223> OTHER INFORMATION: partial Hdj-1 sequence 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 198
atgggtaaag attactacca ggagcaggtt cttccaatat ag                        42

<210> SEQ ID NO 199
<211> LENGTH: 42
<212> TYPE: DNA
<213> ORGANISM: unknown
<220> FEATURE:
<223> OTHER INFORMATION: partial Hdj-1 sequence 5' and 3' complement
      sequence
<220> FEATURE:
<221> NAME/KEY: misc_difference
<222> LOCATION: 21-22
<223> OTHER INFORMATION: non-consecutive nucleotides

<400> SEQUENCE: 199
ctatattgga agaacctgct cctggtagta atctttaccc at                        42

<210> SEQ ID NO 200
<211> LENGTH: 17
<212> TYPE: DNA
<213> ORGANISM: Artificial Sequence
<220> FEATURE:
<223> OTHER INFORMATION: primer

<400> SEQUENCE: 200
acgcgtctat attggaa                                                    17

<210> SEQ ID NO 201
<211> LENGTH: 20
<212> TYPE: DNA
<213> ORGANISM: Artificial Sequence
<220> FEATURE:
<223> OTHER INFORMATION: primer

<400> SEQUENCE: 201
ggatccgcca ccatggccaa                                                 20

<210> SEQ ID NO 202
<211> LENGTH: 13
<212> TYPE: PRT
<213> ORGANISM: unknown
<220> FEATURE:
<223> OTHER INFORMATION: partial Hsp70 sequence
```

```
<220> FEATURE:
<221> NAME/KEY: NON_CONS
<222> LOCATION: 7-8

<400> SEQUENCE: 202

Met Ala Lys Ala Ala Ala Val Thr Ile Glu Glu Val Asp
 1               5                  10

<210> SEQ ID NO 203
<211> LENGTH: 42
<212> TYPE: DNA
<213> ORGANISM: unknown
<220> FEATURE:
<223> OTHER INFORMATION: partial Hsp70 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 203
atggccaaag ccgcggcagt caccattgag gaggtagatt ag                     42

<210> SEQ ID NO 204
<211> LENGTH: 42
<212> TYPE: DNA
<213> ORGANISM: Unknown
<220> FEATURE:
<223> OTHER INFORMATION: partial Hsp70 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 204
ctaatctacc tcctcaatgg tgactgccgc ggctttggcc at                     42

<210> SEQ ID NO 205
<211> LENGTH: 17
<212> TYPE: DNA
<213> ORGANISM: Artificial Sequence
<220> FEATURE:
<223> OTHER INFORMATION: primer

<400> SEQUENCE: 205
acgcgtctaa tctacct                                                 17

<210> SEQ ID NO 206
<211> LENGTH: 21
<212> TYPE: DNA
<213> ORGANISM: Artificial Sequence
<220> FEATURE:
<223> OTHER INFORMATION: primer

<400> SEQUENCE: 206
acgcgtgcca ccatgcctga g                                            21

<210> SEQ ID NO 207
<211> LENGTH: 13
<212> TYPE: PRT
<213> ORGANISM: unknown
<220> FEATURE:
<223> OTHER INFORMATION: partial Hsp90 sequence
<220> FEATURE:
<221> NAME/KEY: NON_CONS
<222> LOCATION: 7-8

<400> SEQUENCE: 207

Met Pro Glu Glu Val His His Arg Met Glu Glu Val Asp
```

```
<210> SEQ ID NO 208
<211> LENGTH: 42
<212> TYPE: DNA
<213> ORGANISM: unknown
<220> FEATURE:
<223> OTHER INFORMATION: partial Hsp90 5' and 3' sequence
<220> FEATURE:
<221> NAME/KEY: misc_difference
<222> LOCATION: 21-22
<223> OTHER INFORMATION: non-consecutive nucleotides

<400> SEQUENCE: 208
atgcctgagg aagtgcacca tcgcatggaa gaagtcgatt ag                              42

<210> SEQ ID NO 209
<211> LENGTH: 42
<212> TYPE: DNA
<213> ORGANISM: unknown
<220> FEATURE:
<223> OTHER INFORMATION: partial Hsp90 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 209
ctaatcgact tcttccatgc gatggtgcac ttcctcaggc at                              42

<210> SEQ ID NO 210
<211> LENGTH: 26
<212> TYPE: DNA
<213> ORGANISM: Artificial Sequence
<220> FEATURE:
<223> OTHER INFORMATION: primer

<400> SEQUENCE: 210
gcggccgcct aatcgacttc ttccat                                                26

<210> SEQ ID NO 211
<211> LENGTH: 11
<212> TYPE: PRT
<213> ORGANISM: unknown
<220> FEATURE:
<223> OTHER INFORMATION: TAT protein transduction domain (PTD) tag

<400> SEQUENCE: 211

Tyr Gly Arg Lys Lys Arg Arg Gln Arg Arg
 1               5                   10

<210> SEQ ID NO 212
<211> LENGTH: 11
<212> TYPE: PRT
<213> ORGANISM: Unknown
<220> FEATURE:
<223> OTHER INFORMATION: PTD-4 protein transduction domain (PTD) tag

<400> SEQUENCE: 212

Tyr Ala Arg Ala Ala Ala Arg Gln Ala Arg Ala
 1               5                   10

<210> SEQ ID NO 213
<211> LENGTH: 11
<212> TYPE: PRT
<213> ORGANISM: unknown
<220> FEATURE:
<223> OTHER INFORMATION: Arg protein transudction domain (PTD) tag
```

-continued

<400> SEQUENCE: 213

Arg Arg Gly Arg Arg Gly Arg Gly Arg Arg
1               5                   10

<210> SEQ ID NO 214
<211> LENGTH: 10
<212> TYPE: PRT
<213> ORGANISM: Artificial Sequence
<220> FEATURE:
<223> OTHER INFORMATION: translated sequence

<400> SEQUENCE: 214

Gly Tyr Gly Arg Lys Lys Arg Arg Gln Arg
1               5                   10

<210> SEQ ID NO 215
<211> LENGTH: 36
<212> TYPE: DNA
<213> ORGANISM: Artificial Sequence
<220> FEATURE:
<223> OTHER INFORMATION: primer

<400> SEQUENCE: 215
caccggctat ggccgcaaga aacgtcgcca gcgtcg                                36

<210> SEQ ID NO 216
<211> LENGTH: 7
<212> TYPE: PRT
<213> ORGANISM: Artificial Sequence
<220> FEATURE:
<223> OTHER INFORMATION: translated sequence

<400> SEQUENCE: 216

Arg Arg Gln Arg Arg Arg Gly
1               5

<210> SEQ ID NO 217
<211> LENGTH: 38
<212> TYPE: DNA
<213> ORGANISM: Artificial Sequence
<220> FEATURE:
<223> OTHER INFORMATION: primer

<400> SEQUENCE: 217
cgtcgccagc gtcgccgtgg catgaccagc gaacaata                              38

<210> SEQ ID NO 218
<211> LENGTH: 10
<212> TYPE: PRT
<213> ORGANISM: Artificial Sequence
<220> FEATURE:
<223> OTHER INFORMATION: translated sequence

<400> SEQUENCE: 218

Gly Tyr Ala Arg Ala Ala Ala Arg Gln Ala
1               5                   10

<210> SEQ ID NO 219
<211> LENGTH: 35
<212> TYPE: DNA
<213> ORGANISM: Artificial Sequence
<220> FEATURE:
<223> OTHER INFORMATION: primer

<400> SEQUENCE: 219

```
caccggctat gcgcgcgcag cggctcgcca ggcgc                    35
```

<210> SEQ ID NO 220
<211> LENGTH: 7
<212> TYPE: PRT
<213> ORGANISM: Artificial Sequence
<220> FEATURE:
<223> OTHER INFORMATION: translated sequence

<400> SEQUENCE: 220

Ala Arg Gln Ala Arg Ala Gly
 1               5

<210> SEQ ID NO 221
<211> LENGTH: 38
<212> TYPE: DNA
<213> ORGANISM: Artificial Sequence
<220> FEATURE:
<223> OTHER INFORMATION: primer

<400> SEQUENCE: 221

```
gctcgccagg cgcgcgcagg catgaccagc gaacaata                 38
```

<210> SEQ ID NO 222
<211> LENGTH: 10
<212> TYPE: PRT
<213> ORGANISM: Artificial Sequence
<220> FEATURE:
<223> OTHER INFORMATION: translated sequence

<400> SEQUENCE: 222

Gly Arg Arg Gly Arg Arg Gly Arg Arg Gly
 1               5                  10

<210> SEQ ID NO 223
<211> LENGTH: 35
<212> TYPE: DNA
<213> ORGANISM: Artificial Sequence
<220> FEATURE:
<223> OTHER INFORMATION: primer

<400> SEQUENCE: 223

```
caccggccgc cggggtcggc gtggacgtcg cgggc                    35
```

<210> SEQ ID NO 224
<211> LENGTH: 7
<212> TYPE: PRT
<213> ORGANISM: Artificial Sequence
<220> FEATURE:
<223> OTHER INFORMATION: translated sequence

<400> SEQUENCE: 224

Gly Arg Arg Gly Arg Arg Gly
 1               5

<210> SEQ ID NO 225
<211> LENGTH: 38
<212> TYPE: DNA
<213> ORGANISM: Artificial Sequence
<220> FEATURE:
<223> OTHER INFORMATION: primer

<400> SEQUENCE: 225

```
ggacgtcgcg ggcggcgcgg catgaccagc gaacaata                 38
```

<210> SEQ ID NO 226

-continued

```
<211> LENGTH: 24
<212> TYPE: DNA
<213> ORGANISM: Artificial Sequence
<220> FEATURE:
<223> OTHER INFORMATION: primer

<400> SEQUENCE: 226
caccggcatg accagcgaac aata                                              24

<210> SEQ ID NO 227
<211> LENGTH: 12
<212> TYPE: PRT
<213> ORGANISM: unknown
<220> FEATURE:
<223> OTHER INFORMATION: partial aequorin N and C terminal sequence
<220> FEATURE:
<221> NAME/KEY: NON_CONS
<222> LOCATION: 6-7

<400> SEQUENCE: 227

Met Thr Ser Glu Gln Tyr Tyr Gly Gly Ala Val Pro
 1               5                  10

<210> SEQ ID NO 228
<211> LENGTH: 39
<212> TYPE: DNA
<213> ORGANISM: unknown
<220> FEATURE:
<223> OTHER INFORMATION: partial aequorin 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 228
atgaccagcg aacaatacta cggtggagct gtcccctaa                              39

<210> SEQ ID NO 229
<211> LENGTH: 39
<212> TYPE: DNA
<213> ORGANISM: unknown
<220> FEATURE:
<223> OTHER INFORMATION: partial aequorin 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 229
ttaggggaca gctccaccgt agtattgttc gctggtcat                              39

<210> SEQ ID NO 230
<211> LENGTH: 16
<212> TYPE: DNA
<213> ORGANISM: Artificial Sequence
<220> FEATURE:
<223> OTHER INFORMATION: primer

<400> SEQUENCE: 230
ttaggggaca gctcca                                                       16

<210> SEQ ID NO 231
<211> LENGTH: 10
<212> TYPE: PRT
<213> ORGANISM: Artificial Sequence
<220> FEATURE:
<223> OTHER INFORMATION: translated sequence

<400> SEQUENCE: 231
```

Gly Tyr Gly Arg Lys Lys Arg Arg Gln Arg
 1               5                  10

<210> SEQ ID NO 232
<211> LENGTH: 36
<212> TYPE: DNA
<213> ORGANISM: Artificial Sequence
<220> FEATURE:
<223> OTHER INFORMATION: primer

<400> SEQUENCE: 232
caccggctat ggccgcaaga aacgtcgcca gcgtcg                          36

<210> SEQ ID NO 233
<211> LENGTH: 7
<212> TYPE: PRT
<213> ORGANISM: Artificial Sequence
<220> FEATURE:
<223> OTHER INFORMATION: translated sequence

<400> SEQUENCE: 233

Arg Arg Gln Arg Arg Arg Gly
 1               5

<210> SEQ ID NO 234
<211> LENGTH: 36
<212> TYPE: DNA
<213> ORGANISM: Artificial Sequence
<220> FEATURE:
<223> OTHER INFORMATION: primer

<400> SEQUENCE: 234
cgtcgccagc gtcgccgtgg catggtgagc aagggc                          36

<210> SEQ ID NO 235
<211> LENGTH: 10
<212> TYPE: PRT
<213> ORGANISM: Artificial Sequence
<220> FEATURE:
<223> OTHER INFORMATION: translated sequence

<400> SEQUENCE: 235

Gly Tyr Ala Arg Ala Ala Ala Arg Gln Ala
 1               5                  10

<210> SEQ ID NO 236
<211> LENGTH: 35
<212> TYPE: DNA
<213> ORGANISM: Artificial Sequence
<220> FEATURE:
<223> OTHER INFORMATION: primer

<400> SEQUENCE: 236
caccggctat gcgcgcgcag cggctcgcca ggcgc                           35

<210> SEQ ID NO 237
<211> LENGTH: 7
<212> TYPE: PRT
<213> ORGANISM: Artificial Sequence
<220> FEATURE:
<223> OTHER INFORMATION: translated sequence

<400> SEQUENCE: 237

Ala Arg Gln Ala Arg Ala Gly
 1               5

```
<210> SEQ ID NO 238
<211> LENGTH: 36
<212> TYPE: DNA
<213> ORGANISM: Artificial Sequence
<220> FEATURE:
<223> OTHER INFORMATION: primer

<400> SEQUENCE: 238
gctcgccagg cgcgcgcagg catggtgagc aagggc                               36

<210> SEQ ID NO 239
<211> LENGTH: 10
<212> TYPE: PRT
<213> ORGANISM: Artificial Sequence
<220> FEATURE:
<223> OTHER INFORMATION: translated sequence

<400> SEQUENCE: 239

Gly Arg Arg Gly Arg Arg Gly Arg Arg Gly
 1               5                  10

<210> SEQ ID NO 240
<211> LENGTH: 35
<212> TYPE: DNA
<213> ORGANISM: Artificial Sequence
<220> FEATURE:
<223> OTHER INFORMATION: primer

<400> SEQUENCE: 240
caccggccgc cggggtcggc gtggacgtcg cgggc                                35

<210> SEQ ID NO 241
<211> LENGTH: 7
<212> TYPE: PRT
<213> ORGANISM: Artificial Sequence
<220> FEATURE:
<223> OTHER INFORMATION: translated sequence

<400> SEQUENCE: 241

Gly Arg Arg Gly Arg Arg Gly
 1               5

<210> SEQ ID NO 242
<211> LENGTH: 36
<212> TYPE: DNA
<213> ORGANISM: Artificial Sequence
<220> FEATURE:
<223> OTHER INFORMATION: primer

<400> SEQUENCE: 242
ggacgtcgcg ggcggcgcgg catggtgagc aagggc                               36

<210> SEQ ID NO 243
<211> LENGTH: 22
<212> TYPE: DNA
<213> ORGANISM: Artificial Sequence
<220> FEATURE:
<223> OTHER INFORMATION: primer

<400> SEQUENCE: 243
caccggcatg gtgagcaagg gc                                              22

<210> SEQ ID NO 244
<211> LENGTH: 12
<212> TYPE: PRT
<213> ORGANISM: unknown
```

```
<220> FEATURE:
<223> OTHER INFORMATION: partial EGFP N and C terminal sequence
<220> FEATURE:
<221> NAME/KEY: NON_CONS
<222> LOCATION: 6-7

<400> SEQUENCE: 244

Met Val Ser Lys Gly Glu Met Asp Glu Leu Tyr Lys
 1               5                  10

<210> SEQ ID NO 245
<211> LENGTH: 39
<212> TYPE: DNA
<213> ORGANISM: unknown
<220> FEATURE:
<223> OTHER INFORMATION: partial EGFP 5' and 3' sequence
<220> FEATURE:
<221> NAME/KEY: misc_difference
<222> LOCATION: 18-19
<223> OTHER INFORMATION: non-consecutive nucleotides

<400> SEQUENCE: 245
atggtgagca agggcgagat ggacgagctg tacaagtaa                       39

<210> SEQ ID NO 246
<211> LENGTH: 39
<212> TYPE: DNA
<213> ORGANISM: unknown
<220> FEATURE:
<223> OTHER INFORMATION: partial EGFP 5' and 3' complement sequence
<220> FEATURE:
<221> NAME/KEY: misc_difference
<222> LOCATION: 21-22
<223> OTHER INFORMATION: non-consecutive nucleotides

<400> SEQUENCE: 246
ttacttgtac agctcgtcca tctcgcccatt gctcaccat                      39

<210> SEQ ID NO 247
<211> LENGTH: 17
<212> TYPE: DNA
<213> ORGANISM: Artificial Sequence
<220> FEATURE:
<223> OTHER INFORMATION: primer

<400> SEQUENCE: 247
ttacttgtac agctcgt                                               17

<210> SEQ ID NO 248
<211> LENGTH: 10
<212> TYPE: PRT
<213> ORGANISM: Artificial Sequence
<220> FEATURE:
<223> OTHER INFORMATION: translated sequence

<400> SEQUENCE: 248

Gly Tyr Gly Arg Lys Lys Arg Arg Gln Arg
 1               5                  10

<210> SEQ ID NO 249
<211> LENGTH: 36
<212> TYPE: DNA
<213> ORGANISM: Artificial Sequence
<220> FEATURE:
<223> OTHER INFORMATION: primer

<400> SEQUENCE: 249
caccggctat ggccgcaaga aacgtcgcca gcgtcg                          36
```

<210> SEQ ID NO 250
<211> LENGTH: 7
<212> TYPE: PRT
<213> ORGANISM: Artificial Sequence
<220> FEATURE:
<223> OTHER INFORMATION: translated sequence

<400> SEQUENCE: 250

Arg Arg Gln Arg Arg Arg Gly
 1               5

<210> SEQ ID NO 251
<211> LENGTH: 38
<212> TYPE: DNA
<213> ORGANISM: Artificial Sequence
<220> FEATURE:
<223> OTHER INFORMATION: primer

<400> SEQUENCE: 251
cgtcgccagc gtcgccgtgg catggctggt gatctttc                              38

<210> SEQ ID NO 252
<211> LENGTH: 10
<212> TYPE: PRT
<213> ORGANISM: Artificial Sequence
<220> FEATURE:
<223> OTHER INFORMATION: translated sequence

<400> SEQUENCE: 252

Gly Tyr Ala Arg Ala Ala Ala Arg Gln Ala
 1               5                  10

<210> SEQ ID NO 253
<211> LENGTH: 35
<212> TYPE: DNA
<213> ORGANISM: Artificial Sequence
<220> FEATURE:
<223> OTHER INFORMATION: primer

<400> SEQUENCE: 253
caccggctat gcgcgcgcag cggctcgcca ggcgc                                 35

<210> SEQ ID NO 254
<211> LENGTH: 7
<212> TYPE: PRT
<213> ORGANISM: Artificial Sequence
<220> FEATURE:
<223> OTHER INFORMATION: translated sequence

<400> SEQUENCE: 254

Ala Arg Gln Ala Arg Ala Gly
 1               5

<210> SEQ ID NO 255
<211> LENGTH: 38
<212> TYPE: DNA
<213> ORGANISM: Artificial Sequence
<220> FEATURE:
<223> OTHER INFORMATION: primer

<400> SEQUENCE: 255
gctcgccagg cgcgcgcagg catggctggt gatctttc                              38

<210> SEQ ID NO 256
<211> LENGTH: 10

```
<212> TYPE: PRT
<213> ORGANISM: Artificial Sequence
<220> FEATURE:
<223> OTHER INFORMATION: translated sequence

<400> SEQUENCE: 256

Gly Arg Arg Gly Arg Arg Gly Arg Arg Gly
  1               5                  10

<210> SEQ ID NO 257
<211> LENGTH: 35
<212> TYPE: DNA
<213> ORGANISM: Artificial Sequence
<220> FEATURE:
<223> OTHER INFORMATION: primer

<400> SEQUENCE: 257
caccggccgc cggggtcggc gtggacgtcg cgggc                          35

<210> SEQ ID NO 258
<211> LENGTH: 7
<212> TYPE: PRT
<213> ORGANISM: Artificial Sequence
<220> FEATURE:
<223> OTHER INFORMATION: translated sequence

<400> SEQUENCE: 258

Gly Arg Arg Gly Arg Arg Gly
  1               5

<210> SEQ ID NO 259
<211> LENGTH: 38
<212> TYPE: DNA
<213> ORGANISM: Artificial Sequence
<220> FEATURE:
<223> OTHER INFORMATION: primer

<400> SEQUENCE: 259
ggacgtcgcg ggcggcgcgg catggctggt gatctttc                       38

<210> SEQ ID NO 260
<211> LENGTH: 24
<212> TYPE: DNA
<213> ORGANISM: Artificial Sequence
<220> FEATURE:
<223> OTHER INFORMATION: primer

<400> SEQUENCE: 260
caccggcatg gctggtgatc tttc                                      24

<210> SEQ ID NO 261
<211> LENGTH: 20
<212> TYPE: DNA
<213> ORGANISM: Artificial Sequence
<220> FEATURE:
<223> OTHER INFORMATION: primer

<400> SEQUENCE: 261
ttagtgataa aaatagagtt                                           20

<210> SEQ ID NO 262
<211> LENGTH: 10
<212> TYPE: PRT
<213> ORGANISM: Artificial Sequence
<220> FEATURE:
<223> OTHER INFORMATION: translated sequence
```

```
<400> SEQUENCE: 262

Gly Tyr Gly Arg Lys Lys Arg Arg Gln Arg
 1               5                  10

<210> SEQ ID NO 263
<211> LENGTH: 36
<212> TYPE: DNA
<213> ORGANISM: Artificial Sequence
<220> FEATURE:
<223> OTHER INFORMATION: primer

<400> SEQUENCE: 263
caccggctat ggccgcaaga aacgtcgcca gcgtcg                                 36

<210> SEQ ID NO 264
<211> LENGTH: 7
<212> TYPE: PRT
<213> ORGANISM: Artificial Sequence
<220> FEATURE:
<223> OTHER INFORMATION: translated sequence

<400> SEQUENCE: 264

Arg Arg Gln Arg Arg Arg Gly
 1               5

<210> SEQ ID NO 265
<211> LENGTH: 38
<212> TYPE: DNA
<213> ORGANISM: Artificial Sequence
<220> FEATURE:
<223> OTHER INFORMATION: primer

<400> SEQUENCE: 265
cgtcgccagc gtcgccgtgg catggctggt gatctttc                               38

<210> SEQ ID NO 266
<211> LENGTH: 10
<212> TYPE: PRT
<213> ORGANISM: Artificial Sequence
<220> FEATURE:
<223> OTHER INFORMATION: translated sequence

<400> SEQUENCE: 266

Gly Tyr Ala Arg Ala Ala Ala Arg Gln Ala
 1               5                  10

<210> SEQ ID NO 267
<211> LENGTH: 35
<212> TYPE: DNA
<213> ORGANISM: Artificial Sequence
<220> FEATURE:
<223> OTHER INFORMATION: primer

<400> SEQUENCE: 267
caccggctat gcgcgcgcag cggctcgcca ggcgc                                  35

<210> SEQ ID NO 268
<211> LENGTH: 7
<212> TYPE: PRT
<213> ORGANISM: Artificial Sequence
<220> FEATURE:
<223> OTHER INFORMATION: translated sequence

<400> SEQUENCE: 268

Ala Arg Gln Ala Arg Ala Gly
 1               5
```

```
<210> SEQ ID NO 269
<211> LENGTH: 38
<212> TYPE: DNA
<213> ORGANISM: Artificial Sequence
<220> FEATURE:
<223> OTHER INFORMATION: primer

<400> SEQUENCE: 269
gctcgccagg cgcgcgcagg catggctggt gatctttc                          38

<210> SEQ ID NO 270
<211> LENGTH: 10
<212> TYPE: PRT
<213> ORGANISM: Artificial Sequence
<220> FEATURE:
<223> OTHER INFORMATION: translated sequence

<400> SEQUENCE: 270

Gly Arg Arg Gly Arg Arg Gly Arg Arg Gly
 1               5                  10

<210> SEQ ID NO 271
<211> LENGTH: 35
<212> TYPE: DNA
<213> ORGANISM: Artificial Sequence
<220> FEATURE:
<223> OTHER INFORMATION: primer

<400> SEQUENCE: 271
caccggccgc cggggtcggc gtggacgtcg cgggc                             35

<210> SEQ ID NO 272
<211> LENGTH: 7
<212> TYPE: PRT
<213> ORGANISM: Artificial Sequence
<220> FEATURE:
<223> OTHER INFORMATION: translated sequence

<400> SEQUENCE: 272

Gly Arg Arg Gly Arg Arg Gly
 1               5

<210> SEQ ID NO 273
<211> LENGTH: 38
<212> TYPE: DNA
<213> ORGANISM: Artificial Sequence
<220> FEATURE:
<223> OTHER INFORMATION: primer

<400> SEQUENCE: 273
ggacgtcgcg ggcggcgcgg catggctggt gatctttc                          38

<210> SEQ ID NO 274
<211> LENGTH: 24
<212> TYPE: DNA
<213> ORGANISM: Artificial Sequence
<220> FEATURE:
<223> OTHER INFORMATION: primer

<400> SEQUENCE: 274
caccggcatg gctggtgatc tttc                                         24

<210> SEQ ID NO 275
<211> LENGTH: 17
<212> TYPE: DNA
```

```
<213> ORGANISM: Artificial Sequence
<220> FEATURE:
<223> OTHER INFORMATION: primer

<400> SEQUENCE: 275
ttacttggtg tctgaga                                                   17

<210> SEQ ID NO 276
<211> LENGTH: 10
<212> TYPE: PRT
<213> ORGANISM: Artificial Sequence
<220> FEATURE:
<223> OTHER INFORMATION: translated sequence

<400> SEQUENCE: 276

Gly Tyr Gly Arg Lys Lys Arg Arg Gln Arg
 1               5                   10

<210> SEQ ID NO 277
<211> LENGTH: 36
<212> TYPE: DNA
<213> ORGANISM: Artificial Sequence
<220> FEATURE:
<223> OTHER INFORMATION: primer

<400> SEQUENCE: 277
caccggctat ggccgcaaga aacgtcgcca gcgtcg                              36

<210> SEQ ID NO 278
<211> LENGTH: 7
<212> TYPE: PRT
<213> ORGANISM: Artificial Sequence
<220> FEATURE:
<223> OTHER INFORMATION: translated sequence

<400> SEQUENCE: 278

Arg Arg Gln Arg Arg Arg Gly
 1               5

<210> SEQ ID NO 279
<211> LENGTH: 37
<212> TYPE: DNA
<213> ORGANISM: Artificial Sequence
<220> FEATURE:
<223> OTHER INFORMATION: primer

<400> SEQUENCE: 279
cgtcgccagc gtcgccgtgg catggagagc agggatc                             37

<210> SEQ ID NO 280
<211> LENGTH: 10
<212> TYPE: PRT
<213> ORGANISM: Artificial Sequence
<220> FEATURE:
<223> OTHER INFORMATION: translated sequence

<400> SEQUENCE: 280

Gly Tyr Ala Arg Ala Ala Ala Arg Gln Ala
 1               5                   10

<210> SEQ ID NO 281
<211> LENGTH: 35
<212> TYPE: DNA
<213> ORGANISM: Artificial Sequence
<220> FEATURE:
<223> OTHER INFORMATION: primer
```

<400> SEQUENCE: 281
caccggctat gcgcgcgcag cggctcgcca ggcgc    35

<210> SEQ ID NO 282
<211> LENGTH: 7
<212> TYPE: PRT
<213> ORGANISM: Artificial Sequence
<220> FEATURE:
<223> OTHER INFORMATION: translated sequence

<400> SEQUENCE: 282

Ala Arg Gln Ala Arg Ala Gly
 1               5

<210> SEQ ID NO 283
<211> LENGTH: 37
<212> TYPE: DNA
<213> ORGANISM: Artificial Sequence
<220> FEATURE:
<223> OTHER INFORMATION: primer

<400> SEQUENCE: 283
gctcgccagg cgcgcgcagg catggagagc agggatc    37

<210> SEQ ID NO 284
<211> LENGTH: 10
<212> TYPE: PRT
<213> ORGANISM: Artificial Sequence
<220> FEATURE:
<223> OTHER INFORMATION: translated sequence

<400> SEQUENCE: 284

Gly Arg Arg Gly Arg Arg Gly Arg Arg Gly
 1               5                  10

<210> SEQ ID NO 285
<211> LENGTH: 35
<212> TYPE: DNA
<213> ORGANISM: Artificial Sequence
<220> FEATURE:
<223> OTHER INFORMATION: primer

<400> SEQUENCE: 285
caccggccgc cggggtcggc gtggacgtcg cgggc    35

<210> SEQ ID NO 286
<211> LENGTH: 7
<212> TYPE: PRT
<213> ORGANISM: Artificial Sequence
<220> FEATURE:
<223> OTHER INFORMATION: translated sequence

<400> SEQUENCE: 286

Gly Arg Arg Gly Arg Arg Gly
 1               5

<210> SEQ ID NO 287
<211> LENGTH: 37
<212> TYPE: DNA
<213> ORGANISM: Artificial Sequence
<220> FEATURE:
<223> OTHER INFORMATION: primer

<400> SEQUENCE: 287
ggacgtcgcg ggcggcgcgg catggagagc agggatc    37

```
<210> SEQ ID NO 288
<211> LENGTH: 23
<212> TYPE: DNA
<213> ORGANISM: Artificial Sequence
<220> FEATURE:
<223> OTHER INFORMATION: primer

<400> SEQUENCE: 288
caccggcatg gagagcaggg atc                                              23

<210> SEQ ID NO 289
<211> LENGTH: 18
<212> TYPE: DNA
<213> ORGANISM: Artificial Sequence
<220> FEATURE:
<223> OTHER INFORMATION: primer

<400> SEQUENCE: 289
ttaggaagaa gagacaac                                                    18

<210> SEQ ID NO 290
<211> LENGTH: 10
<212> TYPE: PRT
<213> ORGANISM: Artificial Sequence
<220> FEATURE:
<223> OTHER INFORMATION: translated sequence

<400> SEQUENCE: 290

Gly Tyr Gly Arg Lys Lys Arg Arg Gln Arg
 1               5                  10

<210> SEQ ID NO 291
<211> LENGTH: 36
<212> TYPE: DNA
<213> ORGANISM: Artificial Sequence
<220> FEATURE:
<223> OTHER INFORMATION: primer

<400> SEQUENCE: 291
caccggctat ggccgcaaga aacgtcgcca gcgtcg                                36

<210> SEQ ID NO 292
<211> LENGTH: 7
<212> TYPE: PRT
<213> ORGANISM: Artificial Sequence
<220> FEATURE:
<223> OTHER INFORMATION: translated sequence

<400> SEQUENCE: 292

Arg Arg Gln Arg Arg Arg Gly
 1               5

<210> SEQ ID NO 293
<211> LENGTH: 36
<212> TYPE: DNA
<213> ORGANISM: Artificial Sequence
<220> FEATURE:
<223> OTHER INFORMATION: primer

<400> SEQUENCE: 293
cgtcgccagc gtcgccgtgg cgtcaaccct ggcgtc                                36

<210> SEQ ID NO 294
<211> LENGTH: 10
<212> TYPE: PRT
<213> ORGANISM: Artificial Sequence
```

```
<220> FEATURE:
<223> OTHER INFORMATION: translated sequence

<400> SEQUENCE: 294

Gly Tyr Ala Arg Ala Ala Ala Arg Gln Ala
 1               5                  10

<210> SEQ ID NO 295
<211> LENGTH: 35
<212> TYPE: DNA
<213> ORGANISM: Artificial Sequence
<220> FEATURE:
<223> OTHER INFORMATION: primer

<400> SEQUENCE: 295
caccggctat gcgcgcgcag cggctcgcca ggcgc                              35

<210> SEQ ID NO 296
<211> LENGTH: 7
<212> TYPE: PRT
<213> ORGANISM: Artificial Sequence
<220> FEATURE:
<223> OTHER INFORMATION: translated sequence

<400> SEQUENCE: 296

Ala Arg Gln Ala Arg Ala Gly
 1               5

<210> SEQ ID NO 297
<211> LENGTH: 36
<212> TYPE: DNA
<213> ORGANISM: Artificial Sequence
<220> FEATURE:
<223> OTHER INFORMATION: primer

<400> SEQUENCE: 297
gctcgccagg cgcgcgcagg cgtcaaccct ggcgtc                             36

<210> SEQ ID NO 298
<211> LENGTH: 10
<212> TYPE: PRT
<213> ORGANISM: Artificial Sequence
<220> FEATURE:
<223> OTHER INFORMATION: translated sequence

<400> SEQUENCE: 298

Gly Arg Arg Gly Arg Arg Gly Arg Arg Gly
 1               5                  10

<210> SEQ ID NO 299
<211> LENGTH: 35
<212> TYPE: DNA
<213> ORGANISM: Artificial Sequence
<220> FEATURE:
<223> OTHER INFORMATION: primer

<400> SEQUENCE: 299
caccggccgc cggggtcggc gtggacgtcg cgggc                              35

<210> SEQ ID NO 300
<211> LENGTH: 7
<212> TYPE: PRT
<213> ORGANISM: Artificial Sequence
<220> FEATURE:
<223> OTHER INFORMATION: translated sequence

<400> SEQUENCE: 300
```

Gly Arg Arg Gly Arg Arg Gly
1               5

<210> SEQ ID NO 301
<211> LENGTH: 36
<212> TYPE: DNA
<213> ORGANISM: Artificial Sequence
<220> FEATURE:
<223> OTHER INFORMATION: primer

<400> SEQUENCE: 301
ggacgtcgcg ggcggcgcgg cgtcaaccct ggcgtc                            36

<210> SEQ ID NO 302
<211> LENGTH: 22
<212> TYPE: DNA
<213> ORGANISM: Artificial Sequence
<220> FEATURE:
<223> OTHER INFORMATION: primer

<400> SEQUENCE: 302
caccggcgtc aaccctggcg tc                                           22

<210> SEQ ID NO 303
<211> LENGTH: 18
<212> TYPE: DNA
<213> ORGANISM: Artificial Sequence
<220> FEATURE:
<223> OTHER INFORMATION: primer

<400> SEQUENCE: 303
ttaggaagaa gagacaac                                                18

<210> SEQ ID NO 304
<211> LENGTH: 10
<212> TYPE: PRT
<213> ORGANISM: Artificial Sequence
<220> FEATURE:
<223> OTHER INFORMATION: translated sequence

<400> SEQUENCE: 304

Gly Tyr Gly Arg Lys Lys Arg Arg Gln Arg
1               5                   10

<210> SEQ ID NO 305
<211> LENGTH: 36
<212> TYPE: DNA
<213> ORGANISM: Artificial Sequence
<220> FEATURE:
<223> OTHER INFORMATION: primer

<400> SEQUENCE: 305
caccggctat ggccgcaaga aacgtcgcca gcgtcg                            36

<210> SEQ ID NO 306
<211> LENGTH: 7
<212> TYPE: PRT
<213> ORGANISM: Artificial Sequence
<220> FEATURE:
<223> OTHER INFORMATION: translated sequence

<400> SEQUENCE: 306

Arg Arg Gln Arg Arg Arg Gly
1               5

<210> SEQ ID NO 307
<211> LENGTH: 38
<212> TYPE: DNA
<213> ORGANISM: Artificial Sequence
<220> FEATURE:
<223> OTHER INFORMATION: primer

<400> SEQUENCE: 307
cgtcgccagc gtcgccgtgg catggctggt gatctttc                          38

<210> SEQ ID NO 308
<211> LENGTH: 10
<212> TYPE: PRT
<213> ORGANISM: Artificial Sequence
<220> FEATURE:
<223> OTHER INFORMATION: translated sequence

<400> SEQUENCE: 308

Gly Tyr Ala Arg Ala Ala Ala Arg Gln Ala
 1               5                  10

<210> SEQ ID NO 309
<211> LENGTH: 35
<212> TYPE: DNA
<213> ORGANISM: Artificial Sequence
<220> FEATURE:
<223> OTHER INFORMATION: primer

<400> SEQUENCE: 309
caccggctat gcgcgcgcag cggctcgcca ggcgc                             35

<210> SEQ ID NO 310
<211> LENGTH: 7
<212> TYPE: PRT
<213> ORGANISM: Artificial Sequence
<220> FEATURE:
<223> OTHER INFORMATION: translated sequence

<400> SEQUENCE: 310

Ala Arg Gln Ala Arg Ala Gly
 1               5

<210> SEQ ID NO 311
<211> LENGTH: 38
<212> TYPE: DNA
<213> ORGANISM: Artificial Sequence
<220> FEATURE:
<223> OTHER INFORMATION: primer

<400> SEQUENCE: 311
gctcgccagg cgcgcgcagg catggctggt gatctttc                          38

<210> SEQ ID NO 312
<211> LENGTH: 10
<212> TYPE: PRT
<213> ORGANISM: Artificial Sequence
<220> FEATURE:
<223> OTHER INFORMATION: translated sequence

<400> SEQUENCE: 312

Gly Arg Arg Gly Arg Arg Gly Arg Arg Gly
 1               5                  10

<210> SEQ ID NO 313
<211> LENGTH: 35
<212> TYPE: DNA
<213> ORGANISM: Artificial Sequence
<220> FEATURE:
<223> OTHER INFORMATION: primer

<400> SEQUENCE: 313
caccggccgc cggggtcggc gtggacgtcg cgggc                    35

<210> SEQ ID NO 314
<211> LENGTH: 7
<212> TYPE: PRT
<213> ORGANISM: Artificial Sequence
<220> FEATURE:
<223> OTHER INFORMATION: translated sequence

<400> SEQUENCE: 314

Gly Arg Arg Gly Arg Arg Gly
 1               5

<210> SEQ ID NO 315
<211> LENGTH: 38
<212> TYPE: DNA
<213> ORGANISM: Artificial Sequence
<220> FEATURE:
<223> OTHER INFORMATION: primer

<400> SEQUENCE: 315
ggacgtcgcg ggcggcgcgg catggctggt gatctttc                 38

<210> SEQ ID NO 316
<211> LENGTH: 24
<212> TYPE: DNA
<213> ORGANISM: Artificial Sequence
<220> FEATURE:
<223> OTHER INFORMATION: primer

<400> SEQUENCE: 316
caccggcatg gctggtgatc tttc                                24

<210> SEQ ID NO 317
<211> LENGTH: 18
<212> TYPE: DNA
<213> ORGANISM: Artificial Sequence
<220> FEATURE:
<223> OTHER INFORMATION: primer

<400> SEQUENCE: 317
ttaggaagaa gagacaac                                       18

<210> SEQ ID NO 318
<211> LENGTH: 10
<212> TYPE: PRT
<213> ORGANISM: Artificial Sequence
<220> FEATURE:
<223> OTHER INFORMATION: translated sequence

<400> SEQUENCE: 318

Gly Tyr Gly Arg Lys Lys Arg Arg Gln Arg
 1               5                  10

<210> SEQ ID NO 319
<211> LENGTH: 36
<212> TYPE: DNA
<213> ORGANISM: Artificial Sequence
<220> FEATURE:
<223> OTHER INFORMATION: primer

<400> SEQUENCE: 319

```
caccggctat ggccgcaaga aacgtcgcca gcgtcg                                    36
```

<210> SEQ ID NO 320
<211> LENGTH: 7
<212> TYPE: PRT
<213> ORGANISM: Artificial Sequence
<220> FEATURE:
<223> OTHER INFORMATION: translated sequence

<400> SEQUENCE: 320

Arg Arg Gln Arg Arg Arg Gly
 1               5

<210> SEQ ID NO 321
<211> LENGTH: 37
<212> TYPE: DNA
<213> ORGANISM: Artificial Sequence
<220> FEATURE:
<223> OTHER INFORMATION: primer

<400> SEQUENCE: 321

```
cgtcgccagc gtcgccgtgg catggagagc aggatc                                    37
```

<210> SEQ ID NO 322
<211> LENGTH: 10
<212> TYPE: PRT
<213> ORGANISM: Artificial Sequence
<220> FEATURE:
<223> OTHER INFORMATION: translated sequence

<400> SEQUENCE: 322

Gly Tyr Ala Arg Ala Ala Ala Arg Gln Ala
 1               5                  10

<210> SEQ ID NO 323
<211> LENGTH: 35
<212> TYPE: DNA
<213> ORGANISM: Artificial Sequence
<220> FEATURE:
<223> OTHER INFORMATION: primer

<400> SEQUENCE: 323

```
caccggctat gcgcgcgcag cggctcgcca ggcgc                                     35
```

<210> SEQ ID NO 324
<211> LENGTH: 7
<212> TYPE: PRT
<213> ORGANISM: Artificial Sequence
<220> FEATURE:
<223> OTHER INFORMATION: translated sequence

<400> SEQUENCE: 324

Ala Arg Gln Ala Arg Ala Gly
 1               5

<210> SEQ ID NO 325
<211> LENGTH: 37
<212> TYPE: DNA
<213> ORGANISM: Artificial Sequence
<220> FEATURE:
<223> OTHER INFORMATION: primer

<400> SEQUENCE: 325

```
gctcgccagg cgcgcgcagg catggagagc aggatc                                    37
```

<210> SEQ ID NO 326

-continued

```
<211> LENGTH: 10
<212> TYPE: PRT
<213> ORGANISM: Artificial Sequence
<220> FEATURE:
<223> OTHER INFORMATION: translated sequence

<400> SEQUENCE: 326

Gly Arg Arg Gly Arg Arg Gly Arg Arg Gly
 1               5                  10

<210> SEQ ID NO 327
<211> LENGTH: 35
<212> TYPE: DNA
<213> ORGANISM: Artificial Sequence
<220> FEATURE:
<223> OTHER INFORMATION: primer

<400> SEQUENCE: 327
caccggccgc cggggtcggc gtggacgtcg cgggc                              35

<210> SEQ ID NO 328
<211> LENGTH: 7
<212> TYPE: PRT
<213> ORGANISM: Artificial Sequence
<220> FEATURE:
<223> OTHER INFORMATION: translated sequence

<400> SEQUENCE: 328

Gly Arg Arg Gly Arg Arg Gly
 1               5

<210> SEQ ID NO 329
<211> LENGTH: 37
<212> TYPE: DNA
<213> ORGANISM: Artificial Sequence
<220> FEATURE:
<223> OTHER INFORMATION: primer

<400> SEQUENCE: 329
ggacgtcgcg gcggcgcgg catggagagc agggatc                             37

<210> SEQ ID NO 330
<211> LENGTH: 23
<212> TYPE: DNA
<213> ORGANISM: Artificial Sequence
<220> FEATURE:
<223> OTHER INFORMATION: primer

<400> SEQUENCE: 330
caccggcatg gagagcaggg atc                                           23

<210> SEQ ID NO 331
<211> LENGTH: 20
<212> TYPE: DNA
<213> ORGANISM: Artificial Sequence
<220> FEATURE:
<223> OTHER INFORMATION: primer

<400> SEQUENCE: 331
ttagtgataa aaatagagtt                                               20

<210> SEQ ID NO 332
<211> LENGTH: 10
<212> TYPE: PRT
<213> ORGANISM: Artificial Sequence
<220> FEATURE:
<223> OTHER INFORMATION: translated sequence
```

```
<400> SEQUENCE: 332

Gly Tyr Gly Arg Lys Lys Arg Arg Gln Arg
1               5                   10

<210> SEQ ID NO 333
<211> LENGTH: 36
<212> TYPE: DNA
<213> ORGANISM: Artificial Sequence
<220> FEATURE:
<223> OTHER INFORMATION: primer

<400> SEQUENCE: 333
caccggctat ggccgcaaga aacgtcgcca gcgtcg                              36

<210> SEQ ID NO 334
<211> LENGTH: 7
<212> TYPE: PRT
<213> ORGANISM: Artificial Sequence
<220> FEATURE:
<223> OTHER INFORMATION: translated sequence

<400> SEQUENCE: 334

Arg Arg Gln Arg Arg Arg Gly
1               5

<210> SEQ ID NO 335
<211> LENGTH: 36
<212> TYPE: DNA
<213> ORGANISM: Artificial Sequence
<220> FEATURE:
<223> OTHER INFORMATION: primer

<400> SEQUENCE: 335
cgtcgccagc gtcgccgtgg cgtcaaccct ggcgtc                              36

<210> SEQ ID NO 336
<211> LENGTH: 10
<212> TYPE: PRT
<213> ORGANISM: Artificial Sequence
<220> FEATURE:
<223> OTHER INFORMATION: translated sequence

<400> SEQUENCE: 336

Gly Tyr Ala Arg Ala Ala Ala Arg Gln Ala
1               5                   10

<210> SEQ ID NO 337
<211> LENGTH: 35
<212> TYPE: DNA
<213> ORGANISM: Artificial Sequence
<220> FEATURE:
<223> OTHER INFORMATION: primer

<400> SEQUENCE: 337
caccggctat gcgcgcgcag cggctcgcca ggcgc                               35

<210> SEQ ID NO 338
<211> LENGTH: 7
<212> TYPE: PRT
<213> ORGANISM: Artificial Sequence
<220> FEATURE:
<223> OTHER INFORMATION: translated sequence

<400> SEQUENCE: 338

Ala Arg Gln Ala Arg Ala Gly
```

```
<210> SEQ ID NO 339
<211> LENGTH: 36
<212> TYPE: DNA
<213> ORGANISM: Artificial Sequence
<220> FEATURE:
<223> OTHER INFORMATION: primer

<400> SEQUENCE: 339
gctcgccagg cgcgcgcagg cgtcaaccct ggcgtc                          36

<210> SEQ ID NO 340
<211> LENGTH: 10
<212> TYPE: PRT
<213> ORGANISM: Artificial Sequence
<220> FEATURE:
<223> OTHER INFORMATION: translated sequence

<400> SEQUENCE: 340

Gly Arg Arg Gly Arg Arg Gly Arg Arg Gly
1               5                   10

<210> SEQ ID NO 341
<211> LENGTH: 35
<212> TYPE: DNA
<213> ORGANISM: Artificial Sequence
<220> FEATURE:
<223> OTHER INFORMATION: primer

<400> SEQUENCE: 341
caccggccgc cggggtcggc gtggacgtcg cgggc                           35

<210> SEQ ID NO 342
<211> LENGTH: 7
<212> TYPE: PRT
<213> ORGANISM: Artificial Sequence
<220> FEATURE:
<223> OTHER INFORMATION: translated sequence

<400> SEQUENCE: 342

Gly Arg Arg Gly Arg Arg Gly
1               5

<210> SEQ ID NO 343
<211> LENGTH: 36
<212> TYPE: DNA
<213> ORGANISM: Artificial Sequence
<220> FEATURE:
<223> OTHER INFORMATION: primer

<400> SEQUENCE: 343
ggacgtcgcg ggcggcgcgg cgtcaaccct ggcgtc                          36

<210> SEQ ID NO 344
<211> LENGTH: 22
<212> TYPE: DNA
<213> ORGANISM: Artificial Sequence
<220> FEATURE:
<223> OTHER INFORMATION: primer

<400> SEQUENCE: 344
caccggcgtc aaccctggcg tc                                         22

<210> SEQ ID NO 345
<211> LENGTH: 20
```

```
<212> TYPE: DNA
<213> ORGANISM: Artificial Sequence
<220> FEATURE:
<223> OTHER INFORMATION: primer

<400> SEQUENCE: 345
ttagtgataa aaatagagtt                                              20

<210> SEQ ID NO 346
<211> LENGTH: 10
<212> TYPE: PRT
<213> ORGANISM: Artificial Sequence
<220> FEATURE:
<223> OTHER INFORMATION: translated sequence

<400> SEQUENCE: 346

Gly Tyr Gly Arg Lys Lys Arg Arg Gln Arg
 1               5                  10

<210> SEQ ID NO 347
<211> LENGTH: 36
<212> TYPE: DNA
<213> ORGANISM: Artificial Sequence
<220> FEATURE:
<223> OTHER INFORMATION: primer

<400> SEQUENCE: 347
caccggctat ggccgcaaga aacgtcgcca gcgtcg                            36

<210> SEQ ID NO 348
<211> LENGTH: 7
<212> TYPE: PRT
<213> ORGANISM: Artificial Sequence
<220> FEATURE:
<223> OTHER INFORMATION: translated sequence

<400> SEQUENCE: 348

Arg Arg Gln Arg Arg Arg Gly
 1               5

<210> SEQ ID NO 349
<211> LENGTH: 38
<212> TYPE: DNA
<213> ORGANISM: Artificial Sequence
<220> FEATURE:
<223> OTHER INFORMATION: primer

<400> SEQUENCE: 349
cgtcgccagc gtcgccgtgg cgccaggaaa ctactttc                          38

<210> SEQ ID NO 350
<211> LENGTH: 10
<212> TYPE: PRT
<213> ORGANISM: Artificial Sequence
<220> FEATURE:
<223> OTHER INFORMATION: translated sequence

<400> SEQUENCE: 350

Gly Tyr Ala Arg Ala Ala Ala Arg Gln Ala
 1               5                  10

<210> SEQ ID NO 351
<211> LENGTH: 35
<212> TYPE: DNA
<213> ORGANISM: Artificial Sequence
<220> FEATURE:
<223> OTHER INFORMATION: primer
```

```
<400> SEQUENCE: 351
caccggctat gcgcgcgcag cggctcgcca ggcgc                              35

<210> SEQ ID NO 352
<211> LENGTH: 7
<212> TYPE: PRT
<213> ORGANISM: Artificial Sequence
<220> FEATURE:
<223> OTHER INFORMATION: translated sequence

<400> SEQUENCE: 352

Ala Arg Gln Ala Arg Ala Gly
 1               5

<210> SEQ ID NO 353
<211> LENGTH: 38
<212> TYPE: DNA
<213> ORGANISM: Artificial Sequence
<220> FEATURE:
<223> OTHER INFORMATION: primer

<400> SEQUENCE: 353
gctcgccagg cgcgcgcagg cgccaggaaa ctactttc                           38

<210> SEQ ID NO 354
<211> LENGTH: 10
<212> TYPE: PRT
<213> ORGANISM: Artificial Sequence
<220> FEATURE:
<223> OTHER INFORMATION: translated sequence

<400> SEQUENCE: 354

Gly Arg Arg Gly Arg Arg Gly Arg Arg Gly
 1               5                  10

<210> SEQ ID NO 355
<211> LENGTH: 35
<212> TYPE: DNA
<213> ORGANISM: Artificial Sequence
<220> FEATURE:
<223> OTHER INFORMATION: primer

<400> SEQUENCE: 355
caccggccgc cggggtcggc gtggacgtcg cgggc                              35

<210> SEQ ID NO 356
<211> LENGTH: 7
<212> TYPE: PRT
<213> ORGANISM: Artificial Sequence
<220> FEATURE:
<223> OTHER INFORMATION: translated sequence

<400> SEQUENCE: 356

Gly Arg Arg Gly Arg Arg Gly
 1               5

<210> SEQ ID NO 357
<211> LENGTH: 38
<212> TYPE: DNA
<213> ORGANISM: Artificial Sequence
<220> FEATURE:
<223> OTHER INFORMATION: primer

<400> SEQUENCE: 357
ggacgtcgcg ggcggcgcgg cgccaggaaa ctactttc                           38
```

<210> SEQ ID NO 358
<211> LENGTH: 24
<212> TYPE: DNA
<213> ORGANISM: Artificial Sequence
<220> FEATURE:
<223> OTHER INFORMATION: primer

<400> SEQUENCE: 358
caccggcgcc aggaaactac tttc                                    24

<210> SEQ ID NO 359
<211> LENGTH: 18
<212> TYPE: DNA
<213> ORGANISM: Artificial Sequence
<220> FEATURE:
<223> OTHER INFORMATION: primer

<400> SEQUENCE: 359
ctaaaagtta aaggtccc                                           18

<210> SEQ ID NO 360
<211> LENGTH: 10
<212> TYPE: PRT
<213> ORGANISM: Artificial Sequence
<220> FEATURE:
<223> OTHER INFORMATION: translated sequence

<400> SEQUENCE: 360

Gly Tyr Gly Arg Lys Lys Arg Arg Gln Arg
 1               5                  10

<210> SEQ ID NO 361
<211> LENGTH: 36
<212> TYPE: DNA
<213> ORGANISM: Artificial Sequence
<220> FEATURE:
<223> OTHER INFORMATION: primer

<400> SEQUENCE: 361
caccggctat ggccgcaaga aacgtcgcca gcgtcg                       36

<210> SEQ ID NO 362
<211> LENGTH: 7
<212> TYPE: PRT
<213> ORGANISM: Artificial Sequence
<220> FEATURE:
<223> OTHER INFORMATION: translated sequence

<400> SEQUENCE: 362

Arg Arg Gln Arg Arg Arg Gly
 1               5

<210> SEQ ID NO 363
<211> LENGTH: 39
<212> TYPE: DNA
<213> ORGANISM: Artificial Sequence
<220> FEATURE:
<223> OTHER INFORMATION: primer

<400> SEQUENCE: 363
cgtcgccagc gtcgccgtgg cgcaagaaaa ctgttatcc                    39

<210> SEQ ID NO 364
<211> LENGTH: 10
<212> TYPE: PRT

<213> ORGANISM: Artificial Sequence
<220> FEATURE:
<223> OTHER INFORMATION: translated sequence

<400> SEQUENCE: 364

Gly Tyr Ala Arg Ala Ala Ala Arg Gln Ala
 1               5                  10

<210> SEQ ID NO 365
<211> LENGTH: 35
<212> TYPE: DNA
<213> ORGANISM: Artificial Sequence
<220> FEATURE:
<223> OTHER INFORMATION: primer

<400> SEQUENCE: 365
caccggctat gcgcgcgcag cggctcgcca ggcgc                           35

<210> SEQ ID NO 366
<211> LENGTH: 7
<212> TYPE: PRT
<213> ORGANISM: Artificial Sequence
<220> FEATURE:
<223> OTHER INFORMATION: translated sequence

<400> SEQUENCE: 366

Ala Arg Gln Ala Arg Ala Gly
 1               5

<210> SEQ ID NO 367
<211> LENGTH: 39
<212> TYPE: DNA
<213> ORGANISM: Artificial Sequence
<220> FEATURE:
<223> OTHER INFORMATION: primer

<400> SEQUENCE: 367
gctcgccagg cgcgcgcagg cgcaagaaaa ctgttatcc                       39

<210> SEQ ID NO 368
<211> LENGTH: 10
<212> TYPE: PRT
<213> ORGANISM: Artificial Sequence
<220> FEATURE:
<223> OTHER INFORMATION: translated sequence

<400> SEQUENCE: 368

Gly Arg Arg Gly Arg Arg Gly Arg Arg Gly
 1               5                  10

<210> SEQ ID NO 369
<211> LENGTH: 35
<212> TYPE: DNA
<213> ORGANISM: Artificial Sequence
<220> FEATURE:
<223> OTHER INFORMATION: primer

<400> SEQUENCE: 369
caccggccgc cggggtcggc gtggacgtcg cgggc                           35

<210> SEQ ID NO 370
<211> LENGTH: 7
<212> TYPE: PRT
<213> ORGANISM: Artificial Sequence
<220> FEATURE:
<223> OTHER INFORMATION: translated sequence -continued

```
<400> SEQUENCE: 370

Gly Arg Arg Gly Arg Arg Gly
  1               5

<210> SEQ ID NO 371
<211> LENGTH: 39
<212> TYPE: DNA
<213> ORGANISM: Artificial Sequence
<220> FEATURE:
<223> OTHER INFORMATION: primer

<400> SEQUENCE: 371
ggacgtcgcg ggcggcgcgg cgcaagaaaa ctgttatcc                    39

<210> SEQ ID NO 372
<211> LENGTH: 25
<212> TYPE: DNA
<213> ORGANISM: Artificial Sequence
<220> FEATURE:
<223> OTHER INFORMATION: primer

<400> SEQUENCE: 372
caccggcgca agaaaactgt tatcc                                   25

<210> SEQ ID NO 373
<211> LENGTH: 23
<212> TYPE: DNA
<213> ORGANISM: Artificial Sequence
<220> FEATURE:
<223> OTHER INFORMATION: primer

<400> SEQUENCE: 373
ttaaaaatta aattcttttg ttt                                     23

<210> SEQ ID NO 374
<211> LENGTH: 10
<212> TYPE: PRT
<213> ORGANISM: Artificial Sequence
<220> FEATURE:
<223> OTHER INFORMATION: tranlsated sequence

<400> SEQUENCE: 374

Gly Tyr Gly Arg Lys Lys Arg Arg Gln Arg
  1               5                  10

<210> SEQ ID NO 375
<211> LENGTH: 36
<212> TYPE: DNA
<213> ORGANISM: Artificial Sequence
<220> FEATURE:
<223> OTHER INFORMATION: primer

<400> SEQUENCE: 375
caccggctat ggccgcaaga aacgtcgcca gcgtcg                       36

<210> SEQ ID NO 376
<211> LENGTH: 7
<212> TYPE: PRT
<213> ORGANISM: Artificial Sequence
<220> FEATURE:
<223> OTHER INFORMATION: translated sequence

<400> SEQUENCE: 376

Arg Arg Gln Arg Arg Gly
  1               5
```

```
<210> SEQ ID NO 377
<211> LENGTH: 40
<212> TYPE: DNA
<213> ORGANISM: Artificial Sequence
<220> FEATURE:
<223> OTHER INFORMATION: primer

<400> SEQUENCE: 377
cgtcgccagc gtcgccgtgg ctttagaaag ctgctttcta                           40

<210> SEQ ID NO 378
<211> LENGTH: 10
<212> TYPE: PRT
<213> ORGANISM: Artificial Sequence
<220> FEATURE:
<223> OTHER INFORMATION: translated sequence

<400> SEQUENCE: 378

Gly Tyr Ala Arg Ala Ala Ala Arg Gln Ala
 1               5                  10

<210> SEQ ID NO 379
<211> LENGTH: 35
<212> TYPE: DNA
<213> ORGANISM: Artificial Sequence
<220> FEATURE:
<223> OTHER INFORMATION: primer

<400> SEQUENCE: 379
caccggctat gcgcgcgcag cggctcgcca ggcgc                                35

<210> SEQ ID NO 380
<211> LENGTH: 7
<212> TYPE: PRT
<213> ORGANISM: Artificial Sequence
<220> FEATURE:
<223> OTHER INFORMATION: translated sequence

<400> SEQUENCE: 380

Ala Arg Gln Ala Arg Ala Gly
 1               5

<210> SEQ ID NO 381
<211> LENGTH: 40
<212> TYPE: DNA
<213> ORGANISM: Artificial Sequence
<220> FEATURE:
<223> OTHER INFORMATION: primer

<400> SEQUENCE: 381
gctcgccagg cgcgcgcagg ctttagaaag ctgctttcta                           40

<210> SEQ ID NO 382
<211> LENGTH: 10
<212> TYPE: PRT
<213> ORGANISM: Artificial Sequence
<220> FEATURE:
<223> OTHER INFORMATION: translated sequence

<400> SEQUENCE: 382

Gly Arg Arg Gly Arg Arg Gly Arg Arg Gly
 1               5                  10

<210> SEQ ID NO 383
<211> LENGTH: 35
<212> TYPE: DNA
```

<210> SEQ ID NO 383
<211> LENGTH: 35
<212> TYPE: DNA
<213> ORGANISM: Artificial Sequence
<220> FEATURE:
<223> OTHER INFORMATION: primer

<400> SEQUENCE: 383
caccggccgc cggggtcggc gtggacgtcg cgggc                          35

<210> SEQ ID NO 384
<211> LENGTH: 7
<212> TYPE: PRT
<213> ORGANISM: Artificial Sequence
<220> FEATURE:
<223> OTHER INFORMATION: translated sequence

<400> SEQUENCE: 384

Gly Arg Arg Gly Arg Arg Gly
 1               5

<210> SEQ ID NO 385
<211> LENGTH: 40
<212> TYPE: DNA
<213> ORGANISM: Artificial Sequence
<220> FEATURE:
<223> OTHER INFORMATION: primer

<400> SEQUENCE: 385
ggacgtcgcg ggcggcgcgg ctttagaaag ctgctttcta                     40

<210> SEQ ID NO 386
<211> LENGTH: 26
<212> TYPE: DNA
<213> ORGANISM: Artificial Sequence
<220> FEATURE:
<223> OTHER INFORMATION: primer

<400> SEQUENCE: 386
caccggcttt agaaagctgc tttcta                                    26

<210> SEQ ID NO 387
<211> LENGTH: 19
<212> TYPE: DNA
<213> ORGANISM: Artificial Sequence
<220> FEATURE:
<223> OTHER INFORMATION: primer

<400> SEQUENCE: 387
ttaaagttga aatccatcc                                            19

<210> SEQ ID NO 388
<211> LENGTH: 10
<212> TYPE: PRT
<213> ORGANISM: Artificial Sequence
<220> FEATURE:
<223> OTHER INFORMATION: translated sequence

<400> SEQUENCE: 388

Gly Tyr Gly Arg Lys Lys Arg Arg Gln Arg
 1               5                  10

<210> SEQ ID NO 389
<211> LENGTH: 36
<212> TYPE: DNA
<213> ORGANISM: Artificial Sequence
<220> FEATURE:
<223> OTHER INFORMATION: primer

<400> SEQUENCE: 389

```
caccggctat ggccgcaaga aacgtcgcca gcgtcg                                    36
```

<210> SEQ ID NO 390
<211> LENGTH: 7
<212> TYPE: PRT
<213> ORGANISM: Artificial Sequence
<220> FEATURE:
<223> OTHER INFORMATION: translated sequence

<400> SEQUENCE: 390

Arg Arg Gln Arg Arg Arg Gly
 1               5

<210> SEQ ID NO 391
<211> LENGTH: 39
<212> TYPE: DNA
<213> ORGANISM: Artificial Sequence
<220> FEATURE:
<223> OTHER INFORMATION: primer

<400> SEQUENCE: 391

```
cgtcgccagc gtcgccgtgg catgaacccc atcgtaatt                                 39
```

<210> SEQ ID NO 392
<211> LENGTH: 10
<212> TYPE: PRT
<213> ORGANISM: Artificial Sequence
<220> FEATURE:
<223> OTHER INFORMATION: translated sequence

<400> SEQUENCE: 392

Gly Tyr Ala Arg Ala Ala Ala Arg Gln Ala
 1               5                  10

<210> SEQ ID NO 393
<211> LENGTH: 35
<212> TYPE: DNA
<213> ORGANISM: Artificial Sequence
<220> FEATURE:
<223> OTHER INFORMATION: primer

<400> SEQUENCE: 393

```
caccggctat gcgcgcgcag cggctcgcca ggcgc                                     35
```

<210> SEQ ID NO 394
<211> LENGTH: 7
<212> TYPE: PRT
<213> ORGANISM: Artificial Sequence
<220> FEATURE:
<223> OTHER INFORMATION: translated sequence

<400> SEQUENCE: 394

Ala Arg Gln Ala Arg Ala Gly
 1               5

<210> SEQ ID NO 395
<211> LENGTH: 39
<212> TYPE: DNA
<213> ORGANISM: Artificial Sequence
<220> FEATURE:
<223> OTHER INFORMATION: primer

<400> SEQUENCE: 395

```
gctcgccagg cgcgcgcagg catgaacccc atcgtaatt                                 39
```

```
<210> SEQ ID NO 396
<211> LENGTH: 10
<212> TYPE: PRT
<213> ORGANISM: Artificial Sequence
<220> FEATURE:
<223> OTHER INFORMATION: translated sequence

<400> SEQUENCE: 396

Gly Arg Arg Gly Arg Arg Gly Arg Arg Gly
 1               5                  10

<210> SEQ ID NO 397
<211> LENGTH: 35
<212> TYPE: DNA
<213> ORGANISM: Artificial Sequence
<220> FEATURE:
<223> OTHER INFORMATION: primer

<400> SEQUENCE: 397
caccggccgc cggggtcggc gtggacgtcg cgggc                                35

<210> SEQ ID NO 398
<211> LENGTH: 7
<212> TYPE: PRT
<213> ORGANISM: Artificial Sequence
<220> FEATURE:
<223> OTHER INFORMATION: translated sequence

<400> SEQUENCE: 398

Gly Arg Arg Gly Arg Arg Gly
 1               5

<210> SEQ ID NO 399
<211> LENGTH: 39
<212> TYPE: DNA
<213> ORGANISM: Artificial Sequence
<220> FEATURE:
<223> OTHER INFORMATION: primer

<400> SEQUENCE: 399
ggacgtcgcg ggcggcgcgg catgaacccc atcgtaatt                            39

<210> SEQ ID NO 400
<211> LENGTH: 25
<212> TYPE: DNA
<213> ORGANISM: Artificial Sequence
<220> FEATURE:
<223> OTHER INFORMATION: primer

<400> SEQUENCE: 400
caccggcatg aacccatcg taatt                                            25

<210> SEQ ID NO 401
<211> LENGTH: 17
<212> TYPE: DNA
<213> ORGANISM: Artificial Sequence
<220> FEATURE:
<223> OTHER INFORMATION: primer

<400> SEQUENCE: 401
tcattccagc tccagtt                                                    17

<210> SEQ ID NO 402
<211> LENGTH: 10
<212> TYPE: PRT
<213> ORGANISM: Artificial Sequence
<220> FEATURE:
```

<223> OTHER INFORMATION: translated sequence

<400> SEQUENCE: 402

Gly Tyr Gly Arg Lys Lys Arg Arg Gln Arg
 1               5                  10

<210> SEQ ID NO 403
<211> LENGTH: 36
<212> TYPE: DNA
<213> ORGANISM: Artificial Sequence
<220> FEATURE:
<223> OTHER INFORMATION: primer

<400> SEQUENCE: 403
caccggctat ggccgcaaga aacgtcgcca gcgtcg                                36

<210> SEQ ID NO 404
<211> LENGTH: 7
<212> TYPE: PRT
<213> ORGANISM: Artificial Sequence
<220> FEATURE:
<223> OTHER INFORMATION: translated sequence

<400> SEQUENCE: 404

Arg Arg Gln Arg Arg Gly
 1               5

<210> SEQ ID NO 405
<211> LENGTH: 40
<212> TYPE: DNA
<213> ORGANISM: Artificial Sequence
<220> FEATURE:
<223> OTHER INFORMATION: primer

<400> SEQUENCE: 405
cgtcgccagc gtcgccgtgg catgacaaat cttgatactg                            40

<210> SEQ ID NO 406
<211> LENGTH: 10
<212> TYPE: PRT
<213> ORGANISM: Artificial Sequence
<220> FEATURE:
<223> OTHER INFORMATION: translated sequence

<400> SEQUENCE: 406

Gly Tyr Ala Arg Ala Ala Ala Arg Gln Ala
 1               5                  10

<210> SEQ ID NO 407
<211> LENGTH: 35
<212> TYPE: DNA
<213> ORGANISM: Artificial Sequence
<220> FEATURE:
<223> OTHER INFORMATION: primer

<400> SEQUENCE: 407
caccggctat gcgcgcgcag cggctcgcca ggcgc                                 35

<210> SEQ ID NO 408
<211> LENGTH: 7
<212> TYPE: PRT
<213> ORGANISM: Artificial Sequence
<220> FEATURE:
<223> OTHER INFORMATION: translated sequence

<400> SEQUENCE: 408

Ala Arg Gln Ala Arg Ala Gly
1               5

<210> SEQ ID NO 409
<211> LENGTH: 40
<212> TYPE: DNA
<213> ORGANISM: Artificial Sequence
<220> FEATURE:
<223> OTHER INFORMATION: primer

<400> SEQUENCE: 409
gctcgccagg cgcgcgcagg catgacaaat cttgatactg                40

<210> SEQ ID NO 410
<211> LENGTH: 10
<212> TYPE: PRT
<213> ORGANISM: Artificial Sequence
<220> FEATURE:
<223> OTHER INFORMATION: translated sequence

<400> SEQUENCE: 410

Gly Arg Arg Gly Arg Arg Gly Arg Arg Gly
1               5                   10

<210> SEQ ID NO 411
<211> LENGTH: 35
<212> TYPE: DNA
<213> ORGANISM: Artificial Sequence
<220> FEATURE:
<223> OTHER INFORMATION: primer

<400> SEQUENCE: 411
caccggccgc cggggtcggc gtggacgtcg cgggc                35

<210> SEQ ID NO 412
<211> LENGTH: 7
<212> TYPE: PRT
<213> ORGANISM: Artificial Sequence
<220> FEATURE:
<223> OTHER INFORMATION: translated sequence

<400> SEQUENCE: 412

Gly Arg Arg Gly Arg Arg Gly
1               5

<210> SEQ ID NO 413
<211> LENGTH: 40
<212> TYPE: DNA
<213> ORGANISM: Artificial Sequence
<220> FEATURE:
<223> OTHER INFORMATION: primer

<400> SEQUENCE: 413
ggacgtcgcg ggcggcgcgg catgacaaat cttgatactg                40

<210> SEQ ID NO 414
<211> LENGTH: 26
<212> TYPE: DNA
<213> ORGANISM: Artificial Sequence
<220> FEATURE:
<223> OTHER INFORMATION: primer

<400> SEQUENCE: 414
caccggcatg acaaatcttg atactg                26

<210> SEQ ID NO 415

```
<211> LENGTH: 20
<212> TYPE: DNA
<213> ORGANISM: Artificial Sequence
<220> FEATURE:
<223> OTHER INFORMATION: primer

<400> SEQUENCE: 415
ttatgtaatt aaaaagcgtg                                                  20

<210> SEQ ID NO 416
<211> LENGTH: 10
<212> TYPE: PRT
<213> ORGANISM: Artificial Sequence
<220> FEATURE:
<223> OTHER INFORMATION: translated sequence

<400> SEQUENCE: 416

Gly Tyr Gly Arg Lys Lys Arg Arg Gln Arg
1               5                   10

<210> SEQ ID NO 417
<211> LENGTH: 36
<212> TYPE: DNA
<213> ORGANISM: Artificial Sequence
<220> FEATURE:
<223> OTHER INFORMATION: primer

<400> SEQUENCE: 417
caccggctat ggccgcaaga aacgtcgcca gcgtcg                                36

<210> SEQ ID NO 418
<211> LENGTH: 7
<212> TYPE: PRT
<213> ORGANISM: Artificial Sequence
<220> FEATURE:
<223> OTHER INFORMATION: translated sequence

<400> SEQUENCE: 418

Arg Arg Gln Arg Arg Arg Gly
1               5

<210> SEQ ID NO 419
<211> LENGTH: 39
<212> TYPE: DNA
<213> ORGANISM: Artificial Sequence
<220> FEATURE:
<223> OTHER INFORMATION: primer

<400> SEQUENCE: 419
cgtcgccagc gtcgccgtgg catgctggca gttttaaaa                             39

<210> SEQ ID NO 420
<211> LENGTH: 10
<212> TYPE: PRT
<213> ORGANISM: Artificial Sequence
<220> FEATURE:
<223> OTHER INFORMATION: translated sequence

<400> SEQUENCE: 420

Gly Tyr Ala Arg Ala Ala Ala Arg Gln Ala
1               5                   10

<210> SEQ ID NO 421
<211> LENGTH: 35
<212> TYPE: DNA
<213> ORGANISM: Artificial Sequence
<220> FEATURE:
```

<223> OTHER INFORMATION: primer

<400> SEQUENCE: 421
caccggctat gcgcgcgcag cggctcgcca ggcgc               35

<210> SEQ ID NO 422
<211> LENGTH: 7
<212> TYPE: PRT
<213> ORGANISM: Artificial Sequence
<220> FEATURE:
<223> OTHER INFORMATION: translated sequence

<400> SEQUENCE: 422

Ala Arg Gln Ala Arg Ala Gly
 1               5

<210> SEQ ID NO 423
<211> LENGTH: 39
<212> TYPE: DNA
<213> ORGANISM: Artificial Sequence
<220> FEATURE:
<223> OTHER INFORMATION: primer

<400> SEQUENCE: 423
gctcgccagg cgcgcgcagg catgctggca gttttaaaa           39

<210> SEQ ID NO 424
<211> LENGTH: 10
<212> TYPE: PRT
<213> ORGANISM: Artificial Sequence
<220> FEATURE:
<223> OTHER INFORMATION: translated sequence

<400> SEQUENCE: 424

Gly Arg Arg Gly Arg Arg Gly Arg Arg Gly
 1               5                  10

<210> SEQ ID NO 425
<211> LENGTH: 35
<212> TYPE: DNA
<213> ORGANISM: Artificial Sequence
<220> FEATURE:
<223> OTHER INFORMATION: primer

<400> SEQUENCE: 425
caccggccgc cggggtcggc gtggacgtcg cgggc               35

<210> SEQ ID NO 426
<211> LENGTH: 7
<212> TYPE: PRT
<213> ORGANISM: Artificial Sequence
<220> FEATURE:
<223> OTHER INFORMATION: translated sequence

<400> SEQUENCE: 426

Gly Arg Arg Gly Arg Arg Gly
 1               5

<210> SEQ ID NO 427
<211> LENGTH: 39
<212> TYPE: DNA
<213> ORGANISM: Artificial Sequence
<220> FEATURE:
<223> OTHER INFORMATION: primer

<400> SEQUENCE: 427

-continued

```
ggacgtcgcg ggcggcgcgg catgctggca gttttaaaa                                  39

<210> SEQ ID NO 428
<211> LENGTH: 25
<212> TYPE: DNA
<213> ORGANISM: Artificial Sequence
<220> FEATURE:
<223> OTHER INFORMATION: primer

<400> SEQUENCE: 428
caccggcatg ctggcagttt taaaa                                                 25

<210> SEQ ID NO 429
<211> LENGTH: 17
<212> TYPE: DNA
<213> ORGANISM: Artificial Sequence
<220> FEATURE:
<223> OTHER INFORMATION: primer

<400> SEQUENCE: 429 ttataccca cccgaat                                                           17

<210> SEQ ID NO 430
<211> LENGTH: 10
<212> TYPE: PRT
<213> ORGANISM: Artificial Sequence
<220> FEATURE:
<223> OTHER INFORMATION: translated sequence

<400> SEQUENCE: 430

Gly Tyr Gly Arg Lys Lys Arg Arg Gln Arg
 1               5                  10

<210> SEQ ID NO 431
<211> LENGTH: 36
<212> TYPE: DNA
<213> ORGANISM: Artificial Sequence
<220> FEATURE:
<223> OTHER INFORMATION: primer

<400> SEQUENCE: 431
caccggctat ggccgcaaga aacgtcgcca gcgtcg                                     36

<210> SEQ ID NO 432
<211> LENGTH: 7
<212> TYPE: PRT
<213> ORGANISM: Artificial Sequence
<220> FEATURE:
<223> OTHER INFORMATION: translated sequence

<400> SEQUENCE: 432

Arg Arg Gln Arg Arg Arg Gly
 1               5

<210> SEQ ID NO 433
<211> LENGTH: 39
<212> TYPE: DNA
<213> ORGANISM: Artificial Sequence
<220> FEATURE:
<223> OTHER INFORMATION: primer

<400> SEQUENCE: 433
cgtcgccagc gtcgccgtgg catgggtaaa gattactac                                  39

<210> SEQ ID NO 434
<211> LENGTH: 10
```

<212> TYPE: PRT
<213> ORGANISM: Artificial Sequence
<220> FEATURE:
<223> OTHER INFORMATION: translated sequence

<400> SEQUENCE: 434

Gly Tyr Ala Arg Ala Ala Ala Arg Gln Ala
1               5                   10

<210> SEQ ID NO 435
<211> LENGTH: 35
<212> TYPE: DNA
<213> ORGANISM: Artificial Sequence
<220> FEATURE:
<223> OTHER INFORMATION: primer

<400> SEQUENCE: 435
caccggctat gcgcgcgcag cggctcgcca ggcgc                              35

<210> SEQ ID NO 436
<211> LENGTH: 7
<212> TYPE: PRT
<213> ORGANISM: Artificial Sequence
<220> FEATURE:
<223> OTHER INFORMATION: translated sequence

<400> SEQUENCE: 436

Ala Arg Gln Ala Arg Ala Gly
1               5

<210> SEQ ID NO 437
<211> LENGTH: 39
<212> TYPE: DNA
<213> ORGANISM: Artificial Sequence
<220> FEATURE:
<223> OTHER INFORMATION: primer

<400> SEQUENCE: 437
gctcgccagg cgcgcgcagg catgggtaaa gattactac                          39

<210> SEQ ID NO 438
<211> LENGTH: 10
<212> TYPE: PRT
<213> ORGANISM: Artificial Sequence
<220> FEATURE:
<223> OTHER INFORMATION: translated sequence

<400> SEQUENCE: 438

Gly Arg Arg Gly Arg Arg Gly Arg Arg Gly
1               5                   10

<210> SEQ ID NO 439
<211> LENGTH: 35
<212> TYPE: DNA
<213> ORGANISM: Artificial Sequence
<220> FEATURE:
<223> OTHER INFORMATION: primer

<400> SEQUENCE: 439
caccggccgc cggggtcggc gtggacgtcg cgggc                              35

<210> SEQ ID NO 440
<211> LENGTH: 7
<212> TYPE: PRT
<213> ORGANISM: Artificial Sequence
<220> FEATURE:
<223> OTHER INFORMATION: translated sequence -continued

<400> SEQUENCE: 440

Gly Arg Arg Gly Arg Arg Gly
1               5

<210> SEQ ID NO 441
<211> LENGTH: 39
<212> TYPE: DNA
<213> ORGANISM: Artificial Sequence
<220> FEATURE:
<223> OTHER INFORMATION: primer

<400> SEQUENCE: 441
ggacgtcgcg ggcggcgcgg catgggtaaa gattactac                      39

<210> SEQ ID NO 442
<211> LENGTH: 25
<212> TYPE: DNA
<213> ORGANISM: Artificial Sequence
<220> FEATURE:
<223> OTHER INFORMATION: primer

<400> SEQUENCE: 442
caccggcatg ggtaaagatt actac                                     25

<210> SEQ ID NO 443
<211> LENGTH: 18
<212> TYPE: DNA
<213> ORGANISM: Artificial Sequence
<220> FEATURE:
<223> OTHER INFORMATION: primer

<400> SEQUENCE: 443
ctatattgga agaacctg                                             18

<210> SEQ ID NO 444
<211> LENGTH: 10
<212> TYPE: PRT
<213> ORGANISM: Artificial Sequence
<220> FEATURE:
<223> OTHER INFORMATION: translated sequence

<400> SEQUENCE: 444

Gly Tyr Gly Arg Lys Lys Arg Arg Gln Arg
1               5                   10

<210> SEQ ID NO 445
<211> LENGTH: 36
<212> TYPE: DNA
<213> ORGANISM: Artificial Sequence
<220> FEATURE:
<223> OTHER INFORMATION: primer

<400> SEQUENCE: 445
caccggctat ggccgcaaga aacgtcgcca gcgtcg                         36

<210> SEQ ID NO 446
<211> LENGTH: 7
<212> TYPE: PRT
<213> ORGANISM: Artificial Sequence
<220> FEATURE:
<223> OTHER INFORMATION: translated sequence

<400> SEQUENCE: 446

Arg Arg Gln Arg Arg Arg Gly
1               5

<210> SEQ ID NO 447
<211> LENGTH: 36
<212> TYPE: DNA
<213> ORGANISM: Artificial Sequence
<220> FEATURE:
<223> OTHER INFORMATION: primer

<400> SEQUENCE: 447
cgtcgccagc gtcgccgtgg catggccaaa gccgcg                                 36

<210> SEQ ID NO 448
<211> LENGTH: 10
<212> TYPE: PRT
<213> ORGANISM: Artificial Sequence
<220> FEATURE:
<223> OTHER INFORMATION: translated sequence

<400> SEQUENCE: 448

Gly Tyr Ala Arg Ala Ala Ala Arg Gln Ala
 1               5                  10

<210> SEQ ID NO 449
<211> LENGTH: 35
<212> TYPE: DNA
<213> ORGANISM: Artificial Sequence
<220> FEATURE:
<223> OTHER INFORMATION: primer

<400> SEQUENCE: 449
caccggctat gcgcgcgcag cggctcgcca ggcgc                                  35

<210> SEQ ID NO 450
<211> LENGTH: 7
<212> TYPE: PRT
<213> ORGANISM: Artificial Sequence
<220> FEATURE:
<223> OTHER INFORMATION: translated sequence

<400> SEQUENCE: 450

Ala Arg Gln Ala Arg Ala Gly
 1               5

<210> SEQ ID NO 451
<211> LENGTH: 36
<212> TYPE: DNA
<213> ORGANISM: Artificial Sequence
<220> FEATURE:
<223> OTHER INFORMATION: primer

<400> SEQUENCE: 451
gctcgccagg cgcgcgcagg catggccaaa gccgcg                                 36

<210> SEQ ID NO 452
<211> LENGTH: 10
<212> TYPE: PRT
<213> ORGANISM: Artificial Sequence
<220> FEATURE:
<223> OTHER INFORMATION: translated sequence

<400> SEQUENCE: 452

Gly Arg Arg Gly Arg Arg Gly Arg Arg Gly
 1               5                  10

<210> SEQ ID NO 453
<211> LENGTH: 35

```
<212> TYPE: DNA
<213> ORGANISM: Artificial Sequence
<220> FEATURE:
<223> OTHER INFORMATION: primer

<400> SEQUENCE: 453
caccggccgc cggggtcggc gtggacgtcg cgggc                                    35

<210> SEQ ID NO 454
<211> LENGTH: 7
<212> TYPE: PRT
<213> ORGANISM: Artificial Sequence
<220> FEATURE:
<223> OTHER INFORMATION: translated sequence

<400> SEQUENCE: 454

Gly Arg Arg Gly Arg Arg Gly
 1               5

<210> SEQ ID NO 455
<211> LENGTH: 36
<212> TYPE: DNA
<213> ORGANISM: Artificial Sequence
<220> FEATURE:
<223> OTHER INFORMATION: primer

<400> SEQUENCE: 455
ggacgtcgcg ggcggcgcgg catggccaaa gccgcg                                   36

<210> SEQ ID NO 456
<211> LENGTH: 22
<212> TYPE: DNA
<213> ORGANISM: Artificial Sequence
<220> FEATURE:
<223> OTHER INFORMATION: primer

<400> SEQUENCE: 456
caccggcatg gccaaagccg cg                                                  22

<210> SEQ ID NO 457
<211> LENGTH: 18
<212> TYPE: DNA
<213> ORGANISM: Artificial Sequence
<220> FEATURE:
<223> OTHER INFORMATION: primer

<400> SEQUENCE: 457
ctaatctacc tcctcaat                                                       18

<210> SEQ ID NO 458
<211> LENGTH: 10
<212> TYPE: PRT
<213> ORGANISM: Artificial Sequence
<220> FEATURE:
<223> OTHER INFORMATION: translated sequence

<400> SEQUENCE: 458

Gly Tyr Gly Arg Lys Lys Arg Arg Gln Arg
 1               5                  10

<210> SEQ ID NO 459
<211> LENGTH: 36
<212> TYPE: DNA
<213> ORGANISM: Artificial Sequence
<220> FEATURE:
<223> OTHER INFORMATION: primer
```

```
<400> SEQUENCE: 459
caccggctat ggccgcaaga aacgtcgcca gcgtcg                                    36

<210> SEQ ID NO 460
<211> LENGTH: 7
<212> TYPE: PRT
<213> ORGANISM: Artificial Sequence
<220> FEATURE:
<223> OTHER INFORMATION: translated sequence

<400> SEQUENCE: 460

Arg Arg Gln Arg Arg Arg Gly
 1               5

<210> SEQ ID NO 461
<211> LENGTH: 37
<212> TYPE: DNA
<213> ORGANISM: Artificial Sequence
<220> FEATURE:
<223> OTHER INFORMATION: primer

<400> SEQUENCE: 461
cgtcgccagc gtcgccgtgg catgcctgag gaagtgc                                   37

<210> SEQ ID NO 462
<211> LENGTH: 10
<212> TYPE: PRT
<213> ORGANISM: Artificial Sequence
<220> FEATURE:
<223> OTHER INFORMATION: translated sequence

<400> SEQUENCE: 462

Gly Tyr Ala Arg Ala Ala Ala Arg Gln Ala
 1               5                  10

<210> SEQ ID NO 463
<211> LENGTH: 35
<212> TYPE: DNA
<213> ORGANISM: Artificial Sequence
<220> FEATURE:
<223> OTHER INFORMATION: primer

<400> SEQUENCE: 463
caccggctat gcgcgcgcag cggctcgcca ggcgc                                     35

<210> SEQ ID NO 464
<211> LENGTH: 7
<212> TYPE: PRT
<213> ORGANISM: Artificial Sequence
<220> FEATURE:
<223> OTHER INFORMATION: translated sequence

<400> SEQUENCE: 464

Ala Arg Gln Ala Arg Ala Gly
 1               5

<210> SEQ ID NO 465
<211> LENGTH: 37
<212> TYPE: DNA
<213> ORGANISM: Artificial Sequence
<220> FEATURE:
<223> OTHER INFORMATION: primer

<400> SEQUENCE: 465
gctcgccagg cgcgcgcagg catgcctgag gaagtgc                                   37
```

<210> SEQ ID NO 466
<211> LENGTH: 10
<212> TYPE: PRT
<213> ORGANISM: Artificial Sequence
<220> FEATURE:
<223> OTHER INFORMATION: translated sequence

<400> SEQUENCE: 466

Gly Arg Arg Gly Arg Arg Gly Arg Arg Gly
1               5                   10

<210> SEQ ID NO 467
<211> LENGTH: 35
<212> TYPE: DNA
<213> ORGANISM: Artificial Sequence
<220> FEATURE:
<223> OTHER INFORMATION: primer

<400> SEQUENCE: 467
caccggccgc cggggtcggc gtggacgtcg cgggc                          35

<210> SEQ ID NO 468
<211> LENGTH: 7
<212> TYPE: PRT
<213> ORGANISM: Artificial Sequence
<220> FEATURE:
<223> OTHER INFORMATION: translated sequence

<400> SEQUENCE: 468

Gly Arg Arg Gly Arg Arg Gly
1               5

<210> SEQ ID NO 469
<211> LENGTH: 37
<212> TYPE: DNA
<213> ORGANISM: Artificial Sequence
<220> FEATURE:
<223> OTHER INFORMATION: primer

<400> SEQUENCE: 469
ggacgtcgcg ggcggcgcgg catgcctgag gaagtgc                        37

<210> SEQ ID NO 470
<211> LENGTH: 23
<212> TYPE: DNA
<213> ORGANISM: Artificial Sequence
<220> FEATURE:
<223> OTHER INFORMATION: primer

<400> SEQUENCE: 470
caccggcatg cctgaggaag tgc                                       23

<210> SEQ ID NO 471
<211> LENGTH: 18
<212> TYPE: DNA
<213> ORGANISM: Artificial Sequence
<220> FEATURE:
<223> OTHER INFORMATION: primer

<400> SEQUENCE: 471
ctaatcgact tcttccat                                             18

<210> SEQ ID NO 472
<211> LENGTH: 11
<212> TYPE: PRT
<213> ORGANISM: Artificial Sequence

```
-continued

<220> FEATURE:
<223> OTHER INFORMATION: peptide

<400> SEQUENCE: 472

Arg Arg Ala Asp Asp Ser Asp Asp Asp Asp
 1               5                   10

<210> SEQ ID NO 473
<211> LENGTH: 12
<212> TYPE: PRT
<213> ORGANISM: Artificial Sequence
<220> FEATURE:
<223> OTHER INFORMATION: peptide

<400> SEQUENCE: 473

Ala Ala Val Leu Leu Pro Val Leu Leu Ala Ala Pro
 1               5                   10
```

ANTI-PATHOGEN TREATMENTS

RELATED APPLICATIONS

This application is a Divisional of U.S. application Ser. No. 10/361,208, filed on Feb. 7, 2003, now U.S. Pat. No. 7,125, 839, issued Oct. 24, 2006, which claims the benefit of U.S. Provisional Application No. 60/355,359, filed Feb. 7, 2002, U.S. Provisional Application No. 60/355,022, filed Feb. 7, 2002, and U.S. Provisional Application No. 60/432,386, filed Dec. 10, 2002.

The entire teachings of the above applications are incorporated herein by reference.

GOVERNMENT SUPPORT

The invention was supported, in whole or in part, by contract number F19628-00-C-0002 from the United States Air Force. The Government has certain rights in the invention.

BACKGROUND OF THE INVENTION

Many pathogens have the ability to evade the natural defenses of an infected host cell or organism. Consequently, the infected host develops the disease or disorder which is associated with that pathogen.

Treatments for pathogenic infections typically target a distinguishing feature or characteristic of a specific pathogen. For example, acyclovir targets the replication stage of herpesvirus infection, zidovudine/AZT targets the reverse transcriptase of human immunodeficiency virus (HIV), and various protease inhibitors target HIV protease. Generally, however, these therapies have many disadvantages, including limited usefulness for only a specific pathogen, ineffectiveness due to pathogen variation, and toxic side effects. In addition, many of these therapies tend to be slow to develop.

A need exists therefore, for the development of anti-pathogen therapies that are effective for a broad spectrum of pathogens and which overcome disadvantages of existing therapies.

SUMMARY OF THE INVENTION

The present invention relates to an agent, such as a chimeric molecule, or components thereof, which are capable of being assembled together to form said chimeric molecule or agent, as described herein. The chimeric molecule or agent of the invention has at least one pathogen-detection domain (or a pathogen-recognition domain), or molecular structure that is capable of specifically interacting with a pathogen, pathogen component, pathogen product or pathogen-induced product, and/or at least one effector domain, or molecular structure capable of eliciting a desired effector function, these domains or molecular structures not being typically associated or bound together in nature. This invention also relates to the use of this agent for the treatment or prevention of a pathogen infection in a cell or an organism.

In one embodiment, a method for treating or preventing a pathogen infection in a cell includes administering to a cell chimeric molecules having at least one pathogen-detection domain and at least one effector domain, such pathogen-detection domain and effector domain being not normally bound to each other, and wherein in the presence of a pathogen in the cell, the chimeric molecules bind to the pathogen, pathogen component or pathogen product, and activate the effector domain, thus treating or preventing the pathogen infection in the cell.

In another embodiment, a method for treating or preventing a pathogen infection in a cell includes administering to a cell chimeric molecules having at least one pathogen-induced product-detection domain and at least one effector domain, such pathogen-induced product-detection domain and effector domain being not normally bound to each other, and wherein in the presence of a pathogen-induced product in a cell, the chimeric molecules bind to the pathogen-induced product and activate the effector domain, thus treating or preventing the pathogen infection in the cell.

In a further embodiment, a method for treating or preventing the spread of a pathogen infection in an organism, includes administering to the organism, chimeric molecules having at least one pathogen-detection domain and at least one effector domain, such pathogen-detection domain and effector domain being not normally bound to each other, and wherein in the presence of a pathogen in the organism, the chimeric molecules bind to the pathogen, pathogen component or pathogen product, and activate the effector domain, thus treating or preventing the spread of the pathogen infection in the organism.

In a still further embodiment, a method for treating or preventing the spread of a pathogen infection in an organism, includes administering to the organism, chimeric molecules having at least one pathogen-induced product-detection domain and at least one effector domain, such pathogen-induced product-detection domain and effector domain being not normally bound to each other, and wherein in the presence of a pathogen-induced product in the organism, the chimeric molecules bind to the pathogen-induced product and activate the effector domain, thus treating or preventing the spread of the pathogen infection in the organism.

In another embodiment of the invention, a method of treating or preventing a pathogen infection in a cell includes administering to a cell an agent having at least one pathogen-interacting molecular structure and at least one effector-mediating molecular structure, such pathogen-interacting molecular structure and effector-mediating molecular structure being a non-naturally occurring agent in a cell, and wherein in the presence of a pathogen in a cell, the agent binds to the pathogen, pathogen component or pathogen product, and activates the effector-mediating molecular structure, thus treating or preventing the pathogen infection in the cell.

In still another embodiment of the invention, a method of treating or preventing a pathogen infection in a cell includes administering to a cell an agent having at least one pathogen-induced product-interacting molecular structure and at least one effector-mediating molecular structure, such pathogen-induced product-interacting molecular structure and effector-mediating molecular structure being a non-naturally occurring agent in a cell, and wherein in the presence of a pathogen-induced product in a cell, the agent binds to the pathogen-induced product and activates the effector-mediating molecular structure, thus treating or preventing the pathogen infection in the cell.

In a further embodiment, a method for treating or preventing the spread of a pathogen infection in an organism, includes administering to the organism an agent having at least one pathogen-interacting molecular structure and at least one effector-mediating molecular structure, such pathogen-interacting molecular structure and effector-mediating molecular structure being a non-naturally occurring agent in a cell, and wherein in the presence of a pathogen in the organism, the agent binds to the pathogen, pathogen component or pathogen product, and activates the effector-mediating molecular structure, thus treating or preventing the spread of the pathogen infection in the organism.

In another embodiment, a method for treating or preventing the spread of a pathogen infection in an organism, includes administering to the organism an agent having at least one pathogen-induced product-interacting molecular structure and at least one effector-mediating molecular structure, such pathogen-induced product-interacting molecular structure and effector-mediating molecular structure being a non-naturally occurring agent in a cell, and wherein in the presence of a pathogen in the organism, the agent binds to the pathogen-induced product and activates the effector-mediating molecular structure, thus treating or preventing the spread of the pathogen infection in the organism.

In yet another embodiment of the invention, a method of treating or preventing a pathogen infection in a cell includes administering to the cell individual components of a chimeric molecule, such components being assembled together to form a chimeric molecule having at least one pathogen-detection domain and at least one effector domain, such pathogen-detection domain and effector domain being not normally bound to each other, and wherein in the presence of a pathogen, pathogen component or pathogen product in the cell, the chimeric molecules bind to the pathogen, pathogen component or pathogen product in the cell, and activate the effector domain, thus treating or preventing the pathogen infection in the cell.

In another embodiment of the invention, a method of treating or preventing a pathogen infection in a cell includes administering to the cell individual components of a chimeric molecule, such components being assembled together to form a chimeric molecule having at least one pathogen-induced product-detection domain and at least one effector domain, such pathogen-induced product-detection domain and effector domain being not normally bound to each other, and wherein in the presence of a pathogen-induced product in a cell, the chimeric molecules bind to the pathogen-induced product and activate the effector domain, thus treating or preventing the pathogen infection in the cell.

In still another embodiment of the invention, a method of treating or preventing a pathogen infection in an organism includes administering to the organism individual components of a chimeric molecule, such components being assembled together to form a chimeric molecule having at least one pathogen-detection domain and at least one effector domain, such pathogen-detection domain and effector domain being not normally bound to each other, and wherein in the presence of a pathogen in the organism, the chimeric molecules bind to the pathogen, pathogen component or pathogen product, and activate the effector domain, thus treating or preventing the spread of the pathogen infection in the organism.

In another embodiment of the invention, a method of treating or preventing a pathogen infection in an organism includes administering to the organism individual components of a chimeric molecule, such components being assembled together to form a chimeric molecule having at least one pathogen-induced product-detection domain and at least one effector domain, such pathogen-induced product-detection domain and effector domain being not normally bound to each other, and wherein in the presence of a pathogen-induced product in the organism, the chimeric molecules bind to the pathogen-induced product and activate the effector domain, thus treating or preventing the spread of the pathogen infection in the organism.

In a further embodiment of the invention, a chimeric molecule is provided which has at least one pathogen-detection domain and at least one effector domain, such pathogen-detection domain and effector domain being one that is non-naturally-occurring in a cell.

In a still further embodiment of the invention, a chimeric molecule is provided which has at least one pathogen-induced product-detection domain and at least one effector domain, such pathogen-induced product-detection domain and effector domain being one that is non-naturally-occurring in a cell.

In yet another embodiment of the invention, an agent is provided which has at least one pathogen-interacting molecular structure and at least one effector-mediating molecular structure, such agent being one that is non-naturally-occurring in a cell.

In a further embodiment of the invention, an agent is provided which has at least one pathogen-induced product-interacting molecular structure and at least one effector-mediating molecular structure, such agent being one that is non-naturally-occurring in a cell.

In another embodiment of the invention, an assay for the detection of a pathogen infection in a cell includes culturing the cell in a suitable cell culture medium and administering to the cell chimeric molecules having at least one pathogen-detection domain and at least one effector domain, such chimeric molecule being one that is non-naturally-occurring in a cell, wherein in the presence of a pathogen, pathogen component or pathogen product in the cell, the chimeric molecules bind to the pathogen, pathogen component or pathogen product, and activate the effector domain, thus determining the presence or absence of apoptosis in the cell indicates the presence or absence of a pathogen infection in the cell.

In yet another embodiment of the invention, an assay for the detection of a pathogen infection in an organism includes obtaining a cell or cells from the organism and culturing the cell(s) in a suitable cell culture medium and administering to the cell(s) chimeric molecules having at least pathogen-detection domain and at least one effector domain, such chimeric molecule being one that is non-naturally-occurring in a cell, wherein in the presence of a pathogen, pathogen component or pathogen product, chimeric molecules bind to the pathogen, pathogen component or pathogen product, and activate the effector domain. Thus, determining the presence or absence of apoptosis in the cell isolated from the organism indicates the presence or absence of a pathogen infection in the organism.

In a still further embodiment of the invention, an assay for the detection of a pathogen infection in an organism, includes obtaining a sample from the organism and adding the sample to an uninfected cell, then culturing this cell in a suitable cell culture medium and administering to that cell chimeric molecules having at least one pathogen-detection domain and at least one effector domain, such chimeric molecules are non-naturally-occurring in a cell, wherein in the presence of a pathogen, pathogen component or pathogen product, the chimeric molecules bind to the pathogen, pathogen component or pathogen product, and activate the effector domain. Thus, determining the presence or absence of effector domain activation indicates the presence or absence of a pathogen infection in the sample obtained from the organism.

In a still further embodiment of the invention, an assay for the detection of a pathogen infection in an organism, includes obtaining a sample from the organism and adding the sample to an uninfected cell, then culturing this cell in a suitable cell culture medium and administering to that cell an agent having at least one pathogen-interacting molecular structure and at least one effector-mediating molecular structure, such agent being one that is non-naturally-occurring in a cell, wherein in the presence of a pathogen, pathogen component or pathogen product in the cell, the agent binds to the pathogen, pathogen component or pathogen product, and activates the effector-mediating molecular structure. Thus, determining the presence or absence of activation of the effector-mediating molecular structure in the cell indicates the presence or absence of a pathogen infection in the sample obtained from the organism.

In further embodiment of the invention, an assay for the detection of a pathogen infection in a cell includes culturing the cell in a suitable cell culture medium and administering to that cell an agent having at least one pathogen-interacting molecular structure and at least one effector-mediating molecular structure, such agent being one that is non-naturally-occurring in a cell, wherein in the presence of a pathogen, pathogen component or pathogen product in the cell, the agent binds to the pathogen, pathogen component or pathogen product, and activates the effector-mediating molecular structure. Thus, determining the presence or absence of activation of the effector-mediating molecular structure in the cell indicates the presence or absence of a pathogen infection in the cell.

In another embodiment of the invention, an assay for the detection of a pathogen infection in an organism includes obtaining a cell or cells from the organism and culturing the cell(s) in a suitable cell culture medium and administering to the cell(s) an agent having at least one pathogen-interacting molecular structure and at least one effector-mediating molecular structure, such agent being one that is non-naturally-occurring in a cell, wherein in the presence of a pathogen, pathogen component or pathogen product, chimeric molecules bind to the pathogen, pathogen component or pathogen product, and activate the effector-mediating molecular structure. Thus, determining the presence or absence of activation of the effector-mediating molecular structure in the cell indicates the presence or absence of a pathogen infection in the organism.

In another embodiment of the invention, an assay for the detection of a pathogen infection in a cell includes culturing the cell in a suitable cell culture medium and administering to the cell chimeric molecules having at least one pathogen-induced product-detection domain and at least one effector domain, such chimeric molecule being one that is non-naturally-occurring in a cell, wherein in the presence of a pathogen-induced product in the cell, the chimeric molecules bind to the pathogen-induced product, and activate the effector domain, thus determining the presence or absence of apoptosis in the cell indicates the presence or absence of a pathogen infection in the cell.

In yet another embodiment of the invention, an assay for the detection of a pathogen infection in an organism includes obtaining a cell or cells from the organism and culturing the cell(s) in a suitable cell culture medium and administering to the cell(s) chimeric molecules having at least pathogen-induced product-detection domain and at least one effector domain, such chimeric molecule being one that is non-naturally-occurring in a cell, wherein in the presence of a pathogen, pathogen component or pathogen product, chimeric molecules bind to the pathogen-induced product, and activate the effector domain. Thus, determining the presence or absence of apoptosis in the cell isolated from the organism indicates the presence or absence of a pathogen infection in the organism.

In further embodiment of the invention, an assay for the detection of a pathogen infection in a cell includes culturing the cell in a suitable cell culture medium and administering to that cell an agent having at least one pathogen-induced product-interacting molecular structure and at least one effector-mediating molecular structure, such agent being one that is non-naturally-occurring in a cell, wherein in the presence of a pathogen-induced product in the cell, the agent binds to the pathogen-induced product, and activates the effector-mediating molecular structure. Thus, determining the presence or absence of activation of the effector-mediating molecular structure in the cell indicates the presence or absence of a pathogen infection in the cell.

In a still further embodiment of the invention, an assay for the detection of a pathogen infection in an organism, includes obtaining a sample from the organism and adding the sample to an uninfected cell, then culturing this cell in a suitable cell culture medium and administering to that cell chimeric molecules having at least one pathogen-induced product-detection domain and at least one effector domain, such chimeric molecules are non-naturally-occurring in a cell, wherein in the presence of a pathogen-induced product, the chimeric molecules bind to the pathogen-induced product, and activate the effector domain. Thus, determining the presence or absence of effector domain activation indicates the presence or absence of a pathogen infection in the sample obtained from the organism.

In a still further embodiment of the invention, an assay for the detection of a pathogen infection in an organism, includes obtaining a sample from the organism and adding the sample to an uninfected cell, then culturing this cell in a suitable cell culture medium and administering to that cell an agent having at least one pathogen-induced product-interacting molecular structure and at least one effector-mediating molecular structure, such agent being one that is non-naturally-occurring in a cell, wherein in the presence of a pathogen-induced product, chimeric molecules bind to the pathogen-induced product, and activate the effector-mediating molecular structure. Thus, determining the presence or absence of activation of the effector-mediating molecular structure in the cell indicates the presence or absence of a pathogen infection in the sample obtained from the organism.

In another embodiment of the invention, an assay for the detection of a pathogen infection in an organism includes obtaining a cell or cells from the organism and culturing the cell(s) in a suitable cell culture medium and administering to the cell(s) an agent having at least one pathogen-induced product-interacting molecular structure and at least one effector-mediating molecular structure, such agent being one that is non-naturally-occurring in a cell, wherein in the presence of a pathogen-induced product, chimeric molecules bind to the pathogen-induced product, and activate the effector-mediating molecular structure. Thus, determining the presence or absence of activation of the effector-mediating molecular structure in the cell indicates the presence or absence of a pathogen infection in the organism.

In another embodiment, a method for treating or preventing the spread of a pathogen infection in an organism, includes administering to the organism, chimeric molecules having at least one pathogen-detection domain and at least one effector domain, such pathogen-detection domain and effector domain being not normally bound to each other, and wherein the presence of a pathogen in the organism, the chimeric molecules bind to the pathogen, pathogen component or pathogen product and activate the effector domain, thus treating or preventing the spread of the pathogen infection in the organism.

In yet another embodiment, the method includes administering to a cell chimeric molecules which have at least one double-stranded RNA binding domain and at least one apoptosis mediator domain, the chimeric molecule being one that is non-naturally-occurring in a cell, such that in the presence of a pathogen in the cell, chimeric molecules bind to the double-stranded RNA produced by the pathogen and activate the apoptosis mediator domain, thereby causing apoptosis of the cell, thus treating or preventing the pathogen infection in the cell.

In a further embodiment, the method includes administering to a cell an agent which has at least one double-stranded RNA-interacting molecular structure and at least one apoptosis-effector mediating molecular structure, the agent being one that is non-naturally-occurring in a cell, such that in the presence of a pathogen in the cell, the agent binds to the double-stranded RNA produced by the pathogen and activates the apoptosis-effector mediating molecular structure, thereby causing apoptosis of the cell, thus treating or preventing the pathogen infection in the cell.

In another embodiment of the invention, a method for treating or preventing a virus infection in a cell includes administering to the cell chimeric molecules that have at least one double-stranded RNA binding domain and at least one apoptosis mediator domain, the chimeric molecule being one not naturally-occurring in a cell, such that in the presence of a virus in the cell, the chimeric molecules bind to a double-stranded RNA produced by the virus and activate the apoptosis mediator domain, thereby causing apoptosis of the cell, thus treating or preventing the virus infection in the cell.

In an additional embodiment of the invention, a method of treating or preventing a pathogen infection in a cell includes administering to the cell chimeric molecules having at least one double-stranded RNA binding domain isolated from protein kinase R and at least one pro-enzymatic caspase-3 domain, such that in the presence of a pathogen in the cell, these chimeric molecules bind to the double-stranded RNA produced by the pathogen and activate the pro-enzymatic caspase-3 domain thereby causing apoptosis of the cell, thus treating or preventing the pathogen infection in the cell.

In another embodiment of the invention, a method of treating or preventing a pathogen infection in a cell comprises administering to the cell chimeric molecules having at least one double-stranded RNA binding domain isolated from protein kinase R and at least one apoptosis mediator domain isolated from Fas-associated protein with death domain (FADD), such that in the presence of a pathogen in the cell, the chimeric molecules bind to double-stranded RNA produced by the pathogen and activate the apoptosis mediator domain and cause apoptosis of the cell, thus treating or preventing the pathogen infection in the cell.

In still another embodiment of the invention, a method of treating or preventing the spread of a pathogen infection in an organism, includes administering to the organism chimeric molecules that have at least one double-stranded RNA binding domain and at least one apoptosis mediator domain, the double-stranded RNA binding domain being one that is not naturally bound to the apoptosis mediator domain, such that in the presence of a pathogen in a cell or cells of the organism, the chimeric molecules bind to double-stranded RNA produced by the pathogen and activate the apoptosis mediator domain, thereby causing apoptosis of the cell in the organism, thus treating or preventing the spread of the pathogen in the organism.

In yet another embodiment, a method of treating or preventing the spread of a pathogen infection in an organism, includes administering to the organism an agent which has at least one double-stranded RNA-interacting molecular structure and at least one apoptosis-effector mediating molecular structure whereby, the agent being one that is non-naturally-occurring in a cell, such that in the presence of a pathogen in a cell or cells of the organism, the agent binds to the double-stranded RNA produced by the pathogen and activates the apoptosis-effector mediating molecular structure, thereby causing apoptosis of the cell in the organism, thus treating or preventing the spread of the pathogen in the organism.

In a further embodiment of the invention, a method of treating or preventing the spread of a pathogen infection in an organism, includes administering to the organism chimeric molecules having at least one double-stranded RNA binding domain isolated from protein kinase R and at least one pro-enzymatic caspase-3 domain, such that in the presence of the pathogen in a cell or cells of the organism, the chimeric molecules bind to the double-stranded RNA produced by the pathogen and activate the pro-enzymatic caspase-3 domain, thereby causing apoptosis of the cell in the organism, thus treating or preventing the spread of the pathogen in the organism.

In another embodiment of the invention, a method for treating or preventing the spread of a pathogen infection in an organism, includes administering to the organism chimeric molecules that have at least one double-stranded RNA binding domain isolated from protein kinase R and at least one apoptosis mediator domain isolated from FADD, such that in the presence of the pathogen in a cell or cells of an organism, the chimeric molecules bind to double-stranded RNA produced by that pathogen and activate the apoptosis mediator domain, thereby causing apoptosis of the cell in the organism, thus treating or preventing the spread of the pathogen in the organism.

In yet another embodiment of the invention, a method of treating or preventing a pathogen infection in a cell includes administering to the cell individual components of a chimeric molecule, such components being assembled together to form a chimeric molecule at least one double-stranded RNA binding domain and at least one apoptosis mediator domain, such that in the presence of a pathogen in the cell, the chimeric molecules bind to double-stranded RNA produced by the pathogen and activate the apoptosis mediator domain, thus treating or preventing the pathogen infection in the cell.

In still another embodiment of the invention, a method of treating or preventing the spread of a pathogen infection in an organism includes administering to the organism individual components of a chimeric molecule, such components being assembled together to form a chimeric molecule having at least one double-stranded RNA binding domain and at least one apoptosis mediator domain, such that in the presence of a pathogen, the chimeric molecules bind to double-stranded RNA produced by the pathogen and activate the apoptosis mediator domain, thus treating or preventing the spread of a pathogen infection in the organism.

In a further embodiment of the invention, a method of mediating apoptosis in a cell infected with a pathogen, includes administering to the cell chimeric molecules having at least one double-stranded RNA binding domain and at least one apoptosis mediator domain, the double-stranded RNA binding domain being one that is not naturally bound to the apoptosis mediator domain, such that in the presence of a pathogen in the cell, the chimeric molecules bind to the double-stranded RNA produced by that pathogen and activate the apoptosis mediator domain, thus causing apoptosis of the cell.

In a further embodiment of the invention, a method of mediating apoptosis in a cell infected with a pathogen, includes administering to the cell an agent which has at least one double-stranded RNA-interacting molecular structure and at least one apoptosis-effector mediating molecular structure, the agent being one that is non-naturally-occurring in a cell, such that in the presence of a pathogen, the agent binds to the double-stranded RNA produced by the pathogen and activates the apoptosis-effector mediating molecular structure, thereby causing apoptosis of the cell.

In another embodiment of the invention, a method of mediating apoptosis in a cell infected with a pathogen, includes administering to the cell chimeric molecules having at least one double-stranded RNA binding domain isolated from protein kinase R and at least one pro-enzymatic caspase-3 domain, the double-stranded RNA binding domain being one that is not naturally bound to the apoptosis mediator domain, such that in the presence of the pathogen in the cell, the chimeric molecules bind to the double-stranded RNA produced by the pathogen and activate pro-enzymatic caspase-3, thus causing apoptosis of the cell.

In a further embodiment of the invention, a method of mediating apoptosis in a cell infected with a pathogen, includes administering to the cell chimeric molecules having at least one double-stranded RNA binding domain isolated from protein kinase R and at least one apoptosis mediator domain isolated from FADD, the double-stranded RNA binding domain being one that is not naturally bound to the apoptosis mediator domain, such that in the presence of the pathogen in the cell, the chimeric molecules bind to the double-stranded RNA produced by that pathogen and activate the apoptosis mediator domain, and cause apoptosis of the cell.

In still another embodiment of the invention, a method of mediating apoptosis in an organism infected with a pathogen, includes administering to the organism chimeric molecules having at least one double-stranded RNA binding domain and at least one apoptosis mediator domain, the double-stranded RNA binding domain being one that is not naturally bound to the apoptosis mediator domain, such that in the presence of the pathogen in a cell or cells of the organism, the chimeric molecules bind to the double-stranded RNA produced by the pathogen and activate apoptosis mediator domain, thereby causing apoptosis of the cell in the organism.

In another embodiment of the invention, a method of mediating apoptosis in an organism infected with a pathogen, includes administering to the organism an agent having at least one double-stranded RNA-interacting molecular structure and at least one apoptosis-effector mediating molecular structure, the agent being one that is non-naturally-occurring in a cell, such that in the presence of the pathogen in a cell or cells of the organism, the agent binds to the double-stranded RNA produced by the pathogen and activates the apoptosis-effector mediating molecular structure, thereby causing apoptosis of the cell in the organism.

In further embodiment of the invention, a method of mediating apoptosis in an organism infected with a pathogen, includes administering to the organism chimeric molecules having at least one double-stranded RNA binding domain isolated from protein kinase R and at least one pro-enzymatic caspase-3 domain, the double-stranded RNA binding domain being one that is not naturally bound to the apoptosis mediator domain, such that in the presence of a pathogen in a cell or cells of the organism, the chimeric molecules bind to the double-stranded RNA produced by that pathogen and activate the pro-enzymatic caspase-3 domain, causing apoptosis of the cell in the organism.

Another embodiment of the invention is a method of mediating apoptosis in an organism infected with a pathogen, by administering to the organism chimeric molecules having at least one double-stranded RNA binding domain isolated from protein kinase R and at least one apoptosis mediator domain isolated from FADD, the double-stranded RNA binding domain being one that is not naturally bound to the apoptosis mediator domain, such that in the presence of a pathogen in a cell or cells of the organism, the chimeric molecules bind to the double-stranded RNA produced by that pathogen and activate the apoptosis mediator domain, causing apoptosis of the cell in the organism.

In another embodiment of the invention, a chimeric molecule is provided which has at least one double-stranded pathogen-RNA binding domain and at least one apoptosis mediator domain.

In still another embodiment, is an agent that has at least one double-stranded RNA-interacting molecular structure and at least one apoptosis-effector mediating molecular structure.

In a further embodiment, a chimeric molecule is provided that has at least one double-stranded RNA binding domain isolated from protein kinase R and at least one apoptosis mediator domain isolated from pro-enzymatic caspase-3, the double-stranded RNA binding domain being one that is not naturally bound to the apoptosis mediator domain.

In another embodiment, a chimeric molecule is provided that has at least one double-stranded RNA binding domain isolated from protein kinase R and at least one apoptosis mediator domain isolated from FADD apoptosis mediator, the double-stranded RNA binding domain being one that is not naturally bound to the apoptosis mediator domain.

In a further embodiment of the invention, a chimeric molecule having more than one double-stranded RNA binding domain and at least one apoptosis mediator domain, the double-stranded RNA binding domains being ones that are not naturally bound to the apoptosis mediator domain, is provided.

In an alternative embodiment, a chimeric molecule of the invention has at least one double-stranded RNA binding domain and more than one apoptosis mediator domain, the double-stranded RNA binding domain being one that is not naturally bound to the apoptosis mediator domains.

In further embodiment of the invention, an assay for the detection of a pathogen infection in a cell includes, culturing the cell in a suitable cell culture medium and administering to that cell chimeric molecules having at least one double-stranded RNA binding domain and at least one apoptosis mediator domain, the double-stranded RNA binding domain being one that is not naturally bound to the apoptosis mediator domain, such that in the presence of a pathogen in the cell, the chimeric molecules bind to the double-stranded RNA produced by the pathogen and activate the apoptosis mediator domain, thus determining the presence or absence of apoptosis in the cell indicates the presence or absence of a pathogenic infection in the cell.

In further embodiment of the invention, an assay for the detection of a pathogen infection in a cell includes, culturing the cell in a suitable cell culture medium and administering to that cell an agent having at least one double-stranded RNA-interacting molecular structure, and at least one apoptosis-effector mediating molecular structure, the agent being one that is non-naturally occurring in a cell, such that in the presence of a pathogen in the cell, the agent binds to the double-stranded RNA produced by the pathogen and activates the apoptosis-effector mediating molecular structure, thus determining the presence or absence of apoptosis in the cell indicates the presence or absence of a pathogenic infection in the cell.

In still a further embodiment of the invention, an assay for the detection of double-stranded RNA in a sample includes the steps of administering to the sample chimeric molecules having at least one double-stranded RNA binding domain and at least one apoptosis mediator domain, the double-stranded RNA binding domain being one that is not naturally bound to the apoptosis mediator domain, such that in the presence of double-stranded RNA in the sample, the chimeric molecules will bind to that double-stranded RNA and activate the apoptosis mediator domain. A determination of the presence or absence of activation of the apoptosis mediator domain will indicate the presence or absence of double-stranded RNA in the sample.

In another embodiment of the invention, an assay for the detection of double-stranded RNA in a sample includes the steps of administering to the sample an agent having at least one double-stranded RNA-interacting molecular structure and at least one apoptosis-effector mediating molecular structure, the agent being one that is non-naturally occurring in a cell, such that in the presence of double-stranded RNA in the sample, the agent binds to that double-stranded RNA and activates the apoptosis-effector mediating molecular structure, thus a determination of the presence or absence of activation of the apoptosis-effector mediating molecular structure will indicate the presence or absence of double-stranded RNA in the sample.

In further embodiment of the invention, an assay for the detection of a pathogen infection in an organism includes, obtaining a cell or cells from the organism, culturing the cell(s) in a suitable cell culture medium, and administering to the cell(s) chimeric molecules having at least one double-stranded RNA binding domain and at least one apoptosis mediator domain, the double-stranded RNA binding domain being one that is not naturally bound to the apoptosis mediator domain, such that in the presence of a pathogen in the cell, the chimeric molecules bind to the double-stranded RNA produced by the pathogen and activate the apoptosis mediator domain. Determining the presence or absence of apoptosis in the cell indicates the presence or absence of a pathogenic infection in the organism.

In another embodiment of the invention, an assay for the detection of a pathogen infection in an organism includes, obtaining a cell or cells from the organism, culturing the cell(s) in a suitable cell culture medium and administering to the cell(s) an agent having at least one double-stranded RNA-interacting molecular structure, and at least one apoptosis-effector mediating molecular structure, the agent being one that is non-naturally occurring in a cell, such that in the presence of a pathogen in the cell, the agent binds to the double-stranded RNA produced by the pathogen and activates the apoptosis-effector mediating molecular structure. Determining the presence or absence of apoptosis in the cell indicates the presence or absence of a pathogenic infection in the organism.

The invention described herein provides chimeric molecules, and methods of use of said chimeric molecules, for treatment and prevention of pathogenic infections in a cell or an organism. Advantages of the claimed invention include, for example, its applicability to a broad spectrum of pathogenic infections, in addition to its use in both prophylactic methods and post-infection treatments. Furthermore, the claimed invention can overcome at least some disadvantages of existing therapies.

BRIEF DESCRIPTION OF THE DRAWINGS

FIG. 1 is a chart illustrating some of the possible cellular methods for detecting and responding (by mediating one or more effects or effector functions) to pathogens. Detection methods include, but are not limited to, detection of interferon, double-stranded RNA (dsRNA), lipopolysaccharide (LPS), and apoptosis signals. Cellular responses with anti-pathogen effects (effector functions) include, but are not limited to, various responses from the interferon pathway, apoptosis, heat shock, and other stress responses, enhancing or inducing the immune response by upregulating MHC Class I molecules on cell surfaces or by other methods, dsRNase activity, inhibition of endosome function, and nuclear localization signal inhibitors.

FIG. 25 is a diagram of an interferon-induced heat shock protein which selectively protects uninfected cells near infected ones. An interferon-induced heat shock protein gene is a new anti-pathogen defense that can be added to cells via gene therapy or other methods to inhibit pathogen replication in cells. Because its effect is localized in both space and time, only occurring in cells near infected ones, side-effects are minimized.

FIG. 35 is a diagram of an interferon-inducible heat shock protein (HSP) expression vector on the left panel and on the right panel is a photograph of interferon-inducible HSP expression vectors electrophoresed on an agarose gel.

FIG. 48 is a schematic of further chimeric caspases.

FIG. 51 is a schematic of using IFN-induced defenses. Illustrated is a vector with an ISRE-containing promoter regulating the expression of at least one defense gene.

FIG. 55 is a schematic for the production of PCR product 31. It encodes a truncated form of importin α4 that lacks the importin-β-binding domain but includes an HA epitope.

FIG. 57 is a schematic for the production of PCR product 32. PCR was carried out using the illustrated PCR primers and the vector pCMV/Bsd/ISRE/α6. It encodes a truncated form of importin α6 that lacks the importin-β-binding domain but includes an HA epitope.

FIG. 58 illustrates the creation of a gene encoding E. coli RNase III with an HA epitope, and its subsequent insertion into the pCMV/Bsd/ISRE vector to produce the new vector pCMV/Bsd/ISRE/RNase III.

FIG. 63 is a schematic for the production of PCR product 35. It encodes the *Salmonella* SpiC protein with an HA epitope.

FIG. 69 illustrates PCR primers for producing a DNA sequence encoding aequorin fused to one of the following protein transduction tags: TAT, PTD-4, an arginine-rich sequence Arg, or no protein transduction tag.

FIG. 70 illustrates PCR primers for producing a DNA sequence encoding enhanced green fluorescent protein (EGFP) fused to one of the following protein transduction tags: TAT, PTD-4, an arginine-rich sequence Arg, or no protein transduction tag.

FIG. 71 illustrates PCR primers for producing a DNA sequence that includes the coding sequence from PCR product 7 or 8 fused to one of the following protein transduction tags: TAT, PTD-4, an arginine-rich sequence Arg, or no protein transduction tag.

FIG. 72 illustrates PCR primers for producing a DNA sequence that includes the coding sequence from PCR product 9 or 10 fused to one of the following protein transduction tags: TAT, PTD-4, an arginine-rich sequence Arg, or no protein transduction tag.

FIG. 73 illustrates PCR primers for producing a DNA sequence that includes the coding sequence from PCR product 25 fused to one of the following protein transduction tags: TAT, PTD-4, an arginine-rich sequence Arg, or no protein transduction tag.

FIG. 75 illustrates PCR primers for producing a DNA sequence that includes the coding sequence from PCR product 27 fused to one of the following protein transduction tags: TAT, PTD-4, an arginine-rich sequence Arg, or no protein transduction tag.

FIG. 76 illustrates PCR primers for producing a DNA sequence that includes the coding sequence from PCR product 28 fused to one of the following protein transduction tags: TAT, PTD-4, an arginine-rich sequence Arg, or no protein transduction tag.

FIG. 77 illustrates PCR primers for producing a DNA sequence that includes the coding sequence from PCR product 29 fused to one of the following protein transduction tags: TAT, PTD-4, an arginine-rich sequence Arg, or no protein transduction tag.

FIG. 78 illustrates PCR primers for producing a DNA sequence that includes the coding sequence from PCR product 30 fused to one of the following protein transduction tags: TAT, PTD-4, an arginine-rich sequence Arg, or no protein transduction tag.

FIG. 79 illustrates PCR primers for producing a DNA sequence that includes the coding sequence from PCR product 31 fused to one of the following protein transduction tags: TAT, PTD-4, an arginine-rich sequence Arg, or no protein transduction tag.

FIG. 80 illustrates PCR primers for producing a DNA sequence that includes the coding sequence from PCR product 32 fused to one of the following protein transduction tags: TAT, PTD-4, an arginine-rich sequence Arg, or no protein transduction tag.

FIG. 81 illustrates PCR primers for producing a DNA sequence that includes the coding sequence from PCR product 33 fused to one of the following protein transduction tags: TAT, PTD-4, an arginine-rich sequence Arg, or no protein transduction tag.

FIG. 82 illustrates PCR primers for producing a DNA sequence that includes the coding sequence from PCR product 34 fused to one of the following protein transduction tags: TAT, PTD-4, an arginine-rich sequence Arg, or no protein transduction tag.

FIG. 83 illustrates PCR primers for producing a DNA sequence that includes the coding sequence from PCR product 35 fused to one of the following protein transduction tags: TAT, PTD-4, an arginine-rich sequence Arg, or no protein transduction tag.

FIG. 84 illustrates PCR primers for producing a DNA sequence that includes the coding sequence from PCR product 36 fused to one of the following protein transduction tags: TAT, PTD-4, an arginine-rich sequence Arg, or no protein transduction tag.

FIG. 85 illustrates PCR primers for producing a DNA sequence that includes the coding sequence from PCR product 37 fused to one of the following protein transduction tags: TAT, PTD-4, an arginine-rich sequence Arg, or no protein transduction tag.

FIG. 86 illustrates PCR primers for producing a DNA sequence that includes the coding sequence from PCR product 38 fused to one of the following protein transduction tags: TAT, PTD-4, an arginine-rich sequence Arg, or no protein transduction tag.

DETAILED DESCRIPTION OF THE INVENTION

Figure 2:
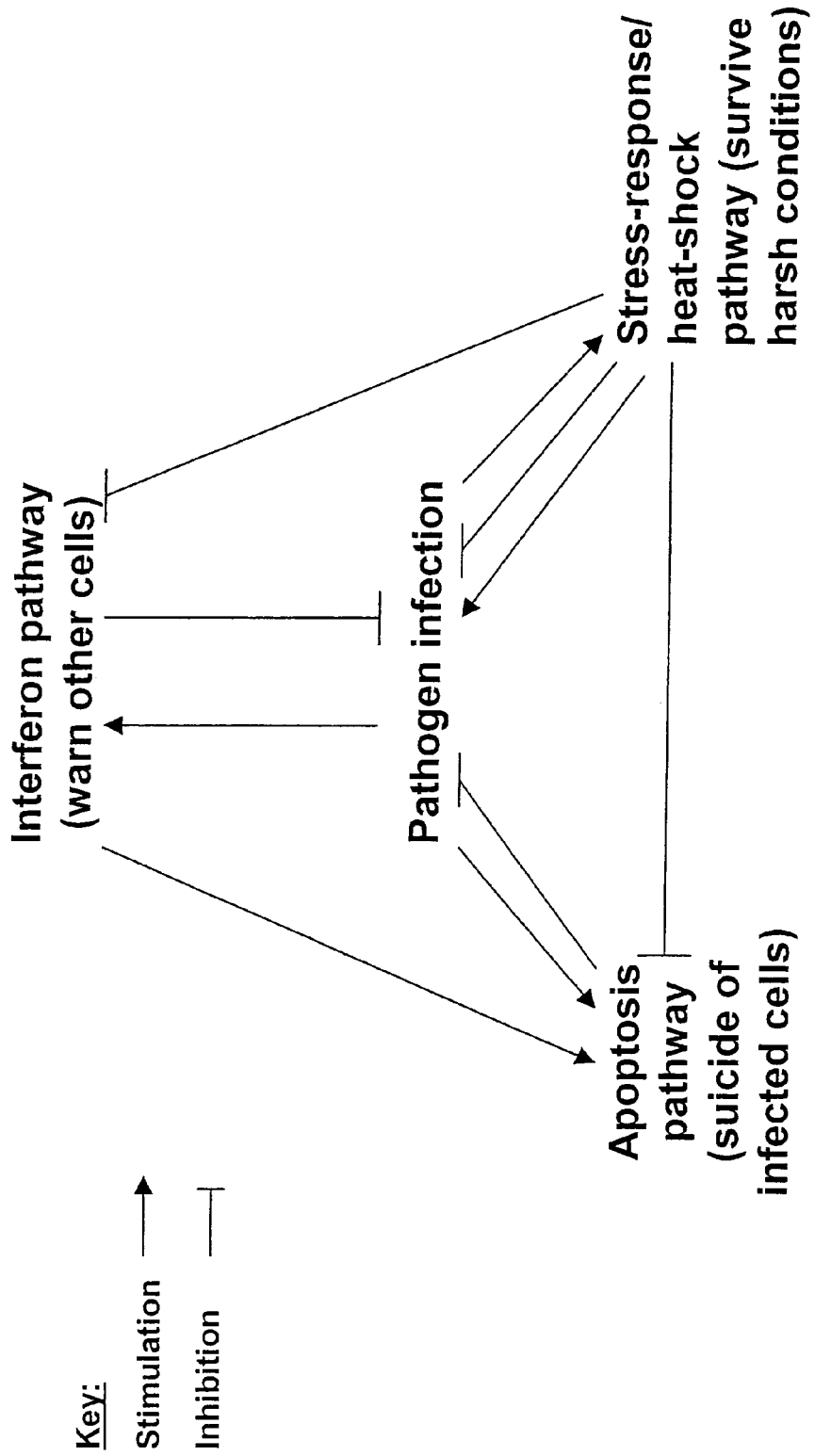
FIG. 2 is a simplified diagram showing three of the natural cellular pathways that interact with viruses or other pathogens. As shown, a line ending in an arrow indicates a general tendency to stimulate, while a line ending in a bar indicates a general tendency to inhibit.
Figure 3:
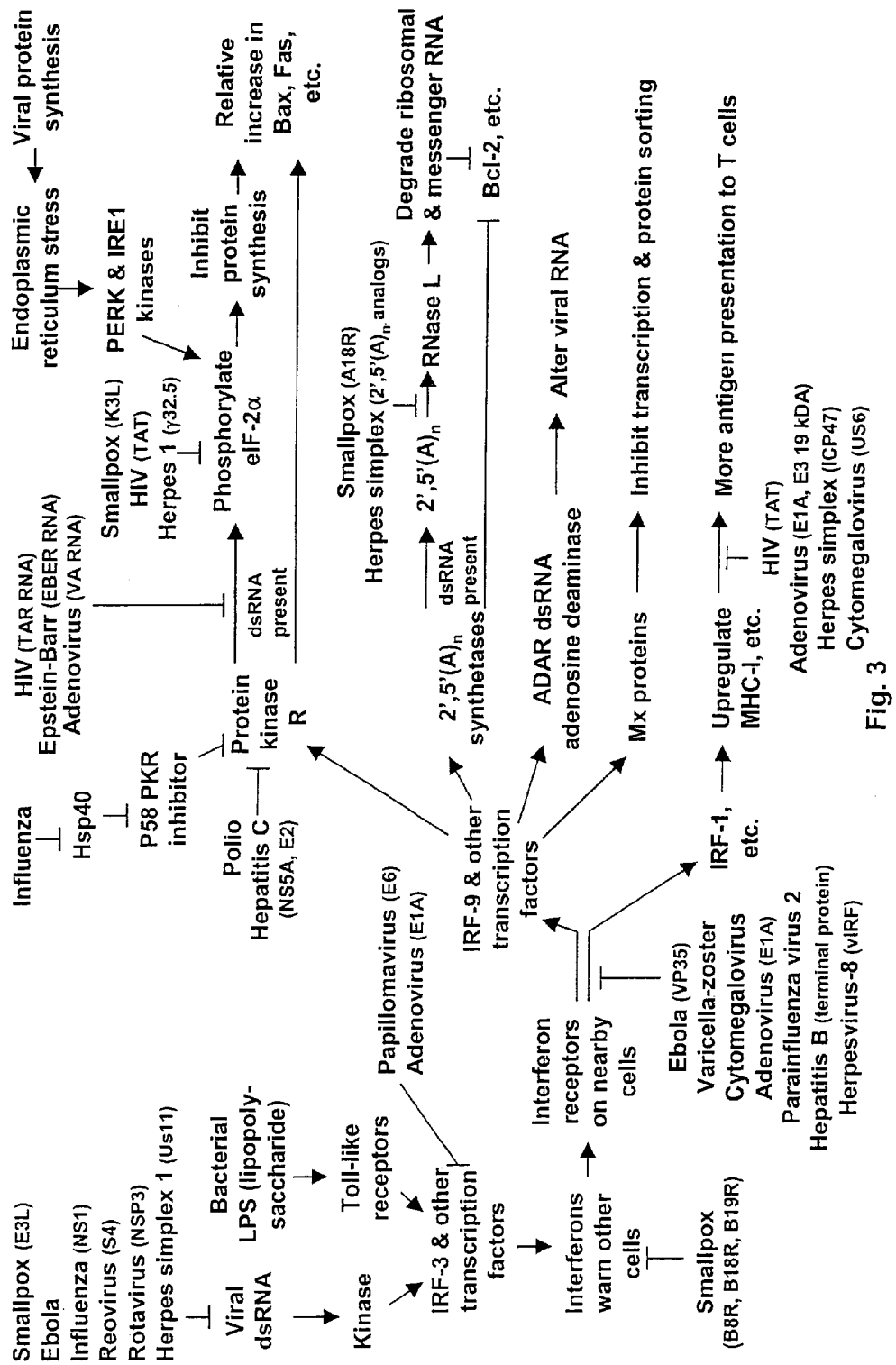
FIG. 3 is a simplified diagram depicting the interferon pathway and the methods by which some pathogens inhibit it. As shown, a line ending in an arrow indicates a general tendency to stimulate, while a line ending in a bar indicates a general tendency to inhibit.
Figure 4:
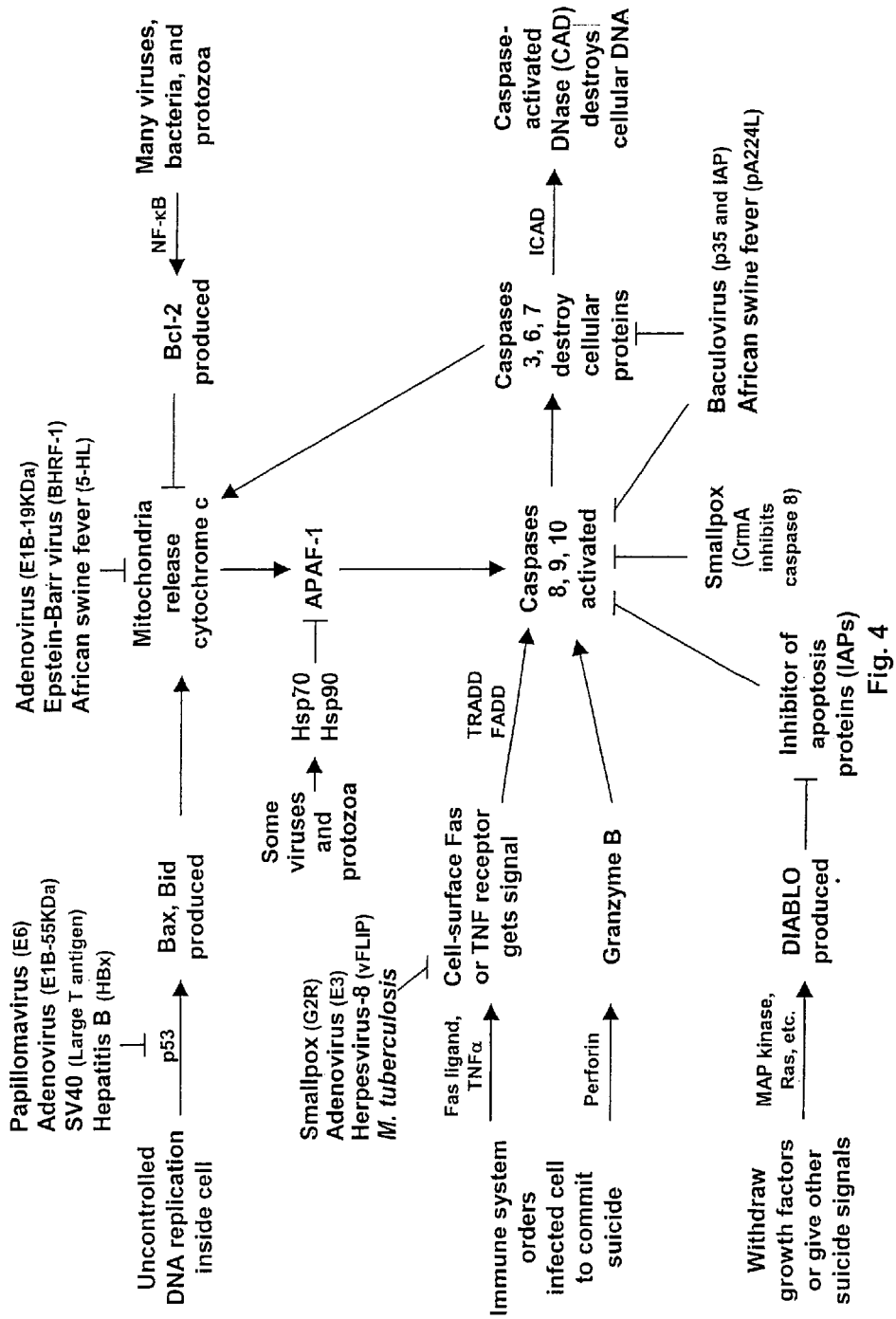
FIG. 4 is a simplified diagram showing the apoptosis pathway and the methods by which some pathogens inhibit it. As shown, a line ending in an arrow indicates a general tendency to stimulate, while a line ending in a bar indicates a general tendency to inhibit. The diagram illustrates some of the ways by which pathogens can inhibit apoptosis to prevent premature death of the host cells.
Figure 5:
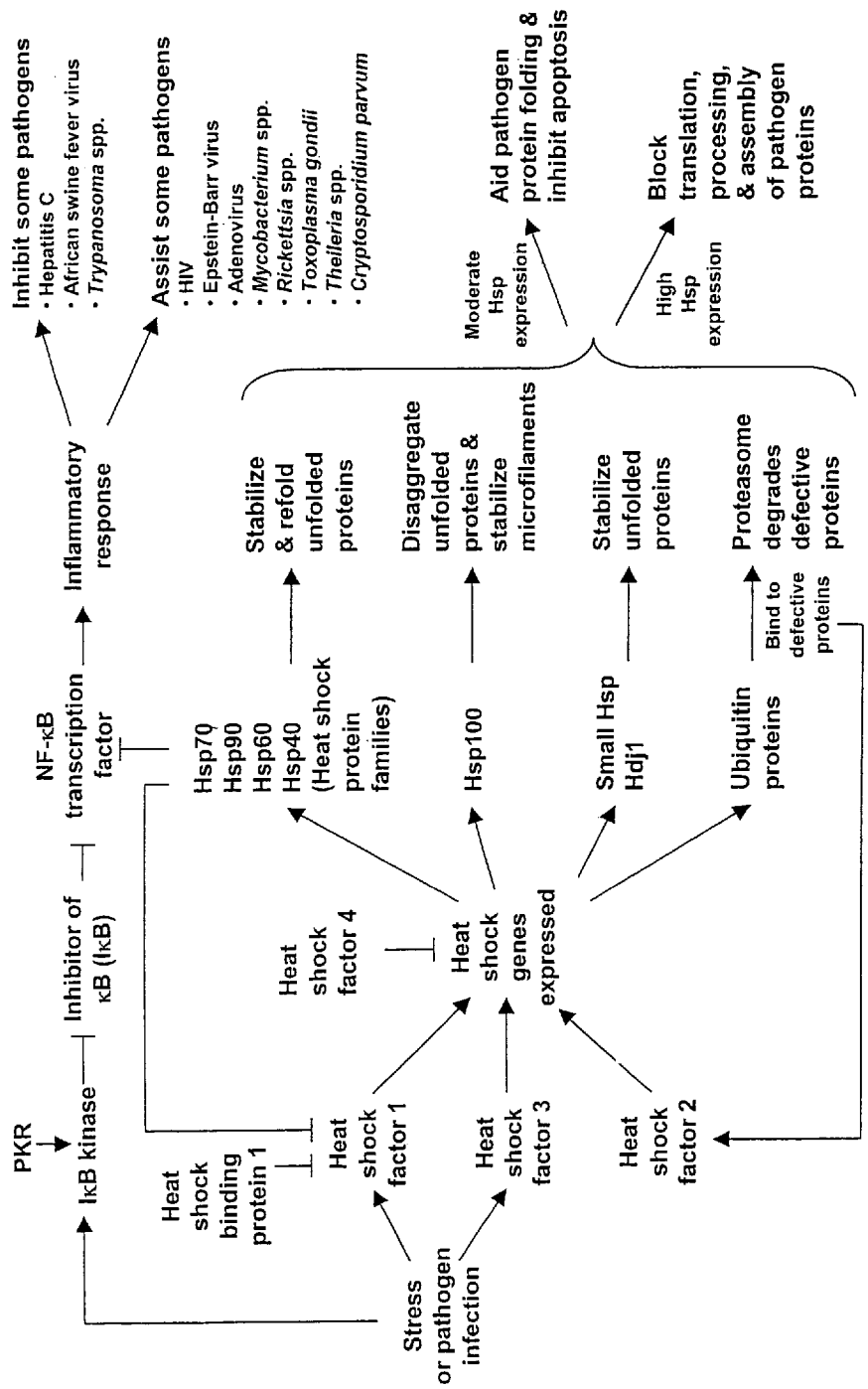
FIG. 5 is a simplified diagram depicting the pathway involving heat shock and other stress responses, as well as its interactions with some pathogens. As shown, a line ending in an arrow indicates a general tendency to stimulate, while a line ending in a bar indicates a general tendency to inhibit.
Figure 6:
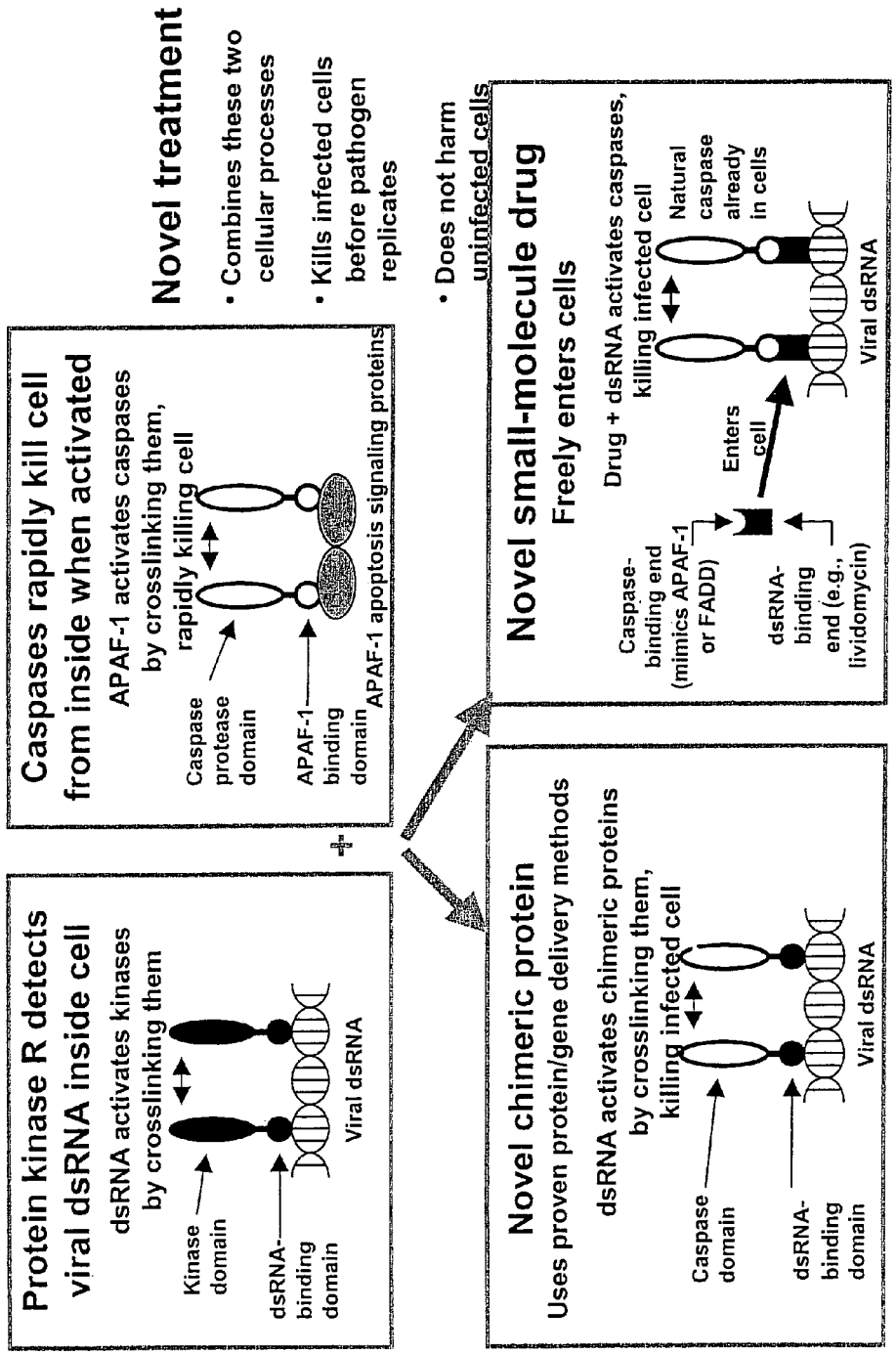
FIG. 6 is a diagram representing how parts of the interferon and apoptosis pathways can be combined to create a novel dsRNA-activated caspase or related treatments that selectively kill pathogen-infected cells. A chimeric (pro)caspase protein with a dsRNA-binding domain such as that from PKR will selectively kill infected cells. Alternatively, a small-molecule drug that binds both dsRNA (e.g., lividomycin) and caspases (e.g., by mimicking the caspase-binding region of APAF-1 or FADD) will selectively kill infected cells by crosslinking and thereby activating endogenous caspases when dsRNA is present.

Organisms, such as humans, other animals, and plants, and their cells have natural defenses against pathogens, such as viruses, viroids, bacteria, rickettsia, chlamydia, mycoplasma, fungi, protozoa, helminths, and prions. These natural defenses include, for example and without limitation: (1) the interferon pathway, by which an infected cell can warn or prime nearby uninfected cells to increase their resistance to infection; (2) apoptosis, in which an infected cell can commit cell suicide to prevent further spread of the infection; (3) heat shock and other stress responses, which help cells survive under stress conditions, such as infection; (4) inflammatory responses, which can combat infections; (5) unfolded-protein responses or endoplasmic reticulum-associated protein degradation responses, which help cells respond to endoplasmic reticulum stress or protein accumulation, such as can be caused by a pathogen; (6) innate immune responses, which inhibit a broad spectrum of pathogens; and (7) adaptive immune responses, which identify and respond to specific pathogens.

However, many pathogens, for example: viruses such as variola major (smallpox), Ebola, HIV, hepatitis viruses, influenza viruses, papillomaviruses, herpesviruses, and adenoviruses; bacteria such as *Mycobacterium* species, *Salmonella* species, *Yersinia* species, *Chlamydia* species, *Coxiella burnetti*, *Francisella tularensis*, *Brucella* species, *Bordetella* species, *Listeria monocytogenes*, and *Legionella pneumophila*; fungi such as *Histoplasma capsulatum*; and protozoa such as *Plasmodium* species, *Trypanosoma* species, *Leish-*

*mania* species, and *Toxoplasma gondii*, have developed methods to evade some or all of these natural defenses.

This invention provides chimeric molecules, agents, and methods of use thereof, which manipulate or modify the natural defenses to be more effective against pathogen infections. This invention is also known as "Pharmacological Augmentation of Nonspecific Anti-pathogen Cellular Enzymes and Activities (PANACEA)."

A chimeric molecule of the invention, as described herein, is composed of at least two domains, said domains being not normally found in association together, or bound to one another, in a cell.

An agent of the invention, as described herein, is one that is non-naturally-occurring in a cell.

A broad spectrum of pathogens will be susceptible to treatment with the agents and chimeric molecules described herein, and include, for example and without limitation: viruses, including those belonging to the families of poxvirus (such as variola major), herpesvirus (such as herpes simplex virus types 1 and 2, varicella-zoster virus, cytomegaloviruses, and Epstein-Barr virus), adenovirus (such as various human adenovirus serotypes), papovavirus (such as human papillomaviruses), hepadnavirus (such as hepatitis B virus), parvovirus (such as parvovirus-like agent), picornavirus (such as poliovirus, Coxsachie viruses A and B, rhinoviruses, and foot-and-mouth disease virus), calicivirus (such as Norwalk agent and hepatitis E virus), togavirus (such as equine encephalitis viruses and rubella virus), flavivirus (such as West Nile virus, yellow fever virus, and Powassan), coronavirus (such as human coronaviruses), reovirus (such as Colorado tick fever virus), rhabdovirus (such as rabies virus), filovirus (such as Ebola and Marburg viruses), paramyxovirus (such as parainfluenza viruses, measles, distemper, rinderpest, and respiratory syncytial virus), orthomyxovirus (such as influenza viruses), bunyavirus (such as Rift Valley fever virus and Hantaan virus), arenavirus (such as Lassa virus), retrovirus (such as human immunodeficiency virus and human T cell leukemia virus), plant viruses, for example: dsDNA plant viruses (such as cauliflower mosaic virus and badnaviruses); ssDNA plant viruses (such as geminiviruses); dsRNA plant viruses (such as plant reoviruses and cryptoviruses); negative-sense or ambisense RNA plant viruses (such as rhabdoviruses, tomato spotted wilt virus, and tenuiviruses); positive-sense ssRNA plant viruses (such as tobacco mosaic virus, tobacco rattle virus, and alfalfa mosaic virus); and viroids (such as potato spindle tuber viroid); and other hepatitis viruses or other viruses; bacteria, such as *Treponema pallidum, Borrelia bergdorferi, Helicobacter pylori, Pseudomonas aeruginosa, Legionella pneumophila, Neisseria meningitidis, Neisseria gonorrhoeae, Brucella* species, *Bordetella pertussis, Francisella tularensis, Escherichia coli, Shigella dysenteriae, Salmonella* species, *Klebsiella pneumoniae, Proteus* species, *Yersinia* species, *Vibrio cholerae, Haemophilus influenzae, Rickettsia* species, *Coxiella burnetii, Chlamydia* species, *Mycoplasma* species, *Staphylococcus* species, *Streptococcus* species, *Bacillus anthracis, Clostridium* species, *Listeria monocytogenes, Corynebacterium diphtheriae, Mycobacterium tuberculosis, Mycobacterium leprae*, and other *Mycobacterium* species, and *Nocardia asteroides*; prions, such as the causitive agents of kuru, Creutzfeldt-Jakob disease, Gerstmann-Straussler syndrome, scrapie, bovine spongiform encephalopathy, and transmissible mink encephalopathy; protozoa, such as *Plasmodium vivax, Plasmodium ovale, Plasmodium malariae, Plasmodium falciparum, Toxoplasma gondii, Pneumocystis carinii, Trypanosoma cruzi, Trypanasoma brucei gambiense, Trypanasoma brucei rhodesiense, Leishmania* species, *Naegleria, Acanthamoeba, Trichomonas vaginalis, Cryptosporidium* species, *Isospora* species, *Balantidium coli, Giardia lamblia, Entamoeba histolytica,* and *Dientamoeba fragilis*; fungi, such as *Candida albicans, Candida parasilosis, Cryptococcus neoformans, Apergillus fumigatus conidia* and *Aspergillus fumigatus hyphae*; or multicellular parasites including *Trichinella spiralis*, nematode larvae, *Schistosome* larvae, *Ascaris, Tricuris,* filarila worms and the like.

As used herein, a pathogen, which can be detected by a chimeric molecule or agent of the invention, include those parts of the pathogen that are sufficient for their detection by the chimeric molecule or agent. For example, a pathogen component, a pathogen product or an epitope that is pathogen-specific are all encompassed by the term pathogen as used herein.

A pathogen-detection domain, as used herein, is generally directed to a domain that is capable of recognizing or binding a pathogen, pathogen component or product of the pathogen. As used herein, the term pathogen-detection domain is a region of the molecule that includes at least the minimal region necessary to perform the pathogen recognition (also referred to herein as pathogen detection) function of the domain. The pathogen-detection domain can also be encompassed within a larger region or structure, or smaller region or structure, but it still retains the pathogen recognition function of the domain.

More particularly, a detector domain, as used herein, is a molecule that binds to, is stimulated by, or is inhibited by one or more of the following: a pathogen (such as, for example, an extracellular domain of a toll-like receptor that binds to bacteria or other pathogens); a pathogen component (such as, for example, the domain from approximately amino acids 1-199 of human bactericidal/permeability-increasing protein (BPI) that binds to bacterial lipopolysaccharide (LPS)); a pathogen-produced product (such as, for example, the domain from approximately amino acids 1-174 of human PKR that binds to dsRNA produced in virus-infected cells); a pathogen-induced product (such as, for example, the domain from approximately amino acids 1-335 of human RNase L that binds to 2',5'-oligoadenylate produced in virus-infected cells); or a pathogen-induced signaling molecule (such as, for example, the domain from approximately amino acids 98-1194 that binds to cytochrome c during pathogen-induced apoptotic pathway signaling). A molecule or structure that is detected can belong to multiple categories described supra. For example, dsRNA can be considered a pathogen component, a pathogen-produced product, or a pathogen-induced product.

Pathogen-detection domains can be isolated from naturally-occurring molecules that normally recognize a pathogen, pathogen component or product of said pathogen, such as a cellular protein. Suitable pathogen-detection domains can be isolated from a wide range of known cellular proteins from a number of different organisms, including for example, humans, non-human primates, rodents, plants, *Drosophila*, yeast, bacteria and the like, as will be appreciated by one of skill in the art. Alternatively, the pathogen-detection domain can be synthetically-derived, such as by chemically modifying a naturally-occurring molecule, or otherwise manipulating a naturally-occurring molecule to enhance, optimize, or modify the pathogen-detection domain, using standard techniques known to those of skill in the art. Additionally, the pathogen-detection domain can be a synthetic product such as a small molecule or a peptidomimetic. Furthermore, a pathogen-detection domain can be an antibody (including, for example, antibody fragments, such as Fab, Fab', F(ab')$_2$, and fragments including either a $V_L$ or $V_H$ domain, single chain antibodies, bi-specific, chimeric or humanized antibodies), that recognizes a specific pathogen epitope, an epitope of a pathogen component or an epitope of a product of the pathogen.

In one embodiment, a pathogen, pathogen component or product of the pathogen, to which a pathogen-detection domain of the chimeric molecule of the invention can bind is double-stranded RNA (dsRNA), which is produced by said pathogen. In a preferred embodiment, the dsRNA is produced by a virus or a virus-infected cell.

Suitable dsRNA binding domains can be isolated from a wide range of known dsRNA-binding proteins from a number of different organisms, including for example, humans, non-human primates, rodents, plants, *Drosophila*, yeast, bacteria and the like, as will be appreciated by one of skill in the art. Examples of dsRNA-binding proteins include protein kinase R, 2',5'-oligoadenylate synthases, RNA-specific adenosine deaminase 1 (ADAR1), vaccinia E3L, RNase III, Rnt1p, and Pac1. The identification and isolation of suitable domains from proteins or other molecules of interest can be readily achieved using standard techniques, as will be appreciated by one of skill in the art.

Examples of some dsRNA binding domain-containing proteins and the approximate amino acid position of the dsRNA binding domains are provided in Table 1. The protein, the approximate amino acid location of the dsRNA binding domain region within the protein, and the National Center for Biotechnology Information (NCBI) database accession number are provided in Table 1.

(NCBI Accession #SYMS02); 2',5'-oligoadenylate synthetase 3, *Mus musculus* (NCBI Accession #SYMS03); RNase III, *Homo sapiens* (NCBI Accession #AAF80558); RNase III, *Escherichia coli* (NCBI Accession #NP_417062); Rnt1, *Saccharomyces cerevisiae* (NCBI Accession #S56053); and Pac1, *Schizosaccharomyces pombe* (NCBI Accession #S12605). Identification and isolation of a dsRNA binding domain from these or any other proteins will be readily appreciated by one of skill in the art using standard techniques.

Other pathogen-detection domains can be isolated from other dsRNA-binding compounds, including for example, antibiotics such as lividomycin or tobramycin.

A pathogen detection domain can also be a molecule that binds to lipopolysaccharide (LPS), such as the domain of approximately amino acids 1-197 of LPS-binding protein (LBP) (S. L. Abrahamson et al. (1997) *Journal of Biological Chemistry* 272, 2149-2155; L. J. Beamer et al. (1998) *Protein Science* 7, 906-914), the domain of approximately amino acids 1-193 of bactericidal/permeability-increasing protein (BPI) (S. L. Abrahamson et al. (1997) *Journal of Biological Chemistry* 272, 2149-2155; L. J. Beamer et al. (1998) *Protein Science* 7, 906-914), or a single-chain antibody that binds to LPS.

A pathogen-detection domain can also be a domain that recognizes an epitope which is present in multiple copies or is reiterated on the pathogen, pathogen component or pathogen product.

TABLE 1

| Protein, organism | Domain type: sequence location (amino acids) | NCBI Accession number |
|---|---|---|
| Protein kinase R, *Homo sapiens* | dsRNA binding domain: 1-174 | AAC50768 |
| Protein kinase R, *Mus musculus* | dsRNA binding domain: 1-160 | Q03963 |
| E3L protein, Vaccinia virus | dsRNA binding domain: 114-185 | B35928 |
| RNase III, *E. coli* | dsRNA binding domain: 153-226 | NP_417062 |
| RNT1p, *Saccharomyces cerevisiae* | dsRNA binding domain: 330-471 | S56053 |
| 2',5'-oligoadenylate synthetase, 41- and 46-kDa forms, *Homo sapiens* | dsRNA-binding domain: 104-158 | P00973 |
| 2',5'-oligoadenylate synthetase, 69- and 71-kDa forms, *Homo sapiens* | dsRNA-binding domains: 102-149 and 438-493 | P29728 |
| 2',5'-oligoadenylate synthetase, 100-kDa form, *Homo sapiens* | dsRNA-binding domains: 103-155, 502-554, and 845-898 | AAD28543 |
| 2',5'-oligoadenylate synthetase 1A, *Mus musculus* | dsRNA-binding domain: 105-159 | P11928 |
| ADAR1-a (RNA-specific adenosine deaminase), *Homo sapiens* | dsRNA-binding domains: 553-569, 664-680, and 776-792 | U18121 |
| ADAR1 (RNA-specific adenosine deaminase), *Mus musculus* | dsRNA-binding domains: 457-506, 568-617, and 676-741 | NP_062629 | dsRNA binding proteins that contain one or more dsRNA binding domains suitable for use in this invention include, for example and without limitation: 2',5'-oligoadenylate synthetase 100 kDa form, *Homo sapiens* (NCBI Accession #AAD28543); 2',5'-oligoadenylate synthetase 69 and 71 kDa forms, *Homo sapiens* (NCBI Accession #P29728); 2',5'-oligoadenylate synthetase 41 and 46 kDa forms, *Homo sapiens* (NCBI Accession #P00973); 2',5'-oligoadenylate synthetase 1A, *Mus musculus* (NCBI Accession #P11928); 2',5'-oligoadenylate synthetase 1B, *Mus musculus* (NCBI Accession #P29080); 2',5'-oligoadenylate synthetase 2, *Mus musculus*

A pathogen-induced product-detection domain is generally directed to an isolated domain that is capable of recognizing or binding a pathogen-induced product. As used herein, the term pathogen-induced product-detection domain is a region of the molecule that includes at least the minimal region necessary to perform the function of the domain. The pathogen-induced product-detection domain can also be encompassed within a larger or smaller region or structure, but it still retains the pathogen-induced product-detection function of the domain Pathogen-induced product-detection domains can be isolated from naturally-occurring molecules that normally rec.

ognize a pathogen-induced product, such as a cellular protein that is induced to be expressed by a cell in response to a pathogen or pathogen stimulus. Suitable pathogen-induced product-detection domains can be isolated from a wide range of known cellular proteins from a number of different organisms, including for example, humans, non-human primates, rodents, plants, *Drosophila*, yeast, bacteria and the like, as will be appreciated by one of skill in the art. The pathogen-induced product-detection domain can also be synthetically-derived, such as by chemically modifying a naturally-occurring molecule, or otherwise manipulating a naturally-occurring molecule to enhance, optimize, or modify the pathogen-induced product-detection domain, using standard techniques known to those of skill in the art, or alternatively, they can be a synthetic product such as a small molecule or a peptidomimetic. Furthermore, a pathogen-induced product-detection domain can be an antibody (including, for example, antibody fragments, such as Fab, Fab', F(ab')$_2$, and fragments including either a $V_L$ or $V_H$ domain, single chain antibodies, bi-specific, chimeric or humanized antibodies), that recognizes a specific pathogen-induced product.

A pathogen-induced product which can be recognized by a pathogen-induced product-detection domain includes, for example and without limitation, cytokines such as an interferon or interleukin, 2',5'-oligoadenylate, unfolded-protein response or endoplasmic reticulum-associated protein degradation response signaling molecules, stress response or inflammatory response signaling molecules, and apoptosis signaling molecules.

Cytokines such as interferon alpha, interferon beta, or interferon omega are produced by cells in response to a pathogen infection and many genes are responsive to stimulation by such cytokines through suitable inducible promoters, for example and without limitation, promoters that contain one or more interferon-stimulated response elements (ISREs). Examples of suitable promoters are well known to those of skill in the art and include the promoters of the following genes: protein kinase R (K. L. Kuhen and C. E. Samuel (1999) Virology 254, 182-195; H. Tanaka and C. E. Samuel (2000) Gene 246, 373-382); 2',5'-oligoadenylate synthetases (F. Yu, Q. Wang, and G. Floyd-Smith (1999) Gene 237, 177-184; G. Floyd-Smith, Q. Wang, and G. C. Sen (1999) Exp. Cell Res. 246, 138-147; Q. Wang and G. Floyd-Smith (1998) Gene 222, 83-90); Mx genes (T. Ronni et al. (1998) J. Interferon Cytokine Res. 18, 773-781); ADAR1 (C. X. George and C. E. Samuel (1999) Gene 229, 203-213). The ISRE-containing promoter of the Stratagene PathDetect® ISRE vector (Stratagene #219092) is another example of a promoter that can be induced by cytokines such as interferon alpha, interferon beta, or interferon omega. A pathogen-induced product-detection domain can be an ISRE-containing or other suitable promoter as defined supra that is operatively linked to a polynucleotide sequence encoding an effector domain as described herein, the effector domain being one not typically or normally associated with the promoter.

Cytokines such as interferon gamma, interleukin 1, interleukin 2, interleukin 3, interleukin 4, interleukin 5, interleukin 6, interleukin 7, interleukin 9, interleukin 12, or interleukin 15 are produced by cells in response to a pathogen infection, and many genes are responsive to stimulation by such cytokines through suitable inducible promoters, for example, and without limitation, promoters that contain one or more gamma-activated sequences (GASs), GAS-related sequences, or STAT-protein-binding sequences. Examples of suitable promoters are well known to those of skill in the art (T. Kisseleva et al. (2002) Gene 285, 1-24). The GAS-containing promoter of the Stratagene PathDetect® GAS vector (Stratagene #219093) is an example of a promoter that can be induced by cytokines such as interferon gamma. A pathogen-induced product-detection domain can be an GAS-containing promoter, GAS-related sequence containing promoter, STAT protein binding sequence-containing promoter, or other suitable promoter as defined supra that is operatively linked to a polynucleotide sequence encoding an effector domain as described herein, the effector domain being one not typically or normally associated with the promoter.

In another preferred embodiment, the pathogen-induced product-detection domain is a dsRNA-inducible promoter that is responsive to dsRNA-stimulated cellular signaling. In one embodiment, the promoter is operatively linked to a polynucleotide sequence encoding an effector domain as described herein, said effector domain being one not typically or normally associated with said promoter. Examples of suitable promoters will be appreciated by one of skill in the art and include the promoters of the following genes: interferon-beta (R. Lin et al. (2000) Molecular and Cellular Biology 20, 6342-6353); RANTES (R. Lin et al. (2000) Molecular and Cellular Biology 20, 6342-6353); and other interferon genes (R. M. Roberts et al. (1998) J. Interferon Cytokine Res. 18, 805-816).

Optionally, a promoter that is a pathogen-induced product-detection domain can be conditionally-regulated. For example, the promoter can include a control region that is responsive to drug stimulation, such as an antibiotic. Examples of drug-inducible promoters include a tetracycline-inducible or doxycycline-inducible promoter (for example, Clontech pTRE2hyg vector), which is stimulated with the appropriate transcription factor (for example, Clontech TetOn); a synthetic receptor recognition element promoter (for example, Stratagene pEGSH vector) which is responsive to a synthetic ecdysone-inducible receptor (for example, as expressed by the Stratagene pERV3 vector); or an IPTG-inducible promoter (for example, Stratagene pOPI3CAT and pOPRSVI/MCS vectors) which is responsive via a Lac repressor protein.

Alternatively, a pathogen-induced product-detection domain can be a 2',5'-oligoadenylate binding domain, such as, for example, isolated from human Rnase L (NCBI Accession #CAA52920). The 2',5'-oligoadenylate binding domain of human RNase L is approximately amino acids 1-335 (B. Dong and R. H. Silverman (1997) *Journal of Biological Chemistry* 272, 22236-22242). Rnase L is expressed in a cell in response to a pathogen infection and it contains a 2',5'-oligoadenylate binding domain which can be isolated using standard techniques, and used as a pathogen-induced product-detection domain in the invention. Furthermore, a single-chain antibody or other molecular structure that binds to 2',5'-oligoadenylate can be used as a pathogen-induced product-detection domain.

Further pathogen-induced product-detection domains of the invention include apoptosis-activated molecules, for example, and without limitation, an apoptosis-inducible promoter isolated from one or more of the following genes: DIABLO/Smac (P. G. Ekert et al. (2001) J. Cell Biology 152, 483-490; S. M. Srinivasula et al. (2001) Nature 410, 112-116); Fas/APO-1/CD95 (D. Munsch et al. (2000) J. Biological Chemistry 275, 3867-3872; M. Mueller et al. (1998) J. Exp. Med. 188, 2033-2045); Apaf-1 (A. Fortin et al. (2001) J. Cell Biology 155, 207-216); Bax (E. C. Thomborrow and J. J. Manfredi (2001) J. Biological Chemistry 276, 15598-15608); or other genes whose expression is induced in apoptosis, as will be appreciated by one of skill in the art. Another example of an apoptosis-inducible promoter is the p53-binding-site-containing promoter of the Stratagene PathDetect® p53 vector (Stratagene #219083).

Still other pathogen-induced product-detection domains of the invention include promoters that are activated during an unfolded-protein response or endoplasmic reticulum-associated protein degradation responses, for example and without limitation, a suitable promoter containing an endoplasmic reticulum stress response element (ERSE: C. Patil and P. Walter (2001) Current Opinion in Cell Biology 13, 349-356; K. Lee et al. (2002) Genes & Development 16, 452-466; S. Oyadomari et al. (2002) Apoptosis 7, 335-345), ATF6-binding motif (K. Lee et al. (2002) Genes & Development 16, 452-466), or amino-acid response element (AARE: T. Okada et al. (2002) Biochem. J. 366, 585-594), or a promoter from a gene whose expression is induced during unfolded-protein responses or endoplasmic reticulum-associated protein degradation responses, as will be appreciated by one of skill in the art.

Other pathogen-induced product-detection domains of the invention include promoters that are activated during stress responses, for example and without limitation, a promoter containing a heat shock element (HSE: S. Ahn et al. (2001) Genes & Development 15, 2134-2145; A. Mathew et al. (2001) Mol. Cell. Biol. 21, 7163-7171), a promoter from hsp70 or hsp90 genes, or a promoter from another gene whose expression is induced during stress responses, as will be appreciated by one of skill in the art.

Still other pathogen-induced product-detection domains of the invention include promoters that are activated during inflammatory responses, for example and without limitation, a promoter containing an NF-kappa-B binding site (F. E. Chen and G. Ghosh (1999) Oncogene 18, 6845-6852; H. L. Pahl (1999) Oncogene 18, 6853-6866), the NF-kappa-B-inducible promoter of the Stratagene PathDetect® NF-kappaB vector (Stratagene #219077), or a promoter from another gene whose expression is induced during inflammatory responses, as will be appreciated by one of skill in the art.

Other pathogen-induced product-detection domains can be isolated from molecules that are activated or inhibited during apoptosis or other forms of pathogen-triggered cell death (A. Muller and T. Rudel (2001) Int. J. Med. Microbiol. 291, 197-207; C. A. Benedict et al. (2002) Nature Immunology 3, 1013-1018; V. T. Heussler et al. (2001) International Journal for Parasitology 31, 1166-1176; L.-Y. Gao and Y. A. Kwaik (2000) Microbes and Infection 2, 1705-1719; L.-Y. Gao and Y. A. Kwaik (2000) Trends Microbiol. 8, 306-313; K. C. Zimmermann et al. (2001) Pharmacology & Therapeutics 92, 57-70; H. R. Stennicke and G. S. Salvesen (2000) Biochimica et Biophysica Acta 1477, 299-306; S. Nagata (1997) Cell 88, 355-365; Z. Song & H. Steller (1999) Trends Cell Biol. 9, M49-52), for example and without limitation: p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); Bcl-2 (K. C. Zimmermann et al. (2001) Pharmacology & Therapeutics 92, 57-70; inhibitor of apoptosis proteins (IAPs: H. R. Stennicke et al. (2002) TRENDS in Biochemical Sciences 27, 94-101; S. M. Srinivasula et al. (2001) Nature 410, 112-116); mitochondrial cytochrome c (K. C. Zimmermann et al. (2001) Pharmacology & Therapeutics 92, 57-70; S. B. Bratton et al. (2001) EMBO Journal 20, 998-1009); apoptotic protease activating factor 1 (Apaf-1: *Homo sapiens*, #NM_013229, NM_001160; *Mus musculus*, #NP_033814); Fas ligand (*Homo sapiens*, #D38122; *Mus musculus* U58995); Fas/CD95 (*Homo sapiens*, #AAC16236, AAC16237; *Mus musculus*, #AAG02410); tumor necrosis factor alpha (TNF-α: *Homo sapiens*, #CAA01558, CAB63904, CAB63905; *Mus musculus*, #CAA68530); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); perforin (*Homo sapiens*, #CAA01809, NP_005032; *Mus musculus*, #CAA42731, CAA35721, AAB01574); granzyme B (*Homo sapiens*, #AAH30195, NP_004122; *Mus musculus*, #AAH02085, NP_038570); Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); calpains (T. Lu et al., (2002) Biochimica et Biophysica Acta 1590, 16-26); caspase-activated DNase (CAD: *Homo sapiens*, #AB013918; *Mus musculus*, #AB009377); or inhibitor of caspase-activated DNase (ICAD: *Mus musculus*, #AB009375, AB009376). A pathogen-induced product-detection domain can also be isolated from a molecule that binds to, is activated by, or is inhibited by natural apoptosis or cell death signaling molecules such as those listed supra.

Other pathogen-detection or pathogen-induced product-detection domains can be isolated from molecules that are activated stimulated or inhibited during interferon-related or cytokine-related responses (T. Kisseleva et al. (2002) Gene 285, 1-24; A. Garcia-Sastre (2002) Microbes and Infection 4, 647-655; C. E. Samuel (2001) Clinical Microbiology Reviews 14, 778-809; S. Landolfo et al. (1995) Pharmacol. Ther. 65, 415-442), for example and without limitation: interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439; *Mus musculus*, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12:

Homo sapiens, #NM_000882, NM_002187; Mus musculus, #NM_008351, NM_008352); interleukin 15 (IL-15: Homo sapiens, #NM_172174, NM_172175, NM_000585; Mus musculus, #NM_008357); cytokine receptors and related signaling molecules (W. E. Paul (ed.), Fundamental immunology (4th ed., Lippincott-Raven, Philadelphia, 1999), Chapters 21 and 22); interferon type I receptor subunit 1 (IFNAR1: Homo sapiens, #NM_000629; Mus musculus, #NM_010508); interferon type I receptor subunit 2 (IFNAR2: Homo sapiens, #NM_000874; Mus musculus, #NM_010509); janus kinase 1 (JAK1: Homo sapiens, #NP_002218; Mus musculus, #NP_666257); janus kinase 2 (JAK2: Homo sapiens, #AAC23653, AAC23982, NP_004963; Mus musculus, #NP_032439, AAN62560); JAK3; Tyk2; signal transducer and activator of transcription 1 (STAT1: Homo sapiens, #NM_007315, NM_139266; Mus musculus, #U06924); signal transducer and activator of transcription 2 (STAT2: Homo sapiens, #NM_005419; Mus musculus, AF206162); STAT3; STAT4; STAT5; STAT6; IRF9/interferon-stimulated gene factor 3 gamma (ISGF3 gamma: Homo sapiens, #Q00978, NM_006084; Mus musculus, #NM_008394) interferon regulatory factor 1 (IRF1: Homo sapiens, #NM_002198, P10914; Mus musculus, #NM_008390); interferon regulatory factor 3 (IRF3: Homo sapiens, #NM_001571, Z56281; Mus musculus, #NM_016849, U75839, U75840); interferon regulatory factor 5 (IRF5: Homo sapiens, #Q13568, U51127; Mus musculus, #AAB81997, NP_036187); interferon regulatory factor 6 (IRF6: Homo sapiens, #AF027292, NM_006147; Mus musculus, #U73029); interferon regulatory factor 7 (IRF7: Homo sapiens, #U53830, U53831, U53832, AF076494, U73036; Mus musculus, #NM_016850, U73037); IRF8; protein kinase R (PKR: Homo sapiens, #AAC50768; Mus musculus, #Q03963; S. Nanduri et al. (1998) EMBO J. 17, 5458-5465); eukaryotic translation initiation factor 2 alpha (eIF-2alpha: Homo sapiens, #NP_004085); p58 (Homo sapiens, #NP_006251); 2',5'-oligoadenylate synthetases (Homo sapiens forms including #P00973, P29728, AAD28543; Mus musculus forms including P11928; S. Y. Desai et al. (1995) J. Biol. Chem. 270, 3454-3461); 2',5'-oligoadenylate (C. E. Samuel (2001) Clinical Microbiology Reviews 14, 778-809); RNase L (Homo sapiens, #CAA52920); promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (Homo sapiens, #U18121; Mus musculus, #NP_062629); Mx1 (Homo sapiens, #NM_002462); or Mx2 (Homo sapiens, #NM_002463). A pathogen-induced product-detection domain can also be isolated from a molecule that binds to, is activated by, or is inhibited by natural interferon-response-related signaling or cytokine response-related molecules such as those listed supra.

Other pathogen-detection domains or pathogen-induced product-detection domains can be isolated from toll-like receptors, their accessory molecules, or molecules that they activate directly or indirectly, (S. Akira (2003) Current Opinion in Immunology 15, 5-11; T. Vasselon and P. A. Detmers (2002) Infection and Immunity 70, 1033-1041; C. A. Janeway Jr. and R. Medzhitov (2002) Annu. Rev. Immunol. 20, 197-216), including for example and without limitation: toll-like receptor 1, Homo sapiens (NCBI Accession #NP_003254, AAC34137); toll-like receptor 2, Homo sapiens (NCBI Accession #AAH33756, AAM23001, AAC34133); toll-like receptor 3, Homo sapiens (NCBI Accession #AAC34134, NP_003256); toll-like receptor 4, Homo sapiens (NCBI Accession #AAC34135, AAF89753, AAF07823, AAF05316); toll-like receptor 5, Homo sapiens (NCBI Accession #AAC34136, BAB43955); toll-like receptor 6, Homo sapiens (NCBI Accession #NP_006059, BAA78631); toll-like receptor 7, Homo sapiens (NCBI Accession #AAF60188, AAF78035, NP_057646, AAH33651); toll-like receptor 8, Homo sapiens (NCBI Accession #AAF64061, AAF78036); toll-like receptor 9 Homo sapiens (NCBI Accession # AAG01734, AAG01735, AAG01736, BAB19259); toll-like receptor 10, Homo sapiens (NCBI Accession #AAK26744, NP_112218); CD14, Homo sapiens (NCBI Accession #AAH10507, AAL02401, CAD36116); MD-2, Homo sapiens (NCBI Accession #NP_056179, BAA78717, AAH20690); MD-1, Homo sapiens (NCBI Accession #AAC98152, NP_004262); RP105, Homo sapiens (NCBI Accession #BAA12019); toll/IL-1 receptor domain containing adaptor protein (TIRAP), Homo sapiens (NCBI Accession #NP_683708, NP_443119, AAL05627); MyD88, Homo sapiens (NCBI Accession #AAB49967, AAC50954); IL-IR activated kinase 4 (IRAK-4), Homo sapiens (NCBI Accession #CAC60090); TNF-receptor-associated factor 6 (TRAF6), Homo sapiens (NCBI Accession #NP_665802, NP_004611); toll-like receptor 1, Mus musculus (NCBI Accession #AAG35062, AAG37302, NP_109607); toll-like receptor 2, Mus musculus (NCBI Accession #AAD46481, AAF04277, AAD49335, NP_036035, AAF28345); toll-like receptor 3, Mus musculus (NCBI Accession #AAK26117, AAL27007, NP_569054); toll-like receptor 4, Mus musculus (NCBI Accession #AAD29272, AAF04278, AAF05317, NP_067272, AAH29856); toll-like receptor 5, Mus musculus (NCBI Accession #AAF65625, NP_058624); toll-like receptor 6, Mus musculus (NCBI Accession #BAA78632, AAG38563, NP_035734); toll-like receptor 7, Mus musculus (NCBI Accession #AAK62676, NP_573474, AAL73191, AAL73192); toll-like receptor 8, Mus musculus (NCBI Accession #NP_573475, AAK62677); toll-like receptor 9, Mus musculus (NCBI Accession #BAB19260, AAK29625, AAK28488, NP_112455); CD14, Mus musculus (NCBI Accession #CAA32166, BAB68578, NP_033971); MD-2, Mus musculus (NCBI Accession #BAA93619); MD-1, Mus musculus (NCBI Accession #BAA32399); RP105, Mus musculus (NCBI Accession #BAA07043); toll/IL-1 receptor domain containing adaptor protein (TIRAP), Mus musculus (NCBI Accession #AAL05628, NP_473437); MyD88, Mus musculus (NCBI Accession #AAC53013); IL-IR activated kinase 4 (IRAK-4), Mus musculus (NCBI Accession #AAM15773, NP_084202); and TNF-receptor-associated factor 6 (TRAF6), Mus musculus (NCBI Accession #BAA12705, NP_033450). A pathogen-induced product-detection domain can also be isolated from a molecule that binds to, is activated by, or is inhibited by toll-like-receptor-pathway-related molecules.

Still other pathogen-detection domains or pathogen-induced product-detection domains can be isolated from nucleotide-binding oligomerization domain (NOD) proteins, or nucleotide-binding-domain (NBD)proteins, or nucleotide-binding-site (NBS)) proteins, or molecules that they activate directly or indirectly, (N. Inohara et al. (2002) Current Opinion in Microbiology 5, 76-80; S. E. Girardin et al. (2002) TRENDS in Microbiology 10, 193-199; J. A. Harton et al. (2002) Journal of Immunology 169, 4088-4093; N. Inohara et al. (2000) Journal of Biological Chemistry 275, 27823-27831), including but not limited to:Nod1/CARD4 (Homo sapiens, #AAD28350, AAD43922; N. Inohara et al. (1999) Journal of Biological Chemistry 274, 14560-14567); Nod2, (Homo sapiens, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM-021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH01140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876). A pathogen-induced product-detection domain can also be isolated from a molecule that binds to, is activated by, or is inhibited by NOD protein pathway-related molecules.

Other pathogen-detection domains or pathogen-induced product-detection domains can also be isolated from pentraxins or molecules that they activate directly or indirectly, (H. Gewurz et al. (1995) Current Opinion in Immunology 7, 54-64), including, but not limited to, C-reactive protein (CRP), *Homo sapiens* (NCBI Accession #1GNHA, 1GNHB, 1GNHC, 1GNHD, 1GNHE, 1GNHF, 1GNHG, 1GNHH, 1GNHI, 1GNHJ); C-reactive protein (CRP), *Mus musculus* (NCBI Accession #CAA31928, NP 031794); serum amyloid P component (SAP), *Homo sapiens* (NCBI Accession #1SACA, 1SACB, 1SACC, 1SACD, 1SACE); and serum amyloid P component (SAP), *Mus musculus* (NCBI Accession #NP_035448, CAA34774). A pathogen-induced product-detection domain can also be isolated from a molecule that binds to, is activated by, or is inhibited by pentraxin pathway-related molecules.

Other pathogen-detection domains or pathogen-induced product-detection domains can be isolated from collectins or molecules that they activate directly or indirectly, (M. Gadjeva et al. (2001) Current Opinion in Immunology 13, 74-78; U. L. Holmskov (2000) APMIS Suppl. 100, 1-59), including for example and without limitation, mannan/mannose binding lectin (MBL), *Homo sapiens* (NCBI Accession #AAK52907, CAB56120, CAB56044); mannan/mannose binding lectin (MBL), *Mus musculus* (NCBI Accession #NP_034905, NP_034906); MBL-associated serine protease 1 (MASP1), *Homo sapiens* (NCBI Accession #NP_001870, NP_624302); MBL-associated serine protease 2 (MASP2), *Homo sapiens* (NCBI Accession #NP_006601, NP_631947, AAG50274, BAA85659); MBL-associated serine protease 1 (MASP1), *Mus musculus* (NCBI Accession #XP_193834); MBL-associated serine protease 2 (MASP2), *Mus musculus* (NCBI Accession #BAA34674, CAB65247, CAB65250); MBL-associated serine protease 3 (MASP3), *Mus musculus* (NCBI Accession #BAB69688); surfactant protein A (SP-A), *Homo sapiens* (NCBI Accession #NP_005402, NP_008857); surfactant protein D (SP-D), *Homo sapiens* (NCBI Accession #CAA46152, NP_003010); surfactant protein D (SP-D), *Mus musculus* (NCBI Accession #AAF15277); surfactant protein D (SP-D), *Bos taurus* (NCBI Accession #CAA53510, S33603); conglutinin, *Bos taurus* (NCBI Accession #CAA50665, BAA03170); collectin-43 (CL-43), *Bos taurus* (NCBI Accession #CAA53511, P42916, A53570); collectin-L1, *Mus musculus* (NCBI Accession #BAC53954); and collectin placenta 1 (CL-P1), *Homo sapiens* (NCBI Accession #AB005145). A pathogen-induced product-detection domain can also be isolated from a molecule that binds to, is activated by, or is inhibited by collectin pathway-related molecules.

Still other pathogen-detection domains or pathogen-induced product-detection domains can be isolated from mannose receptors or molecules that they activate directly or indirectly, (L. East and C. M. Isacke (2002) Biochimica et Biophysica Acta 1572, 364-386; S. Zamze et al. (2002) Journal of Biological Chemistry 277, 41613-41623), including for example and without limitation, mannose receptor (MR), *Homo sapiens*(NCBI Accession #NM_002438); and mannose receptor (MR), *Mus musculus* (NCBI Accession #CAA78028, NP_032651, NP_032652). A pathogen-induced product-detection domain can also be isolated from a molecule that binds to, is activated by, or is inhibited by mannose receptor pathway-related molecules.

Other pathogen-detection domains or pathogen-induced product-detection domains can also be isolated from scavenger receptors or molecules that they activate directly or indirectly, (L. Peiser et al. (2002) Current Opinion in Immunology 14, 123-128; A. Brannstrom et al. (2002) Biochemical and Biophysical Research Communications 290, 1462-1469), including for example and without limitation, scavenger receptor A I (SR-A I), *Homo sapiens* (NCBI Accession #D90187); scavenger receptor A II (SR-A II), *Homo sapiens* (NCBI Accession #D90188); scavenger receptor A I (SR-A I), *Mus musculus* (NCBI Accession #L04274); scavenger receptor A II (SR-A II), *Mus musculus* (NCBI Accession #L04275); macrophage receptor with collagenous structure (MARCO), *Homo sapiens* (NCBI Accession #NP_006761); macrophage receptor with collagenous structure (MARCO), *Mus musculus* (NCBI Accession #NP_034896); scavenger receptor with C-type lectin I (SR-CL I), *Homo sapiens* (NCBI Accession #BAB39147); scavenger receptor with C-type lectin II (SR-CL II), *Homo sapiens* (NCBI Accession #BAB39148); and scavenger receptor with C-type lectin (SR-CL), *Mus musculus* (NCBI Accession #BAB82497). A pathogen-induced product-detection domain can also be isolated from a molecule that binds to, is activated by, or is inhibited by scavenger-receptor-pathway-related molecules.

Other pathogen-detection domains or pathogen-induced product-detection domains can be isolated from molecules that initiate, signal, or detect immune-related responses (W. E. Paul (ed.), Fundamental Immunology (4th ed., Lippincott-Raven, Philadelphia, 1999); M. T. M. Vossen et al. (2002) Immunogenetics 54, 527-542), for example and without limitation the following molecules or DNA or RNA encoding them: MHC Class I; MHC Class II; antibodies; single-chain antibodies; T cell receptors; Fc receptors; NK cell activation receptors (including but not limited to NKp46, Ly49H, and NKG2D; A. Diefenbach and D. H. Raulet (2003) Current Opinion in Immunology 15, 37-44; A. R. French and W. M. Yokoyama (2003) Current Opinion in Immunology 15, 45-51); NK cell inhibitory receptors; receptor-associated tyrosine kinases; or phospholipase C. A pathogen-detection domain or pathogen-induced product-detection domain can also be isolated from a molecule that binds to, is activated by, or is inhibited by immune-response-pathway-related molecules.

Other pathogen-detection domains or pathogen-induced product-detection domains can be isolated from molecules that are activated or inhibited during unfolded protein response-related or endoplasmic reticulum-associated protein degradation-related responses (C. Patil and P. Walter (2001) Current Opinion in Cell Biology 13, 349-356; K. Lee et al. (2002) Genes & Development 16, 452-466; S. Oyadomari et al. (2002) Apoptosis 7, 335-345), for example and without limitation: BiP/GRP78/SHPA5 (*Homo sapiens*, #AJ271729, AF216292, X87949, NM_005347; *Mus musculus*, #NM_022310); PKR-like endoplasmic reticulum kinase (PERK: *Homo sapiens*, #NP_004827; *Mus musculus*, #AAD03337, NP_034251); IRE1 alpha (*Homo sapiens*, #AF059198; *Mus musculus*, #AB031332, AF071777); IRE1 beta (*Homo sapiens*, #AB047079); RNA for IRE1 alpha or IRE1 beta (W. Tirasophon et al. (2000) Genes & Development 14, 2725-2736); p58 (*Homo sapiens*, #NP_006251; W. Yan et al. (2002) Proc. Natl. Acad. Sci. USA 99, 15920-15925); activating transcription factor 4 (ATF4: *Homo sapiens*, #NM_001675; *Mus musculus*, #NM_009716); activating transcription factor 6 alpha or beta (ATF6 alpha or beta: *Homo sapiens*, #NM_007348, AF005887, AB015856; *Mus musculus*, #XM_129579); X-box binding protein 1 (XBP1: *Homo sapiens*, #AB076383, AB076384; *Mus musculus*, #AF443192, AF027963, NM_013842); XBP1 RNA (K. Lee et al. (2002) Genes & Development 16, 452-466; H. Yoshida et al. (2001) Cell 107, 881-891); CHOP-10/GADD153/DDIT3 (*Homo sapiens*, #NM_004083; *Mus musculus*, #X67083, NM_007837); site-1 protease (S1P: *Homo sapiens*, #NM_003791; *Mus musculus*, #NM_019709); site-2 protease (S2P: *Homo sapiens*, #NM_015884); presenilin-1 (*Homo sapiens*, #AH004968, AF416717; *Mus musculus*, #BC030409, NM_008943, AF149111); TNF receptor-associated factor 2 (TRAF2: *Homo sapiens*, #NM_021138, NM_145718, *Mus musculus*, #XM_203851, XM_130119, L35303); cJUN NH2-terminal kinases (JNKs: S. Oyadomari et al. (2002) Apoptosis 7, 335-345); or eukaryotic translation initiation factor 2 alpha (eIF-2alpha: *Homo sapiens*, #NP_004085). A pathogen-detection domain or pathogen-induced product-detection domain can also be isolated from a molecule that binds to, is activated by, or is inhibited by natural unfolded protein response-related or endoplasmic reticulum-associated protein degradation-related molecules such as those listed supra.

Still other pathogen-induced product-detection domains of the invention include a promoter that is activated or inhibited during an unfolded-protein response or endoplasmic-reticulum-associated-protein-degradation response, for example and without limitation, an isolated promoter containing an endoplasmic reticulum stress response element (ERSE: C. Patil and P. Walter (2001) Current Opinion in Cell Biology 13, 349-356; K. Lee et al. (2002) Genes & Development 16, 452-466; S. Oyadomari et al. (2002) Apoptosis 7, 335-345), ATF6-binding motif (K. Lee et al. (2002) Genes & Development 16, 452-466), or amino-acid response element (AARE: T. Okada et al. (2002) Biochem. J. 366, 585-594), or a promoter from a gene whose expression is induced or repressed during an unfolded-protein response or endoplasmic-reticulum-associated-protein-degradation response, as will be appreciated by one of skill in the art.

Other pathogen-detection domains or pathogen-induced product-detection domains can be isolated from molecules that are activated or inhibited during a stress or inflammatory response (R. I. Morimoto and M. G. Santoro (1998) Nature Biotech. 16, 833-838; R. I. Morimoto (1998) Genes & Dev. 12, 3788-3796; M. G. Santoro (2000) Biochem. Pharmacol. 59, 55-63; A. De Marco et al. (1998) Eur. J. Biochem. 256, 334-341; C. Conti et al. (1999) Antimicrobial Agents and Chemotherapy 43, 822-829; M. G. Santoro (1996) EXS 77, 337-357; E. A. A. Nollen and R. I. Morimoto (2002) Journal of Cell Science 115, 2809-2816; J. Hiscott et al. (2001) J. Clinical Investigation 107, 143-151; E. N. Hatada et al. (2000) Curr. Opin. Immunol. 12, 52-58; T. Wang et al. (2002) Int. Immunopharmacol. 2, 1509-1520; X. Li and G. R. Stark (2002) Exp. Hematol. 30, 285-296; Z. Sun and R. Andersson (2002) Shock 18, 99-106; H. L. Pahl (1999) Oncogene 18, 6853-6866; F. Mercurio and A. M. Manning Oncogene 18, 6163-6167)), for example and without limitation: heat shock protein 70 or related proteins (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM_015765, NM_010481, NM_008301, M76613); Hsp90 (*Homo sapiens*, #M16660, NM_005348, NM_007355); Hsp40/Hdj-1 (*Homo sapiens*, #X62421, NM_006145, NM_005880); Hsc70 (*Homo sapiens*, #AF352832); Hsp47/CBP-2 (*Homo sapiens*, #D83174); cdc48 (S. Thoms (2002) FEBS Lett. 520, 107-110); Bip/GRP78; Hsp60 (*Homo sapiens*, #NM_002156); Hsp100 (*Homo sapiens*, #NM_006660); Alpha-A-crystallin (*Homo sapiens*, #NM_000394); Alpha-B-crystallin (*Homo sapiens*, #NM_001885); Hsp27-1 (*Homo sapiens*, #NM_001540); Hsp27-2 (*Homo sapiens*, #XM_012054); heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131); heat shock factor 2 (HSF2: *Homo sapiens*, #NM_004506; *Mus musculus*, #X61754, AH007205, NM_008297); heat shock factor 3 (HSF3: L. Pirkkala et al. (2001) FASEB J. 15, 1.118-1131); heat shock factor 4 (HSF4: *Homo sapiens*, #NM_001538, D87673, AB029348; *Mus musculus*, #AF160965, AF160966, AB029349, AB029350); heat shock factor binding protein 1 (HSBP1: *Homo sapiens*, #NM_001537, BC007515, AF068754); heat shock factor 2 binding protein (HSF2BP: *Homo sapiens*, #NM_007031); RelA/p65 (*Homo sapiens*, #NM_021975, Z22948, L19067; *Mus musculus*, #NM_009045, AF199371); RelB (*Homo sapiens*, #NM_006509; *Mus musculus*, #NM_009046, M83380); c-Rel (*Homo sapiens*, #X75042, NM_002908; *Mus musculus*, #NM_009044, X15842); p50/p105/NF-kappa B 1 (*Homo sapiens*, #NM_003998, S76638, AF213884, AH009144; *Mus musculus*, #NM_008689, AK052726, M57999); p52/p100/NF-kappa B 2 (*Homo sapiens*, #NM_002502; *Mus musculus*, #AF155372, AF155373, NM_019408); inhibitors of kappa B (I kappa B: *Homo sapiens*, #AY033600, NM_020529; S. Ghosh and M. Karin (2002) Cell 109, S81-S96); IKK1/I kappa B kinase alpha (IKK alpha: *Homo sapiens*, # AF009225, AF080157); IKK2/I kappa B kinase beta (IKK beta: *Homo sapiens*, #AF080158; *Mus musculus*, #AF026524, AF088910); NEMO/I kappa B kinase gamma (IKK gamma: *Homo sapiens*, #AF261086, AF091453; *Mus musculus*, #AF069542). A pathogen detection domain or pathogen-induced product-detection domain can also be isolated from a molecule that binds to, is activated by, or is inhibited by a stress response-related or inflammatory response-related molecule such as those listed supra.

Still other pathogen-induced product-detection domains of the invention include promoters that are activated or inhibited during stress or inflammatory responses, for example and without limitation, a promoter containing a heat shock element (HSE: S. Ahn et al. (2001) Genes & Development 15, 2134-2145; A. Mathew et al. (2001) Mol. Cell. Biol. 21, 7163-7171) or NF-kappa-B binding site (F. E. Chen and G. Ghosh (1999) Oncogene 18, 6845-6852; H. L. Pahl (1999) Oncogene 18, 6853-6866), a promoter from hsp70 or hsp90 genes, or a promoter from another gene whose expression is induced or repressed during stress or inflammatory responses as will be appreciated by one of skill in the art.

Other pathogen-detection domains or pathogen-induced product-detection domains can be isolated from complement pathway-related molecules (W. E. Paul (ed.), Fundamental Immunology (4th ed., Lippincott-Raven, Philadelphia, 1999), Chapter 29; M. K. Pangburn et al. (2000) Journal of Immunology 164, 4742-4751), for example and without limitation: C3 alpha, C3 beta, factor B, factor D, properdin, C1q, C1r, C1s, C4, C2, C5, C6, C7, C8, C9, factor I, factor H, C1-INH, C4 bp, S protein, clusterin, carboxypeptidase N, FHL-1, FHR-1, FHR-2, FHR-3, FHR-4, CR1, or DAF. A pathogen detection domain or pathogen-induced product-detection domain can also be isolated from a molecule that binds to, is activated by, or is inhibited by natural complement pathway-related molecules such as those listed supra.

Effector domains of this invention can mediate, either directly or indirectly, a wide range of effector functions. These include, for example and without limitation, one or more of the following responses: (1) an interferon response; (2) an apoptosis response; (3) stress response; (4) an enhanced immune response; (5) the expression of a double-stranded RNase; (6) inhibition of nuclear localization of targets; (7) inhibition of endosome function or activity; and other anti-pathogen responses.

As used herein, the effector domain is a region of the molecule that includes at least the minimal region necessary to perform the described effector function of the domain. The effector domain can also be encompassed within a larger or smaller region or structure, but it still retains the effector function of the domain.

More particularly, an effector domain as used herein is a molecule that binds to or acts on one or more of the following: a pathogen (for example: a peptide containing amino acids 119-136 of hamster prion protein that binds to and inhibits a pathogenic prion); a pathogen component (for example, a molecule that binds to a viral late domain motif, thereby inhibiting viral budding or release, as described herein); a molecule produced or induced by a pathogen (for example, an RNase III that degrades dsRNA produced in a virus-infected cell, as described herein); a natural anti-pathogen molecule (for example, a molecule that activates caspases in an infected cell, thereby killing said cell and preventing further spread of the infection); a component that is naturally occurring in a cell or organism and that directly or indirectly activates or inhibits an anti-pathogen molecule, or a component that is naturally occurring within a cell or organism and that aids a pathogen or pathogenic effect (for example, a molecule that binds to vacuolar ATPase and inhibits acidification of endosomes in a cell, thereby inhibiting infection of the cell by a virus, as described herein). By binding or acting as described supra and herein, the effector domain exerts an anti-pathogen effect, for example, and without limitation, by performing one or more of the following functions: inhibiting infection of a cell or organism by a pathogen; inhibiting replication of a pathogen; destroying or neutralizing a pathogen; or making a pathogen more vulnerable to other therapeutic anti-pathogen molecules or to natural anti-pathogen molecules. An effector domain can belong to multiple categories described herein.

Effector domains can be isolated from naturally-occurring molecules that normally mediate the function of an effector domain as described herein, such as a cellular protein. Effector domains can be isolated from a wide range of known cellular proteins from a number of different organisms, including for example, humans, non-human primates, rodents, plants, Drosophila, yeast, bacteria and the like, as will be appreciated by one of skill in the art. The effector domain can also be synthetically-derived, such as by chemically modifying a naturally-occurring molecule, or otherwise manipulating a naturally-occurring molecule to enhance, optimize, or modify the effector domain, using standard techniques known to those of skill in the art. Alternatively, an effector domain can be a synthetic product such as a small molecule or a peptidomimetic. Furthermore, an effector domain can be an antibody (including, for example, antibody fragments, such as Fab, Fab', F(ab')$_2$, and fragments including either a $V_L$ or $V_H$ domain, single chain antibodies, bi-specific, chimeric or humanized antibodies), that performs the function of an effector domain.

Effector domains can be isolated from molecules that execute, stimulate, or inhibit apoptosis or other forms of cell death (A. Muller and T. Rudel (2001) Int. J. Med. Microbiol. 291, 197-207; C. A. Benedict et al. (2002) Nature Immunology 3, 1013-1018; V. T. Heussler et al. (2001) International Journal for Parasitology 31, 1166-1176; L.-Y. Gao and Y. A. Kwaik (2000) Microbes and Infection 2, 1705-1719; L.-Y. Gao and Y. A. Kwaik (2000) Trends Microbiol. 8, 306-313; K. C. Zimmermann et al. (2001) Pharmacology & Therapeutics 92, 57-70; H. R. Stennicke and G. S. Salvesen (2000) Biochimica et Biophysica Acta 1477, 299-306; S. Nagata (1997) Cell 88, 355-365; Z. Song & H. Steller (1999) Trends Cell Biol. 9, M49-52), for example and without limitation, the following molecules or DNA or RNA encoding them: p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); Bcl-2 (K. C. Zimmermann et al. (2001) Pharmacology & Therapeutics 92, 57-70); inhibitor of apoptosis proteins (IAPs: H. R. Stennicke et al. (2002) TRENDS in Biochemical Sciences 27, 94-101; S. M. Srinivasula et al. (2001) Nature 410, 112-116); mitochondrial cytochrome c (K. C. Zimmermann et al. (2001) Pharmacology & Therapeutics 92, 57-70; S. B. Bratton et al. (2001) EMBO Journal 20, 998-1009); apoptotic protease activating factor 1 (Apaf-1: *Homo sapiens*, #NM_013229, NM_001160; *Mus musculus*, #NP_033814); Fas ligand (*Homo sapiens*, #D38122; *Mus musculus* U58995); Fas/CD95 (*Homo sapiens*, #AAC16236, AAC16237; *Mus musculus*, #AAG02410); tumor necrosis factor alpha (TNF-a: *Homo sapiens*, #CAA01558, CAB63904, CAB63905; *Mus musculus*, #CAA68530); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); perforin (*Homo sapiens*, #CAA01809, NP_005032; *Mus musculus*, #CAA42731, CAA35721, AAB01574); granzyme B (*Homo sapiens*, #AAH30195, NP_004122; *Mus musculus*, #AAH02085, NP_038570); Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*,

BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); calpains (T. Lu et al., (2002) Biochimica et Biophysica Acta 1590, 16-26); caspase-activated DNase (CAD: *Homo sapiens*, #AB013918; *Mus musculus*, #AB009377); or inhibitor of caspase-activated DNase (ICAD: *Mus musculus*, #AB009375, AB009376). An effector domain can also be isolated from a molecule that binds to, stimulates, or inhibits natural apoptosis or cell death signaling molecules such as those listed supra.

Other effector domains can be isolated from molecules that execute, stimulate, or inhibit interferon-related or cytokine-related responses (T. Kisseleva et al. (2002) Gene 285, 1-24; A. Garcia-Sastre (2002) Microbes and Infection 4, 647-655; C. E. Samuel (2001) Clinical Microbiology Reviews 14, 778-809; S. Landolfo et al. (1995) Pharmacol. Ther. 65, 415-442), for example and without limitation, the following molecules or DNA or RNA encoding them: interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439; *Mus musculus*, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12: *Homo sapiens*, #NM_000882, NM_002187; *Mus musculus*, #NM_008351, NM_008352); interleukin 15 (IL-15: *Homo sapiens*, #NM_172174, NM_172175, NM_000585; *Mus musculus*, #NM_008357); cytokine receptors and related signaling molecules (W. E. Paul (ed.), Fundamental Immunology (4th ed., Lippincott-Raven, Philadelphia, 1999), Chapters 21 and 22); interferon type I receptor subunit 1 (IFNAR1: *Homo sapiens*, #NM_000629; *Mus musculus*, #NM_010508); interferon type I receptor subunit 2 (IFNAR2: *Homo sapiens*, #NM_000874; *Mus musculus*, #NM_010509); janus kinase 1 (JAK1: *Homo sapiens*, #NP_002218; *Mus musculus*, #NP_666257); janus kinase 2 (JAK2: *Homo sapiens*, #AAC23653, AAC23982, NP_004963; *Mus musculus*, #NP_032439, AAN62560); JAK3; Tyk2; signal transducer and activator of transcription 1 (STAT1: *Homo sapiens*, #NM_007315, NM_139266; *Mus musculus*, #U06924); signal transducer and activator of transcription 2 (STAT2: *Homo sapiens*, #NM_005419; *Mus musculus*, AF206162); STAT3; STAT4; STAT5; STAT6; IRF9/interferon-stimulated gene factor 3 gamma (ISGF3 gamma: *Homo sapiens*, #Q00978, NM_006084; *Mus musculus*, #NM_008394) interferon regulatory factor 1 (IRF1: *Homo sapiens*, #NM_002198, P10914; *Mus musculus*, #NM_008390); interferon regulatory factor 3 (IRF3: *Homo sapiens*, #NM_001571, Z56281; *Mus musculus*, #NM_016849, U75839, U75840); interferon regulatory factor 5 (IRF5: *Homo sapiens*, #Q13568, U51127; *Mus musculus*, #AAB81997, NP_036187); interferon regulatory factor 6 (IRF6: *Homo sapiens*, #AF027292, NM_006147; *Mus musculus*, #U73029); interferon regulatory factor 7 (IRF7: *Homo sapiens*, #U53830, U53831, U53832, AF076494, U73036; *Mus musculus*, #NM_016850, U73037); protein kinase R (PKR: *Homo sapiens*, #AAC50768; *Mus musculus*, #Q03963; S. Nanduri et al. (1998) EMBO J. 17, 5458-5465); eukaryotic translation initiation factor 2 alpha (eIF-2alpha: *Homo sapiens*, #NP_004085); p58 (*Homo sapiens*, #NP_006251); 2',5'-oligoadenylate synthetases (*Homo sapiens* forms including #P00973, P29728, AAD28543; *Mus musculus* forms including P11928; S. Y. Desai et al. (1995) J. Biol. Chem. 270, 3454-3461); 2',5'-oligoadenylate (C. E. Samuel (2001) Clinical Microbiology Reviews 14, 778-809); RNase L (*Homo sapiens*, #CAA52920); promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (*Homo sapiens*, #U18121; *Mus musculus*, #NP_062629); Mx1 (*Homo sapiens*, #NM_002462); or Mx2 (*Homo sapiens*, #NM_002463). An effector domain can also be isolated from a molecule that binds to, stimulates, or inhibits natural interferon-response-related or cytokine-response related molecules such as those listed supra.

Other effector domains can be isolated from molecules that execute, stimulate, or inhibit stress or inflammatory responses (R. I. Morimoto and M. G. Santoro (1998) Nature Biotech. 16, 833-838; R. I. Morimoto (1998) Genes & Dev. 12, 3788-3796; M. G. Santoro (2000) Biochem. Pharmacol. 59, 55-63; A. De Marco et al. (1998) Eur. J. Biochem. 256, 334-341; C. Conti et al. (1999) Antimicrobial Agents and Chemotherapy 43, 822-829; M. G. Santoro (1996) EXS 77, 337-357; E. A. A. Nollen and R. I. Morimoto (2002) Journal of Cell Science 115, 2809-2816; J. Hiscott et al. (2001) J. Clinical Investigation 107, 143-151; E. N. Hatada et al. (2000) Curr. Opin. Immunol. 12, 52-58; T. Wang et al. (2002) Int. Immunopharmacol. 2, 1509-1520; X. Li and G. R. Stark (2002) Exp. Hematol. 30, 285-296; Z. Sun and R. Andersson (2002) Shock 18, 99-106; H. L. Pahl (1999) Oncogene 18, 6853-6866; F. Mercurio and A. M. Manning Oncogene 18, 6163-6167)), for example and without limitation, the following molecules or DNA or RNA encoding them: heat shock protein 70 or related proteins (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM_015765, NM_010481, NM_008301, M76613); Hsp90 (*Homo sapiens*, #M16660, NM_005348, NM_007355); Hsp40/Hdj-1 (*Homo sapiens*, #X62421, NM_006145, NM_005880); Hsc70 (*Homo sapiens*, #AF352832); Hsp47/CBP-2 (*Homo sapiens*, #D83174); cdc48 (S. Thoms (2002) FEBS Lett. 520, 107-110); Bip/GRP78; Hsp60 (*Homo sapiens*, #NM_002156); Hsp100 (*Homo sapiens*, #NM_006660); Alpha-A-crystallin (*Homo sapiens*, #NM_000394); Alpha-B-crystallin (*Homo sapiens*, #NM_001885); Hsp27-1 (*Homo sapiens*, #NM_001540); Hsp27-2 (*Homo sapiens*, #XM_012054); heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131); heat shock factor 2 (HSF2: *Homo sapiens*, #NM_004506; *Mus musculus*, #X61754, AH007205, NM_008297); heat shock factor 3 (HSF3: L. Pirkkala et al. (2001) FASEB J. 15, 1118-1131); heat shock factor 4 (HSF4: *Homo sapiens*, #NM_001538, D87673, AB029348; *Mus musculus*, #AF160965, AF160966, AB029349, AB029350); heat shock factor binding protein 1 (HSBP1: *Homo sapiens*, #NM_001537, BC007515, AF068754); heat shock factor 2 binding protein (HSF2BP: *Homo sapiens*, #NM_007031); RelA/p65 (*Homo sapiens*, #NM_021975, Z22948, L19067; *Mus musculus*, #NM_009045, AF199371); RelB (*Homo sapiens*, #NM_006509; *Mus musculus*, #NM_009046, M83380); c-Rel (*Homo sapiens*, #X75042, NM_002908; *Mus musculus*, #NM_009044, X15842); p50/p105/NF-kappa B 1 (*Homo sapiens*, #NM_003998, S76638, AF213884, AH009144; *Mus musculus*, #NM_008689, AK052726, M57999); p52/p100/NF-kappa B 2 (*Homo sapiens*, #NM_002502; *Mus musculus*, #AF155372, AF155373, NM_019408); inhibitors of kappa B (I kappa B: *Homo sapiens*, #AY033600, NM_020529; S. Ghosh and M. Karin (2002) Cell 109, S81-S96); IKK1/I kappa B kinase alpha (IKK alpha: *Homo sapiens*, # AF009225, AF080157); IKK2/I kappa B kinase beta (IKK beta: *Homo sapiens*, #AF080158; *Mus musculus*, #AF026524, AF088910); NEMO/I kappa B kinase gamma (IKK gamma: *Homo sapiens*, #AF261086, AF091453; *Mus musculus*, #AF069542). An effector domain can also be isolated from a molecule that binds to, stimulates, or inhibits natural stress-response-related or inflammatory-response-related molecules such as those listed supra.

Other effector domains can be isolated from molecules that execute, stimulate, or inhibit unfolded protein response-related or endoplasmic reticulum-associated protein degradation-related responses (C. Patil and P. Walter (2001) Current Opinion in Cell Biology 13, 349-356; K. Lee et al. (2002) Genes & Development 16, 452-466; S. Oyadomari et al. (2002) Apoptosis 7, 335-345), for example and without limitation, the following molecules or DNA or RNA encoding them: BiP/GRP78/SHPA5 (*Homo sapiens*, #AJ271729, AF216292, X87949, NM_005347; *Mus musculus*, #NM_022310); PKR-like endoplasmic reticulum kinase (PERK: *Homo sapiens*, #NP_004827; *Mus musculus*, #AAD03337, NP_034251); IRE1 alpha (*Homo sapiens*, #AF059198; *Mus musculus*, #AB031332, AF071777); IRE1 beta (*Homo sapiens*, #AB047079); RNA for IRE1 alpha or IRE1 beta (W. Tirasophon et al. (2000) Genes & Development 14, 2725-2736); p58 (*Homo sapiens*, #NP_006251; W. Yan et al. (2002) Proc. Natl. Acad. Sci. USA 99, 15920-15925); activating transcription factor 4 (ATF4: *Homo sapiens*, #NM_001675; *Mus musculus*, #NM_009716); activating transcription factor 6 alpha or beta (ATF6 alpha or beta: *Homo sapiens*, #NM_007348, AF005887, AB015856; *Mus musculus*, #XM_129579); X-box binding protein 1 (XBP1: *Homo sapiens*, #AB076383, AB076384; *Mus musculus*, #AF443192, AF027963, NM_013842); XBP1 RNA (K. Lee et al. (2002) Genes & Development 16, 452-466; H. Yoshida et al. (2001) Cell 107, 881-891); CHOP-10/GADD153/DDIT3 (*Homo sapiens*, #NM_004083; *Mus musculus*, #X67083, NM_007837); site-1 protease (S1P: *Homo sapiens*, #NM_003791; *Mus musculus*, #NM_019709); site-2 protease (S2P: *Homo sapiens*, #NM_015884); presenilin-1 (*Homo sapiens*, #AH004968, AF416717; *Mus musculus*, #BC030409, NM_008943, AF149111); TNF receptor-associated factor 2 (TRAF2: *Homo sapiens*, #NM_021138, NM_145718, *Mus musculus*, #XM_203851, XM_130119, L35303); cJUN NH2-terminal kinases (JNKs: S. Oyadomari et al. (2002) Apoptosis 7, 335-345); or eukaryotic translation initiation factor 2 alpha (eIF-2alpha: *Homo sapiens*, #NP_004085). An effector domain can also be isolated from a molecule that binds to, stimulates, or inhibits natural unfolded protein response-related or endoplasmic reticulum-associated protein degradation-related molecules such as those listed supra.

An effector domain can be any naturally or non-naturally occurring molecule that binds to a pathogen, pathogen component, or cellular component that directly or indirectly aids a pathogen. Such effector domains include, for example and without limitation, an antibody, antibody fragment, single-chain antibody, peptidomimetic, or synthesized molecule. An effector domain can also be an antisense polynucleotide or small interfering RNA (G. M. Barton and R. Medzhitov (2002) Proc. Natl. Acad. Sci. USA 99, 14943-14945) that inhibits expression of a pathogen gene or a host gene that aids a pathogen. An effector domain can also be DNA or RNA that encodes a molecule that binds to a pathogen, pathogen component, or cellular component that directly or indirectly aids a pathogen. In addition, an effector domain can be any molecule that synthesizes a molecule that binds to a pathogen, pathogen component, or cellular component that directly or indirectly aids a pathogen.

Other effector domains can be isolated from complement pathway-related molecules (W. E. Paul (ed.), Fundamental Immunology (4th ed., Lippincott-Raven, Philadelphia, 1999), Chapter 29; M. K. Pangburn et al. (2000) Journal of Immunology 164, 4742-4751), for example and without limitation, the following molecules or DNA or RNA encoding them: C3 alpha, C3 beta, factor B, factor D, properdin, C1q, C1r, C1s, C4, C2, C5, C6, C7, C8, C9, factor I, factor H, C1-INH, C4 bp, S protein, clusterin, carboxypeptidase N, FHL-1, FHR-1, FHR-2, FHR-3, FHR-4, CR1, or DAF. An effector domain can also be isolated from a molecule that binds to, stimulates, or inhibits natural complement pathway-related molecules such as those listed supra.

Other effector domains can be isolated from toll-like receptors, their accessory molecules, or molecules that they activate directly or indirectly, (S. Akira (2003) Current Opinion in Immunology 15, 5-11; T. Vasselon and P. A. Detmers (2002) Infection and Immunity 70, 1033-1041; C. A. Janeway Jr. and R. Medzhitov (2002) Annu. Rev. Immunol. 20, 197-216), including for example and without limitation, the following molecules or DNA or RNA encoding them: toll-like receptor 1, *Homo sapiens* (NCBI Accession #NP_003254, AAC34137); toll-like receptor 2, *Homo sapiens* (NCBI Accession #AAH33756, AAM23001, AAC34133); toll-like receptor 3, *Homo sapiens* (NCBI Accession #AAC34134, NP_003256); toll-like receptor 4, *Homo sapiens* (NCBI Accession #AAC34135, AAF89753, AAF07823, AAF05316); toll-like receptor 5, *Homo sapiens* (NCBI Accession #AAC34136, BAB43955); toll-like receptor 6, *Homo sapiens* (NCBI Accession #NP_006059, BAA78631); toll-like receptor 7, *Homo sapiens* (NCBI Accession #AAF60188, AAF78035, NP_057646, AAH33651); toll-like receptor 8, *Homo sapiens* (NCBI Accession #AAF64061, AAF78036); toll-like receptor 9 *Homo sapiens* (NCBI Accession # AAG01734, AAG01735, AAG01736, BAB19259); toll-like receptor 10, *Homo sapiens* (NCBI Accession #AAK26744, NP_112218); CD 14, *Homo sapiens* (NCBI Accession #AAH10507, AAL02401, CAD36116); MD-2, *Homo sapiens* (NCBI Accession #NP_056179, BAA78717, AAH20690); MD-1, *Homo sapiens* (NCBI Accession #AAC98152, NP_004262); RP105, *Homo sapiens* (NCBI Accession #BAA12019); toll/IL-1 receptor domain containing adaptor protein (TIRAP), *Homo sapiens* (NCBI Accession #NP_683708, NP_443119, AAL05627); MyD88, *Homo sapiens* (NCBI Accession #AAB49967, AAC50954); IL-1R activated kinase 4 (IRAK-4), *Homo sapiens* (NCBI Accession #CAC60090); TNF-receptor-associated factor 6 (TRAF6), *Homo sapiens* (NCBI Accession #NP_665802, NP_004611); toll-like receptor 1, *Mus musculus* (NCBI Accession #AAG35062, AAG37302, NP_109607); toll-like receptor 2, *Mus musculus* (NCBI Accession #AAD46481, AAF04277, AAD49335, NP_036035, AAF28345); toll-like receptor 3, *Mus musculus* (NCBI Accession #AAK26117, AAL27007, NP_569054); toll-like receptor 4, *Mus musculus* (NCBI Accession #AAD29272, AAF04278, AAF05317, NP_067272, AAH29856); toll-like receptor 5, *Mus musculus* (NCBI Accession #AAF65625, NP_058624); toll-like receptor 6, *Mus musculus* (NCBI Accession #BAA78632, AAG38563, NP_035734); toll-like receptor 7, *Mus musculus* (NCBI Accession #AAK62676, NP_573474, AAL73191, AAL73192); toll-like receptor 8, *Mus musculus* (NCBI Accession #NP_573475, AAK62677); toll-like receptor 9, *Mus musculus* (NCBI Accession #BAB19260, AAK29625, AAK28488, NP_112455); CD14, *Mus musculus* (NCBI Accession #CAA32166, BAB68578, NP_033971); MD-2, *Mus musculus* (NCBI Accession #BAA93619); MD-1, *Mus musculus* (NCBI Accession #BAA32399); RP105, *Mus musculus* (NCBI Accession #BAA07043); toll/IL-1 receptor domain containing adaptor protein (TIRAP), *Mus musculus* (NCBI Accession #AAL05628, NP_473437); MyD88, *Mus musculus* (NCBI Accession #AAC53013); IL-lR activated kinase 4 (IAK-4), *Mus musculus* (NCBI Accession #AAM15773, NP_084202); or TNF-receptor-associated factor 6 (TRAF6), *Mus musculus* (NCBI Accession #BAA12705, NP_033450). An effector domain can also be isolated from a molecule that binds to, stimulates, or inhibits natural toll-like-receptor response-related molecules such as those listed supra.

Still other effector domains can be isolated from nucleotide-binding oligomerization domain (NOD), or nucleotide-binding-domain (NBD), or nucleotide-binding-site (NBS), proteins or molecules that they activate directly or indirectly, (N. Inohara et al. (2002) Current Opinion in Microbiology 5, 76-80; S. E. Girardin et al. (2002) TRENDS in Microbiology 10, 193-199; J. A. Harton et al. (2002) Journal of Immunology 169, 4088-4093; N. Inohara et al. (2000) Journal of Biological Chemistry 275, 27823-27831), including for example and without limitation, the following molecules or DNA or RNA encoding them:Nod1/CARD4 (*Homo sapiens*, #AAD28350, AAD43922; N. Inohara et al. (1999) Journal of Biological Chemistry 274, 14560-14567); Nod2, (*Homo sapiens*, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM_021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH011140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876). An effector domain can also be isolated from a molecule that binds to, stimulates, or inhibits natural NOD-response-related molecules such as those listed supra.

Effector domains can also be isolated from pentraxins or molecules that they activate directly or indirectly, (H. Gewurz et al. (1995) Current Opinion in Immunology 7, 54-64), including for example and without limitation, the following molecules or DNA or RNA encoding them: C-reactive protein (CRP), *Homo sapiens* (NCBI Accession #1GNHA, 1GNHB, 1GNHC, 1GNHD, 1GNHE, 1GNHF, 1GNHG, 1GNHH, 1GNHI, 1GNHJ); C-reactive protein (CRP), *Mus musculus* (NCBI Accession #CAA31928, NP_031794); serum amyloid P component (SAP), *Homo sapiens* (NCBI Accession #1SACA, 1SACB, 1SACC, 1SACD, 1SACE); and serum amyloid P component (SAP), *Mus musculus* (NCBI Accession #NP_035448, CAA34774). An effector domain can also be isolated from a molecule that binds to, stimulates, or inhibits natural pentraxin-response-related molecules such as those listed supra.

Other effector domains can be isolated from collectins or molecules that they activate directly or indirectly, (M. Gadjeva et al. (2001) Current Opinion in Immunology 13, 74-78; U. L. Holmskov (2000) APMIS Suppl. 100, 1-59), including for example and without limitation, the following molecules or DNA or RNA encoding them: mannan/mannose binding lectin (MBL), *Homo sapiens* (NCBI Accession #AAK52907, CAB56120, CAB56044); mannan/mannose binding lectin (MBL), *Mus musculus* (NCBI Accession #NP_034905, NP_034906); MBL-associated serine protease 1 (MASP1), *Homo sapiens* (NCBI Accession #NP_001870, NP_624302); MBL-associated serine protease 2 (MASP2), *Homo sapiens* (NCBI Accession #NP_006601, NP_631947, AAG50274, BAA85659); MBL-associated serine protease 1 (MASP1), *Mus musculus* (NCBI Accession #XP_193834); MBL-associated serine protease 2 (MASP2), *Mus musculus* (NCBI Accession #BAA34674, CAB65247, CAB65250); MBL-associated serine protease 3 (MASP3), *Mus musculus* (NCBI Accession #BAB69688); surfactant protein A (SP-A), *Homo sapiens* (NCBI Accession #NP_005402, NP_008857); surfactant protein D (SP-D), *Homo sapiens* (NCBI Accession #CAA46152, NP_003010); surfactant protein D (SP-D), *Mus musculus* (NCBI Accession #AAF15277); surfactant protein D (SP-D), *Bos taurus* (NCBI Accession #CAA53510, S33603); conglutinin, *Bos taurus* (NCBI Accession #CAA50665, BAA03170); collectin-43 (CL-43), *Bos taurus* (NCBI Accession #CAA53511, P42916, A53570); collectin-L1, *Mus musculus* (NCBI Accession #BAC53954); or collectin placenta 1 (CL-P1), *Homo sapiens* (NCBI Accession #AB005145). An effector domain can also be isolated from a molecule that binds to, stimulates, or inhibits natural collectin response-related molecules such as those listed supra.

Still other effector domains can be isolated from mannose receptors or molecules that they activate directly or indirectly, (L. East and C. M. Isacke (2002) Biochimica et Biophysica Acta 1572, 364-386; S. Zamze et al. (2002) Journal of Biological Chemistry 277, 41613-41623), including for example and without limitation, the following molecules or DNA or RNA encoding them: mannose receptor (MR), *Homo sapiens* (NCBI Accession #NM_002438); and mannose receptor (MR), *Mus musculus* (NCBI Accession #CAA78028, NP_032651, NP_032652). An effector domain can also be isolated from a molecule that binds to, stimulates, or inhibits natural mannose-receptor-response-related molecules such as those listed supra.

Effector domains can also be isolated from scavenger receptors or molecules that they activate directly or indirectly, (L. Peiser et al. (2002) Current Opinion in Immunology 14, 123-128; A. Brannstrom et al. (2002) Biochemical and Biophysical Research Communications 290, 1462-1469), including for example and without limitation, the following molecules or DNA or RNA encoding them: scavenger receptor A I (SR-A I), *Homo sapiens* (NCBI Accession #D90187); scavenger receptor A II (SR-A II), *Homo sapiens* (NCBI Accession #D90188); scavenger receptor A I (SR-A I), *Mus musculus* (NCBI Accession #L04274); scavenger receptor A II (SR-A II), *Mus musculus* (NCBI Accession #L04275); macrophage receptor with collagenous structure (MARCO), *Homo sapiens* (NCBI Accession #NP_006761); macrophage receptor with collagenous structure (MARCO), *Mus musculus* (NCBI Accession #NP_034896); scavenger receptor with C-type lectin I (SR-CL I), *Homo sapiens* (NCBI Accession #BAB39147); scavenger receptor with C-type lectin II (SR-CL II), *Homo sapiens* (NCBI Accession #BAB39148); and scavenger receptor with C-type lectin (SR-CL), *Mus musculus* (NCBI Accession #BAB82497). An effector domain can also be isolated from a molecule that binds to, stimulates, or inhibits natural scavenger receptor response-related molecules such as those listed supra.

An effector domain can be isolated from a molecule that inhibits transport between the cytoplasm and the nucleus of a cell, including for example and without limitation, the following molecules or DNA or RNA encoding them: importin alpha 1 (*Homo sapiens*, #NM_002266) with the importin beta binding domain (approximately amino acids 3-99) removed; importin alpha 3 (*Homo sapiens*, #NM_002268) with the importin beta binding domain (approximately amino acids 3-94) removed; importin alpha 4 (*Homo sapiens*, #NM_002267) with the importin beta binding domain (approximately amino acids 3-94) removed; importin alpha 5 (*Homo sapiens*, #U28386) with the importin beta binding domain (approximately amino acids 3-94) removed; importin alpha 6 (*Homo sapiens*, #NM_002269) with the importin beta binding domain (approximately amino acids 3-94) removed; importin alpha 7 (*Homo sapiens*, #NM_012316) with the importin beta binding domain (approximately amino acids 3-103) removed; importin alpha with the importin beta binding domain removed as described supra and also with the last two armadillo repeats removed (Y. Miyamoto et al. (2002) EMBO Journal 21, 5833-5842), as will be understood by one of skill in the art; the autoinhibitory domain of an importin alpha mutated to have a higher than normal affinity for wild-type importin alpha (B. Catimel et al. (2001) Journal of Biological Chemistry 276, 34189-34198), as will be understood by one of skill in the art; a modified importin alpha that does not enable nuclear import, but still binds to one or more pathogen nuclear localization signals (NLSs), preferably with a higher affinity than it binds to cellular NLSs, as will be understood by one of skill in the art; the importin beta binding domain of importin alpha 1 (*Homo sapiens*, #NM_002266, approximately amino acids 1-99); the importin beta binding domain of importin alpha 3 (*Homo sapiens*, #NM_002268, approximately amino acids 1-94); the importin beta binding domain of importin alpha 4 (*Homo sapiens*, #NM_002267, approximately amino acids 1-94); the importin beta binding domain of importin alpha 5 (*Homo sapiens*, #U28386, approximately amino acids 1-94); the importin beta binding domain of importin alpha 6 (*Homo sapiens*, #NM_002269, approximately amino acids 1-94); the importin beta binding domain of importin alpha 7 (*Homo sapiens*, #NM_012316, approximately amino acids 1-103); importin beta 1 (*Homo sapiens*, #NM_002265, #NP_002256) modified to not bind nucleoporins, for example by deleting the region between HEAT-5 and HEAT-6 (approximately amino acids 203-211) and the region between HEAT-6 and HEAT-7 (approximately amino acids 246-252) or by replacing those regions with nonhomologous linker regions (Y. M. Chook and G. Blobel (2001) Current Opinion in Structural Biology 11, 703-715); importin beta 1 (*Homo sapiens*, #NM_002265, #NP_002256) modified to not bind importin alpha, for example by deleting the acidic loop importin-alpha-binding region spanning from approximately amino acid 333 through approximately amino acid 343 (G. Cingolani et al. (1999) Nature 399, 221-229); a defective mutant of an exportin (I. G. Macara (2001) Microbiology and Molecular Biology Reviews 65, 570-594) as will be understood by one of skill in the art; a mutant p10/NTF2 that inhibits import by importin beta 1, for example, p10 D23A (C. M. Lane et al. (2000) Journal of Cell Biology 151, 321-331) or N77Y (B. B. Quimby et al. (2001) Journal of Biological Chemistry 276, 38820-38829); vesicuovirus matrix protein or a portion thereof that inhibits nuclear import and/or nuclear export (J. M. Petersen et al. (2001) Proc. Natl. Acad. Sci. USA 98, 8590-8595; J. M. Petersen et al. (2000) Molecular and Cellular Biology 20, 8590-8601; C. von Kobbe et al. (2000) Molecular Cell 6, 1243-1252); a peptide or other molecule that resembles the classical nuclear localization signal of SV40 T antigen (E. Merle et al. (1999) Journal of Cellular Biochemistry 74, 628-637); peptides with FxFG repeats or GLFG repeats (R. Bayliss et al. (2002) Journal of Biological Chemistry 277, 50597-50606); leptomycin B; or a mutant of Ran that interferes with nuclear import or export, for example and without limitation, RanC4A (R. H. Kehlenbach et al. (2001) Journal of Biological Chemistry 276, 14524-14531).

An effector domain can be isolated from any naturally or non-naturally occurring molecule that binds to a pathogen, pathogen component, or cellular component that is involved in transport between the cytoplasm and the nucleus of a cell (I. G. Macara (2001) Microbiology and Molecular Biology Reviews 65, 570-594; B. Ossareh-Nazari (2001) Traffic 2, 684-689). Such effector molecules include, for example and without limitation, an antibody, antibody fragment, single-chain antibody, peptidomimetic, or synthesized molecule. An effector molecule can also be DNA or RNA that encodes a molecule that binds to a pathogen, pathogen component, or cellular component that is involved in transport between the cytoplasm and the nucleus of a cell. In addition, an effector molecule can be any molecule that synthesizes a molecule that binds to a pathogen, pathogen component, or cellular component that is involved in transport between the cytoplasm and the nucleus of a cell.

Cellular components that are involved in transport between the cytoplasm and the nucleus of a cell (I. G. Macara (2001) Microbiology and Molecular Biology Reviews 65, 570-594; E. Conti and E. Izaurralde (2001) Current Opinion in Cell Biology 13, 310-319) include, for example, importin alpha proteins, importin beta proteins, importin 7, Ran, Nup358 (S. K. Vasu and D. J. Forbes (2001) Current Opinion in Cell Biology 13, 363-375), CAN/Nup214 (L. C. Trotman et al. (2001) Nature Cell Biology 3, 1092-1100; S. K. Vasu and D. J. Forbes (2001) Current Opinion in Cell Biology 13, 363-375), CRM1, CAS, calreticulin, or kinases or phosphatases that regulate nuclear import or export (R. H. Kehlenbach and L. Gerace (2000) Journal of Biological Chemistry 275, 17848-17856). In one embodiment, the effector domain inhibits pathogen transport more efficiently than cellular transport.

An effector domain can be isolated from a molecule that alters the endocytic or phagocytic pathways (for example and without restriction, the properties of endosomes, phagosomes, lysosomes, other intracellular compartments, or vesicular trafficking) to produce an anti-pathogen effect, (L. A. Knodler, J. Celli, and B. B. Finlay (2001) Nat. Rev. Mol. Cell. Biol. 2, 578-588; D. Sacks and A. Sher (2002) Nature Immunology 3, 1041-1047; M. W. Hornef et al. (2002) Nature Immunology 3, 1033-1040; J. Pieters (2001) Current-Opinion in Immunology 13, 37-44), for example and without limitation, the following molecules or DNA or RNA encoding them: dynamin-1 mutant K44A (M. Huber et al. (2001) Traffic 2, 727-736), particularly when overexpressed; cellubrevin (R. A. Fratti et al. (2002) Journal of Biological Chemistry 277, 17320-17326), particularly when overexpressed; *Salmonella* SpiC protein (NCBI Accession #U51927); a defective mutant of TassC (A. H. Lee et al. (2002) Cell. Microbiol. 4, 739-750); other vesicular trafficking inhibitors; Nramp1 (P. Cuellar-Mata et al. (2002) Journal of Biological Chemistry 277, 2258-2265; C. Frehel et al. (2002) Cellular Microbiology 4, 541-556; D. J. Hackam et al. (1998) J. Exp. Med. 188, 351-364), particularly when overexpressed; NADPH oxidase subunits or cofactors (P. V. Vignais (2002) Cell. Mol. Life Sci. 59, 1428-1459), particularly when overexpressed; NOS2 nitric oxide synthase (J. D. MacMicking et al. (1997) Proc. Natl. Acad. Sci. USA 94, 5243-5248), particularly when overexpressed; human papillomavirus 16 E5 protein (NCBI Accession #W5WLHS); bafilomycin A1; an antibody, single-chain antibody, or other molecule that binds to V-ATPase subunit a (S. B. Sato and S. Toyama (1994) J. Cell. Biol. 127, 39-53), preferably a1 or a2; antisense oligonucleotides that inhibit vacuolar ATPase subunits (J. E. Strasser et al. (1999) Journal of Immunology 162, 6148-6154); a peptide composed of approximately the 78 amino-terminal amino acids of vacuolar H+-ATPase subunit E (M. Lu et al. (2002) Journal of Biological Chemistry 277, 38409-38415); A2-cassette mutant of vacuolar H+-ATPase subunit A (N. Hernando et al. (1999) Eur. J. Biochem. 266, 293-301); a defective mutant of subunit a1 or a2 of vacuolar H+-ATPase (S. Kawasaki-Nishi et al. (2001) Proc. Natl. Acad. Sci. USA 98, 12397-12402; S. Kawasaki-Nishi et al. (2001) 276, 47411-47420; T. Nishi and M. Forgac (2000) J. Biol. Chem. 275, 6824-6830; S. B. Peng et al. (1999) J. Biol. Chem. 274, 2549-2555; T. Toyomura et al. (2000) J. Biol. Chem. 275, 8760-8765); overexpression of the C and/or H subunits of vacuolar H+-ATPase subunit E (K. K. Curtis and P. M. Kane (2002) Journal of Biological Chemistry 277, 2716-2724); other defective vacuolar ATPase subunit or portion of a subunit (examples of wild-type human vacuolar ATPase subunits that can be made defective for anti-pathogen effects will be understood by one of skill in the art, and include, without limitation, those vacuolar ATPase subunits with Accession numbers: NM_004231, NM_130463, NM_015994, NM_001694, NM_004047, NM_001696, NM_004691, NM_001695, NM_001693, NM_001690, NM_020632, NM_004888); other vacuolar H+-ATPase inhibitors, particularly inhibitors that alter pH in endosomes, phagosomes, or lysosomes with minimal undesirable effects on cells such as osteoclasts and renal intercalated cells; molecules that inhibit intracellular compartment acidification and can be isolated from intracellular pathogens (for example and without limitation, *Mycobacterium* spp., *Salmonella* spp., *Yersinia* spp., *Chlamydia* spp., *Histoplasma capsulatum* (J. E. Strasser et al. (1999) Journal of Immunology 162, 6148-6154), or *Toxoplasma gondii*); molecules that promote intracellular compartment acidification and can be isolated from intracellular pathogens (for example and without limitation, *Coxiella burnetti, Francisella tularensis, Brucella* spp. (F. Porte et al. (1999) Infection and Immunity 67, 4041-4047), *Leishmania* spp., *Listeria monocytogenes, Bordetella bronchiseptica*, or *Legionella pneumophila*); or molecules that interfere with vesicular trafficking or other properties of intracellular compartments can be isolated from intracellular pathogens (for example and without limitation, *Mycobacterium* spp., *Salmonella* spp., *Yersinia* spp., *Chlamydia* spp., *Histoplasma capsulatum* (J. E. Strasser et al. (1999) Journal of Immunology 162, 6148-6154), *Toxoplasma gondii, Coxiella burnetti, Francisella tularensis, Brucella* spp. (F. Porte et al. (1999) Infection and Immunity 67, 4041-4047), *Leishmania* spp., *Listeria monocytogenes, Bordetella bronchiseptica*, or *Legionella pneumophila*)

An effector domain can be isolated from a molecule that stimulates, inhibits, or binds to a component of the ubiquitin-proteasome degradative pathway (M. H. Glickman and A. Ciechanover (2002) Physiol. Rev. 82, 373-428; K. M. Sakamoto (2002) Molecular Genetics and Metabolism 77, 44-56) to produce an anti-pathogen effect, for example and without limitation, the following molecules or DNA or RNA encoding them: CHIP (D. M. Cyr et al. (2002) Trends Biochem. Sci. 27, 368-375; J. Demand et al. (2001) Curr. Biol. 11, 1569-1577; S. Murata et al. (2001) EMBO Rep. 2, 1133-1138), particularly when overexpressed; Fbx2 (Y. Yoshida et al. (2002) Nature 418, 438-442), particularly when overexpressed; molecules that ubiquitinate pathogens, pathogen components, or cellular components that assist pathogens (P. Zhou et al. (2000) Mol. Cell 6, 751-756; K. M. Sakamoto et al. (2001) Proc. Natl. Acad. Sci. USA 98, 8554-8559; N. Zheng et al. (2000) Cell 102, 533-539; D. Oyake et al. (2002) Biochemical and Biophysical Research Communications 295, 370-375); or inhibitors of ubiquitination or proteasomes (J. Myung et al. (2001) Medicinal Research Reviews 21, 245-273; G. Lennox et al. (1988) Neurosci. Lett. 94, 211-217; N. F. Bence et al. (2001) Science 292, 1552-1555), for example and without limitation, lactacystin or epoxomicin.

Effector domains can be isolated from molecules that execute, stimulate, or inhibit defensin-related responses (R. I. Lehrer and T. Ganz (2002) Current Opinion in Immunology 14, 96-102; D. Yang et al. (2002) TRENDS in Immunology 23, 291-296; P. A. Raj and A. R. Dentino (2002) FEMS Microbiology Letters 206, 9-18; G. T.-J. Huang et al. (2002) Human Gene Therapy 13, 2017-2025; J. Cohn et al. (2001) Current Opinion in Immunology 13, 55-62), for example and without limitation, the following molecules or DNA or RNA encoding them: alpha defensins, beta defensins, theta defensins, plant defensins, or arthropod defensins. An effector domain can be isolated from a molecule that binds to, stimulates, or inhibits natural defensin-response related molecules such as those listed supra.

Other effector domains can be isolated from molecules that execute, stimulate, or inhibit cathelicidin-related responses (R. I. Lehrer and T. Ganz (2002) Curr. Opin. Hematol. 9, 18-22; B. Ramanathan et al. (2002) Microbes Infect. 4, 361-372; M. Zaiou and R. L. Gallo (2002) J. Mol. Med. 80, 549-561), for example and without limitation, the following molecules or DNA or RNA encoding them: hCAP-18/LL-37, CRAMP, Bac4, OaBac5; prophenin-1, protegrin-1, or PR-39. An effector domain can be isolated from a molecule that binds to, stimulates, or inhibits natural cathelicidin-response related molecules such as those listed supra.

Still other effector domains can be isolated from molecules that execute, stimulate, or inhibit chemokine-related or thrombocidin-related responses (M. Durr and A. Peschel (2002) Infection and Immunity 70, 6515-6517; Y. Tang et al. (2002) Infection and Immunity 70, 6524-6533; J. Krijgsveld et al. (2000) Journal of Biological Chemistry 275, 20374-20381; A. D. Luster (2002) Current Opinion in Immunology 14, 129-135; M. Mellado et al. (2001) Annu. Rev. Immunol. 19, 397-421), for example and without limitation, the following molecules or DNA or RNA encoding them: CC chemokines, CXC chemokines, C chemokines, CX3C chemokines, CC chemokine receptors, CXC chemokine receptors, C chemokine receptors, CX3C chemokine receptors, JAK proteins, STAT proteins, fibrinopeptide A, fibrinopeptide B, or thymosin beta 4. An effector domains can be isolated from a molecule that binds to, stimulates, or inhibits natural chemokine-response-related or thrombocidin-response-related molecules such as those listed supra.

An effector domain can be isolated from a molecule that is toxic to an infected host cell or a pathogen cell. In one embodiment, the effector molecule is toxic to an infected host cell is not toxic to uninfected host cells, for example and without limitation, an intracellular bacterial toxin (B. B. Finlay and P. Cossart (1997) Science 276, 718-725; C. Montecucco et al. (1994) FEBS Lett. 346, 92-98; P. O. Falnes et al. (2001) Biochemistry 40, 4349-4358) that has been modified so that it cannot cross cellular plasma membranes, such as the A (21 kDa) fragment of diptheria toxin. An effector domains can be isolated from a molecule that is toxic to a pathogen cell, including but not limited to penicillin, erythromycin, tetracycline, rifampin, amphotericin B, metronidazole, or mefloquine. An effector domains can be isolated from an ATP inhibitor (E. K. Hui and D. P. Nayak (2001) Virology 290, 329-341). An effector molecule can be a toxin that inhibits transcription, translation, replication, oxidative phosphorylation, cytoskeletal processes, or other cell and/or pathogen functions.

An effector domain can be isolated from a molecule that inhibits budding or release of pathogens from an infected cell, for example and without limitation, the following molecules or DNA or RNA encoding them: Hrs, particularly when overexpressed (N. Bishop et al. (2002) Journal of Cell Biology 157, 91-101; L. Chin et al. (2001) Journal of Biological Chemistry 276, 7069-7078; C. Raiborg et al. (2002) Nature Cell Biology 4, 394-398); defective Vps4 mutants such as K173Q or E228Q, particularly when overexpressed (J. E. Garrus et al. (2001) Cell 107, 55-65); small interfering RNA that inhibits Tsg101 expression (N. Bishop et al. (2002) Journal of Cell Biology 157, 91-101; J. E. Garrus et al. (2001) Cell 107, 55-65); truncated AP-50 consisting of approximately amino acids 121-435, or other defective mutant of AP-50, particularly when overexpressed (B. A. Puffer et al. (1998) Journal of Virology 72, 10218-10221); WW-domain-containing fragment of LDI-1, Nedd4, Yes-associated protein, KIAA0439 gene product, or other defective Nedd4-related proteins, particularly when overexpressed (A. Kikonyogo et al. (2001) Proc. Natl. Acad. Sci. USA 98, 11199-11204; A. Patnaik and J. W. Wills (2002) Journal of Virology 76, 2789-2795); a peptide consisting of the HIV p6 Gag PTAPP-motif-containing late (L) domain (L. VerPlank et al. (2001) Proc. Natl. Acad. Sci. USA 98, 7724-7729) or other viral late (L) domain containing PTAP, PSAP, PPXY, YPDL, or YXXL motifs (J. Martin-Serrano et al. (2001) Nature Medicine 7, 1313-1319; A. Patnaik and J. W. Wills (2002) Journal of Virology 76, 2789-2795); amino acids 1-167 of Tsg101, TSG-5' fragment of Tsg101, or similar amino-terminal fragment of Tsg101, particularly when overexpressed (D. G. Demirov et al. (2002) Proc. Natl. Acad. Sci. USA 99, 955-9601; E. L. Myers and J. F. Allen (2002) Journal of Virology 76, 11226-11235); a mutant of Tsg101 (M. Babst et al. (2000) Traffic 1, 248-258; L. VerPlank et al. (2001) Proc. Natl. Acad. Sci. USA 98, 7724-7729; J. Martin-Serrano et al. (2001) Nature Medicine 7, 1313-1319; O. Pornillos et al. (2002) EMBO Journal 21, 2397-2406) with reduced capacity to aid viral budding; a casein kinase 2 (CK2) inhibitor, such as the peptide RRADDSDDDDD (SEQ ID NO: 472)(E. K. Hui and D. P. Nayak (2002) Journal of General Virology 83, 3055-3066); or G protein signalling inhibitors (E. K. Hui and D. P. Nayak (2002) Journal of General Virology 83, 3055-3066). An effector domain can be isolated from a molecule that binds to a cellular or pathogen molecule (for example and without limitation, to one or more of the following molecules: Tsg101, Vps4, casein kinase 2, Hrs, hVps28, Eap30, Eap20, Eap45, Chmp1, Chmp2, Chmp3, Chmp4, Chmp5, Chmp6, AP-50, Nedd4-related proteins, WW-domain-containing proteins, or L-domain-containing proteins; O. Pornillos et al. (2002) TRENDS in Cell Biology 12, 569-579; P. Gomez-Puertas et al. (2000) Journal of Virology 74, 11538-11547; E. Katz et al. (2002) Journal of Virology 76, 11637-11644) that is involved in budding or release of pathogens from an infected cell.

An effector domain can be isolated from a molecule that degrades components of cells or pathogens, for example and without limitation: proteases, including chymotrypsin, trypsin, or elastase; DNases, including caspase-activated DNase (CAD), constitutively active CAD (N. Inohara et al. (1999) Journal of Biological Chemistry 274, 270-274), or restriction enzymes; RNases, including RNase II (*Homo sapiens*, #AF189011; *Escherichia coli*, #NP_417062, NC_000913), RNt1p (*Saccharomyces cerevisiae*, #U27016), Pac1, (*Schizosaccharomyces pombe*, #X54998), RNase A, or RNase L; glycosidases, including N-glycanase, endoglycosidase H, O-glycanase, endoglycosidase F2, sialidase, or beta-galactosidase; or lipases, including to phospholipase A1, phospholipase A2, phospholipase C, or phospholipase D. An effector domain can be encoded by DNA or RNA which encodes a molecule that degrades components of cells or pathogens. An effector domain can be isolated from a molecule that binds to, stimulates, or inhibits a molecule such as those described supra that degrades components of cells or pathogens.

Other effector domain can be isolated from molecules that execute, stimulate, or inhibit immune-related responses (W. E. Paul (ed.), Fundamental Immunology (4th ed., Lippincott-Raven, Philadelphia, 1999)), for example and without limitation, the following molecules or DNA or RNA encoding them: MHC Class I, MHC Class II, antibodies, single-chain antibodies, T cell receptors, Fc receptors, NK cell activation receptors (including but not limited to NKp46, Ly49H, and NKG2D; A. Diefenbach and D. H. Raulet (2003) Current Opinion in Immunology 15, 37-44; A. R. French and W. M. Yokoyama (2003) Current Opinion in Immunology 15, 45-51), NK cell inhibitory receptors, receptor-associated tyrosine kinases, or phospholipase C. An effector domain can be isolated from a molecule that binds to, stimulates, or inhibits natural immune-response related molecules.

A chimeric molecule of the invention that has at least one dsRNA binding domain as described supra, can be bound to, or is associated with, an effector domain that mediates the activation or induction of apoptosis. For example, caspases (also known as pro-caspases) 1 to 14 (Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*,

BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; CED-3 caspase, and *Caenorhabditis elegans*, #AF210702) can be effector domains. Such caspases are widely recognized in the art and include homologs from a variety of organisms, including *Homo sapiens, Mus musculus, Drosophila melanogaster* and *C. elegans*. Both a full-length pro-caspase and a fragment of a pro-caspase that contains the active caspase subunits and the activation cleavage sites are suitable for use in the invention, as will be appreciated by one of skill in the art.

Other effector domains that mediate the activation or induction of apoptosis include apoptosis-associated proteins, such as a death effector domain (DED) isolated from FADD, a caspase recruitment domain (CARD) isolated from Apaf-1, or a death domain (DD) isolated from either Fas or TRADD (tumor necrosis factor receptor type 1 (TNFR1)-associated death domain protein). Table 2 provides examples of these effector domain-containing proteins and the approximate amino acid position of the effector domains.

TABLE 2

| Protein, organism | Domain type: sequence location (amino acids) | NCBI Accession number |
|---|---|---|
| FADD, *Homo sapiens* | Death effector domain (DED): 1-100 | U24231 |
| FADD, *Mus musculus* | Death effector domain (DED): 18-69 | NM_010175 |
| Apaf-1, *Homo sapiens* | Caspase recruitment domain (CARD): 1-89 | NM_013229, NM_001160 |
| Apaf-1, *Mus musculus* | Caspase recruitment domain (CARD): 1-87 | NP_033814 |
| TRADD, *Homo sapiens* | Death domain (DD): 226-301 | NP_003780, CAC38018 |

In a preferred embodiment, the chimeric molecule or agent of the invention has one or more dsRNA-binding domains, as described supra, fused in frame with or bound to or associated with one or more of the following effector molecules: an apoptosis effector domain as described supra; an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more 2',5'-oligoadenylate-binding domains, as described supra, fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more endoplasmic-reticulum-stress-detection domains from PERK (for example, approximately amino acids 1-542 of human PERK), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more endoplasmic-reticulum-stress-detection domains from IRE1 alpha (for example, approximately amino acids 1-469 of human IRE1 alpha), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more endoplasmic-reticulum-stress-detection domains from IRE1 beta (for example, approximately amino acids 1-451 of human IRE1 beta), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more stress-detection domains from HSF1 (for example, approximately amino acids 125-503 of human HSF1), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod 1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more LPS-binding domains, as described supra, fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example and without limitation, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis signal-detection domains from Apaf-1 (for example, approximately amino acids 97-1194 of human Apaf-1), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis-signal-detection domains from FADD (for example, approximately amino acids 117-208 of human FADD), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example and without limitation, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis-signal-detection domains from caspase 8 (for example, approximately amino acids 1-215 of human caspase 8), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis-signal-detection domains from caspase 9 (for example, approximately amino acids 1-92 of human caspase 9), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis-signal-detection domains from TNF alpha receptor 1 (for example, the extracellular and transmembrane domain of human TNF-RI), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example and without limitation, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more apoptosis-signal-detection domains from Fas/CD95 (for example, the extracellular and transmembrane domain of human Fas/CD95), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-detection domains from Nod1/CARD4 (for example, approximately amino acids 127-953 of human Nod1/CARD4), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-detection domains from Nod2 (for example, approximately amino acids 251-1040 of human Nod2), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-detection domains from Ipaf-1/CLAN/CARD12 (for example, approximately amino acids 126-1024 of human Ipaf-1/CLAN/CARD12), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-detection domains from CIITA (for example, approximately amino acids 341-1130 of CARD-less human CIITA), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-binding domains or pathogen-induced-product-binding domains (for example, a single-chain antibody that binds to one or more pathogens, pathogen components, pathogen-produced products, or pathogen-induced products), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); a protease that is activated by crosslinking; an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more domains that specifically bind to one or more pathogenic forms of prions (for example, a portion of a nonpathogenic prion form (such as approximately amino acids 119-136 of hamster prion protein; J. Chabry et al. (1999) Journal of Virology 73, 6245-6250) that binds to a pathogenic prion form, or a single-chain antibody that binds to one or more pathogenic forms of prions), fused in frame with or bound to or associated with one or more of the following effector molecules: an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from HSF1 (for example, approximately amino acids 1-227 of human HSF1); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); a protease that is activated by crosslinking; an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more inflammatory-signal-detection domains from IKK gamma (for example, full-length human IKK gamma), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-induced-signal-detection domains from RIP (for example, approximately amino acids 301-671 of human RIP), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); or an effector domain from Rip2/RICK/CARDIAK (for example, approximately amino acids 1-300 of human Rip2/RICK/CARDIAK).

In another preferred embodiment, the chimeric molecule or agent of the invention has one or more pathogen-induced-signal-detection domains from Rip2/RICK/CARDIAK (for example, approximately amino acids 301-540 of human Rip2/RICK/CARDIAK), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); or an effector domain from RIP (for example, approximately amino acids 1-300 of human RIP).

In another preferred embodiment, the chimeric molecule or agent of the invention has one or more pathogen-detection domains isolated from toll-like receptors (for example, the extracellular domain of the following human toll-like receptors: TLR1, TLR2, TLR3, TLR4, TLR5, TLR6, TLR7, TLR8, TLR9, or TLR10), fused in frame with or bound to or associated with one or more of the following effector molecules: an apoptosis effector domain as described supra; an effector domain from protein kinase R (for example, approximately amino acids 175-551 or 274-551 of human protein kinase R); an effector domain from RNase L (for example, approximately amino acids 336-741 of human RNase L); an effector domain from PERK (for example, approximately amino acids 543-1115 of human PERK); an effector domain from IRE1 alpha (for example, approximately amino acids 470-977 of human IRE1 alpha); an effector domain from IRE1 beta (for example, approximately amino acids 452-925 of human IRE1 beta); an effector domain from Nod1/CARD4 (for example, approximately amino acids 1-126 of human Nod1/CARD4); an effector domain from Nod2 (for example, approximately amino acids 1-250 of human Nod2); an effector domain from Ipaf-1/CLAN/CARD12 (for example, approximately amino acids 1-125 of human Ipaf-1/CLAN/CARD12); an acidic domain effector domain from CIITA (for example, approximately amino acids 1-340 of CARD-less human CIITA); a CARD effector domain from dendritic cell CIITA (for example, approximately amino acids 1-100 of human dendritic cell CIITA); a CARD-acidic-domain effector domain from dendritic cell CIITA (for example, approximately amino acids 1-440 of human dendritic cell CIITA); an effector domain from IKK gamma (for example, full-length human IKK gamma or approximately amino acids 1-200 of human IKK gamma); an effector domain from HSF1 (for example, approximately amino acids 1-227 of human HSF1); an effector domain from RIP (for example, approximately amino acids 1-300 of human RIP); or an effector domain from Rip2/RICK/CARDIAK (for example, approximately amino acids 1-300 of human Rip2/RICK/CARDIAK).

A chimeric molecule or agent of the invention can be a molecule that binds to a pathogen or a product produced or induced by a pathogen and that also binds to a natural effector molecule, thereby activating effector molecules by crosslinking on a polyvalent pathogen/pathogen-produced product/pathogen-induced product and/or promoting an anti-pathogen effect by bringing a pathogen/pathogen-produced product into close proximity with a natural anti-pathogen effector molecule. More specifically, and without restriction, an agent of the invention can be a molecule that binds to a pathogen or product produced or induced by a pathogen and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a protease that is activated by crosslinking; a glycosidase as described supra; a lipase as described supra; a heat shock protein as described supra; an E3 ubiquitin ligase as described supra.

A chimeric molecule or agent of the invention can be a molecule that binds to dsRNA (for example, by containing lividomycin or by mimicking the dsRNA-binding domain of lividomycin, protein kinase R, or other dsRNA-binding domains as described supra) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to protein kinase R (for example, by binding within the domain from approximately amino acids 174-551 of human protein kinase R) and that also binds to one or more of the following: RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to 2',5'-oligoadenylate (for example, by mimicking the 2',5'-oligoadenylate-binding domain from approximately amino acids 1-335 of human RNase L) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to RNase L (for example, by binding within the domain from approximately amino acids 364-741 of human RNase L) and that also binds to one or more of the following: protein kinase R (for example, by binding within the domain from approximately amino acids 1-174 of human protein kinase R); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to viral late domains (for example and without restriction, by binding to viral late domain motifs such as PTAP, PSAP, PPXY, YPDL, or YXXL, as described supra) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to viral glycoproteins (for example and without restriction, by mimicking the hemagglutinin-binding domain of human NK cell activation receptor NKp46) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to LPS (for example, by mimicking the LPS-binding domain from approximately amino acids 1-199 of human BPI or other LPS-binding domains as described supra) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to peptidoglycan (for example, by mimicking the peptidoglycan-binding domain from the extracellular domain of human TLR2) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to muramyl dipeptide (for example, by mimicking the muramyl-dipeptide-binding domain from approximately amino acids 744-1040 of human Nod2) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to bacterial flagellin (for example, by mimicking the flagellin-binding domain from the extracellular domain of human TLR5) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to a bacterial type III secretion system and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod 1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to CpG DNA (for example, by mimicking the CpG-DNA-binding domain from the extracellular domain of human TLR9) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to zymosan (for example, by mimicking the zymosan-binding domain from the extracellular domain of human TLR2) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to a pathogenic form of a prion (for example, by mimicking a portion of a nonpathogenic prion form (such as approximately amino acids 119-136 of hamster prion protein; J. Chabry et al. (1999) Journal of Virology 73, 6245-6250), that binds to a pathogenic prion form) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a protease that is activated by crosslinking; a glycosidase as described supra; a lipase as described supra; a heat shock protein as described supra; an E3 ubiquitin ligase as described supra.

A chimeric molecule or agent of the invention can be a molecule that binds to Apaf-1 (for example, by mimicking the CARD domain from approximately amino acids 1-91 of human caspase 9) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to FADD (for example, by mimicking the DED-containing domain from approximately amino acids 1-215 of human caspase 8) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to TRADD (for example, by mimicking the death domain (DD) from approximately amino acids 117-208 of human FADD) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to Fas/CD95 (for example, by mimicking the death domain (DD) from approximately amino acids 117-208 of human FADD) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to PERK (for example, by binding to the cytoplasmic domain of PERK) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to IRE1 alpha (for example, by binding to the cytoplasmic domain of IRE1 alpha) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to IRE1 beta (for example, by binding to the cytoplasmic domain of IRE1 beta) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to Nod1/CARD4 (for example, by binding to the CARD domain from approximately amino acids 1-126 of human Nod1/CARD4) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to Nod2 (for example, by binding to the CARD-containing domain from approximately amino acids 1-220 of human Nod2) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to Ipaf-1/CLAN/CARD12 (for example, by binding to the CARD domain from approximately amino acids 1-125 of human Ipaf-1/CLAN/CARD12) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to CIITA (for example, by binding to the CARD and/or acidic domains from CIITA isoforms) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to RIP (for example, by binding within the domain from approximately amino acids 1-289 of human RIP) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to Rip2/RICK/CARDIAK (for example, by binding within the domain from approximately amino acids 1-292 of human Rip2/RICK/CARDIAK) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to IKK gamma (for example, by binding within the domain from approximately amino acids 201-419 of human IKK gamma) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod 1); HSF1 (for example, by binding within the domain from approximately amino acids 137-503 of human HSF1); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to HSF1 (for example, by binding within the DNA-binding domain from approximately amino acids 1-120 of human HSF1) and that also binds to one or more of the following: protein kinase R (for example, by binding within the domain from approximately amino acids 1-174 of human protein kinase R); RNase L (for example, by containing or by mimicking a short molecule of 2',5'-oligoadenylate that binds to RNase L but does not activate it without a secondary crosslinker, which in this case is a pathogen or a product produced or induced by a pathogen); PERK; IRE1 alpha; IRE1 beta; caspase 3; caspase 8 (for example, by mimicking the caspase-8-binding DED domain from approximately amino acids 1-117 of human FADD); caspase 9 (for example, by mimicking the caspase-9-binding CARD domain from approximately amino acids 1-97 of human Apaf-1); Apaf-1; FADD (for example, by mimicking the death domain (DD) from human Fas/CD95 or TRADD); a caspase or apoptosis signaling molecule; Nod1/CARD4 (for example, by binding within the domain from approximately amino acids 126-953 of human Nod1/CARD4); Nod2 (for example, by binding within the domain from approximately amino acids 220-1040 of human Nod2); Ipaf-1/CLAN/CARD12 (for example, by binding within the domain from approximately amino acids 125-1024 of human Ipaf-1/CLAN/CARD12); CIITA (for example, by binding within the nucleotide oligomerization domain (NOD) or leucine-rich-repeat (LRR) domain of a CIITA isoform); RIP (for example, by mimicking the death domain (DD) of Fas/CD95 or TRADD); Rip2/RICK/CARDIAK (for example, by mimicking the CARD domain from approximately amino acids 1-126 of human Nod1); IKK gamma (for example, by binding with the domain from approximately amino acids 201-419 of human IKK gamma); IKK alpha and/or beta (for example, by mimicking the IKK alpha/beta binding domain from approximately amino acids 1-200 of human IKK gamma); a DNase as described supra; an RNase as described supra; a protease as described supra; a glycosidase as described supra; a lipase as described supra; a heat shock protein as described supra; an E3 ubiquitin ligase as described supra.

A chimeric molecule or agent of the invention can be a molecule that binds to a pathogen or a product produced or induced by a pathogen and that also contains an effector domain, thereby promoting an anti-pathogen effect by bringing a pathogen/pathogen-produced product into close proximity with an anti-pathogen effector domain. More specifically, an agent of the invention can be a molecule (for example and without limitation, a single-chain antibody) that binds to a pathogen or product produced or induced by a pathogen and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to dsRNA (for example, by containing one or more dsRNA-binding domain as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to viral late domains (for example and without restriction, by binding to viral late domain motifs such as PTAP, PSAP, PPXY, YPDL, or YXXL, as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to viral glycoproteins (for example and without restriction, by containing or mimicking the hemagglutinin-binding domain of human NK cell activation receptor NKp46) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to LPS (for example, by containing or mimicking the LPS-binding domain from approximately amino acids 1-199 of human BPI or other LPS-binding domains as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to peptidoglycan (for example, by containing or mimicking the peptidoglycan-binding domain from the extracellular domain of human TLR2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to muramyl dipeptide (for example, by containing or mimicking the muramyl-dipeptide-binding domain from approximately amino acids 744-1040 of human Nod2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to bacterial flagellin (for example, by containing or mimicking the flagellin-binding domain from the extracellular domain of human TLR5) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to a bacterial type III secretion system and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to CpG DNA (for example, by containing or mimicking the CpG-DNA-binding domain from the extracellular domain of human TLR9) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to zymosan (for example, by containing or mimicking the zymosan-binding domain from the extracellular domain of human TLR2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to a pathogenic form of a prion (for example, by containing or mimicking a portion of a non-pathogenic prion form (such as approximately amino acids 119-136 of hamster prion protein; J. Chabry et al. (1999) Journal of Virology 73, 6245-6250) that binds to a pathogenic prion form) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to a pathogen or a product produced or induced by a pathogen and that also contains an effector domain, thereby promoting an anti-pathogen effect by bringing a pathogen/pathogen-produced product into close proximity with an anti-pathogen effector domain. More specifically, an agent of the invention can be a molecule (for example and without limitation, a single-chain antibody) that binds to a pathogen or product produced or induced by a pathogen and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to dsRNA (for example, by containing one or more dsRNA-binding domain as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to viral late domains (for example and without restriction, by binding to viral late domain motifs such as PTAP, PSAP, PPXY, YPDL, or YXXL, as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to viral glycoproteins (for example and without restriction, by containing or mimicking the hemagglutinin-binding domain of human NK cell activation receptor NKp46) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to LPS (for example, by containing or mimicking the LPS-binding domain from approximately amino acids 1-199 of human BPI or other LPS-binding domains as described supra) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to peptidoglycan (for example, by containing or mimicking the peptidoglycan-binding domain from the extracellular domain of human TLR2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to muramyl dipeptide (for example, by containing or mimicking the muramyl-dipeptide-binding domain from approximately amino acids 744-1040 of human Nod2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to bacterial flagellin (for example, by containing or mimicking the flagellin-binding domain from the extracellular domain of human TLR5) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to a bacterial type III secretion system and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to CpG DNA (for example, by containing or mimicking the CpG-DNA-binding domain from the extracellular domain of human TLR9) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to zymosan (for example, by containing or mimicking the zymosan-binding domain from the extracellular domain of human TLR2) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

A chimeric molecule or agent of the invention can be a molecule that binds to a pathogenic form of a prion (for example, by containing or mimicking a portion of a non-pathogenic prion form (such as approximately amino acids 119-136 of hamster prion protein; J. Chabry et al. (1999) Journal of Virology 73, 6245-6250) that binds to a pathogenic prion form) and that also contains one or more of the following effector domains: a DNase as described supra; an RNase as described supra; a protease as described supra; a glycosidase as described supra; a lipase as described supra; a stress response or heat shock protein as described supra; an E3 ubiquitin ligase as described supra; a molecule that is toxic or inhibitory to a pathogen (including but not limited to defensins as described supra or drosomycin).

In a preferred embodiment, the effector domain is a polynucleotide sequence that encodes for the desired effector domain, and said polynucleotide sequence is operatively linked with a pathogen-detection domain or pathogen-induced-product-detection domain that is a promoter.

A dsRNA-inducible promoter, as described supra, can be operatively linked with a wide variety of effector domains encoded by a polynucleotide sequence, as described supra. Similarly, an apoptosis-inducible promoter, as described supra, can be operatively linked with a wide variety of effector domains encoded by a polynucleotide sequence, as described supra. Furthermore, an unfolded-protein-response-inducible promoter or endoplasmic-reticulum-associated-protein-degradation-response-inducible promoter, as described supra, can be operatively linked with a wide variety of effector domains encoded by a polynucleotide sequence, as described supra. Examples of effector domains which are operatively-linked to these promoters include: a chimeric molecule or agent as described herein, including but not limited to, dsRNA-activated caspase, 2',5'-oligoadenylate-activated caspase, dsRNA-activated caspase activator, or 2',5'-oligoadenylate-activated caspase activator; a chimeric transcription factor as described herein; a molecule that contains two or more binding sites for a pathogen, pathogen component, or pathogen product as described herein; an antisense polynucleotide or small interfering RNA (G. M. Barton and R. Medzhitov (2002) Proc. Natl. Acad. Sci. USA 99, 14943-14945) that inhibits expression of a pathogen gene or a host gene that aids a pathogen; a molecule that executes, stimulates, or inhibits stress or inflammatory responses, as described supra (including but not limited to heat shock protein 70 (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM_015765, NM_010481, NM_008301, M76613), Hsc70 (*Homo sapiens*, #AF352832), Hsp90 (*Homo sapiens*, #M16660, NM_005348, NM_007355); Hsp40/Hdj-1 (*Homo sapiens*, #X62421, NM_006145, NM_005880), Hsp60 (*Homo sapiens*, #NM_002156), Hsp47/CBP-2 (*Homo sapiens*, #D83174), Hsp100 (*Homo sapiens*, #NM_006660), Alpha-A-crystallin (*Homo sapiens*, #NM_000394), Alpha-B-crystallin (*Homo sapiens*, #NM_001885), Hsp27-1 (*Homo sapiens*, #NM_001540), Hsp27-2 (*Homo sapiens*, #XM_012054), cdc48 (S. Thoms (2002) FEBS Lett. 520, 107-110), heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131), constitutively active HSF1 as will be understood by one of skill in the art, RelA/p65 (*Homo sapiens*, #NM_021975, Z22948, L19067; *Mus musculus*, #NM_009045, AF199371), RelB (*Homo sapiens*, #NM_006509; *Mus musculus*, #NM_009046, M83380), c-Rel (*Homo sapiens*, #X75042, NM_002908; *Mus musculus*, #NM_009044, X15842), p50/p105/NF-kappa B 1 (*Homo sapiens*, #NM_003998, S76638, AF213884, AH009144; *Mus musculus*, #NM_008689, AK052726, M57999), p52/p100/NF-kappa B 2 (*Homo sapiens*, #NM_002502; *Mus musculus*, #AF155372, AF155373, NM_019408), inhibitors of kappa B (I kappa B: *Homo sapiens*, #AY033600, NM_020529; S. Ghosh and M. Karin (2002) Cell 109, S81-S96), IKK1/I kappa B kinase alpha (IKK alpha: *Homo sapiens*, #AF009225, AF080157), IKK2/I kappa B kinase beta (IKK beta: *Homo sapiens*, #AF080158; *Mus musculus*, #AF026524, AF088910), or NEMO/I kappa B kinase gamma (IKK gamma: *Homo sapiens*, #AF261086, AF091453; *Mus musculus*, #AF069542)); a molecule that executes, stimulates, or inhibits unfolded protein-related or endoplasmic reticulum-associated protein degradation-related responses, as described supra (including but not limited to BiP/GRP78/SHPA5 (*Homo sapiens*, #AJ271729, AF216292, X87949, NM_005347; *Mus musculus*, #NM_022310), PKR-like endoplasmic reticulum kinase (PERK: *Homo sapiens*, #NP_004827; *Mus musculus*, #AAD03337, NP_034251), constitutively active PERK as will be understood by one of skill in the art, IRE1 alpha (*Homo sapiens*, #AF059198; *Mus musculus*, #AB031332, AF071777), constitutively active IRE1 alpha as will be understood by one of skill in the art, IRE1 beta (*Homo sapiens*, #AB047079), constitutively active IRE1 beta as will be understood by one of skill in the art, activating transcription factor 4 (ATF4: *Homo sapiens*, #NM_001675; *Mus musculus*, #NM_009716), activating transcription factor 6 alpha or beta (ATF6 alpha or beta: *Homo sapiens*, #NM_007348, AF005887, AB015856; *Mus musculus*, #XM_129579), X-box binding protein 1 (XBP1: *Homo sapiens*, #AB076383, AB076384; *Mus musculus*, #AF443192, AF027963, NM_013842), CHOP-10/GADD153/DDIT3 (*Homo sapiens*, #NM_004083; *Mus musculus*, #X67083, NM_007837), site-1 protease (S1P: *Homo sapiens*, #NM_003791; *Mus musculus*, #NM_019709), site-2 protease (S2P: *Homo sapiens*, #NM_015884), presenilin-1 (*Homo sapiens*, #AH004968, AF416717; *Mus musculus*, #BC030409, NM_008943, AF149111), TNF receptor-associated factor 2 (TRAF2: *Homo sapiens*, #NM_021138, NM_145718, *Mus musculus*, #XM_203851, XM_130119, L35303), or cJUN NH2-terminal kinases (JNKs: S. Oyadomari et al. (2002) Apoptosis 7, 335-345)); a single-chain antibody or other molecule that binds to a pathogen, pathogen component, or cellular component that directly or indirectly aids a pathogen, as described supra; a molecule that executes or stimulates complement pathway-related responses, as described supra, including but not limited to C3 alpha, C3 beta, factor B, factor D, properdin, C1q, C1r, C1s, C4, C2, C5, C6, C7, C8, C9, factor I, factor H, C1-INH, C4 bp, S protein, clusterin, carboxypeptidase N, FHL-1, FHR-1, FHR-2, FHR-3, FHR-4, CR1, or DAF; a molecule that executes, stimulates, or inhibits toll-like-receptor-related responses, NOD-protein-related responses, (including but not limited to Nod1/CARD4 (*Homo sapiens*, #AAD28350, AAD43922; N. Inohara et al. (1999) Journal of Biological Chemistry 274, 14560-14567); Nod2, (*Homo sapiens*, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM_021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH011140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876)), pentraxin-related responses, collectin-related responses, mannose-receptor-related responses, scavenger-receptor-related responses, or immune-related responses, as described supra; a molecule that inhibits transport between the cytoplasm and the nucleus of a cell, as described supra (including but not limited to importin alpha 1 (*Homo sapiens*, #NM_002266) with the importin beta binding domain (approximately amino acids 3-99) removed, importin alpha 3 (*Homo sapiens*, #NM_002268) with the importin beta binding domain (approximately amino acids 3-94) removed, importin alpha 4 (*Homo sapiens*, #NM_002267) with the importin beta binding domain (approximately amino acids 3-94) removed, importin alpha 5 (*Homo sapiens*, #U28386) with the importin beta binding domain (approximately amino acids 3-94) removed, importin alpha 6 (*Homo sapiens*, #NM_002269) with the importin beta binding domain (approximately amino acids 3-94) removed, importin alpha 7 (*Homo sapiens*, #NM_012316) with the importin beta binding domain (approximately amino acids 3-103) removed, importin alpha with the importin beta binding domain removed as described supra and also with the last two armadillo repeats removed (Y. Miyamoto et al. (2002) EMBO Journal 21, 5833-5842) as will be understood by one of skill in the art, the autoinhibitory domain of an importin alpha mutated to have a higher than normal affinity for wild-type importin alpha (B. Catimel et al. (2001) Journal of Biological Chemistry 276, 34189-34198) as will be understood by one of skill in the art, a modified importin alpha that does not enable nuclear import but still binds to one or more pathogen nuclear localization signals (NLSs) and does so preferably with a higher affinity than it binds to cellular NLSs as will be understood by one of skill in the art, the importin beta binding domain of importin alpha 1 (*Homo sapiens*, #NM_002266, approximately amino acids 1-99), the importin beta binding domain of importin alpha 3 (*Homo sapiens*, #NM_002268, approximately amino acids 1-94), the importin beta binding domain of importin alpha 4 (*Homo sapiens*, #NM_002267, approximately amino acids 1-94), the importin beta binding domain of importin alpha 5 (*Homo sapiens*, #U28386, approximately amino acids 1-94), the importin beta binding domain of importin alpha 6 (*Homo sapiens*, #NM_002269, approximately amino acids 1-94), the importin beta binding domain of importin alpha 7 (*Homo sapiens*, #NM_012316, approximately amino acids 1-103), importin beta 1 (*Homo sapiens*, #NM_002265, #NP_002256) modified to not bind nucleoporins (for example by deleting the region between HEAT-5 and HEAT-6 (approximately amino acids 203-211) and the region between HEAT-6 and HEAT-7 (approximately amino acids 246-252) or by replacing those regions with nonhomologous linker regions (Y. M. Chook and G. Blobel (2001) Current Opinion in Structural Biology 11, 703-715)), importin beta 1 (*Homo sapiens*, #NM_002265, #NP_002256) modified to not bind importin alpha (for example by deleting the acidic loop importin-alpha-binding region spanning from approximately amino acid 333 through approximately amino acid 343 (G. Cingolani et al. (1999) Nature 399, 221-229)), a defective mutant of an exportin (I. G. Macara (2001) Microbiology and Molecular Biology Reviews 65, 570-594) as will be understood by one of skill in the art, a mutant p10/NTF2 that inhibits import by importin beta 1 (for example and without limitation, p10 D23A (C. M. Lane et al. (2000) Journal of Cell Biology 151, 321-331) or N77Y (B. B. Quimby et al. (2001) Journal of Biological Chemistry 276, 38820-38829)), vesicuovirus matrix protein or a portion thereof that inhibits nuclear import and/or nuclear export (J. M. Petersen et al. (2001) Proc. Natl. Acad. Sci. USA 98, 8590-8595; J. M. Petersen et al. (2000) Molecular and Cellular Biology 20, 8590-8601; C. von Kobbe et al. (2000) Molecular Cell 6, 1243-1252), a peptide that resembles the classical nuclear localization signal of SV40 T antigen (E. Merle et al. (1999) Journal of Cellular Biochemistry 74, 628-637), another nuclear localization signal, peptides with FxFG repeats or GLFG repeats (R. Bayliss et al. (2002) Journal of Biological Chemistry 277, 50597-50606), leptomycin B, a mutant of Ran that interferes with nuclear import or export (for example and without limitation, RanC4A (R. H. Kehlenbach et al. (2001) Journal of Biological Chemistry 276, 14524-14531)), or a molecule that binds to a pathogen or pathogen component or cellular component that is involved in transport between the cytoplasm and the nucleus of a cell (I. G. Macara (2001) Microbiology and Molecular Biology Reviews 65, 570-594; B. Ossareh-Nazari (2001) Traffic 2, 684-689)); a molecule that inhibits pathogenic prions (for example, approximately amino acids 119-136 of hamster prion protein; J. Chabry et al. (1999) Journal of Virology 73, 6245-6250); a molecule that alters the properties of the endocytic pathway, phagocytic pathway, endosomes, phagosomes, lysosomes, other intracellular compartments, or vesicular trafficking to produce an anti-pathogen effect, as described supra (including but not limited to dynamin-1 mutant K44A (M. Huber et al. (2001) Traffic 2, 727-736; particularly when overexpressed), cellubrevin (R. A. Fratti et al. (2002) Journal of Biological Chemistry 277, 17320-17326; particularly when overexpressed), *Salmonella* SpiC protein (NCBI Accession #U51927), a defective mutant of TassC (A. H. Lee et al. (2002) Cell. Microbiol. 4, 739-750), other vesicular trafficking inhibitors, Nramp1 (P. Cuellar-Mata et al. (2002) Journal of Biological Chemistry 277, 2258-2265; C. Frehel et al. (2002) Cellular Microbiology 4, 541-556; D. J. Hackam et al. (1998) J. Exp. Med. 188, 351-364; particularly when overexpressed), NADPH oxidase subunits or cofactors (P. V. Vignais (2002) Cell. Mol. Life Sci. 59, 1428-1459; particularly when overexpressed), NOS2 nitric oxide synthase (J. D. MacMicking et al. (1997) Proc. Natl. Acad. Sci. USA 94, 5243-5248; particularly when overexpressed), human papillomavirus 16 E5 protein (NCBI Accession #W5WLHS), bafilomycin A1, a single-chain antibody or other molecule that binds to vacuolar ATPase subunit a (S. B. Sato and S. Toyama (1994) J. Cell. Biol. 127, 39-53; preferably a1 or a2), antisense oligonucleotides that inhibit vacuolar ATPase subunits (J. E. Strasser et al. (1999) Journal of Immunology 162, 6148-6154), a peptide composed of approximately the 78 amino-terminal amino acids of vacuolar H+-ATPase subunit E (M. Lu et al. (2002) Journal of Biological Chemistry 277, 38409-38415), A2-cassette mutant of vacuolar H+-ATPase subunit A (N. Hernando et al. (1999) Eur. J. Biochem. 266, 293-301), a defective mutant of subunit a1 or a2 of vacuolar H+-ATPase (S. Kawasaki-Nishi et al. (2001) Proc. Natl. Acad. Sci. USA 98, 12397-12402; S. Kawasaki-Nishi et al. (2001) 276, 47411-47420; T. Nishi and M. Forgac (2000) J. Biol. Chem. 275, 6824-6830; S. B. Peng et al. (1999) J. Biol. Chem. 274, 2549-2555; T. Toyomura et al. (2000) J. Biol. Chem. 275, 8760-8765) as will be understood by one of skill in the art, overexpression of the C and/or H subunits of vacuolar H+-ATPase subunit E (K. K. Curtis and P. M. Kane (2002) Journal of Biological Chemistry 277, 2716-2724), other defective vacuolar ATPase subunit or portion of a subunit (examples of wild-type human vacuolar ATPase subunits that can be made defective for anti-pathogen effects will be understood by one of skill in the art, and include, without limitation, those vacuolar ATPase subunits with Accession numbers: NM_004231, NM_130463, NM_015994, NM_001694, NM_004047, NM_001696, NM_004691, NM_001695, NM_001693, NM_001690, NM_020632, NM_004888)); a molecule that executes, stimulates, or inhibits ubiquitin proteasome degradative pathway-related responses, as described supra (including but not limited to CHIP (D. M. Cyr et al. (2002) Trends Biochem. Sci. 27, 368-375; J. Demand et al. (2001) Curr. Biol. 11, 1569-1577; S. Murata et al. (2001) EMBO Rep. 2, 1133-1138; particularly when overexpressed), Fbx2 (Y. Yoshida et al. (2002) Nature 418, 438-442; particularly when overexpressed), molecules that ubiquitinate pathogens or pathogen components or cellular components that assist pathogens (P. Zhou et al. (2000) Mol. Cell 6, 751-756; K. M. Sakamoto et al. (2001) Proc. Natl. Acad. Sci. USA 98, 8554-8559; N. Zheng et al. (2000) Cell 102, 533-539; D. Oyake et al. (2002) Biochemical and Biophysical Research Communications 295, 370-375), or inhibitors of ubiquitination or proteasomes (J. Myung et al. (2001) Medicinal Research Reviews 21, 245-273; G. Lennox et al. (1988) Neurosci. Lett. 94, 211-217; N. F. Bence et al. (2001) Science 292, 1552-1555); for example and without limitation, lactacystin or epoxomicin; a molecule that executes, stimulates, or inhibits defensin-related responses, as described supra, including but not limited to alpha defensins, beta defensins, theta defensins, plant defensins, or arthropod defensins; a molecule that executes, stimulates, or inhibits cathelicidin-related responses, as described supra, including but not limited to hCAP-18/LL-37, CRAMP, Bac4, OaBac5; prophenin-1, protegrin-1, or PR-39; a molecule that executes, stimulates, or inhibits chemokine-related or thrombocidin-related responses, as described supra, including but not limited to CC chemokines, CXC chemokines, C chemokines, CX3C chemokines, CC chemokine receptors, CXC chemokine receptors, C chemokine receptors, CX3C chemokine receptors, JAK proteins, STAT proteins, fibrinopeptide A, fibrinopeptide B, or thymosin beta 4; a molecule that executes, stimulates, or inhibits interferon-related or cytokine-related responses, as described supra (including but not limited to interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439; *Mus musculus*, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12: *Homo sapiens*, #NM_000882, NM_002187; *Mus musculus*, #NM_008351, NM_008352); interleukin 15 (IL-15: *Homo sapiens*, #NM_172174, NM_172175, NM_000585; *Mus musculus*, #NM_008357); cytokine receptors and related signaling molecules (W. E. Paul (ed.), Fundamental Immunology (4th ed., Lippincott-Raven, Philadelphia, 1999), Chapters 21 and 22); interferon type I receptor subunit 1 (IFNAR1: *Homo sapiens*, #NM_000629; *Mus musculus*, #NM_010508); interferon type I receptor subunit 2 (IFNAR2: *Homo sapiens*, #NM_000874; *Mus musculus*, #NM_010509); janus kinase 1 (JAK1: *Homo sapiens*, #NP_002218; *Mus musculus*, #NP_666257); janus kinase 2 (JAK2: *Homo sapiens*, #AAC23653, AAC23982, NP_004963; *Mus musculus*, #NP_032439, AAN62560); JAK3; Tyk2; signal transducer and activator of transcription 1 (STAT1: *Homo sapiens*, #NM_007315, NM_139266; *Mus musculus*, #U06924); signal transducer and activator of transcription 2 (STAT2: *Homo sapiens*, #NM_005419; *Mus musculus*, AF206162); STAT3; STAT4; STAT5; STAT6; interferon-stimulated gene factor 3 gamma (ISGF3 gamma: *Homo sapiens*, #Q00978, NM_006084; *Mus musculus*, #NM_008394) interferon regulatory factor 1 (IRF1: *Homo sapiens*, #NM_002198, P10914; *Mus musculus*, #NM_008390); interferon regulatory factor 3 (IRF3: *Homo sapiens*, #NM_001571, Z56281; *Mus musculus*, #NM_016849, U75839, U75840); interferon regulatory factor 5 (IRF5: *Homo sapiens*, #Q13568, U51127; *Mus musculus*, #AAB81997, NP_036187); interferon regulatory factor 6 (IRF6: *Homo sapiens*, #AF027292, NM_006147; *Mus musculus*, #U73029); interferon regulatory factor 7 (IRF7: *Homo sapiens*, #U53830, U53831, U53832, AF076494, U73036; *Mus musculus*, #NM_016850, U73037); interferon regulatory factor 8 (IRF8); a constitutively active interferon regulatory factor; protein kinase R (PKR: *Homo sapiens*, #AAC50768; *Mus musculus*, #Q03963; S. Nanduri et al. (1998) EMBO J. 17, 5458-5465); constitutively active PKR; 2',5'-oligoadenylate synthetases (*Homo sapiens* forms including #P00973, P29728, AAD28543; *Mus musculus* forms including P11928; S. Y. Desai et al. (1995) J. Biol. Chem. 270, 3454-3461); constitutively active 2',5'-oligoadenylate synthetases; RNase L (*Homo sapiens*, #CAA52920); constitutively active RNase L; promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (*Homo sapiens*, #U18121; *Mus musculus*, #NP_062629); Mx1 (*Homo sapiens*, #NM_002462); or Mx2 (*Homo sapiens*, #NM_002463)); a molecule that inhibits budding or release of pathogens from an infected cell, as described supra (including but not limited to Hrs, particularly when overexpressed (N. Bishop et al. (2002) Journal of Cell Biology 157, 91-101; L. Chin et al. (2001) Journal of Biological Chemistry 276, 7069-7078; C. Raiborg et al. (2002) Nature Cell Biology 4, 394-398); defective Vps4 mutants such as K173Q or E228Q, particularly when overexpressed (J. E. Garrus et al. (2001) Cell 107, 55-65); small interfering RNA that inhibits Tsg101 expression (N. Bishop et al. (2002) Journal of Cell Biology 157, 91-101; J. E. Garrus et al. (2001) Cell 107, 55-65); truncated AP-50 consisting of approximately amino acids 121-435, or other defective mutant of AP-50, particularly when overexpressed (B. A. Puffer et al. (1998) Journal of Virology 72, 10218-10221); WW-domain-containing fragment of LDI-1, Nedd4, Yes-associated protein, KIAA0439 gene product, or other defective Nedd4-related proteins, particularly when overexpressed (A. Kikonyogo et al. (2001) Proc. Natl. Acad. Sci. USA 98, 11199-11204; A. Patnaik and J. W. Wills (2002) Journal of Virology 76, 2789-2795); a peptide consisting of the HIV p6 Gag PTAPP-motif-containing late (L) domain (L. VerPlank et al. (2001) Proc. Natl. Acad. Sci. USA 98, 7724-7729) or other viral late (L) domain containing PTAP, PSAP, PPXY, YPDL, or YXXL motifs (J. Martin-Serrano et al. (2001) Nature Medicine 7, 1313-1319; A. Patnaik and J. W. Wills (2002) Journal of Virology 76, 2789-2795); amino acids 1-167 of Tsg101, TSG-5' fragment of Tsg101, or similar amino-terminal fragment of Tsg101, particularly when overexpressed (D. G. Demirov et al. (2002) Proc. Natl. Acad. Sci. USA 99, 955-9601; E. L. Myers and J. F. Allen (2002) Journal of Virology 76, 11226-11235); a mutant of Tsg101 (M. Babst et al. (2000) Traffic 1, 248-258; L. VerPlank et al. (2001) Proc. Natl. Acad. Sci. USA 98, 7724-7729; J. Martin-Serrano et al. (2001) Nature Medicine 7, 1313-1319; O. Pornillos et al. (2002) EMBO Journal 21, 2397-2406) with reduced capacity to aid viral budding; a casein kinase 2 (CK2) inhibitor, such as the peptide RRADDSDDDDD (SEQ ID NO: 472) (E. K. Hui and D. P. Nayak (2002) Journal of General Virology 83, 3055-3066); or G protein signalling inhibitors (E. K. Hui and D. P. Nayak (2002) Journal of General Virology 83, 3055-3066); a molecule that binds to a cellular or pathogen molecule (for example and without limitation, to one or more of the following molecules: Tsg101, Vps4, casein kinase 2, Hrs, hVps28, Eap30, Eap20, Eap45, Chmp1, Chmp2, Chmp3, Chmp4, Chmp5, Chmp6, AP-50, Nedd4-related proteins, WW-domain-containing proteins, or L-domain-containing proteins; O. Pornillos et al. (2002) TRENDS in Cell Biology 12, 569-579; P. Gomez-Puertas et al. (2000) Journal of Virology 74, 11538-11547; E. Katz et al. (2002) Journal of Virology 76, 11637-11644) that is involved in budding or release of pathogens from an infected cell); a molecule that executes or stimulates apoptosis-related or other cell-death-related responses, as described supra (including but not limited to p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); apoptotic protease activating factor 1 (Apaf-1: *Homo sapiens*, #NM_013229, NM_001160; *Mus musculus*, #NP_033814); Fas/CD95 (*Homo sapiens*, #AAC16236, AAC16237; *Mus musculus*, #AAG02410); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); granzyme B (*Homo sapiens*, #AAH30195, NP_004122; *Mus musculus*, #AAH02085, NP_038570); constitutively active granzyme B, as will be understood by one of skill in the art; Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); a constitutively active caspase; calpains (T. Lu et al., (2002) Biochimica et Biophysica Acta 1590, 16-26)); a molecule that degrades components of cells or pathogens, as described supra (for example and without limitation: proteases, including chymotrypsin, trypsin, or elastase; DNases, including caspase-activated DNase (CAD), constitutively active CAD (N. Inohara et al. (1999) Journal of Biological Chemistry 274, 270-274), or restriction enzymes; RNases, including RNase III (*Homo sapiens*, #AF189011; *Escherichia coli*, #NP_417062, NC_000913), RNt1p (*Saccharomyces cerevisiae*, #U27016), Pac1, (*Schizosaccharomyces pombe*, #X54998), RNase A, or RNase L; glycosidases, including N-glycanase, endoglycosidase H, O-glycanase, endoglycosidase F2, sialidase, or beta-galactosidase; or lipases, including phospholipase A1, phospholipase A2, phospholipase C, or phospholipase D); a molecule that is toxic to an infected host cell or a pathogen cell, as described supra (including but not limited to an intracellular bacterial toxin (B. B. Finlay and P. Cossart (1997) Science 276, 718-725; C. Montecucco et al. (1994) FEBS Lett. 346, 92-98; P. O. Falnes et al. (2001) Biochemistry 40, 4349-4358) that has been modified so that it cannot cross cellular plasma membranes, such as the A (21 kDa) fragment of diptheria toxin; a molecule that is toxic to a pathogen cell, including but not limited to penicillin, erythromycin, tetracycline, rifampin, amphotericin B, metronidazole, or mefloquine; an ATP inhibitor (E. K. Hui and D. P. Nayak (2001) Virology 290, 329-341); or a toxin that inhibits transcription, translation, replication, oxidative phosphorylation, cytoskeletal processes, or other cell and/or pathogen functions).

An inflammatory response-inducible promoter, as described supra, can be operatively linked with a wide variety of effector domains encoded by a polynucleotide sequence, as described supra. Similarly, a stress/heat shock-inducible promoter, as described supra, can be operatively linked with a wide variety of effector domains encoded by a polynucleotide sequence, as described supra. Likewise, a promoter that can be induced by cytokines such as interferon alpha, interferon beta, or interferon omega, as described supra, can be operatively linked with a wide variety of effector domains encoded by a polynucleotide sequence, as described supra. Additionally, a promoter that can be induced by cytokines such as interferon gamma, interleukin 1, interleukin 2, interleukin 3, interleukin 4, interleukin 5, interleukin 6, interleukin 7, interleukin 9, interleukin 12, or interleukin 15, as described supra, can be operatively linked with a wide variety of effector domains encoded by a polynucleotide sequence, as described supra. Alternatively, a drug-inducible promoter, as described supra, can be operatively linked with a wide variety of effector domains encoded by a polynucleotide sequence, as described supra. Examples of the effector domains that can be operatively linked to these promoters, include: a chimeric molecule or agent as described herein, including but not limited to, dsRNA-activated caspase, 2',5'-oligoadenylate-activated caspase, dsRNA-activated caspase activator, or 2',5'-oligoadenylate-activated caspase activator; a chimeric transcription factor as described herein; a molecule that contains two or more binding sites for a pathogen, pathogen component, or pathogen product as described herein; an antisense polynucleotide or small interfering RNA (G. M. Barton and R. Medzhitov (2002) Proc. Natl. Acad. Sci. USA 99, 14943-14945) that inhibits expression of a pathogen gene or a host gene that aids a pathogen; a molecule that executes, stimulates, or inhibits stress or inflammatory responses, as described supra (including but not limited to heat shock protein 70 (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM_015765, NM_010481, NM_008301, M76613), Hsc70 (*Homo sapiens*, #AF352832), Hsp90 (*Homo sapiens*, #M16660, NM_005348, NM_007355); Hsp40/Hdj-1 (*Homo sapiens*, #X62421, NM_006145, NM_005880), Hsp60 (*Homo sapiens*, #NM_002156), Hsp47/CBP-2 (*Homo sapiens*, #D83174), Hsp100 (*Homo sapiens*, #NM_006660), Alpha- A-crystallin (*Homo sapiens*, #NM_000394), Alpha-B-crystallin (*Homo sapiens*, #NM_001885), Hsp27-1 (*Homo sapiens*, #NM_001540), Hsp27-2 (*Homo sapiens*, #XM_012054), cdc48 (S. Thoms (2002) FEBS Lett. 520, 107-110), heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131), constitutively active HSF1, RelA/p65 (*Homo sapiens*, #NM_021975, Z22948, L19067; *Mus musculus*, #NM_009045, AF199371), RelB (*Homo sapiens*, #NM_006509; *Mus musculus*, #NM_009046, M83380), c-Rel (*Homo sapiens*, #X75042, NM_002908; *Mus musculus*, #NM_009044, X15842), p50/p105/NF-kappa B 1 (*Homo sapiens*, #NM_003998, S76638, AF213884, AH009144; *Mus musculus*, #NM_008689, AK052726, M57999), p52/p100/NF-kappa B 2 (*Homo sapiens*, #NM_002502; *Mus musculus*, #AF155372, AF155373, NM_019408), inhibitors of kappa B (I kappa B: *Homo sapiens*, #AY033600, NM_020529; S. Ghosh and M. Karin (2002) Cell 109, S81-S96), IKK1/I kappa B kinase alpha (IKK alpha: *Homo sapiens*, #AF009225, AF080157), IKK2/I kappa B kinase beta (IKK beta: *Homo sapiens*, #AF080158; *Mus musculus*, #AF026524, AF088910), or NEMO/I kappa B kinase gamma (IKK gamma: *Homo sapiens*, #AF261086, AF091453; *Mus musculus*, #AF069542)); a molecule that executes, stimulates, or inhibits unfolded-protein-related or endoplasmic reticulum-associated protein degradation-related responses, as described supra (including but not limited to BiP/GRP78/SHPA5 (*Homo sapiens*, #AJ271729, AF216292, X87949, NM_005347; *Mus musculus*, #NM_022310), PKR-like endoplasmic reticulum kinase (PERK: *Homo sapiens*, #NP_004827; *Mus musculus*, #AAD03337, NP_034251), constitutively active PERK, IRE1 alpha (*Homo sapiens*, #AF059198; *Mus musculus*, #AB031332, AF071777), constitutively active IRE1 alpha as will be understood by one of skill in the art, IRE1 beta (*Homo sapiens*, #AB047079), constitutively active IRE1 beta, activating transcription factor 4 (ATF4: *Homo sapiens*, #NM_001675; *Mus musculus*, #NM_009716), activating transcription factor 6 alpha or beta (ATF6 alpha or beta: *Homo sapiens*, #NM_007348, AF005887, AB015856; *Mus musculus*, #XM_129579), X-box binding protein 1 (XBP1: *Homo sapiens*, #AB076383, AB076384; *Mus musculus*, #AF443192, AF027963, NM_013842), CHOP-10/GADD153/DDIT3 (*Homo sapiens*, #NM_004083; *Mus musculus*, #X67083, NM_007837), site-1 protease (S1P: *Homo sapiens*, #NM_003791; *Mus musculus*, #NM_019709), site-2 protease (S2P: *Homo sapiens*, #NM_015884), presenilin-1 (*Homo sapiens*, #AH004968, AF416717; *Mus musculus*, #BC030409, NM_008943, AF149111), TNF receptor-associated factor 2 (TRAF2: *Homo sapiens*, #NM_021138, NM_145718, *Mus musculus*, #XM_203851, XM_130119, L35303), or cJUN NH2-terminal kinases (JNKs: S. Oyadomari et al. (2002) Apoptosis 7, 335-345)); a single-chain antibody or other molecule that binds to a pathogen, pathogen component, or cellular component that directly or indirectly aids a pathogen, as described supra; a molecule that executes or stimulates complement pathway-related responses, as described supra, including but not limited to C3 alpha, C3 beta, factor B, factor D, properdin, C1q, C1r, C1s, C4, C2, C5, C6, C7, C8, C9, factor I, factor H, C1-INH, C4 bp, S protein, clusterin, carboxypeptidase N, FHL-1, FHR-1, FHR-2, FHR-3, FHR-4, CR1, or DAF; a molecule that executes, stimulates, or inhibits toll-like-receptor-related responses, NOD-protein-related responses, (including but not limited to Nod1/CARD4 (*Homo sapiens*, #AAD28350, AAD43922; N. Inohara et al. (1999) Journal of Biological Chemistry 274, 14560-14567); Nod2, (*Homo sapiens*, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM_021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH011140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876)), pentraxin-related responses, collectin-related responses, mannose-receptor-related responses, scavenger receptor-related responses, or immune-related responses, as described supra; a molecule that inhibits transport between the cytoplasm and the nucleus of a cell, as described supra (including but not limited to importin alpha 1 (*Homo sapiens*, #NM_002266) with the importin beta binding domain (approximately amino acids 3-99) removed, importin alpha 3 (*Homo sapiens*, #NM_002268) with the importin beta binding domain (approximately amino acids 3-94) removed, importin alpha 4 (*Homo sapiens*, #NM_002267) with the importin beta binding domain (approximately amino acids 3-94) removed, importin alpha 5 (*Homo sapiens*, #U28386) with the importin beta binding domain (approximately amino acids 3-94) removed, importin alpha 6 (*Homo sapiens*, #NM_002269) with the importin beta binding domain (approximately amino acids 3-94) removed, importin alpha 7 (*Homo sapiens*, #NM_012316) with the importin beta binding domain (approximately amino acids 3-103) removed, importin alpha with the importin beta binding domain removed as described supra and also with the last two armadillo repeats removed (Y. Miyamoto et al. (2002) EMBO Journal 21, 5833-5842), the autoinhibitory domain of an importin alpha mutated to have a higher than normal affinity for wild-type importin alpha (B. Catimel et al. (2001) Journal of Biological Chemistry 276, 34189-34198), a modified importin alpha that does not enable nuclear import but still binds to one or more pathogen nuclear localization signals (NLSs) and does so preferably with a higher affinity than it binds to cellular NLSs, the importin beta binding domain of importin alpha 1 (*Homo sapiens*, #NM_002266, approximately amino acids 1-99), the importin beta binding domain of importin alpha 3 (*Homo sapiens*, #NM_002268, approximately amino acids 1-94), the importin beta binding domain of importin alpha 4 (*Homo sapiens*, #NM_002267, approximately amino acids 1-94), the importin beta binding domain of importin alpha 5 (*Homo sapiens*, #U28386, approximately amino acids 1-94), the importin beta binding domain of importin alpha 6 (*Homo sapiens*, #NM_002269, approximately amino acids 1-94), the importin beta binding domain of importin alpha 7 (*Homo sapiens*, #NM_012316, approximately amino acids 1-103), importin beta 1 (*Homo sapiens*, #NM_002265, #NP_002256) modified to not bind nucleoporins (for example and without limitation, by deleting the region between HEAT-5 and HEAT-6 (approximately amino acids 203-211) and the region between HEAT-6 and HEAT-7 (approximately amino acids 246-252) or by replacing those regions with nonhomologous linker regions (Y. M. Chook and G. Blobel (2001) Current Opinion in Structural Biology 11, 703-715)), importin beta 1 (*Homo sapiens*, #NM_002265, #NP_002256) modified to not bind importin alpha (for example and without limitation, by deleting the acidic loop importin-alpha-binding region spanning from approximately amino acid 333 through approximately amino acid 343 (G. Cingolani et al. (1999) Nature 399, 221-229)), a defective mutant of an exportin (I. G. Macara (2001) Microbiology and Molecular Biology Reviews 65, 570-594), a mutant p10/NTF2 that inhibits import by importin beta 1 (for example and without limitation, p10 D23A (C. M. Lane et al. (2000) Journal of Cell Biology 151, 321-331) or N77Y (B. B. Quimby et al. (2001) Journal of Biological Chemistry 276, 38820-38829)), vesicuovirus matrix protein or a portion thereof that inhibits nuclear import and/or nuclear export (J. M. Petersen et al. (2001) Proc. Natl. Acad. Sci. USA 98, 8590-8595; J. M. Petersen et al. (2000) Molecular and Cellular Biology 20, 8590-8601; C. von Kobbe et al. (2000) Molecular Cell 6, 1243-1252), a peptide that resembles the classical nuclear localization signal of SV40 T antigen (E. Merle et al. (1999) Journal of Cellular Biochemistry 74, 628-637), another nuclear localization signal, peptides with FxFG repeats or GLFG repeats (R. Bayliss et al. (2002) Journal of Biological Chemistry 277, 50597-50606), leptomycin B, a mutant of Ran that interferes with nuclear import or export (for example and without limitation, RanC4A (R. H. Kehlenbach et al. (2001) Journal of Biological Chemistry 276, 14524-14531)), or a molecule that binds to a pathogen or pathogen component or cellular component that is involved in transport between the cytoplasm and the nucleus of a cell (I. G. Macara (2001) Microbiology and Molecular Biology Reviews 65, 570-594; B. Ossareh-Nazari (2001) Traffic 2, 684-689)); a molecule that inhibits pathogenic prions (for example and without restriction, approximately amino acids 119-136 of hamster prion protein; J. Chabry et al. (1999) Journal of Virology 73, 6245-6250); a molecule that alters the properties of the endocytic pathway, phagocytic pathway, endosomes, phagosomes, lysosomes, other intracellular compartments, or vesicular trafficking to produce an anti-pathogen effect, as described supra (including but not limited to dynamin-1 mutant K44A (M. Huber et al. (2001) Traffic 2, 727-736; particularly when overexpressed), cellubrevin (R. A. Fratti et al. (2002) Journal of Biological Chemistry 277, 17320-17326; particularly when overexpressed), *Salmonella* SpiC protein (NCBI Accession #U51927), a defective mutant of TassC (A. H. Lee et al. (2002) Cell. Microbiol. 4, 739-750), other vesicular trafficking inhibitors, Nramp1 (P. Cuellar-Mata et al. (2002) Journal of Biological Chemistry 277, 2258-2265; C. Frehel et al. (2002) Cellular Microbiology 4, 541-556; D. J. Hackam et al. (1998) J. Exp. Med. 188, 351-364; particularly when overexpressed), NADPH oxidase subunits or cofactors (P. V. Vignais (2002) Cell. Mol. Life Sci. 59, 1428-1459; particularly when overexpressed), NOS2 nitric oxide synthase (J. D. MacMicking et al. (1997) Proc. Natl. Acad. Sci. USA 94, 5243-5248; particularly when overexpressed), human papillomavirus 16 E5 protein (NCBI Accession #W5WLHS), bafilomycin A1, a single-chain antibody or other molecule that binds to vacuolar ATPase subunit a (S. B. Sato and S. Toyama (1994) J. Cell. Biol. 127, 39-53; preferably a1 or a2), antisense oligonucleotides that inhibit vacuolar ATPase subunits (J. E. Strasser et al. (1999) Journal of Immunology 162, 6148-6154), a peptide composed of approximately the 78 amino-terminal amino acids of vacuolar H+-ATPase subunit E (M. Lu et al. (2002) Journal of Biological Chemistry 277, 38409-38415), A2-cassette mutant of vacuolar H+-ATPase subunit A (N. Hernando et al. (1999) Eur. J. Biochem. 266, 293-301), a defective mutant of subunit a1 or a2 of vacuolar H+-ATPase (S. Kawasaki-Nishi et al. (2001) Proc. Natl. Acad. Sci. USA 98, 12397-12402; S. Kawasaki-Nishi et al. (2001) 276, 47411-47420; T. Nishi and M. Forgac (2000) J. Biol. Chem. 275, 6824-6830; S. B. Peng et al. (1999) J. Biol. Chem. 274, 2549-2555; T. Toyomura et al. (2000) J. Biol. Chem. 275, 8760-8765), overexpression of the C and/or H subunits of vacuolar H+-ATPase subunit E (K. K. Curtis and P. M. Kane (2002) Journal of Biological Chemistry 277, 2716-2724), other defective vacuolar ATPase subunit or portion of a subunit (examples of wild-type human vacuolar ATPase subunits that can be made defective for anti-pathogen effects will be understood by one of skill in the art, and include, without limitation, those vacuolar ATPase subunits with Accession numbers: NM_004231, NM_130463, NM_015994, NM_001694, NM_004047, NM_001696, NM_004691, NM_001695, NM_001693, NM_001690, NM_020632, NM_004888)); a molecule that executes, stimulates, or inhibits ubiquitin proteasome degradative pathway-related responses, as described supra (including but not limited to CHIP (D. M. Cyr et al. (2002) Trends Biochem. Sci. 27, 368-375; J. Demand et al. (2001) Curr. Biol. 11, 1569-1577; S. Murata et al. (2001) EMBO Rep. 2, 1133-1138; particularly when overexpressed as will be understood by one of skill in the art), Fbx2 (Y. Yoshida et al. (2002) Nature 418, 438-442; particularly when overexpressed), molecules that ubiquitinate pathogens or pathogen components or cellular components that assist pathogens (P. Zhou et al. (2000) Mol. Cell 6, 751-756; K. M. Sakamoto et al. (2001) Proc. Natl. Acad. Sci. USA 98, 8554-8559; N. Zheng et al. (2000) Cell 102, 533-539; D. Oyake et al. (2002) Biochemical and Biophysical Research Communications 295, 370-375), or inhibitors of ubiquitination or proteasomes (J. Myung et al. (2001) Medicinal Research Reviews 21, 245-273; G. Lennox et al. (1988) Neurosci. Lett. 94, 211-217; N. F. Bence et al. (2001) Science 292, 1552-1555; for example and without limitation, lactacystin or epoxomicin)); a molecule that executes, stimulates, or inhibits defensin-related responses, as described supra, including but not limited to alpha defensins, beta defensins, theta defensins, plant defensins, or arthropod defensins; a molecule that executes, stimulates, or inhibits cathelicidin-related responses, as described supra, including but not limited to hCAP-18/LL-37, CRAMP, Bac4, OaBac5; prophenin-1, protegrin-1, or PR-39; a molecule that executes, stimulates, or inhibits chemokine-related or thrombocidin-related responses, as described supra, including but not limited to CC chemokines, CXC chemokines, C chemokines, CX3C chemokines, CC chemokine receptors, CXC chemokine receptors, C chemokine receptors, CX3C chemokine receptors, JAK proteins, STAT proteins, fibrinopeptide A, fibrinopeptide B, or thymosin beta 4; a molecule that executes, stimulates, or inhibits interferon-related or cytokine-related responses, as described supra (including but not limited to interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439;

Mus musculus, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12: *Homo sapiens*, #NM_000882, NM_002187; *Mus musculus*, #NM_008351, NM_008352); interleukin 15 (IL-15: *Homo sapiens*, #NM_172174, NM_172175, NM_000585; *Mus musculus*, #NM_008357); cytokine receptors and related signaling molecules (W. E. Paul (ed.), Fundamental Immunology (4th ed., Lippincott-Raven, Philadelphia, 1999), Chapters 21 and 22); interferon type I receptor subunit 1 (IFNAR1: *Homo sapiens*, #NM_000629; *Mus musculus*, #NM_010508); interferon type I receptor subunit 2 (IFNAR2: *Homo sapiens*, #NM_000874; *Mus musculus*, #NM_010509); janus kinase 1 (JAK1: *Homo sapiens*, #NP_002218; *Mus musculus*, #NP_666257); janus kinase 2 (JAK2: *Homo sapiens*, #AAC23653, AAC23982, NP_004963; *Mus musculus*, #NP_032439, AAN62560); JAK3; Tyk2; signal transducer and activator of transcription 1 (STAT1: *Homo sapiens*, #NM_007315, NM_139266; *Mus musculus*, #U06924); signal transducer and activator of transcription 2 (STAT2: *Homo sapiens*, #NM_005419; *Mus musculus*, AF206162); STAT3; STAT4; STAT5; STAT6; interferon-stimulated gene factor 3 gamma (ISGF3 gamma: *Homo sapiens*, #Q00978, NM_006084; *Mus musculus*, #NM_008394) interferon regulatory factor 1 (IRF1: *Homo sapiens*, #NM_002198, P10914; *Mus musculus*, #NM_008390); interferon regulatory factor 3 (IRF3: *Homo sapiens*, #NM_001571, Z56281; *Mus musculus*, #NM_016849, U75839, U75840); interferon regulatory factor 5 (IRF5: *Homo sapiens*, #Q13568, U51127; *Mus musculus*, #AAB81997, NP_036187); interferon regulatory factor 6 (IRF6: *Homo sapiens*, #AF027292, NM_006147; *Mus musculus*, #U73029); interferon regulatory factor 7 (IRF7: *Homo sapiens*, #U53830, U53831, U53832, AF076494, U73036; *Mus musculus*, #NM_016850, U73037); interferon regulatory factor 8 (IRF8); a constitutively active interferon regulatory factor, as will be understood by one of skill in the art; protein kinase R (PKR: *Homo sapiens*, #AAC50768; *Mus musculus*, #Q03963; S. Nanduri et al. (1998) EMBO J. 17, 5458-5465); 2',5'-oligoadenylate synthetases (*Homo sapiens* forms including #P00973, P29728, AAD28543; *Mus musculus* forms including P11928; S. Y. Desai et al. (1995) J. Biol. Chem. 270, 3454-3461); RNase L (*Homo sapiens*, #CAA52920); promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (*Homo sapiens*, #U18121; *Mus musculus*, #NP_062629); Mx1 (*Homo sapiens*, #NM_002462); or Mx2 (*Homo sapiens*, #NM_002463)); a molecule that inhibits budding or release of pathogens from an infected cell, as described supra (including but not limited to Hrs, particularly when overexpressed (N. Bishop et al. (2002) Journal of Cell Biology 157, 91-101; L. Chin et al. (2001) Journal of Biological Chemistry 276, 7069-7078; C. Raiborg et al. (2002) Nature Cell Biology 4, 394-398); defective Vps4 mutants such as K173Q or E228Q, particularly when overexpressed (J. E. Garrus et al. (2001) Cell 107, 55-65); small interfering RNA that inhibits Tsg101 expression (N. Bishop et al. (2002) Journal of Cell Biology 157, 91-101; J. E. Garrus et al. (2001) Cell 107, 55-65); truncated AP-50 consisting of approximately amino acids 121-435, or other defective mutant of AP-50, particularly when overexpressed (B. A. Puffer et al. (1998) Journal of Virology 72, 10218-10221); WW-domain-containing fragment of LDI-1, Nedd4, Yes-associated protein, KIAA0439 gene product, or other defective Nedd4-related proteins, particularly when overexpressed (A. Kikonyogo et al. (2001) Proc. Natl. Acad. Sci. USA 98, 11199-11204; A. Patnaik and J. W. Wills (2002) Journal of Virology 76, 2789-2795); a peptide consisting of the HIV p6 Gag PTAPP-motif-containing late (L) domain (L. VerPlank et al. (2001) Proc. Natl. Acad. Sci. USA 98, 7724-7729) or other viral late (L) domain containing PTAP, PSAP, PPXY, YPDL, or YXXL motifs (J. Martin-Serrano et al. (2001) Nature Medicine 7, 1313-1319; A. Patnaik and J. W. Wills (2002) Journal of Virology 76, 2789-2795); amino acids 1-167 of Tsg101, TSG-5' fragment of Tsg101, or similar amino-terminal fragment of Tsg101, particularly when overexpressed (D. G. Demirov et al. (2002) Proc. Natl. Acad. Sci. USA 99, 955-9601; E. L. Myers and J. F. Allen (2002) Journal of Virology 76, 11226-11235); a mutant of Tsg101 (M. Babst et al. (2000) Traffic 1, 248-258; L. VerPlank et al. (2001) Proc. Natl. Acad. Sci. USA 98, 7724-7729; J. Martin-Serrano et al. (2001) Nature Medicine 7, 1313-1319; O. Pornillos et al. (2002) EMBO Journal 21, 2397-2406) with reduced capacity to aid viral budding, as will be understood by one of skill in the art; a casein kinase 2 (CK2) inhibitor, such as the peptide RRADDSDDDDD (SEQ ID NO: 472)(E. K. Hui and D. P. Nayak (2002) Journal of General Virology 83, 3055-3066); or G protein signalling inhibitors (E. K. Hui and D. P. Nayak (2002) Journal of General Virology 83, 3055-3066); a molecule that binds to a cellular or pathogen molecule (for example and without limitation, to one or more of the following molecules: Tsg101, Vps4, casein kinase 2, Hrs, hVps28, Eap30, Eap20, Eap45, Chmp1, Chmp2, Chmp3, Chmp4, Chmp5, Chmp6, AP-50, Nedd4-related proteins, WW-domain-containing proteins, or L-domain-containing proteins; O. Pornillos et al. (2002) TRENDS in Cell Biology 12, 569-579; P. Gomez-Puertas et al. (2000) Journal of Virology 74, 11538-11547; E. Katz et al. (2002) Journal of Virology 76, 11637-11644) that is involved in budding or release of pathogens from an infected cell); a molecule that makes a cell more receptive to apoptosis signals, as described supra (including but not limited to p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); apoptotic protease activating factor 1 (Apaf-1: *Homo sapiens*, #NM_013229, NM_001160; *Mus musculus*, #NP_033814); Fas/CD95 (*Homo sapiens*, #AAC16236, AAC16237; *Mus musculus*, #AAG02410); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228;

Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); calpains (T. Lu et al., (2002) Biochimica et Biophysica Acta 1590, 16-26)); a molecule that degrades components of pathogens, as described supra (for example and without limitation: proteases, including chymotrypsin, trypsin, or elastase; DNases, including restriction enzymes; RNases, including RNase III (*Homo sapiens*, #AF189011; *Escherichia coli*, #NP 417062, NC_000913), RNt1p (*Saccharomyces cerevisiae*, #U27016), Pac1, (*Schizosaccharomyces pombe*, #X54998), or RNase L; glycosidases, including N-glycanase, endoglycosidase H, O-glycanase, endoglycosidase F2, sialidase, or beta-galactosidase; or lipases, including phospholipase A1, phospholipase A2, phospholipase C, or phospholipase D); a molecule that inhibits or is toxic to a pathogen cell, as described supra (including but not limited to penicillin, erythromycin, tetracycline, rifampin, amphotericin B, metronidazole, mefloquine, or another molecule that inhibits pathogen functions).

An inducible promoter (for example and without limitation, one of the following promoters as described herein: a dsRNA-inducible promoter; apoptosis-inducible promoter; unfolded protein response-inducible promoter or endoplasmic reticulum-associated protein degradation response-inducible promoter; inflammatory response-inducible promoter; stress/heat shock-inducible promoter; promoter that can be induced by cytokines such as interferon alpha, interferon beta, or interferon omega; promoter that can be induced by cytokines such as interferon gamma, interleukin 1, interleukin 2, interleukin 3, interleukin 4, interleukin 5, interleukin 6, interleukin 7, interleukin 9, interleukin 12, or interleukin 15; or a drug-inducible promoter) can be operatively linked with a polynucleotide sequence encoding an effector molecule that can act within the producing cell, between cells, or on or in other cells. The effector molecule can optionally include a cellular targeting tag or a protein uptake tag as described herein and/or a secretory signal peptide, as will be understood by one of skill in the art. In addition to an optional tag or peptide, the effector molecule can include one or more of the following domains, for example and without limitation: a chimeric molecule or agent as described herein, including but not limited to dsRNA-activated caspase, 2',5'-oligoadenylate-activated caspase, dsRNA-activated caspase activator, or 2',5'-oligoadenylate-activated caspase activator; a chimeric transcription factor as described herein; a molecule that contains two or more binding sites for a pathogen, pathogen component, or pathogen product as described herein; a molecule that executes, stimulates, or inhibits stress or inflammatory responses, as described supra (including but not limited to heat shock protein 70 (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM 015765, NM_010481, NM_008301, M76613), Hsc70 (*Homo sapiens*, #AF352832), Hsp90 (*Homo sapiens*, #M16660, NM_005348, NM_007355); Hsp40/Hdj-1 (*Homo sapiens*, #X62421, NM_006145, NM_005880), Hsp60 (*Homo sapiens*, #NM_002156), Hsp47/CBP-2 (*Homo sapiens*, #D83174), Hsp100 (*Homo sapiens*, #NM_006660), Alpha-A-crystallin (*Homo sapiens*, #NM_000394), Alpha-B-crystallin (*Homo sapiens*, #NM_001885), Hsp27-1 (*Homo sapiens*, #NM_001540), Hsp27-2 (*Homo sapiens*, #XM_012054), cdc48 (S. Thoms (2002) FEBS Lett. 520, 107-110), heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131), constitutively active HSF1, RelA/p65 (*Homo sapiens*, #NM_021975, Z22948, L19067; *Mus musculus*, #NM_009045, AF199371), RelB (*Homo sapiens*, #NM_006509; *Mus musculus*, #NM_009046, M83380), c-Rel (*Homo sapiens*, #X75042, NM_002908; *Mus musculus*, #NM_009044, X15842), p50/p105/NF-kappa B 1 (*Homo sapiens*, #NM_003998, S76638, AF213884, AH009144; *Mus musculus*, #NM_008689, AK052726, M57999), p52/p100/NF-kappa B 2 (*Homo sapiens*, #NM_002502; *Mus musculus*, #AF155372, AF155373, NM_019408), inhibitors of kappa B (I kappa B: *Homo sapiens*, #AY033600, NM_020529; S. Ghosh and M. Karin (2002) Cell 109, S81-S96), IKK1/I kappa B kinase alpha (1 alpha: *Homo sapiens*, #AF009225, AF080157), IKK2/I kappa B kinase beta (IKK beta: *Homo sapiens*, #AF080158; *Mus musculus*, #AF026524, AF088910), or NEMO/I kappa B kinase gamma (IKK gamma: *Homo sapiens*, #AF261086, AF091453; *Mus musculus*, #AF069542)); a molecule that executes, stimulates, or inhibits unfolded-protein-related or endoplasmic reticulum-associated protein degradation-related responses, as described supra (including but not limited to BiP/GRP78/SHPA5 (*Homo sapiens*, #AJ271729, AF216292, X87949, NM_005347; *Mus musculus*, #NM_022310), PKR-like endoplasmic reticulum kinase (PERK: *Homo sapiens*, #NP_004827; *Mus musculus*, #AAD03337, NP_034251), constitutively active PERK, IRE1 alpha (*Homo sapiens*, #AF059198; *Mus musculus*, #AB031332, AF071777), constitutively active IRE1 alpha, IRE1 beta (*Homo sapiens*, #AB047079), constitutively active IRE1 beta, activating transcription factor 4 (ATF4: *Homo sapiens*, #NM_001675; *Mus musculus*, #NM_009716), activating transcription factor 6 alpha or beta (ATF6 alpha or beta: *Homo sapiens*, #NM_007348, AF005887, AB015856; *Mus musculus*, #XM_129579), X-box binding protein 1 (XBP1: *Homo sapiens*, #AB076383, AB076384; *Mus musculus*, #AF443192, AF027963, NM_013842), CHOP-10/GADD153/DDIT3 (*Homo sapiens*, #NM_004083; *Mus musculus*, #X67083, NM_007837), site-1 protease (S1P: *Homo sapiens*, #NM_003791; *Mus musculus*, #NM_019709), site-2 protease (S2P: *Homo sapiens*, #NM_015884), presenilin-1 (*Homo sapiens*, #AH004968, AF416717; *Mus musculus*, #BC030409, NM_008943, AF149111), TNF receptor-associated factor 2 (TRAF2: *Homo sapiens*, #NM_021138, NM_145718, *Mus musculus*, #XM_203851, XM_130119, L35303), or cJUN NH2-terminal kinases (JNKs: S. Oyadomari et al. (2002) Apoptosis 7, 335-345)); a single-chain antibody or other molecule that binds to a pathogen, pathogen component, or cellular component that directly or indirectly aids a pathogen, as described supra; a molecule that executes or stimulates complement pathway-related responses, as described supra, including but not limited to C3 alpha, C3 beta, factor B, factor D, properdin, C1q, C1r, C1s, C4, C2, C5, C6, C7, C8, C9, factor I, factor H, C1-INH, C4bp, S protein, clusterin, carboxypeptidase N, FHL-1, FHR-1, FHR-2, FHR-3, FHR-4, CR1, or DAF; a molecule that executes, stimulates, or inhibits toll-like-receptor-related responses, NOD-protein-related responses, (including but not limited to Nod1/CARD4 (*Homo sapiens*, #AAD28350, AAD43922; N. Inohara et al. (1999) Journal of Biological Chemistry 274, 14560-14567); Nod2, (*Homo sapiens*, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM_021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH011140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876)), pentraxin-related responses, collectin-related responses, mannose-receptor-related responses, scavenger receptor-related responses, or immune-related responses, as described supra; a molecule that inhibits transport between the cytoplasm and the nucleus of a cell, as described supra (including but not limited to importin alpha 1 (*Homo sapiens*, #NM_002266) with the importin beta binding domain (approximately amino acids 3-99) removed, importin alpha 3 (*Homo sapiens*, #NM_002268) with the importin beta binding domain (approximately amino acids 3-94) removed, importin alpha 4 (*Homo sapiens*, #NM_002267) with the importin beta binding domain (approximately amino acids 3-94) removed, importin alpha 5 (*Homo sapiens*, #U28386) with the importin beta binding domain (approximately amino acids 3-94) removed, importin alpha 6 (*Homo sapiens*, #NM_002269) with the importin beta binding domain (approximately amino acids 3-94) removed, importin alpha 7 (*Homo sapiens*, #NM_012316) with the importin beta binding domain (approximately amino acids 3-103) removed, importin alpha with the importin beta binding domain removed as described supra and also with the last two armadillo repeats removed (Y. Miyamoto et al. (2002) EMBO Journal 21, 5833-5842), the autoinhibitory domain of an importin alpha mutated to have a higher than normal affinity for wild-type importin alpha (B. Catimel et al. (2001) Journal of Biological Chemistry 276, 34189-34198), a modified importin alpha that does not enable nuclear import but still binds to one or more pathogen nuclear localization signals (NLSs) and does so preferably with a higher affinity than it binds to cellular NLSs, the importin beta binding domain of importin alpha 1 (*Homo sapiens*, #NM_002266, approximately amino acids 1-99), the importin beta binding domain of importin alpha 3 (*Homo sapiens*, #NM_002268, approximately amino acids 1-94), the importin beta binding domain of importin alpha 4 (*Homo sapiens*, #NM_002267, approximately amino acids 1-94), the importin beta binding domain of importin alpha 5 (*Homo sapiens*, #U28386, approximately amino acids 1-94), the importin beta binding domain of importin alpha 6 (*Homo sapiens*, #NM_002269, approximately amino acids 1-94), the importin beta binding domain of importin alpha 7 (*Homo sapiens*, #NM_012316, approximately amino acids 1-103), importin beta 1 (*Homo sapiens*, #NM_002265, #NP_002256) modified to not bind nucleoporins (for example by deleting the region between HEAT-5 and HEAT-6 (approximately amino acids 203-211) and the region between HEAT-6 and HEAT-7 (approximately amino acids 246-252) or by replacing those regions with nonhomologous linker regions (Y. M. Chook and G. Blobel (2001) Current Opinion in Structural Biology 11, 703-715)), importin beta 1 (*Homo sapiens*, #NM_002265, #NP_002256) modified to not bind importin alpha (for example by deleting the acidic loop importin-alpha-binding region spanning from approximately amino acid 333 through approximately amino acid 343 (G. Cingolani et al. (1999) Nature 399, 221-229)), a defective mutant of an exportin (I. G. Macara (2001) Microbiology and Molecular Biology Reviews 65, 570-594), a mutant p10/NTF2 that inhibits import by importin beta 1 (for example p10 D23A (C. M. Lane et al. (2000) Journal of Cell Biology 151, 321-331) or N77Y (B. B. Quimby et al. (2001) Journal of Biological Chemistry 276, 38820-38829)), vesicuovirus matrix protein or a portion thereof that inhibits nuclear import and/or nuclear export (J. M. Petersen et al. (2001) Proc. Natl. Acad. Sci. USA 98, 8590-8595; J. M. Petersen et al. (2000) Molecular and Cellular Biology 20, 8590-8601; C. von Kobbe et al. (2000) Molecular Cell 6, 1243-1252), a peptide that resembles the classical nuclear localization signal of SV40 T antigen (E. Merle et al. (1999) Journal of Cellular Biochemistry 74, 628-637), another nuclear localization signal, peptides with FxFG repeats or GLFG repeats (R. Bayliss et al. (2002) Journal of Biological Chemistry 277, 50597-50606), leptomycin B, a mutant of Ran that interferes with nuclear import or export (for example RanC4A (R. H. Kehlenbach et al. (2001) Journal of Biological Chemistry 276, 14524-14531)), or a molecule that binds to a pathogen or pathogen component or cellular component that is involved in transport between the cytoplasm and the nucleus of a cell (I. G. Macara (2001) Microbiology and Molecular Biology Reviews 65, 570-594; B. Ossareh-Nazari (2001) Traffic 2, 684-689)); a molecule that inhibits pathogenic prions (for example and without restriction, approximately amino acids 119-136 of hamster prion protein; J. Chabry et al. (1999) Journal of Virology 73, 6245-6250); a molecule that alters the properties of the endocytic pathway, phagocytic pathway, endosomes, phagosomes, lysosomes, other intracellular compartments, or vesicular trafficking to produce an anti-pathogen effect, as described supra (including but not limited to dynamin-1 mutant K44A (M. Huber et al. (2001) Traffic 2, 727-736; particularly when overexpressed), cellubrevin (R. A. Fratti et al. (2002) Journal of Biological Chemistry 277, 17320-17326; particularly when overexpressed), *Salmonella* SpiC protein (NCBI Accession #U51927), a defective mutant of TassC (A. H. Lee et al. (2002) Cell. Microbiol. 4, 739-750), other vesicular trafficking inhibitors as will be understood by one of skill in the art, Nramp1 (P. Cuellar-Mata et al. (2002) Journal of Biological Chemistry 277, 2258-2265; C. Frehel et al. (2002) Cellular Microbiology 4, 541-556; D. J. Hackam et al. (1998) J. Exp. Med. 188, 351-364; particularly when overexpressed), NADPH oxidase subunits or cofactors (P. V. Vignais (2002) Cell. Mol. Life Sci. 59, 1428-1459; particularly when overexpressed), NOS2 nitric oxide synthase (J. D. MacMicking et al. (1997) Proc. Natl. Acad. Sci. USA 94, 5243-5248; particularly when overexpressed), human papillomavirus 16 E5 protein (NCBI Accession #W5WLHS), bafilomycin A1, a single-chain antibody or other molecule that binds to vacuolar ATPase subunit a (S. B. Sato and S. Toyama (1994) J. Cell. Biol. 127, 39-53; preferably a1 or a2), antisense oligonucleotides that inhibit vacuolar ATPase subunits (J. E. Strasser et al. (1999) Journal of Immunology 162, 6148-6154), a peptide composed of approximately the 78 amino-terminal amino acids of vacuolar H+-ATPase subunit E (M. Lu et al. (2002) Journal of Biological Chemistry 277, 38409-38415), A2-cassette mutant of vacuolar H+-ATPase subunit A (N. Hernando et al. (1999) Eur. J. Biochem. 266, 293-301), a defective mutant of subunit a1 or a2 of vacuolar H+-ATPase (S. Kawasaki-Nishi et al. (2001) Proc. Natl. Acad. Sci. USA 98, 12397-12402; S. Kawasaki-Nishi et al. (2001) 276, 47411-47420; T. Nishi and M. Forgac (2000) J. Biol. Chem. 275, 6824-6830; S. B. Peng et al. (1999) J. Biol. Chem. 274, 2549-2555; T. Toyomura et al. (2000) J. Biol. Chem. 275, 8760-8765), overexpression of the C and/or H subunits of vacuolar H+-ATPase subunit E (K. K. Curtis and P. M. Kane (2002) Journal of Biological Chemistry 277, 2716-2724), other defective vacuolar ATPase subunit or portion of a subunit (examples of wild-type human vacuolar ATPase subunits that can be made defective for anti-pathogen effects will be understood by one of skill in the art, and include, without limitation, those vacuolar ATPase subunits with Accession numbers: NM_004231, NM_130463, NM_015994, NM_001694, NM_004047, NM_001696, NM_004691, NM_001695, NM_001693, NM_001690, NM_020632, NM_004888)); a molecule that executes, stimulates, or inhibits ubiquitin proteasome degradative pathway-related responses, as described supra (including but not limited to CHIP (D. M. Cyr et al. (2002) Trends Biochem. Sci. 27, 368-375; J. Demand et al. (2001) Curr. Biol. 11, 1569-1577; S. Murata et al. (2001) EMBO Rep. 2, 1133-1138; particularly when overexpressed), Fbx2 (Y. Yoshida et al. (2002) Nature 418, 438-442; particularly when overexpressed), molecules that ubiquitinate pathogens or pathogen components or cellular components that assist pathogens as will be understood by one of skill in the art (P. Zhou et al. (2000) Mol. Cell 6, 751-756; K. M. Sakamoto et al. (2001) Proc. Natl. Acad. Sci. USA 98, 8554-8559; N. Zheng et al. (2000) Cell 102, 533-539; D. Oyake et al. (2002) Biochemical and Biophysical Research Communications 295, 370-375), or inhibitors of ubiquitination or proteasomes (J. Myung et al. (2001) Medicinal Research Reviews 21, 245-273; G. Lennox et al. (1988) Neurosci. Lett. 94, 211-217; N. F. Bence et al. (2001) Science 292, 1552-1555; for example lactacystin or epoxomicin)); a molecule that executes, stimulates, or inhibits defensin-related responses, as described supra, including but not limited to alpha defensins, beta defensins, theta defensins, plant defensins, or arthropod defensins; a molecule that executes, stimulates, or inhibits cathelicidin-related responses, as described supra, including but not limited to hCAP-18/LL-37, CRAMP, Bac4, OaBac5; prophenin-1, protegrin-1, or PR-39; a molecule that executes, stimulates, or inhibits chemokine-related or thrombocidin-related responses, as described supra, including but not limited to CC chemokines, CXC chemokines, C chemokines, CX3C chemokines, CC chemokine receptors, CXC chemokine receptors, C chemokine receptors, CX3C chemokine receptors, JAK proteins, STAT proteins, fibrinopeptide A, fibrinopeptide B, or thymosin beta 4; a molecule that executes, stimulates, or inhibits interferon-related or cytokine-related responses, as described supra (including but not limited to interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439; *Mus musculus*, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12: *Homo sapiens*, #NM_000882, NM_002187; *Mus musculus*, #NM_008351, NM_008352); interleukin 15 (IL-15: *Homo sapiens*, #NM_172174, NM_172175, NM_000585; *Mus musculus*, #NM_008357); cytokine receptors and related signaling molecules (W. E. Paul (ed.), Fundamental Immunology (4th ed., Lippincott-Raven, Philadelphia, 1999), Chapters 21 and 22); interferon type I receptor subunit 1 (IFNAR1: *Homo sapiens*, #NM_000629; *Mus musculus*, #NM_010508); interferon type I receptor subunit 2 (IFNAR2: *Homo sapiens*, #NM_000874; *Mus musculus*, #NM_010509); janus kinase 1 (JAK1: *Homo sapiens*, #NP_002218; *Mus musculus*, #NP_666257); janus kinase 2 (JAK2: *Homo sapiens*, #AAC23653, AAC23982, NP_004963; *Mus musculus*, #NP_032439, AAN62560); JAK3; Tyk2; signal transducer and activator of transcription 1 (STAT1: *Homo sapiens*, #NM_007315, NM_139266; *Mus musculus*, #U06924); signal transducer and activator of transcription 2 (STAT2: *Homo sapiens*, #NM_005419; *Mus musculus*, AF206162); STAT3; STAT4; STAT5; STAT6; interferon-stimulated gene factor 3 gamma (ISGF3 gamma: *Homo sapiens*, #Q00978, NM_006084; *Mus musculus*, #NM_008394) interferon regulatory factor 1 (IRF1: *Homo sapiens*, #NM_002198, P10914; *Mus musculus*, #NM_008390); interferon regulatory factor 3 (IRF3: *Homo sapiens*, #NM_001571, Z56281; *Mus musculus*, #NM_016849, U75839, U75840); interferon regulatory factor 5 (IRF5: *Homo sapiens*, #Q13568, U51127; *Mus musculus*, #AAB81997, NP_036187); interferon regulatory factor 6 (IRF6: *Homo sapiens*, #AF027292, NM_006147; *Mus musculus*, #U73029); interferon regulatory factor 7 (IRF7: *Homo sapiens*, #U53830, U53831, U53832, AF076494, U73036; *Mus musculus*, #NM_016850, U73037); interferon regulatory factor 8 (IRF8); a constitutively active interferon regulatory factor; protein kinase R (PKR: *Homo sapiens*, #AAC50768; *Mus musculus*, #Q03963; S. Nanduri et al. (1998) EMBO J. 17, 5458-5465); 2',5'-oligoadenylate synthetases (*Homo sapiens* forms including #P00973, P29728, AAD28543; *Mus musculus* forms including P11928; S. Y. Desai et al. (1995) J. Biol. Chem. 270, 3454-3461); RNase L (*Homo sapiens*, #CAA52920); ); promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (*Homo sapiens*, #U18121; *Mus musculus*, #NP_062629); Mx1 (*Homo sapiens*, #NM_002462); or Mx2 (*Homo sapiens*, #NM_002463)); a molecule that inhibits budding or release of pathogens from an infected cell, as described supra (including but not limited to Hrs, particularly when overexpressed (N. Bishop et al. (2002) Journal of Cell Biology 157, 91-101; L. Chin et al. (2001) Journal of Biological Chemistry 276, 7069-7078; C. Raiborg et al. (2002) Nature Cell Biology 4, 394-398); defective Vps4 mutants such as K173Q or E228Q, particularly when overexpressed (J. E. Garrus et al. (2001) Cell 107, 55-65); small interfering RNA that inhibits Tsg101 expression (N. Bishop et al. (2002) Journal of Cell Biology 157, 91-101; J. E. Garrus et al. (2001) Cell 107, 55-65); truncated AP-50 consisting of approximately amino acids 121-435, or other defective mutant of AP-50, particularly when overexpressed (B. A. Puffer et al. (1998) Journal of Virology 72, 10218-10221); WW-domain-containing fragment of LDI-1, Nedd4, Yes-associated protein, KIAA0439 gene product, or other defective Nedd4-related proteins, particularly when overexpressed (A. Kikonyogo et al. (2001) Proc. Natl. Acad. Sci. USA 98, 11199-11204; A. Patnaik and J. W. Wills (2002) Journal of Virology 76, 2789-2795); a peptide consisting of the HIV p6 Gag PTAPP-motif-containing late (L) domain (L. VerPlank et al. (2001) Proc. Natl. Acad. Sci. USA 98, 7724-7729) or other viral late (L) domain containing PTAP, PSAP, PPXY, YPDL, or YXXL motifs (J. Martin-Serrano et al. (2001) Nature Medicine 7, 1313-1319; A. Patnaik and J. W. Wills (2002) Journal of Virology 76, 2789-2795); amino acids 1-167 of Tsg101, TSG-5' fragment of Tsg101, or similar amino-terminal fragment of Tsg101, particularly when overexpressed (D. G. Demirov et al. (2002) Proc. Natl. Acad. Sci. USA 99, 955-9601; E. L. Myers and J. F. Allen (2002) Journal of Virology 76, 11226-11235); a mutant of Tsg101 (M. Babst et al. (2000) Traffic 1, 248-258; L. VerPlank et al. (2001) Proc. Natl. Acad. Sci. USA 98, 7724-7729; J. Martin-Serrano et al. (2001) Nature Medicine 7, 1313-1319; O. Pornillos et al. (2002) EMBO Journal 21, 2397-2406) with reduced capacity to aid viral budding; a casein kinase 2 (CK2) inhibitor, such as the peptide RRADDSDDDDD (SEQ ID NO: 472)(E. K. Hui and D. P. Nayak (2002) Journal of General Virology 83, 3055-3066); or G protein signalling inhibitors (E. K. Hui and D. P. Nayak (2002) Journal of General Virology 83, 3055-3066); a molecule that binds to a cellular or pathogen molecule (for example to one or more of the following molecules: Tsg101, Vps4, casein kinase 2, Hrs, hVps28, Eap30, Eap20, Eap45, Chmp1, Chmp2, Chmp3, Chmp4, Chmp5, Chmp6, AP-50, Nedd4-related proteins, WW-domain-containing proteins, or L-domain-containing proteins; O. Pornillos et al. (2002) TRENDS in Cell Biology 12, 569-579; P. Gomez-Puertas et al. (2000) Journal of Virology 74, 11538-11547; E. Katz et al. (2002) Journal of Virology 76, 11637-11644) that is involved in budding or release of pathogens from an infected cell); a molecule that makes a cell more receptive to apoptosis signals, as described supra (including but not limited to p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); apoptotic protease activating factor 1 (Apaf-1: *Homo sapiens*, #NM_013229, NM_001160; *Mus musculus*, #NP_033814); Fas/CD95 (*Homo sapiens*, #AAC16236, AAC16237; *Mus musculus*, #AAG02410); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992; Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); calpains (T. Lu et al., (2002) Biochimica et Biophysica Acta 1590, 16-26)); a molecule that degrades components of pathogens, as described supra (for example: proteases, including but not limited to chymotrypsin, trypsin, or elastase; DNases, including but not limited to restriction enzymes; RNases, including but not limited to RNase III (*Homo sapiens*, #AF189011; *Escherichia coli*, #NP_417062, NC_000913), RNt1p (*Saccharomyces cerevisiae*, #U27016), Pac1, (*Schizosaccharomyces pombe*, #X54998), or RNase L; glycosidases, including but not limited to N-glycanase, endoglycosidase H, O-glycanase, endoglycosidase F2, sialidase, or beta-galactosidase; or lipases, including but not limited to phospholipase A1, phospholipase A2, phospholipase C, or phospholipase D); a molecule that inhibits or is toxic to a pathogen cell, as described supra (including but not limited to penicillin, erythromycin, tetracycline, rifampin, amphotericin B, metronidazole, mefloquine, or another molecule that inhibits pathogen functions).

A chimeric molecule or agent of the invention can be a messenger RNA (mRNA) molecule that only encodes a functional anti-pathogen domain or molecular structure if the mRNA is naturally spliced within a cell that is undergoing an unfolded protein response or endoplasmic reticulum-associated protein degradation response. For example and without limitation, the mRNA can include within its protein encoding sequence the 5' and 3' splice sites from the intron that is removed from XBP1 mRNA by activated IRE1 alpha (H. Yoshida et al. (2001) Cell 107, 881-891; K. Lee et al. (2002) Genes & Development 16, 452-466; W. Tirasophon et al. (2000) Genes & Development 14, 2725-2736) with nucleotides between the splice sites such that the mRNA encodes an anti-pathogen molecule when the mRNA is spliced by activated IRE1 alpha but only a nonfunctional version of the anti-pathogen molecule with nonsense or frameshift mutations when the mRNA is unspliced, as will be understood by one of skill in the art. The mRNA can encode one or more of the following effector molecules, for example and without limitation: a chimeric molecule or agent as described herein, including but not limited to dsRNA-activated caspase, 2',5'-oligoadenylate-activated caspase, dsRNA-activated caspase activator, or 2',5'-oligoadenylate-activated caspase activator; a chimeric transcription factor as described herein; a molecule that contains two or more binding sites for a pathogen, pathogen component, or pathogen product as described herein; an antisense polynucleotide or small interfering RNA (G. M. Barton and R. Medzhitov (2002) Proc. Natl. Acad. Sci. USA 99, 14943-14945) that inhibits expression of a pathogen gene or a host gene that aids a pathogen; a molecule that executes, stimulates, or inhibits stress or inflammatory responses, as described supra (including but not limited to heat shock protein 70 (Hsp70: *Homo sapiens*, #M11717, M15432, L12723, NM_016299, NM_005346, NM_005345, NM_002155, NM_021979, AF093759; *Mus musculus*, #XM_207065, XM_128584, XM_128585, XM_110217, NM_015765, NM_010481, NM_008301, M76613), Hsc70 (*Homo sapiens*, #AF352832), Hsp90 (*Homo sapiens*, #M16660, NM_005348, NM_007355); Hsp40/Hdj-1 (*Homo sapiens*, #X62421, NM_006145, NM_005880), Hsp60 (*Homo sapiens*, #NM_002156), Hsp47/CBP-2 (*Homo sapiens*, #D83174), Hsp100 (*Homo sapiens*, #NM_006660), Alpha-A-crystallin (*Homo sapiens*, #NM_000394), Alpha-B-crystallin (*Homo sapiens*, #NM_001885), Hsp27-1 (*Homo sapiens*, #NM_001540), Hsp27-2 (*Homo sapiens*, #XM_012054), cdc48 (S. Thoms (2002) FEBS Lett. 520, 107-110), heat shock factor 1 (HSF1: *Homo sapiens*, #NM_005526, M64673; *Mus musculus*, #XM_128055, X61753, Z49206; A. Mathew et al. (2001) Mol. Cell. Biol. 21, 7163-7171; L. Pirkkala et al. (2001) FASEB J. 15, 1118-1131), constitutively active HSF1, RelA/p65 (*Homo sapiens*, #NM_021975, Z22948, L119067; *Mus musculus*, #NM_009045, AF199371), RelB (*Homo sapiens*, #NM_006509; *Mus musculus*, #NM_009046 μM83380), c-Rel (*Homo sapiens*, #X75042, NM_002908; *Mus musculus*, #NM_009044, X15842), p50/p105/NF-kappa B 1 (*Homo sapiens*, #NM_003998, S76638, AF213884, AH009144; *Mus musculus*, #NM_008689, AK052726, M57999), p52/p100/NF-kappa B 2 (*Homo sapiens*, #NM_002502; *Mus musculus*, #AF155372, A-F155373, NM_019408), inhibitors of kappa B (I kappa B: *Homo sapiens*, #AY033600, NM_020529; S. Ghosh and M. Karin (2002) Cell 109, S811-S96), IKK1/I kappa B kinase alpha (IKK alpha: *Homo sapiens*, #AF009225, AF080157), IKK2/I kappa B kinase beta (IKK beta: *Homo sapiens*, #AF080158; *Mus musculus*, #AF026524, AF088910), or NEMO/I kappa B kinase gamma (IKK gamma: *Homo sapiens*, #AF261086, AF091453; *Mus musculus*, #AF069542)); a molecule that executes, stimulates, or inhibits unfolded-protein-related or endoplasmic reticulum-associated protein degradation-related responses, as described supra (including but not limited to BiP/GRP78/SHPA5 (*Homo sapiens*, #AJ271729, AF216292, X87949, NM_005347; *Mus musculus*, #NM_022310), PKR-like endoplasmic reticulum kinase (PERK: *Homo sapiens*, #NP_004827; *Mus musculus*, #AAD03337, NP_034251), constitutively active PERK, IRE1 alpha (*Homo sapiens*, #AF059198; *Mus musculus*, #AB031332, AF071777), constitutively active IRE1 alpha, IRE1 beta (*Homo sapiens*, #AB047079), constitutively active IRE1 beta, activating transcription factor 4 (ATF4: *Homo sapiens*, #NM_001675; *Mus musculus*, #NM_009716), activating transcription factor 6 alpha or beta (ATF6 alpha or beta: *Homo sapiens*, #NM_007348, AF005887, AB015856; *Mus musculus*, #XM_129579), X-box binding protein 1 (XBP1: *Homo sapiens*, #AB076383, AB076384; *Mus musculus*, #AF443192, AF027963, NM 013842), CHOP-10/GADD153/DDIT3 (*Homo sapiens*, #NM_004083; *Mus musculus*, #X67083, NM_007837), site-1 protease (S1P: *Homo sapiens*, #NM_003791; *Mus musculus*, #NM_019709), site-2 protease (S2P: *Homo sapiens*, #NM_015884), presenilin-1 (*Homo sapiens*, #AH004968, AF416717; *Mus musculus*, #BC030409, NM_008943, AF149111), TNF receptor-associated factor 2 (TRAF2: *Homo sapiens*, #NM_021138, NM_145718, *Mus musculus*, #XM_203851, XM_130119, L35303), or cJUN NH2-terminal kinases (JNKs: S. Oyadomari et al. (2002) Apoptosis 7, 335-345)); a single-chain antibody or other molecule that binds to a pathogen, pathogen component, or cellular component that directly or indirectly aids a pathogen, as described supra; a molecule that executes or stimulates complement pathway-related responses, as described supra, including but not limited to C3 alpha, C3 beta, factor B, factor D, properdin, C1q, C1r, C1s, C4, C2, C5, C6, C7, C8, C9, factor I, factor H, C1-INH, C4 bp, S protein, clusterin, carboxypeptidase N, FHL-1, FHR-1, FHR-2, FHR-3, FHR-4, CR1, or DAF; a molecule that executes, stimulates, or inhibits toll-like-receptor-related responses, NOD-protein-related responses, (including but not limited to Nod1/CARD4 (*Homo sapiens*, #AAD28350, AAD43922; N. Inohara et al. (1999) Journal of Biological Chemistry 274, 14560-14567); Nod2, (*Homo sapiens*, #AAG33677, AAK70863, AAK70865, AAK70866, AAK70867, AAK70868; Y. Ogura et al. (2001) Journal of Biological Chemistry 276, 4812-4818; N. Inohara et al. (2003) Journal of Biological Chemistry, PMID: 12514169); Ipaf-1/CLAN/CARD12 (*Homo sapiens*, #NM_021209, AY035391; J.-L. Poyet et al. (2001) Journal of Biological Chemistry 276, 28309-28313); CIITA (*Homo sapiens*, #AY084054, AY084055, AF410154, NM_000246, X74301; M. W. Linhoff et al. (2001) Molecular and Cellular Biology 21, 3001-3011; A. Muhlethaler-Mottet et al. (1997) EMBO Journal 16, 2851-2860); NAIP (*Homo sapiens*, #U21912, U19251); Defcap/NAC/NALP1/CARD7 (*Homo sapiens*, #NM_033004, NM_033005, NM_033006, NM_033007, NM_014922); NBS1/NALP2 (*Homo sapiens*, #AF310106, NM_017852); cryopyrin/CIAS1 (*Homo sapiens*, #AF410477, AF427617, AH011140, NM_004895); RIP (*Homo sapiens*, #U50062; S. Grimm et al. (1996) Proc. Natl. Acad. Sci. USA 93, 10923-10927; H. Hsu et al. (1996) Immunity 4, 387-396); Rip2/RICK/CARDIAK (*Homo sapiens*, #AF064824, AF078530; N. Inohara et al. (1998) Journal of Biological Chemistry 273, 18675; M. Thome et al. (1998) Current Biology 8, 885-888); and PKK (A. Muto et al. (2002) Journal of Biological Chemistry 277, 31871-31876)), pentraxin-related responses, collectin-related responses, mannose-receptor-related responses, scavenger receptor-related responses, or immune-related responses, as described supra; a molecule that inhibits transport between the cytoplasm and the nucleus of a cell, as described supra (including but not limited to importin alpha 1 (*Homo sapiens*, #NM_002266) with the importin beta binding domain (approximately amino acids 3-99) removed, importin alpha 3 (*Homo sapiens*, #NM_002268) with the importin beta binding domain (approximately amino acids 3-94) removed, importin alpha 4 (*Homo sapiens*, #NM_002267) with the importin beta binding domain (approximately amino acids 3-94) removed, importin alpha 5 (*Homo sapiens*, #U28386) with the importin beta binding domain (approximately amino acids 3-94) removed, importin alpha 6 (*Homo sapiens*, #NM_002269) with the importin beta binding domain (approximately amino acids 3-94) removed, importin alpha 7 (*Homo sapiens*, #NM_012316) with the importin beta binding domain (approximately amino acids 3-103) removed, importin alpha with the importin beta binding domain removed as described supra and also with the last two armadillo repeats removed (Y. Miyamoto et al. (2002) EMBO Journal 21, 5833-5842), the autoinhibitory domain of an importin alpha mutated to have a higher than normal affinity for wild-type importin alpha (B. Catimel et al. (2001) Journal of Biological Chemistry 276, 34189-34198), a modified importin alpha that does not enable nuclear import but still binds to one or more pathogen nuclear localization signals (NLSs) and does so preferably with a higher affinity than it binds to cellular NLSs as will be understood by one of skill in the art, the importin beta binding domain of importin alpha 1 (*Homo sapiens*, #NM_002266, approximately amino acids 1-99), the importin beta binding domain of importin alpha 3 (*Homo sapiens*, #NM_002268, approximately amino acids 1-94), the importin beta binding domain of importin alpha 4 (*Homo sapiens*, #NM_002267, approximately amino acids 1-94), the importin beta binding domain of importin alpha 5 (*Homo sapiens*, #U28386, approximately amino acids 1-94), the importin beta binding domain of importin alpha 6 (*Homo sapiens*, #NM_002269, approximately amino acids 1-94), the importin beta binding domain of importin alpha 7 (*Homo sapiens*, #NM_012316, approximately amino acids 1-103), importin beta 1 (*Homo sapiens*, #NM_002265, #NP_

002256) modified to not bind nucleoporins (for example by deleting the region between HEAT-5 and HEAT-6 (approximately amino acids 203-211) and the region between HEAT-6 and HEAT-7 (approximately amino acids 246-252) or by replacing those regions with nonhomologous linker regions (Y. M. Chook and G. Blobel (2001) Current Opinion in Structural Biology 11, 703-715)), importin beta 1 (*Homo sapiens*, #NM_002265, #NP_002256) modified to not bind importin alpha (for example by deleting the acidic loop importin-alpha-binding region spanning from approximately amino acid 333 through approximately amino acid 343 (G. Cingolani et al. (1999) Nature 399, 221-229)), a defective mutant of an exportin (I. G. Macara (2001) Microbiology and Molecular Biology Reviews 65, 570-594), a mutant p10/NTF2 that inhibits import by importin beta 1 (for example p10 D23A (C. M. Lane et al. (2000) Journal of Cell Biology 151, 321-331) or N77Y (B. B. Quimby et al. (2001) Journal of Biological Chemistry 276, 38820-38829)), vesicuovirus matrix protein or a portion thereof that inhibits nuclear import and/or nuclear export (J. M. Petersen et al. (2001) Proc. Natl. Acad. Sci. USA 98, 8590-8595; J. M. Petersen et al. (2000) Molecular and Cellular Biology 20, 8590-8601; C. von Kobbe et al. (2000) Molecular Cell 6, 1243-1252), a peptide that resembles the classical nuclear localization signal of SV40 T antigen (E. Merle et al. (1999) Journal of Cellular Biochemistry 74, 628-637), another nuclear localization signal, peptides with FxFG repeats or GLFG repeats (R. Bayliss et al. (2002) Journal of Biological Chemistry 277, 50597-50606), leptomycin B, a mutant of Ran that interferes with nuclear import or export (for example RanC4A (R. H. Kehlenbach et al. (2001) Journal of Biological Chemistry 276, 14524-14531)), or a molecule that binds to a pathogen or pathogen component or cellular component that is involved in transport between the cytoplasm and the nucleus of a cell (I. G. Macara (2001) Microbiology and Molecular Biology Reviews 65, 570-594; B. Ossareh-Nazari (2001) Traffic 2, 684-689)); a molecule that inhibits pathogenic prions (for example and without restriction, approximately amino acids 119-136 of hamster prion protein; J. Chabry et al. (1999) Journal of Virology 73, 6245-6250); a molecule that alters the properties of the endocytic pathway, phagocytic pathway, endosomes, phagosomes, lysosomes, other intracellular compartments, or vesicular trafficking to produce an anti-pathogen effect, as described supra (including but not limited to dynamin-1 mutant K44A (M. Huber et al. (2001) Traffic 2, 727-736; particularly when overexpressed), cellubrevin (R. A. Fratti et al. (2002) Journal of Biological Chemistry 277, 17320-17326; particularly when overexpressed), *Salmonella* SpiC protein (NCBI Accession #U51927), a defective mutant of TassC (A. H. Lee et al. (2002) Cell. Microbiol. 4, 739-750), other vesicular trafficking inhibitors as will be understood by one of skill in the art, Nramp1 (P. Cuellar-Mata et al. (2002) Journal of Biological Chemistry 277, 2258-2265; C. Frehel et al. (2002) Cellular Microbiology 4, 541-556; D. J. Hackam et al. (1998) J. Exp. Med. 188, 351-364; particularly when overexpressed), NADPH oxidase subunits or cofactors (P. V. Vignais (2002) Cell. Mol. Life Sci. 59, 1428-1459; particularly when overexpressed), NOS2 nitric oxide synthase (J. D. MacMicking et al. (1997) Proc. Natl. Acad. Sci. USA 94, 5243-5248; particularly when overexpressed), human papillomavirus 16 E5 protein (NCBI Accession #W5WLHS), bafilomycin A1, a single-chain antibody or other molecule that binds to vacuolar ATPase subunit a (S. B. Sato and S. Toyama (1994) J. Cell. Biol. 127, 39-53; preferably a1 or a2,), antisense oligonucleotides that inhibit vacuolar ATPase subunits (J. E. Strasser et al. (1999) Journal of Immunology 162, 6148-6154;), a peptide composed of approximately the 78 amino-terminal amino acids of vacuolar H+-ATPase subunit E (M. Lu et al. (2002) Journal of Biological Chemistry 277, 38409-38415), A2-cassette mutant of vacuolar H+-ATPase subunit A (N. Hernando et al. (1999) Eur. J. Biochem. 266, 293-301), a defective mutant of subunit a1 or a2 of vacuolar H+-ATPase (S. Kawasaki-Nishi et al. (2001) Proc. Natl. Acad. Sci. USA 98, 12397-12402; S. Kawasaki-Nishi et al. (2001) 276, 47411-47420; T. Nishi and M. Forgac (2000) J. Biol. Chem. 275, 6824-6830; S. B. Peng et al. (1999) J. Biol. Chem. 274, 2549-2555; T. Toyomura et al. (2000) J. Biol. Chem. 275, 8760-8765), overexpression of the C and/or H subunits of vacuolar H+-ATPase subunit E (K. K. Curtis and P. M. Kane (2002) Journal of Biological Chemistry 277, 2716-2724), other defective vacuolar ATPase subunit or portion of a subunit (examples of wild-type human vacuolar ATPase subunits that can be made defective for anti-pathogen effects will be understood by one of skill in the art, and include, without limitation, those vacuolar ATPase subunits with Accession numbers: NM_004231, NM_130463, NM_015994, NM_001694, NM_004047, NM_001696, NM_004691, NM_001695, NM_001693, NM_001690, NM_020632, NM_004888)); a molecule that executes, stimulates, or inhibits ubiquitin-proteasome-degradative-pathway-related responses, as described supra (including but not limited to CHIP (D. M. Cyr et al. (2002) Trends Biochem. Sci. 27, 368-375; J. Demand et al. (2001) Curr. Biol. 11, 1569-1577; S. Murata et al. (2001) EMBO Rep. 2, 1133-1138; particularly when overexpressed), Fbx2 (Y. Yoshida et al. (2002) Nature 418, 438-442; particularly when overexpressed), molecules that ubiquitinate pathogens or pathogen components or cellular components that assist pathogens as will be understood by one of skill in the art (P. Zhou et al. (2000) Mol. Cell 6, 751-756; K. M. Sakamoto et al. (2001) Proc. Natl. Acad. Sci. USA 98, 8554-8559; N. Zheng et al. (2000) Cell 102, 533-539; D. Oyake et al. (2002) Biochemical and Biophysical Research Communications 295, 370-375), or inhibitors of ubiquitination or proteasomes (J. Myung et al. (2001) Medicinal Research Reviews 21, 245-273; G. Lennox et al. (1988) Neurosci. Lett. 94, 211-217; N. F. Bence et al. (2001) Science 292, 1552-1555; for example lactacystin or epoxomicin)); a molecule that executes, stimulates, or inhibits defensin-related responses, as described supra, including but not limited to alpha defensins, beta defensins, theta defensins, plant defensins, or arthropod defensins; a molecule that executes, stimulates, or inhibits cathelicidin-related responses, as described supra, including but not limited to hCAP-18/LL-37, CRAMP, Bac4, OaBac5; prophenin-1, protegrin-1, or PR-39; a molecule that executes, stimulates, or inhibits chemokine-related or thrombocidin-related responses, as described supra, including but not limited to CC chemokines, CXC chemokines, C chemokines, CX3C chemokines, CC chemokine receptors, CXC chemokine receptors, C chemokine receptors, CX3C chemokine receptors, JAK proteins, STAT proteins, fibrinopeptide A, fibrinopeptide B, or thymosin beta 4; a molecule that executes, stimulates, or inhibits interferon-related or cytokine-related responses, as described supra (including but not limited to interferon-alpha (*Homo sapiens*, #NM_002169, NM_021002, J00207; *Mus musculus*, #NM_010502, NM_010503, NM_010507, NM_008333, M68944, M13710); interferon-beta (*Homo sapiens*, #M25460, NM_002176; *Mus musculus*, #NM_010510); interferon-gamma (*Homo sapiens*, #NM_000619, J00219; *Mus musculus*, #M28621); interferon-delta; interferon-tau; interferon-omega (*Homo sapiens*, #NM_002177); interleukin 1 (IL-1: *Homo sapiens*, #NM_000575, NM_012275, NM_019618, NM_000576, NM_014439; *Mus musculus*, #NM_019450, NM_019451, AF230378); interleukin 2 (IL-2: *Homo sapiens*, #NM_000586); interleukin 3 (IL-3: *Homo sapiens*, #NM_000588; *Mus musculus*, #A02046); interleukin 4 (IL-4: *Homo sapiens*, #NM_000589, NM_172348; *Mus musculus*, #NM_021283); interleukin 5 (IL-5: *Homo sapiens*, #NM_000879; *Mus musculus*, #NM_010558); interleukin 6 (IL-6: *Homo sapiens*, #NM_000600; *Mus musculus*, #NM_031168); interleukin 7 (IL-7: *Homo sapiens*, #NM_000880, AH006906; *Mus musculus*, #NM_008371); interleukin 9 (IL-9: *Homo sapiens*, #NM_000590); interleukin 12 (IL-12: *Homo sapiens*, #NM_000882, NM_002187; *Mus musculus*, #NM_008351, NM_008352); interleukin 15 (IL-15: *Homo sapiens*, #NM_172174, NM_172175, NM_000585; *Mus musculus*, #NM_008357); cytokine receptors and related signaling molecules (W. E. Paul (ed.), Fundamental Immunology (4th ed., Lippincott-Raven, Philadelphia, 1999), Chapters 21 and 22); interferon type I receptor subunit 1 (IFNAR1: *Homo sapiens*, #NM_000629; *Mus musculus*, #NM_010508); interferon type I receptor subunit 2 (IFNAR2: *Homo sapiens*, #NM_000874; *Mus musculus*, #NM_010509); janus kinase 1 (JAK1: *Homo sapiens*, #NP_002218; *Mus musculus*, #NP_666257); janus kinase 2 (JAK2: *Homo sapiens*, #AAC23653, AAC23982, NP_004963; *Mus musculus*, #NP_032439, AAN62560); JAK3; Tyk2; signal transducer and activator of transcription 1 (STAT1: *Homo sapiens*, #NM_007315, NM_139266; *Mus musculus*, #U06924); signal transducer and activator of transcription 2 (STAT2: *Homo sapiens*, #NM_005419; *Mus musculus*, AF206162); STAT3; STAT4; STAT5; STAT6; interferon-stimulated gene factor 3 gamma (ISGF3 gamma: *Homo sapiens*, #Q00978, NM_006084; *Mus musculus*, #NM_008394) interferon regulatory factor 1 (IRF1: *Homo sapiens*, #NM_002198, P10914; *Mus musculus*, #NM_008390); interferon regulatory factor 3 (IRF3: *Homo sapiens*, #NM_001571, Z56281; *Mus musculus*, #NM_016849, U75839, U75840); interferon regulatory factor 5 (IRF5: *Homo sapiens*, #Q13568, U51127; *Mus musculus*, #AAB81997, NP_036187); interferon regulatory factor 6 (IRF6: *Homo sapiens*, #AF027292, NM_006147; *Mus musculus*, #U73029); interferon regulatory factor 7 (IRF7: *Homo sapiens*, #U53830, U53831, U53832, AF076494, U73036; *Mus musculus*, #NM_016850, U73037); interferon regulatory factor 8 (IRF8); a constitutively active interferon regulatory factor; protein kinase R (PKR: *Homo sapiens*, #AAC50768; *Mus musculus*, #Q03963; S. Nanduri et al. (1998) EMBO J. 17, 5458-5465); constitutively active PKR; 2',5'-oligoadenylate synthetases (*Homo sapiens* forms including #P00973, P29728, AAD28543; *Mus musculus* forms including P11928; S. Y. Desai et al. (1995) J. Biol. Chem. 270, 3454-3461); constitutively active 2',5'-oligoadenylate synthetases; RNase L (*Homo sapiens*, #CAA52920); constitutively active RNase L; promyelocytic leukemia protein (PML: W. V. Bonilla et al. (2002) Journal of Virology 76, 3810-3818); p56 or related proteins (J. Guo et al. (2000) EMBO Journal 19, 6891-6899; G. C. Sen (2000) Seminars in Cancer Biology 10, 93-101); p200 or related proteins (G. C. Sen (2000) Seminars in Cancer Biology 10, 93-101); ADAR1 (*Homo sapiens*, #U18121; *Mus musculus*, #NP_062629); Mx1 (*Homo sapiens*, #NM_002462); or Mx2 (*Homo sapiens*, #NM_002463)); a molecule that inhibits budding or release of pathogens from an infected cell, as described supra (including but not limited to Hrs, particularly when overexpressed (N. Bishop et al. (2002) Journal of Cell Biology 157, 91-101; L. Chin et al. (2001) Journal of Biological Chemistry 276, 7069-7078; C. Raiborg et al. (2002) Nature Cell Biology 4, 394-398); defective Vps4 mutants such as K173Q or E228Q, particularly when overexpressed (J. E. Garrus et al. (2001) Cell 107, 55-65); small interfering RNA that inhibits Tsg101 expression (N. Bishop et al. (2002) Journal of Cell Biology 157, 91-101; J. E. Garrus et al. (2001) Cell 107, 55-65); truncated AP-50 consisting of approximately amino acids 121-435, or other defective mutant of AP-50, particularly when overexpressed (B. A. Puffer et al. (1998) Journal of Virology 72, 10218-10221); WW-domain-containing fragment of LDI-1, Nedd4, Yes-associated protein, KIAA0439 gene product, or other defective Nedd4-related proteins, particularly when overexpressed (A. Kikonyogo et al. (2001) Proc. Natl. Acad. Sci. USA 98, 11199-11204; A. Patnaik and J. W. Wills (2002) Journal of Virology 76, 2789-2795); a peptide consisting of the HIV p6 Gag PTAPP-motif-containing late (L) domain (L. VerPlank et al. (2001) Proc. Natl. Acad. Sci. USA 98, 7724-7729) or other viral late (L) domain containing PTAP, PSAP, PPXY, YPDL, or YXXL motifs (J. Martin-Serrano et al. (2001) Nature Medicine 7, 1313-1319; A. Patnaik and J. W. Wills (2002) Journal of Virology 76, 2789-2795); amino acids 1-167 of Tsg101, TSG-5' fragment of Tsg101, or similar amino-terminal fragment of Tsg101, particularly when overexpressed (D. G. Demirov et al. (2002) Proc. Natl. Acad. Sci. USA 99, 955-9601; E. L. Myers and J. F. Allen (2002) Journal of Virology 76, 11226-11235); a mutant of Tsg101 (M. Babst et al. (2000) Traffic 1, 248-258; L. VerPlank et al. (2001) Proc. Natl. Acad. Sci. USA 98, 7724-7729; J. Martin-Serrano et al. (2001) Nature Medicine 7, 1313-1319; O. Pornillos et al. (2002) EMBO Journal 21, 2397-2406) with reduced capacity to aid viral budding; a casein kinase 2 (CK2) inhibitor, such as the peptide RRADDSDDDDD (SEQ ID NO: 472) (E. K. Hui and D. P. Nayak (2002) Journal of General Virology 83, 3055-3066); or G protein signalling inhibitors (E. K. Hui and D. P. Nayak (2002) Journal of General Virology 83, 3055-3066); a molecule that binds to a cellular or pathogen molecule (for example to one or more of the following molecules: Tsg101, Vps4, casein kinase 2, Hrs, hVps28, Eap30, Eap20, Eap45, Chmp1, Chmp2, Chmp3, Chmp4, Chmp5, Chmp6, AP-50, Nedd4-related proteins, WW-domain-containing proteins, or L-domain-containing proteins; O. Pornillos et al. (2002) TRENDS in Cell Biology 12, 569-579; P. Gomez-Puertas et al. (2000) Journal of Virology 74, 11538-11547; E. Katz et al. (2002) Journal of Virology 76, 11637-11644) that is involved in budding or release of pathogens from an infected cell); a molecule that executes or stimulates apoptosis-related or other cell-death-related responses, as described supra (including but not limited to p53 (*Homo sapiens*, #AAF36354 through AAF36382; *Mus musculus*, #AAC05704, AAD39535, AAF43275, AAF43276, AAK53397); Bax (*Homo sapiens*, #NM_004324); Bid (*Homo sapiens*, #NM_001196); apoptotic protease activating factor 1 (Apaf-1: *Homo sapiens*, #NM_013229, NM_001160; *Mus musculus*, #NP_033814); Fas/CD95 (*Homo sapiens*, #AAC16236, AAC16237; *Mus musculus*, #AAG02410); TNF receptors (*Homo sapiens*, #NP_001056; V. Baud and M. Karin (2001) TRENDS in Cell Biology 11, 372-377; U. Sartorius et al. (2001) Chembiochem 2, 20-29); FLICE-activated death domain (FADD: *Homo sapiens*, #U24231; *Mus musculus*, #NM_010175); TRADD (*Homo sapiens*, #NP_003780, CAC38018); granzyme B (*Homo sapiens*, #AAH30195, NP_004122; *Mus musculus*, #AAH02085, NP_038570); constitutively active granzyme B; Smac/DIABLO (*Homo sapiens*, #NM_019887); caspases (including but not restricted to Caspase 1, *Homo sapiens*, #NM_001223; Caspase 2, *Homo sapiens*, #NM_032982, NM_001224, NM_032983, and NM_032984; Caspase 3, *Homo sapiens*, #U26943; Caspase 4, *Homo sapiens*, #AAH17839; Caspase 5, *Homo sapiens*, #NP_004338; Caspase 6, *Homo sapiens*, #NM_001226 and NM_032992;

Caspase 7, *Homo sapiens*, #XM_053352; Caspase 8, *Homo sapiens*, #NM_001228; Caspase 9, *Homo sapiens*, #AB019197; Caspase 10, *Homo sapiens*, #XP_027991; Caspase 13, *Homo sapiens*, #AAC28380; Caspase 14, *Homo sapiens*, #NP_036246; Caspase 1, *Mus musculus*, #BC008152; Caspase 2, *Mus musculus*, #NM_007610; Caspase 3, *Mus musculus*, #NM_009810; Caspase 6, *Mus musculus*, #BC002022; Caspase 7, *Mus musculus*, #BC005428; Caspase 8, *Mus musculus*, #BC006737; Caspase 9, *Mus musculus*, #NM_015733; Caspase 11, *Mus musculus*, #NM_007609; Caspase 12, *Mus musculus*, #NM_009808; Caspase 14, *Mus musculus*, #AF092997; and CED-3 caspase, *Caenorhabditis elegans*, #AF210702); a constitutively active caspase; calpains (T. Lu et al., (2002) Biochimica et Biophysica Acta 1590, 16-26)); a molecule that degrades components of cells or pathogens, as described supra (for example: proteases, including but not limited to chymotrypsin, trypsin, or elastase; DNases, including but not limited to caspase-activated DNase (CAD), constitutively active CAD (N. Inohara et al. (1999) Journal of Biological Chemistry 274, 270-274), or restriction enzymes; RNases, including but not limited to RNase III (*Homo sapiens*, #AF189011; *Escherichia coli*, #NP_417062, NC_000913), RNt1p (*Saccharomyces cerevisiae*, #U27016), Pac1, (*Schizosaccharomyces pombe*, #X54998), RNase A, or RNase L; glycosidases, including but not limited to N-glycanase, endoglycosidase H, O-glycanase, endoglycosidase F2, sialidase, or beta-galactosidase; or lipases, including but not limited to phospholipase A1, phospholipase A2, phospholipase C, or phospholipase D); a molecule that is toxic to an infected host cell or a pathogen cell, as described supra (including but not limited to an intracellular bacterial toxin (B. B. Finlay and P. Cossart (1997) Science 276, 718-725; C. Montecucco et al. (1994) FEBS Lett. 346, 92-98; P. O. Falnes et al. (2001) Biochemistry 40, 4349-4358) that has been modified so that it cannot cross cellular plasma membranes (as will be understood by one of skill in the art), such as the A (21 kDa) fragment of diptheria toxin; a molecule that is toxic to a pathogen cell, including but not limited to penicillin, erythromycin, tetracycline, rifampin, amphotericin B, metronidazole, or mefloquine; an ATP inhibitor (E. K. Hui and D. P. Nayak (2001) Virology 290, 329-341); or a toxin that inhibits transcription, translation, replication, oxidative phosphorylation, cytoskeletal processes, or other cell and/or pathogen functions).

Also included in this invention are chimeric transcriptions factors. The heat shock element (HSE) binding domain is approximately amino acids 13-121 of human heat shock factor 1 (HSF1) (M. Green et al. (1995) *Molecular and Cellular Biology* 15, 3354-3362; S.-G. Ahn et al. (2001) *Genes & Development* 15, 2134-2145). One or more copies of this domain can be isolated and linked together, preferably by flexible hydrophilic amino acid sequences in a chimeric transcription factor. In a preferred embodiment, three copies of the HSF1 DNA binding domain, preferably separated by flexible hydrophilic amino acid sequences are present in the chimeric transcription factor.

Interferon-stimulated gene factor 3 gamma (ISGF-3 gamma) induces transcription in response to type-I interferon. The ISGF-3 gamma DNA binding domain is approximately amino acids 1-112. (NCBI Accession #Q00978; H. A. R. Bluyssen, J. E. Durbin, and D. E. Levy (1996) Cytokine & Growth Factor Reviews 7, 11-17; Y. Mamane et al. (1999) Gene 237, 1-14). The ISGF-3 gamma DNA binding domain can be isolated and used in a genetically-engineered chimeric transcription factor, as described below.

Interferon regulatory factor 3 (IRF-3) induces transcription in response to dsRNA. Excluding regions needed for regulation of its activation, the DNA binding domain of IRF-3 is approximately amino acids 1-97 (Y. Mamane et al. (1999) Gene 237, 1-14; R. Lin, Y. Mamane, and J. Hiscott (1999) *Molecular and Cellular Biology* 19, 2465-2474). The DNA binding domain of IRF-3 can also be isolated and used in a genetically-engineered chimeric transcription factor, as described below.

Interferon regulatory factor 1 (IRF-1) upregulates expression of MHC Class I and functions in other ways to improve immune and antiviral responses. The IRF-1 DNA binding domain is approximately amino acids 1-109 (NCBI Accession # P10914, NP_002189; C. E. Samuel (2001) *Clinical Microbiology Reviews* 14, 778-809; S. J. P. Gobin et al. (1999) *J Immunology* 163, 1428-1434; W.-C. Au et al. (1995) *Proc. Natl. Acad. Sci.* 92, 11657-11661; S. Kirchhoff et al. (2000) *Eur. J. Biochem.* 267, 6753-6761; Y. Mamane et al. (1999) *Gene* 237, 1-14). The IRF-1 DNA binding domain can also be isolated and used in a genetically-engineered chimeric transcription factor, as described below.

p53 upregulates apoptosis-related and other genes when activated. The p53 DNA binding domain is approximately amino acids 100-300. (A. Ayed et al. (2001) *Nature Structural Biology* 8, 756-760; B. F. Mueller-Tiemann et al. (1998) *Proc. Natl. Acad. Sci.* 95, 6079-6084; M. E. Anderson et al. (1997) *Molecular and Cellular Biology* 17, 6255-6264; Y. Wang et al. (1995) *Molecular and Cellular Biology* 15, 2157-2165). In a preferred embodiment, the chimeric transcription factor has four copies of the p53 DNA binding domain, preferably separated by flexible hydrophilic amino acid sequences. The p53 DNA binding domain can be isolated and used in a genetically-engineered chimeric transcription factor, as described below.

XBP1 (K. Lee et al. (2002) *Genes & Development* 16, 452-466; H. Yoshida et al. (2001) *Cell* 107, 881-891) and ATF6 (X. Chen et al. (2002) Journal of Biological Chemistry 277, 13045-13052; J. Shi et al. (2002) *Developmental Cell* 3, 99-111; Y. Wang et al. (2000) Journal of Biological Chemistry 275, 27013-27020) upregulate unfolded-protein-response or endoplasmic-reticulum-associated-protein-degradation-response genes.

CIITA (M. W. Linhoff et al. (2001) Molecular and Cellular Biology 21, 3001-3011; A. Muhlethaler-Mottet et al. (1997) EMBO Journal 16, 2851-2860) upregulates MHC Class II genes when activated. The CARD and/or acidic domains of CIITA isoforms act as transcriptional activators.

NF kappa B upregulates inflammatory-response genes when activated (F. E. Chen and G. Ghosh (1999) Oncogene 18, 6845-6852; H. L. Pahl (1999) Oncogene 18, 6853-6866).

In one embodiment, a chimeric molecule or agent of the invention includes a chimeric transcription factor in which the natural DNA-binding domain of ISGF-3 gamma is replaced with one or more of the following: one or more DNA-binding domains isolated from XBP1; one or more DNA-binding domains isolated from ATF6; one or more transcription activation domains isolated from CIITA; one or more HSE-binding domains; one or more DNA-binding domains isolated from NF kappa B; one or more DNA-binding domains isolated from IRF-1.

In another embodiment, a chimeric molecule or agent of the invention includes a chimeric transcription factor in which the natural DNA-binding domain (approximately amino acids 1-97) of IRF-3 is replaced with one or more of the following: one or more DNA-binding domains isolated from XBP1; one or more DNA-binding domains isolated from ATF6; one or more transcription activation domains isolated from CIITA; one or more DNA-binding domains isolated from ISGF-3 gamma; one or more DNA-binding domains isolated from p53; one or more HSE-binding domains; one or more DNA-binding domains isolated from NF kappa B; one or more DNA-binding domains isolated from IRF-1.

In another embodiment, a chimeric molecule or agent of the invention includes a chimeric transcription factor in which the natural DNA-binding domains of NF kappa B are replaced with one or more of the following: one or more DNA-binding domains isolated from XBP1; one or more DNA-binding domains isolated from ATF6; one or more transcription activation domains isolated from CIITA; one or more DNA-binding domains isolated from ISGF-3 gamma; one or more DNA-binding domains isolated from IRF-3; one or more HSE-binding domains; one or more DNA-binding domains isolated from IRF-1.

In another embodiment, a chimeric molecule or agent of the invention includes a chimeric transcription factor in which the natural DNA-binding domain of ATF6 is replaced with one or more of the following: one or more DNA-binding domains isolated from XBP1; one or more DNA-binding domains isolated from p53; one or more transcription activation domains isolated from CIITA; one or more DNA-binding domains isolated from ISGF-3 gamma; one or more DNA-binding domains isolated from IRF-3; one or more HSE-binding domains; one or more DNA-binding domains isolated from NF kappa B; one or more DNA-binding domains isolated from IRF-1.

In another embodiment, a chimeric molecule or agent of the invention includes a chimeric transcription factor in which the natural DNA-binding domain of p53 is replaced with one or more of the following: one or more DNA-binding domains isolated from XBP1; one or more DNA-binding domains isolated from ATF6; one or more transcription activation domains isolated from CIITA; one or more DNA-binding domains isolated from ISGF-3 gamma; one or more DNA-binding domains isolated from IRF-3; one or more HSE-binding domains; one or more DNA-binding domains isolated from NF kappa B; one or more DNA-binding domains isolated from IRF-1.

In another embodiment, a chimeric molecule or agent of the invention includes a chimeric transcription factor in which the natural transcription activation domain of CIITA (the CARD and/or acidic domain) is replaced with one or more of the following: one or more DNA-binding domains isolated from XBP1; one or more DNA-binding domains isolated from ATF6; one or more DNA-binding domains isolated from ISGF-3 gamma; one or more DNA-binding domains isolated from IRF-3; one or more DNA-binding domains isolated from p53; one or more HSE-binding domains; one or more DNA-binding domains isolated from NF kappa B; one or more DNA-binding domains isolated from IRF-1.

In another embodiment, a chimeric molecule or agent of the invention includes a chimeric transcription factor in which the natural DNA-binding domain of IRF-1 is replaced with one or more of the following: one or more DNA-binding domains isolated from XBP1; one or more DNA-binding domains isolated from ATF6; one or more transcription activation domains isolated from CIITA; one or more DNA-binding domains isolated from ISGF-3 gamma; one or more HSE-binding domains; one or more DNA-binding domains isolated from NF kappa B.

In another embodiment, a chimeric molecule or agent of the invention includes a chimeric transcription factor in which the natural DNA-binding domain (approximately amino acids 13-121) of HSF1 is replaced with one or more of the following: one or more DNA-binding domains isolated from XBP1; one or more DNA-binding domains isolated from ATF6; one or more transcription activation domains isolated from CIITA; one or more DNA-binding domains isolated from ISGF-3 gamma; one or more DNA-binding domains isolated from IRF-3; one or more HSE-binding domains; one or more DNA-binding domains isolated from NF kappa B; one or more DNA-binding domains isolated from IRF-1.

An agent of the invention, as described herein, can comprise at least one pathogen-interacting molecular structure and at least one effector-mediating molecular structure. Alternatively, an agent of the invention can comprise at least one pathogen-induced product-interacting molecular structure and at least one effector-mediating molecular structure.

A pathogen-interacting molecular structure, as used herein, is generally directed to an isolated molecular structure that is capable of recognizing or binding (interacting with) a pathogen, pathogen component or pathogen product. The term pathogen-interacting molecular structure is structure of a molecule that includes at least the minimal region necessary to perform the function of interacting with a pathogen, pathogen component or pathogen product. Isolated pathogen-interacting molecular structures, as used herein, encompass the pathogen-detection domains described supra. Furthermore, a pathogen-interacting molecular structure can be more than or less than a domain of the described proteins or polynucleotide sequences, but still retains the function of interacting with a pathogen, pathogen component or pathogen product.

A pathogen-induced product-interacting molecular structure, as used herein, is generally directed to an isolated molecular structure that is capable of recognizing or binding (interacting with) a pathogen-induced product, as described herein and include, for example and without limitation, cytokines such as an interferons or interleukins, unfolded-protein response or endoplasmic reticulum-associated protein degradation response signaling molecules, stress response or inflammatory response signaling molecules, 2',5'-oligoadenylate, and apoptosis signaling molecules. The term pathogen-induced product-interacting molecular structure is the structure of a molecule that includes at least the minimal region necessary to perform the function of interacting with a pathogen-induced product. Isolated pathogen-induced product-interacting molecular structures, as used herein, encompass the pathogen-induced product-detection domains described supra. Furthermore, a pathogen-induced product-interacting molecular structure can be more than or less than a domain of the described proteins or polynucleotide sequences, but retains the function of interacting with a pathogen-induced product.

The effector-mediating molecular structure, as used herein, is generally directed to an isolated molecular structure that is capable of mediating a wide range of effector functions, as described supra for an effector domain of a chimeric molecule of the invention. In particular, the effector-mediating molecular structure of this invention can mediate the same responses as an effector domain, for example and without limitation: (1) an interferon response; (2) an apoptosis response; (3) a stress response; (4) an inflammatory response; (5) an enhanced immune response; (6) a degradative response; (7) inhibition of transport between the cytoplasm and the nucleus of a cell; (8) an unfolded-protein response or endoplasmic reticulum-associated protein degradation response; or (9) alteration of the endocytic or phagocytic pathway, all of which are discussed supra.

The molecular structures of the described agent can be isolated from naturally-occurring molecules, such as a cellular protein, that normally recognize a pathogen, pathogen component, pathogen product, or pathogen-induced product, or is a mediator of a wide range of effector function. Molecular structures can be isolated from a wide range of known cellular proteins from a number of different organisms, including for example, humans, non-human primates, rodents, plants, *Drosophila*, yeast, bacteria and the like, as will be appreciated by one of skill in the art. The molecular structures can also be synthetically-derived, such as by chemically modifying a naturally-occurring molecule, or otherwise manipulating a naturally-occurring molecule to enhance, optimize, or modify the molecular structures, using standard techniques known to those of skill in the art, or alternatively, they can be a synthetic product such as a small molecule or a peptidomimetic. Furthermore, the molecular structures of the agent can be an antibody (including, for example, antibody fragments, such as Fab, Fab', F(ab')$_2$, and fragments including either a $V_L$ or $V_H$ domain, single chain antibodies, bi-specific, chimeric or humanized antibodies), that performs the function of the molecular structure.

More than one detection and/or effector domain can be present in a chimeric molecule. These can be the same or different domains. Similarly, more than one detection and/or effector molecular structures can be present in an agent of the invention.

A chimeric molecule or agent of the invention can be a nonnaturally occurring molecule that contains two or more binding sites for a pathogen or pathogen product. The two or more binding sites promote agglomeration of pathogens or pathogen products and thereby directly or indirectly promote an anti-pathogen effect. For example, a chimeric molecule or agent of the invention can have two or more binding sites for LPS (for example, sites that mimic the LPS-binding domain from approximately amino acids 1-199 of human BPI or other LPS-binding domains as described supra); two or more binding sites for peptidoglycan (for example, sites that mimic the peptidoglycan-binding domain from the extracellular domain of human TLR2); two or more binding sites for muramyl dipeptide (for example, sites that mimic the muramyl-dipeptide-binding domain from approximately amino acids 744-1040 of human Nod2); two or more binding sites for bacterial flagellin (for example, sites that mimic the flagellin-binding domain from the extracellular domain of human TLR5); two or more binding sites for bacterial type III secretion systems; two or more binding sites for CpG DNA (for example, sites that mimic the CpG-DNA-binding domain from the extracellular domain of human TLR9); two or more binding sites for zymosan (for example, sites that mimic the zymosan-binding domain from the extracellular domain of human TLR2); two or more binding sites for a pathogenic form of a prion (for example, sites that mimic a portion of a nonpathogenic prion form that binds to a pathogenic prion form (such as approximately amino acids 119-136 of hamster prion protein; J. Chabry et al. (1999) Journal of Virology 73, 6245-6250)); two or more binding sites for dsRNA (for example, sites that contain lividomycin or that mimic the dsRNA-binding domain of lividomycin, protein kinase R, or other dsRNA-binding domains as described supra); two or more binding sites for viral late domains (for example and without restriction, sites that bind to viral late domain motifs such as PTAP, PSAP, PPXY, YPDL, or YXXL, as described supra); two or more binding sites for viral glycoproteins (for example and without restriction, sites that mimic the hemagglutinin-binding domain of human NK cell activation receptor NKp46).

The chimeric molecules and agents as described herein can be assembled or joined between the domains or molecular structures by, for example, peptide linkage, covalent bonding, artificial linkage, or a flexible linker region normally associated with either domain or molecular structure.

Alternatively, the domains of the chimeric molecules or molecular structures of the agent can be separated. Separate domains or molecular structures are capable of being assembled or joined through several mechanisms, for example and without limitation, through the interaction with another reagent, for example a bi-specific antibody, a chemical cross-linker, or other methods as will be appreciated by one of skill in the art. The separate domains can also be assembled together via non-covalent bonds, such as through electrostatic interactions and the like. Furthermore, the separate domains or molecular structures can mediate their effects either directly or indirectly through such agents as secondary signaling molecules, as will be understood by one of skill in the art.

Attached to the separate domains or separate molecular structures can be further domains or structures that can mediate the joining of the separate domains or structures to form the chimeric molecule or agent, for example, one domain or molecular structure can have one or more streptavidin molecules attached, and the other domain or molecular structure can have one or more biotin molecules attached, thus the specific biotin-streptavidin interaction mediates the forming of a chimeric molecule or agent. Other suitable interaction domains or structures will be recognized by one of skill in the art.

The chimeric molecule or agent can additionally contain cellular targeting tags. For example, tags that direct the chimeric molecule or agent to the cell membrane or cellular organelles, the nucleus, or other varieties of tags. Such tags can be used to mediate crossing of the membrane by the chimeric molecule or agent. Suitable protein uptake tags include, for example and without limitation: (1) poly-arginine and related peptoid tags (L. Chen et al. (2001) Chem. Biol. 8: 1123-1129, P. A. Wender et al. (2000) Proc. Natl. Acad. Sci. 97: 13003-13008); (2) HIV TAT protein, its Protein Transduction Domain (PTD) spanning approximately amino acids 47-57, or synthetic analogs of the PTD (M. Becker-Hapak, S. S. McAllister, and S. F. Dowdy (2001) Methods 24: 247-256, A. Ho et al. (2001) Cancer Res. 61: 474-477); (3) *Drosophila* Antennapedia protein, the domain spanning approximately amino acids 43-58 also called Helix-3 or Penetratin-1, or synthetic analogs thereof (D. Derossi, G. Chassaing, and A. Prochiantz (1998) Trends Cell Biol. 8: 84-87, A. Prochiantz (1996) Curr. Opin. Neurobiol. 6: 629-63); (4) Herpesvirus VP22 protein, the domain spanning approximately amino acids 159-301, or portions or synthetic analogs thereof (N. Normand, H. van Leeuwen, and P. O'Hare (2001) J. Biol. Chem. 276: 15042-15050, A. Phelan, G. Elliott, and P. O'Hare (1998) Nat. Biotech. 16: 440-443); (5) Membrane-Translocating Sequence (MTS) from Kaposi fibroblast growth factor or related amino acid sequences such as AAV-LLPVLLAAP (SEQ ID NO: 473) (M. Rojas, J. P. Donahue, Z. Tan, and Y.-Z. Lin (1998) Nat. Biotech. 16: 370-375, C. Du, S. Yao, M. Rojas, and Y.-Z. Lin (1998) J. Peptide Res. 51: 235-243); (6) Pep-1, MPG, and similar peptides (M. C. Morris et al. (2001) Nat. Biotech. 19: 1173-1176, M. C. Morris et al. (1999) Nuc. Ac. Res. 27: 3510-3517); (7) Transportan, Transportan 2, and similar peptides (M. Pooga et al. (1998) FASEB J. 12: 67-77; M. Pooga et al. (1998) Ann. New York Acad. Sci. 863: 450-453); (8) Amphipathic model peptide and related peptide sequences (A. Scheller et al. (2000) Eur. J. Biochem. 267: 6043-6049, A. Scheller et al. (1999) J. Pept. Sci. 5: 185-194); (9) Tag protein to be delivered with approximately amino acids 1-254 of *Bacillus anthracis* lethal factor (LF), and administer along with *B. anthracis* protective antigen (PA) to deliver the tagged protein into cells, or similar methods (S. H. Leppla, N. Arora, and M. Varughese (1999) J. App. Micro. 87: 284, T. J. Goletz et al. (1997) Proc. Natl. Acad. Sci. 94: 12059-12064); and (10) Folic acid (C. P. Leamon and P. S. Low (2001) Drug Discov. Today 6: 44-51, C. P. Leamon, R. B. DePrince, and R. W. Hendren (1999) J. Drug Targeting 7: 157-169). Methods for attaching uptake tags to the proteins employ standard methods and will be recognized by one of skill in the art.

Optionally the chimeric molecule or agent can include one or more binding sites for one or more natural inhibitory or regulatory molecules in order to facilitate the inhibitory or regulatory molecule(s) to regulate the activity of the chimeric molecule or agent, and prevent toxicity in uninfected cells. For example and without restriction, the chimeric molecule or agent can include one or more binding sites for one of more of the following: the natural P58 inhibitor of protein kinase R and PERK (W. Yan et al. (2002) Proc. Natl. Acad. Sci. USA 99, 15920-15925); the natural RLI inhibitor of RNase L (C. Bisbal et al. (1995) Journal of Biological Chemistry 270, 13308-13317); the natural XIAP inhibitor of caspase 9 (S. M. Srinivasula et al. (2001) Nature 410, 112-116); or the natural HSBP1 inhibitor of HSF1 (R. I. Morimoto (1998) Genes & Development 12, 3788-3796).

The chimeric molecule and its individual domains, and the agent and its individual molecular structures, can be of a variety of compounds or substances, for example, protein, DNA, RNA, single chain antibodies, small molecule drugs, pro-drugs, or peptidomimetics. A DNA or RNA encoding a molecule of interest can, optionally, be operatively-linked to a promoter. Furthermore, said promoter can be conditionally regulated.

The chimeric molecule or agent can be administered to a cell or organism before (prophylactically) or after infection (therapeutically).

The composition of the present invention can be administered by any known route of administration. For example, the route of administration can be intravenous, intramuscular, intraarterial, intraperitoneal, intrasternal, subcutaneous, intraocular, inhalation, orally and by intraarticular injection or infusion.

The composition of the present invention can be, for example, solid (or semi-solid, such as, creams or a gelatin-type substance), liquid, or aerosol. Examples of solid compositions include pills, creams, and implantable dosage units. The pills can be administered orally, the creams can be administered topically. The implantable dosage unit can be administered locally, or implanted for systemic release of the chimeric molecules or agents, for example subcutaneously. Examples of liquid composition include formulations adapted for injection subcutaneously, intravenously, intraarterially, and formulations for topical and administration. Examples of aersol formulation include inhaler formulation for administration to the lungs.

Pharmaceutical compositions for parenteral injection comprise pharmaceutically acceptable sterile aqueous or non-aqueous solutions, dispersions, suspensions or emulsions, as well as sterile powders for reconstitution into sterile injectable solutions, or dispersions, just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polmer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

The compositions of the present invention can include pharmaceutically-acceptable salts of the compositions described herein, e.g., which can be derived from inorganic or organic acids. A "pharmaceutically-acceptable salt" is meant to describe those salts which are, within the scope of sound medical judgement, suitable for use in contact with the tissues of animals, preferably mammals, without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences* (1977) 66:1 et seq. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable," "physiologically tolerable" and grammatical variations thereof as they refer to compositions, carriers, diluents and reagents, are used interchangeably and represent materials that are capable of administration to or upon an animal, preferably a mammal, with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Use of timed release or sustained release delivery systems are also included in the invention. A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The chimeric molecules and agents described herein can be administered individually, in combinations with each other, or in combination with other treatments, as will be apparent to one of skill in the art. The individual domains of the chimeric molecules, or individual molecular structures of the agent described herein, can be administered separately or simultaneously to the cell or organism. Formation of the chimeric molecules or agent of the invention, from separate domains or molecular structures, can occur prior to administering to the cell or organism (ex vivo or in vitro assembly), or the separate domains or molecular structures can be administered to the cell or organism separately and allowed to assemble as chimeric molecules, or as the agent of the invention, in the cell or organism (in vivo assembly).

Furthermore, one or more chimeric molecules and/or agents of the invention can be administered to a cell or organism to treat or prevent an infection by one or more pathogens. To minimize undesirable effects, one or more pathogen detector or pathogen-induced product detector molecules can optionally be administered together with one or more effector molecules, such that detection of a pathogen or pathogen-induced product by the detector molecule(s) directly or indirectly stimulates, activates, facilitates, or upregulates the effector molecule(s). For example and without limitation: one or more detector molecules can be joined to one or more effector molecules such that binding to a pathogen or pathogen-induced product activates or facilitates the function of the effector molecule(s); a detector molecule can be a genetic promoter which is operatively linked to a gene that encodes an effector molecule; a pathogen or pathogen-induced product can affect a detector molecule, which then stimulates, activates, facilitates, or upregulates the effector molecule(s); a pathogen or pathogen-induced product can affect a detector molecule, which then acts via one or more naturally occurring molecules to stimulate, activate, facilitate, or upregulate the effector molecule(s); the detector and effector molecules can be the same molecule, for example and without limitation, a molecule that binds to one or more pathogens or pathogen components, thereby interfering with the pathogens or pathogen components; the detector and/or effector molecules can bind to or interact with one or more naturally occurring molecules, thereby making use of the pathogen-detection, pathogen-induced-product-detection, or anti-pathogen properties of said naturally occurring molecules.

As will be appreciated by one of skill in the art, the chimeric molecule, agent, domains of the chimeric molecule, or molecular structures of the agent, can be administered alone or as admixtures with conventional excipients, as described supra, and which do not deleteriously react with the chimeric molecule or agent. Such preparations can be mixed with auxilliary agents such a lubricants, preservatives, stablilizers, wetting agents, emulsifiers, buffers, coloring, and/or aromatic substances and the like, which also do not deleteriously react with the chimeric molecules or agents of the invention. Furthermore, the preparations can also be combined with other active substances to reduce metabolic degradation, as desired.

The dosage and frequency (single or multiple dosages) administered to the cell or organism can vary depending on a variety of factors, including the type of pathogen, duration of pathogen infection, extent of disease associated with pathogen infection, weight and health of the recipient and the route of administration of the composition. Those skilled in the art will be readily able to determine suitable dosages and frequencies using standard techniques.

As used herein, the term "therapeutically effective amount" means the total amount of each active component of the composition or method that is sufficient to show a meaningful benefit to the recipient, i.e., treatment, healing, prevention or amelioration of the relevant disease or disorder, or an increase in rate of treatment, healing, prevention or amelioration of such diseases or disorders. When applied to a combination, the term refers to combined amounts of the active ingredients that result in the therapeutic effect, whether administered in combination, serially or simultaneously.

Other methods of treatment include gene therapy. Gene transfer methods for gene therapy fall into three broad categories: physical (e.g., electroporation, direct gene transfer and particle bombardment), chemical (e.g., lipid-based carriers, or other non-viral vectors) and biological (e.g., virus-derived vector and receptor uptake). For example, non-viral vectors can be used which include liposomes coated with DNA. Such liposome/DNA complexes can be directly injected intravenously into the patient. Additionally, vectors or the "naked" DNA of the gene can be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally-mediated gene transfer using a noninfectious virus to deliver the gene in the patient or injecting naked DNA into a site in the patient and the DNA is taken up by a percentage of cells in which the gene product protein is expressed. Additionally, other methods such as use of a "gene gun," can be used for in vitro insertion of the DNA or regulatory sequences controlling production of the chimeric protein or agent described herein.

Chemical methods of gene therapy can involve a lipid based compound, not necessarily a liposome, to transfer the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression.

Viral vectors that have been used for gene therapy protocols include but are not limited to, retroviruses, other RNA viruses such as poliovirus or Sindbis virus, adenovirus, adeno-associated virus, herpes viruses, SV40, vaccinia and other DNA viruses. Replication-defective murine retroviral vectors are the most widely utilized gene transfer vectors. Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs. Another method, ligand-mediated gene therapy, involves complexing the DNA with specific ligands to form ligand-DNA conjugates, to direct the DNA to a specific cell or tissue.

The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells can provide treatments for genetic diseases or for prophylactic use. The DNA could be re-injected periodically to maintain the gene product level without mutations occurring in the genomes of the recipient cells. Non-integration of exogenous DNA can allow for the presence of several different exogenous DNA constructs within one cell with all of the constructs expressing various gene products.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell-specific or organ-specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA can also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Chimeric molecules or agents of the invention can optionally be targeted to certain cells within an organism, for example and without restriction by using a liposome vector, viral vector, or other delivery vector that targets a ligand specifically expressed on said cells, or by using a cell-type-specific promoter operatively linked to a polynucleotide sequence encoding a chimeric molecule or agent of the invention, as will be readily appreciated by one of skill in the art.

The concentration, dose, and duration of treatment with chimeric molecules or agents of the invention can be controlled to maximize the therapeutic benefit while minimizing toxicity or undesirable side-effects. Methods of achieving such control will be readily appreciated by one of skill in the art and include, without restriction, the administered dose of chimeric molecules or agents of the invention, frequency of administration, number of adminstrations, inducible promoters, molecular structures to control rates of metabolism by the liver and excretion by the kidneys, mRNA stability signals, ubiquitination signals or other protein stability signals, and delivery vector.

Suitable recipients of the agents described herein include animals, specifically mammals, such as humans, non-human primates, rodents, cattle, and the like. Also included are avian species, fish, plants, insects and prokaryotes, as will be readily appreciated by one of skill in the art.

Furthermore, it is preferred that these chimeric molecules and agents have minimum toxic side-effects. Even more preferred, the chimeric molecules and agents of the invention have no toxic side-effects. Minimum toxic side-effects can be assessed by those of skill in art. Tolerable toxic side-effects allow the recipient to receive treatment that is effective in preventing or treating a pathogen infection, but which does not cause irreparable or intolerable injury to the recipient. Preferably, the recipient cell or organism exhibits or suffers no deleterious toxic side-effects from administration of the treatment, while sufficiently treating or preventing a pathogen infection.

Optionally, chimeric molecules or agents of the invention can be administered together with stimuli that induce latent viruses to upregulate viral gene expression, thereby enhancing the effect of the chimeric molecules or agents on infected cells, as will be readily appreciated by one of skill in the art.

It is also considered that some of the chimeric molecules and agents described herein can treat illnesses other than pathogen infections and that similar therapeutic agents can be designed that will treat additional illnesses other than pathogen infections. Illnesses that can be treated by chimeric molecules or agents described herein, or by similar therapeutic agents, include, for example and without restriction, the following: cancer, such as lymphomas, carcinomas and sarcomas; autoimmune diseases, such as rheumatoid arthritis, lupus, transplant rejection, and multiple sclerosis; inflammatory disorders such as those associated with hypersensitivity or Crohn's disease (N. Inohara et al. (2003) Journal of Biological Chemistry, PMID: 12514169); primary immunodeficiency diseases; neural disorders such as ischemic neuron injury (W. Paschen and J. Doutheil (1999) J. Cereb. Blood Flow Metab. 19, 1-18), Alzheimer's disease (K. Imaizumi et al. (2001) Biochimica et Biophysica Acta 1536, 85-96; T. Kudo et al. (2002) Ann. N.Y. Acad. Sci. 977, 349-355), Huntington's disease, and Parkinson's disease; diabetes (S. Oyadomari et al. (2002) Apoptosis 7, 335-345); cystic fibrosis (M. H. Glickman and A. Ciechanover (2002) Physiol. Rev. 82, 373-428; K. M. Sakamoto (2002) Molecular Genetics and Metabolism 77, 44-56); atherosclerosis (C. Patterson and D. Cyr (2002) Circulation 106, 2741-2746); and the like. For example, detection domains of chimeric molecules or agents can detect apoptosis signals, endoplasmic reticulum stress signals, inflammatory response signals, protein aggregation, cell-cycle-control signals, specific illness-associated molecular epitopes, or other signals associated with illnesses such as those listed supra. Effector domains of said chimeric molecules or agents can be stimulated or induced by said detection domains to affect apoptosis pathways, inflammatory-response pathways, unfolded-protein response-pathways, endoplasmic-reticulum-associated-protein degradation-response pathways, ubiquitin-proteasome pathways, stress-response pathways, or other pathways such that the illness is slowed, alleviated, cured, or prevented.

Chimeric molecules or agents of the invention can be used to detect pathogens, pathogen components, pathogen products, or other molecules. For example and without restriction, chimeric molecules having a caspase effector domain and a detector domain that recognizes a polyvalent pathogen, pathogen component, pathogen product, cancer antigen, other antigen, or other molecule can be used to detect said pathogen, pathogen component, pathogen product, cancer antigen, other antigen, or molecule in a sample. Colorimetric, fluorometric, and other assays for caspase activity (for example, those from R&D Systems) are well known to those of skill in the art. An increase in caspase activity of the chimeric molecules or agents indicates that said pathogen, pathogen component, pathogen product, cancer antigen, other antigen, or molecule is present in a sample and can optionally be used to determine the concentration of said pathogen, pathogen component, pathogen product, cancer antigen, other antigen, or molecule in said sample, as will be readily appreciated by one of skill in the art. Optionally, another effector domain such as a kinase that activates upon crosslinking can be used with a suitable assay, as will be readily appreciated by one of skill in the art.

The present invention is further illustrated by the following examples, which more specifically illustrate the invention.

EXEMPLIFICATION

Example 1

Materials: dsRNA-Activated Caspases

Plasmids encoding human procaspase 3 (NCBI Accession #U26943) and amino acids 1-125 of human FADD (#U24231) were provided by D. M. Spencer, Baylor College of Medicine. A plasmid encoding human protein kinase R (#U50648) was provided by E. F. Meurs, Institut Pasteur. The mammalian expression vector pTRE2hyg, HeLa Tet-On™ human cell line, doxycycline, and tetracycline-free fetal bovine serum were obtained from Clontech. The pCR®2.1-TOPO vector was supplied by Invitrogen. PCR primers, LIPOFECTIN® reagent, and PLUS reagent were obtained from Gibco BRL/Life Technologies/Invitrogen. Polyclonal goat IgG antibodies specific for human caspase 3 were from R&D Systems, and HRP-conjugated rabbit antibodies specific for goat IgG (H+L) were from Zymed. Polyclonal rabbit IgG antibodies specific for human FADD were from Upstate Biotechnology, and HRP-conjugated goat antibodies specific for rabbit IgG were from Santa Cruz Biotechnology. CellTiter 96® AQueous One Solution was obtained from Promega. Poly(I)•poly(C) double-stranded RNA was from Amersham Pharmacia.

Synthesis of dsRNA-Activated Caspases: PCR Product 7

Figure 7:
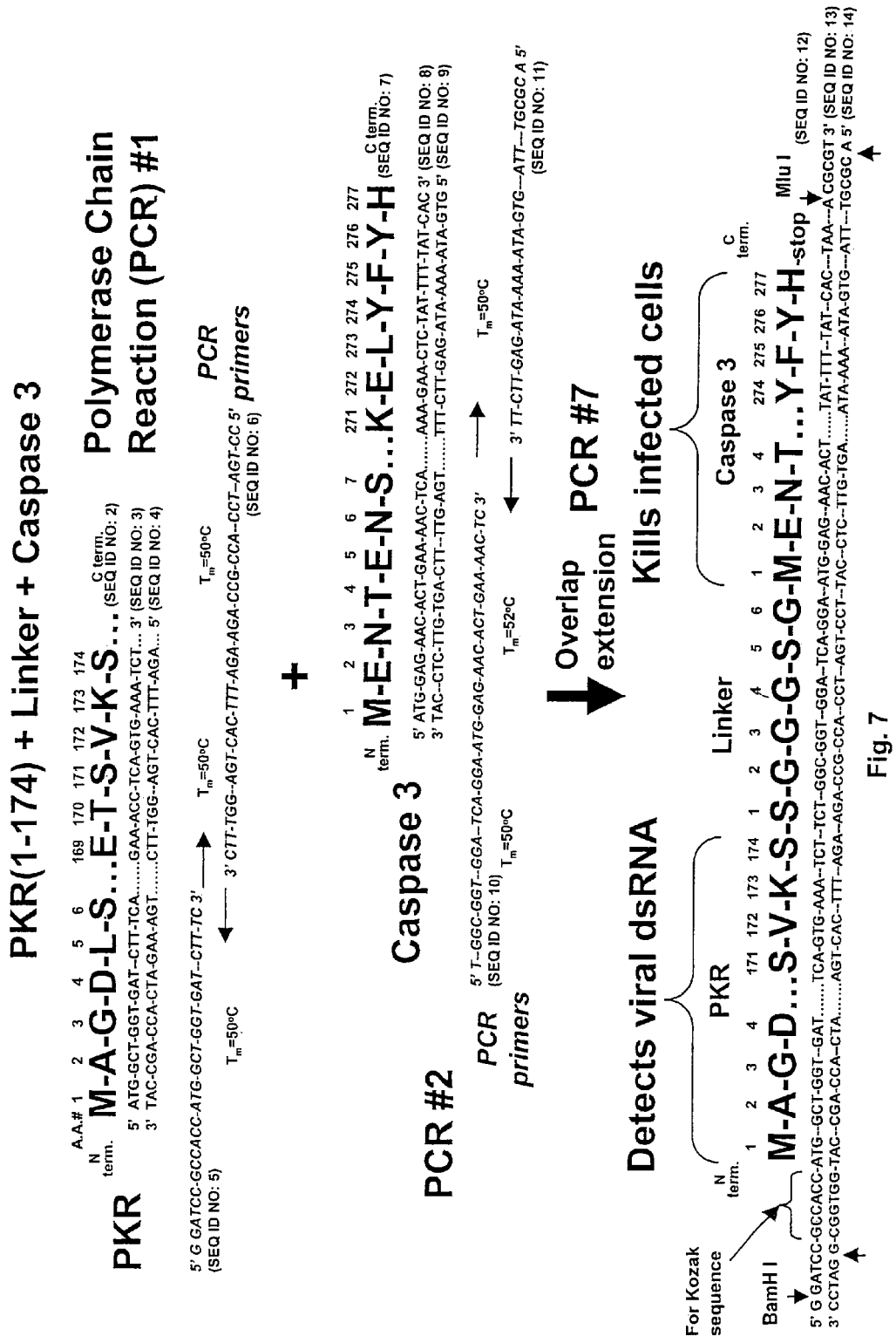
FIG. 7 is an outline of a polymerase chain reaction (PCR) strategy for the synthesis of a dsRNA-activated caspase. PCR was used to produce PCR product 7. The dsRNA-binding domain from PKR (amino acids 1-174) is fused in frame with a short flexible polypeptide linker (S-G-G-G-S-G (SEQ ID NO: 1)) and full-length caspase-3. A Kozak sequence and stop codon are included as shown. BamH I and Mlu I restriction sites are included at the polynucleotide ends for insertion into an appropriate vector.

FIG. 7 illustrates the strategy for the synthesis of PCR Product 7, which encodes a novel dsRNA-activated caspase. The dsRNA-binding domain from PKR (amino acids 1-174) was fused in frame with a short flexible polypeptide linker (S-G-G-G-S-G (SEQ ID NO: 1)) and full-length caspase-3. A Kozak sequence and stop codon were included as shown. BamH I and Mlu I restriction sites were included at the ends for ease of insertion into the pTRE2hyg vector. PCR 1 used the indicated 5' and 3' PCR primers to PCR amplify the region encoding amino acids 1-174 of PKR from the provided plasmid. PCR 2 used the indicated 5' and 3' PCR primers to PCR amplify the coding sequence of caspase-3 from the provided plasmid. PCR 7 used gel-purified products of PCR 1 and 2, 5' primer from PCR 1, and 3' primer from PCR 2, to create the desired product by splicing by overlap extension (C. W. Dieffenbach and G. S. Dveksler (eds.), *PCR Primer: A Laboratory Manual* (1995, Cold Spring Harbor Laboratory Press, Plainview, N.Y.).).

Synthesis of dsRNA-Activated Caspases: PCR Product 8

Figure 8:
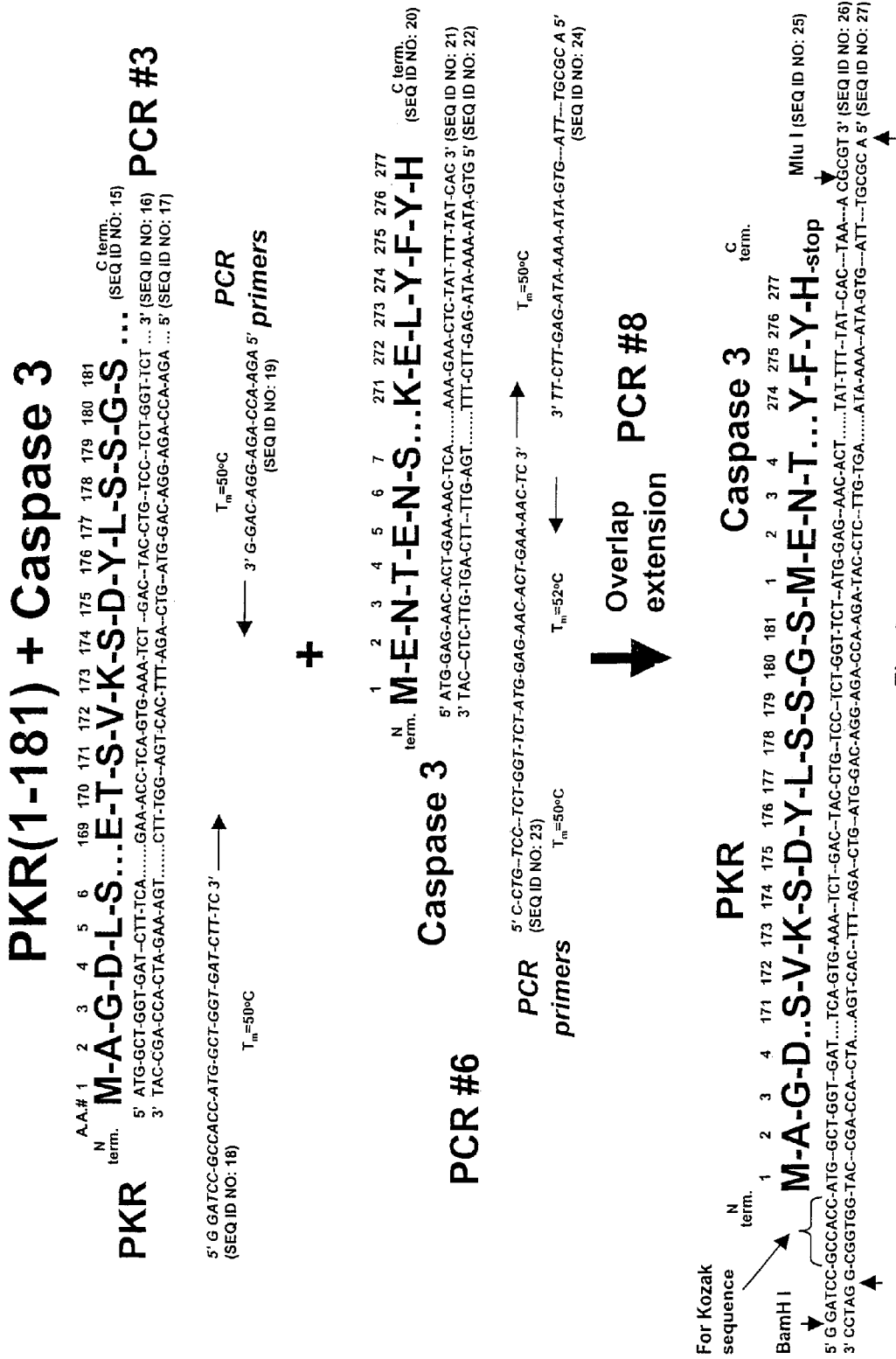
FIG. 8 is an outline of a PCR strategy used to produce PCR product 8, another novel dsRNA-activated caspase. The dsRNA-binding domain from PKR (amino acids 1-174) and part of the natural linker region from PKR (amino acids 175-181) are fused in frame with full-length caspase-3. A Kozak sequence and stop codon are included as shown. BamH I and Mlu I restriction sites are included at the polynucleotide ends for insertion into an appropriate vector.

FIG. 8 illustrates the strategy for the synthesis of PCR product 8, which encodes a novel dsRNA-activated caspase. The dsRNA-binding domain from PKR (amino acids 1-174) and part of the natural linker region from PKR (amino acids 175-181) were fused in frame with full-length caspase-3. A Kozak sequence and stop codon were included as shown. BamH I and Mlu I restriction sites were included at the ends for ease of insertion into the pTRE2hyg vector. PCR 3 used the indicated 5' and 3' PCR primers to PCR amplify the region encoding amino acids 1-181 of PKR from the provided plasmid. PCR 6 used the indicated 5' and 3' PCR primers to copy the coding sequence of caspase-3 from the provided plasmid. PCR 8 used gel-purified products of PCR 3 and 6, 5' primer from PCR 3, and 3' primer from PCR 6, to create the desired product by splicing by overlap extension.

Synthesis of dsRNA-Activated Caspase Activators: PCR Product 9

Figure 9:
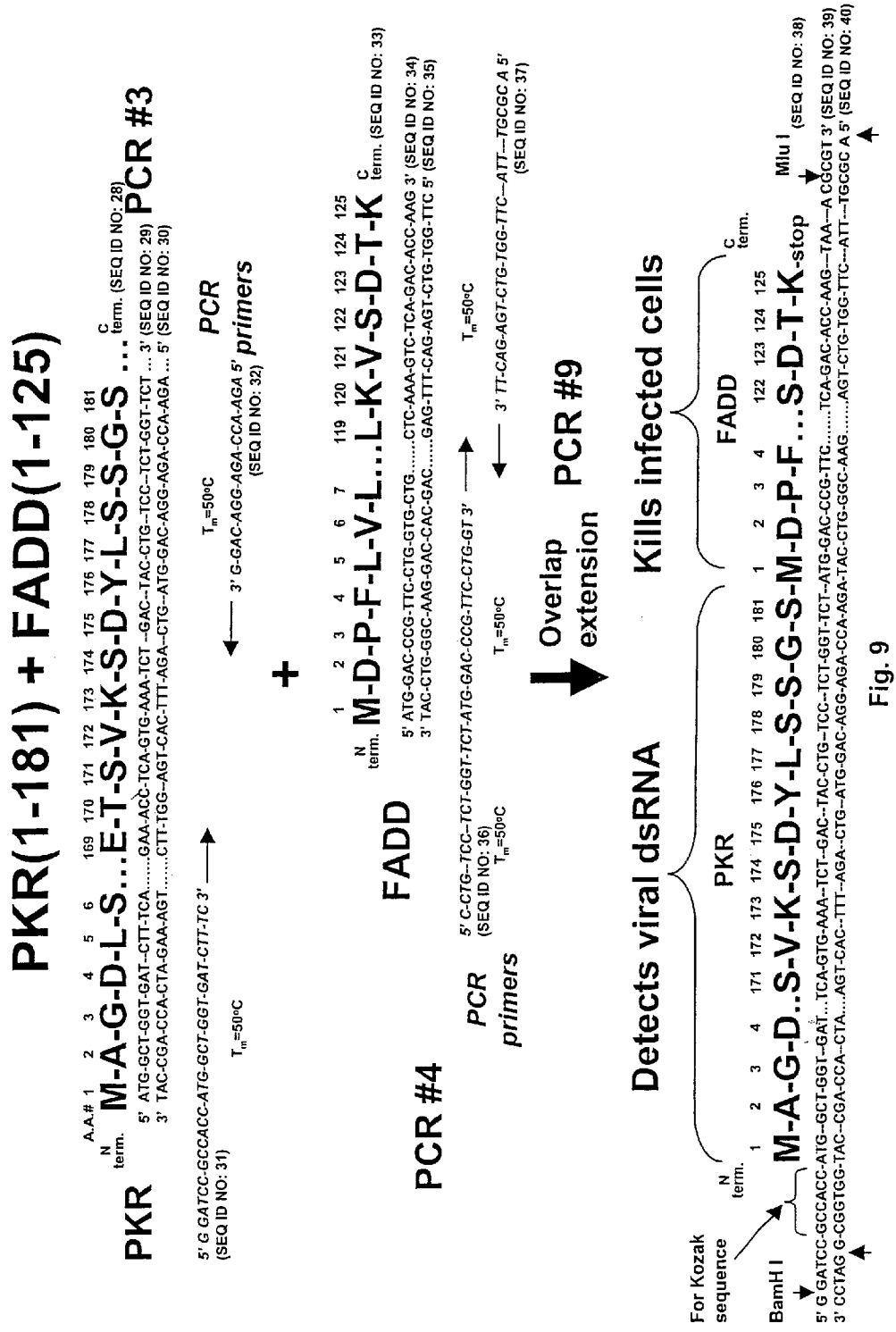
FIG. 9 is an outline of a PCR strategy used to produce PCR product 9, a novel dsRNA-activated caspase activator. The dsRNA-binding domain from PKR (amino acids 1-174) and part of the natural linker region from PKR (amino acids 175-181) are fused in frame with amino acids 1-125 of FADD, which includes the death effector domain (DED) that binds to procaspase-8. A Kozak sequence and stop codon are included as shown. BamH I and Mlu I restriction sites are included at the polynucleotide ends for insertion into an appropriate vector.

FIG. 9 illustrates the strategy for the synthesis of PCR product 9, which encodes a novel dsRNA-activated caspase activator. The dsRNA-binding domain from PKR (amino acids 1-174) and part of the natural linker region from PKR (amino acids 175-181) were fused in frame with amino acids 1-125 of FADD, which includes the death effector domain (DED) that binds to procaspase-8. When two or more copies of the protein encoded by PCR 9 are cross-linked by dsRNA, they will cross-link and activate endogenous (pro)caspase-8. A Kozak sequence and stop codon were included as shown. BamH I and Mlu I restriction sites were included at the ends for ease of insertion into the pTRE2hyg vector. PCR 3 used the indicated 5' and 3' PCR primers to copy the region encoding amino acids 1-181 of PKR from the provided plasmid. PCR 4 used the indicated 5' and 3' PCR primers to PCR amplify the region encoding amino acids 1-125 of FADD from the provided plasmid. PCR 9 used gel-purified products of PCR 3 and 4, 5' primer from PCR 3, and 3' primer from PCR 4 to create the desired product by splicing by overlap extension.

Synthesis of dsRNA-Activated Caspase Activators: PCR Product 10

Figure 10:
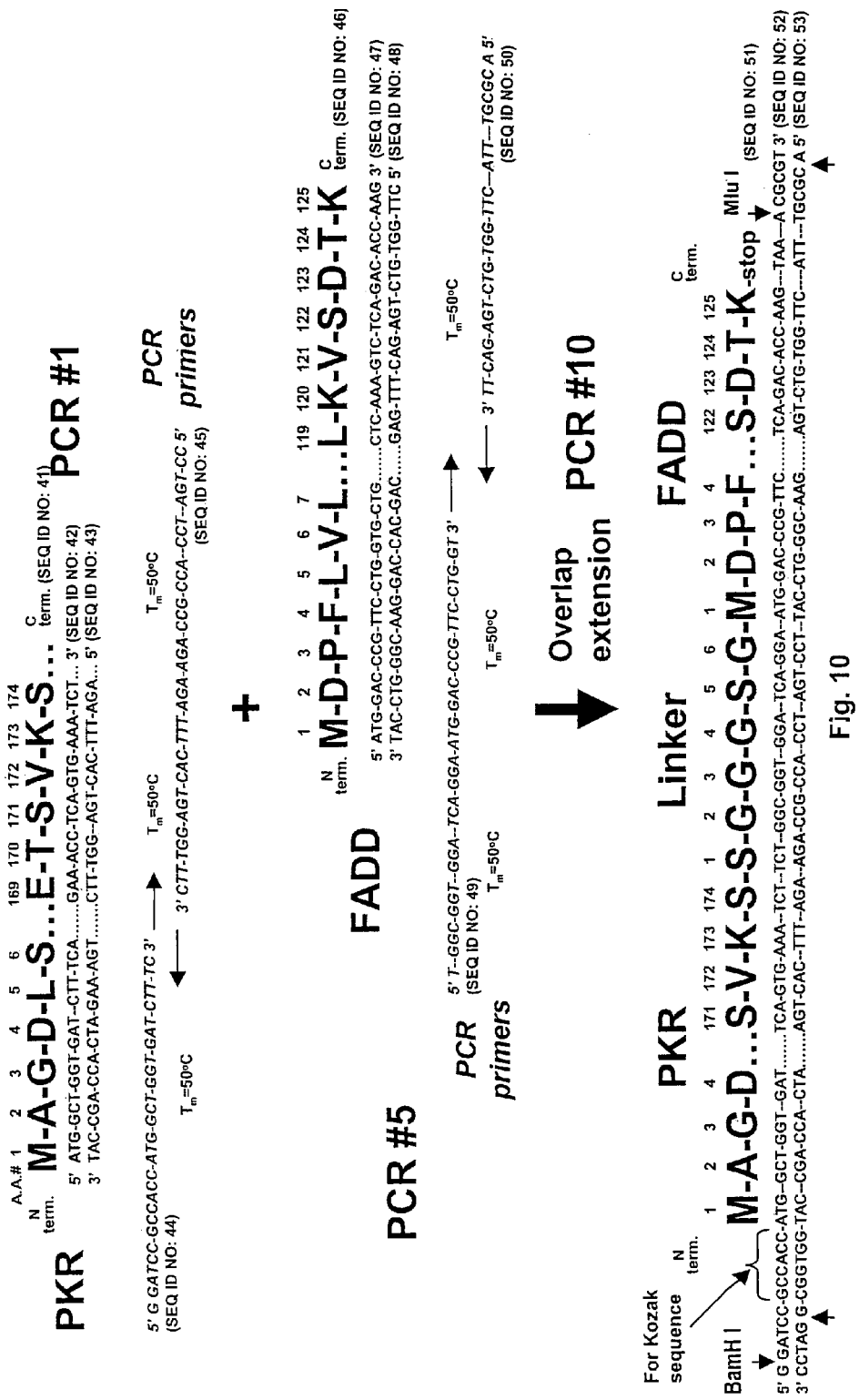
FIG. 10 is an outline of a PCR strategy used to produce PCR product 10, another novel dsRNA-activated caspase activator. The dsRNA-binding domain from PKR (amino acids 1-174) is fused in frame with a short flexible polypeptide linker (S-G-G-G-S-G (SEQ ID NO: 1)) and amino acids 1-125 of FADD, which includes the death effector domain (DED) that binds to procaspase 8. A Kozak sequence and stop codon are included as shown. BamH I and Mlu I restriction sites are included at the ends for ease of insertion into a vector.

FIG. 10 illustrates the strategy for the synthesis of PCR product 10, which encodes a novel dsRNA-activated caspase activator. The dsRNA-binding domain from PKR (amino acids 1-174) was fused in frame with a short flexible polypeptide linker (S-G-G-G-S-G (SEQ ID NO: 1)) and amino acids 1-125 of FADD, which includes the death effector domain (DED) that binds to procaspase-8. When two or more copies of the protein encoded by PCR 10 are cross-linked by dsRNA, they will cross-link and activate endogenous (pro)caspase-8. A Kozak sequence and stop codon were included as shown. BamH I and Mlu I restriction sites were included at the ends for ease of insertion into the pTRE2hyg vector. PCR 1 used the indicated 5' and 3' PCR primers to PCR amplify the region encoding amino acids 1-174 of PKR from the provided plasmid. PCR 5 used the indicated 5' and 3' PCR primers to PCR amplify the region encoding amino acids 1-125 of FADD from the provided plasmid. PCR 10 used the gel-purified products of PCR 1 and 5, 5' primer from PCR 1, and 3' primer from PCR 5 to create the desired product by splicing by overlap extension.

Cloning of PCR Products 7 through 10

Figure 11:
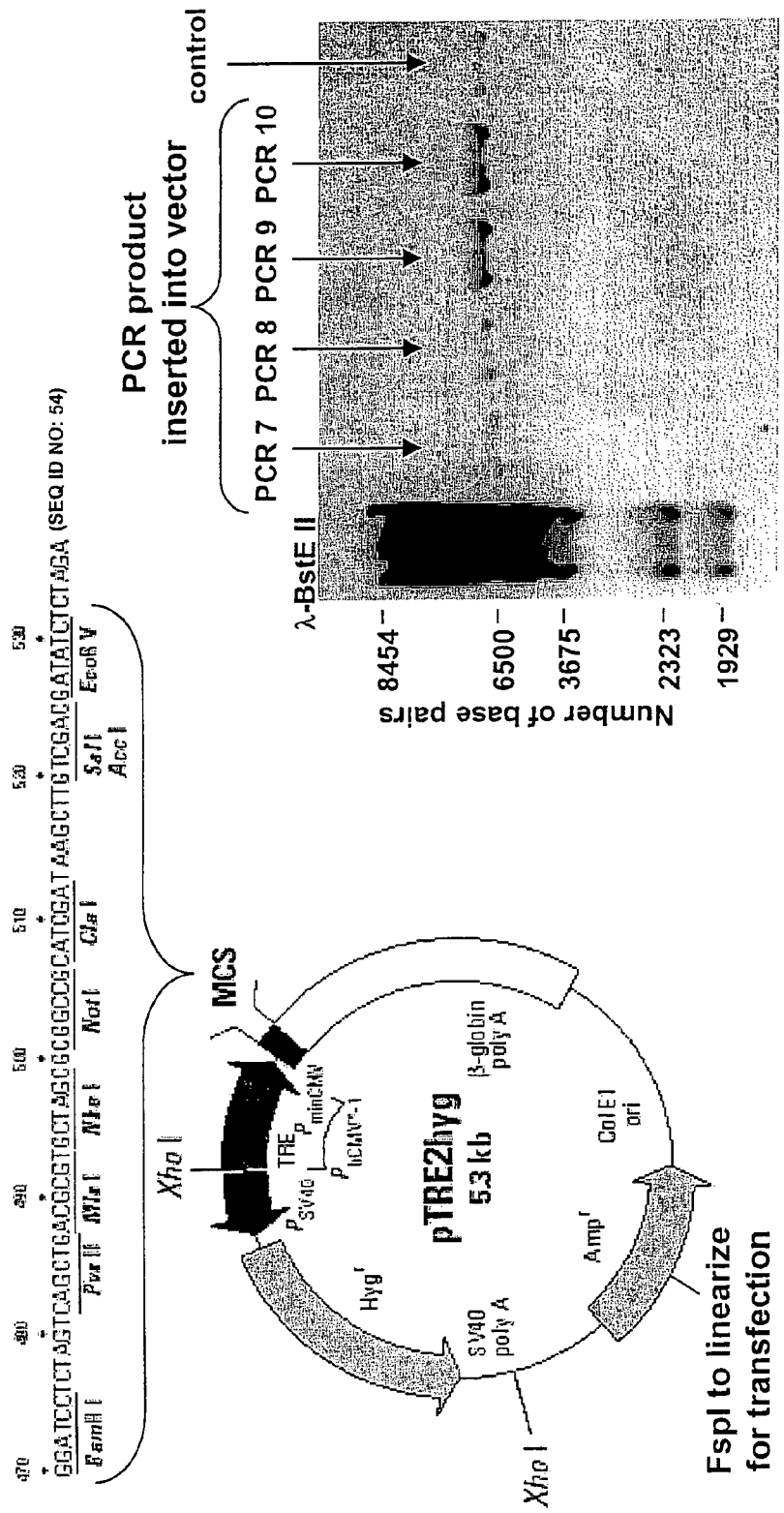
FIG. 11, on the left panel, is a schematic diagram of a Clontech vector (pTRE2hyg), into which PCR products 7 through 10, encoding four different versions of the dsRNA-activated caspase (or caspase activator), are inserted by using the BamH I and Mlu I restriction sites. The vector includes a doxycycline or tetracycline-inducible promoter for the inserted gene, as well as a hygromycin resistance gene for selection of transfected cells. A Clontech-supplied control vector has a luciferase gene inserted after the inducible promoter. All vectors with inserted genes were linearized by digestion with an Fsp I restriction enzyme before transfection. Linearized DNA constructs containing PCR products 7 through 10 and control vector were electrophoresed on an agarose gel as shown in the photograph in the right panel. DNA size markers are in the left-most lane.

PCR products 7, 8, 9, and 10 were gel purified and inserted into the Invitrogen pCR®2.1-TOPO vector following the manufacturer's protocol. The inserts are sequenced on both strands by the Nucleic Acid/Protein Research Core Facility at the Children's Hospital of Philadelphia. The pCR®2.1-TOPO vectors containing PCR products 7 through 10 were digested by BamH I and Mlu I restriction enzymes, and the fragments corresponding to PCR products 7 through 10 were gel purified. The pTRE2hyg vector, shown schematically in FIG. 11, was also digested by BamH I and Mlu I, and the larger resulting fragment gel purified. Then the digested PCR products 7 through 10 were ligated into the digested vector to create expression vectors for PCR 7, 8, 9, and 10. The vectors include a doxycycline or tetracycline-inducible promoter for the inserted gene, as well as a hygromycin resistance gene for selection of transfected cells. A Clontech-supplied control vector has a luciferase gene inserted after the inducible promoter. The inserted region of the new vectors was sequenced on both strands by the Nucleic Acid/Protein Research Core Facility at the Children's Hospital of Philadelphia. All of the vectors with the inserted genes were linearized for transfection using the Fsp I restriction enzyme and are shown in the DNA gel electrophoresis photo in FIG. 11.

Cell Transfections with dsRNA-Activated Caspases and dsRNA-Activated Caspases Acitvators The Clontech Tet-On HeLa human cell line contains the rtTA regulatory protein necessary for the proper functioning of the tetracycline or doxycycline-inducible promoters. Cells were maintained using standard tissue culture practices, humidified incubators at 37° C. and 5% $CO_2$, and DMEM culture medium containing 10% tetracycline-free fetal bovine serum, 100 μM nonessential amino acids, 1 mM sodium pyruvate, 4 mM L-glutamine, 100 units/ml penicillin G, 100 μg/ml streptomycin, 250 ng/ml amphotericin B, and 100 μg/ml G418.

Figure 12:
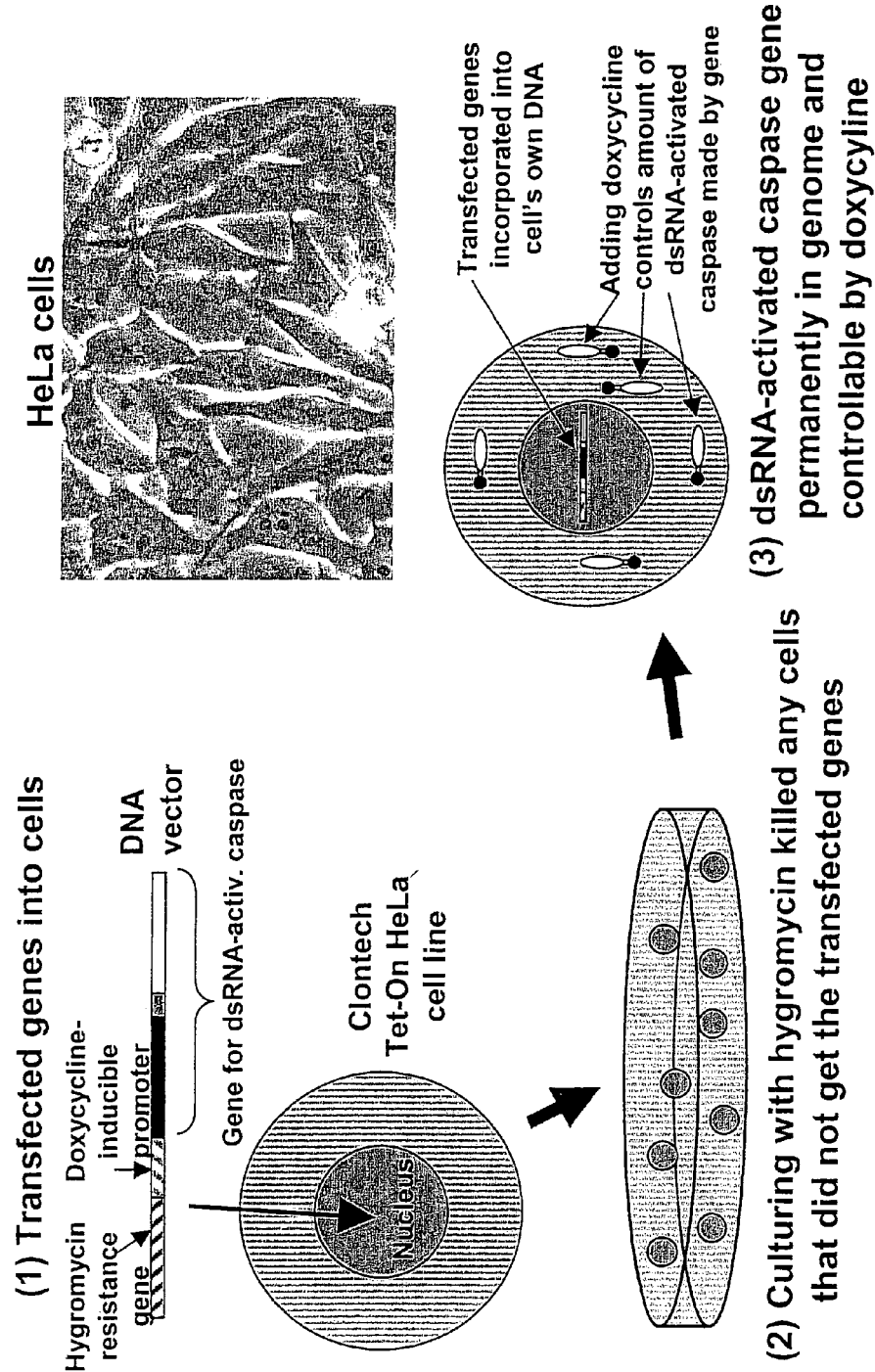
FIG. 12 is a schematic diagram of the linearized vectors with inserted PCR 7, 8, 9, 10, or luciferase transfected into a Clontech Tet-On™ HeLa human cell line, which contains the rtTA regulatory protein necessary for the proper functioning of the tetracycline or doxycycline-inducible promoters. The transfected cells are continuously cultured in the presence of hygromycin to kill any cells without the transfected genes. The resulting cells have the transfected genes stably integrated into their genomes and express them in response to doxycycline.

As shown in FIG. 12, the linearized pTRE2hyg-derived vectors with inserted PCR 7, 8, 9, 10, or luciferase are transfected into the HeLa Tet-On™ cells. The transfections use LIPOFECTIN® and PLUS reagents from Invitrogen and follow Invitrogen's recommended protocol for HeLa cells. One day after transfection, 250 μg/ml hygromycin was added to the cell culture medium to kill any cells that had not been stably transfected with the vectors, and the cells were permanently kept in this concentration of hygromycin as a precaution against the possibility that the cells might lose the transfected genes.

The pools of hygromycin-resistant cells that resulted from each transfection are presumably genetically heterogeneous, with different cells having different copy numbers of the inserted vector or having the vector inserted into different regions of the cellular genome. Therefore, genetically homogeneous clonal cell populations were isolated. Limiting dilutions of the pools of transfected cells are used to deposit approximately 1 cell per well into 96-well plates, and the cells are allowed to multiply. Wells that appear to have received more than one initial cell were disregarded. The resulting clonal cell populations were designated HeLa 7-x, 8-x, 9Ax, or 10-x; the first number indicates which PCR product from FIGS. 7-10 was transfected into the cells, and the x is replaced with the cell clone number. For example, cell line HeLa 7-3 indicates PCR product 7, cell clone 3.

Protein Expression in Transfected Cells

Western blots were used to analyze the cell clones. PKR-Caspase-3 fusion proteins (deriving from PCR 7 and 8) were detected using caspase-3-specific polyclonal goat IgG antibodies from R&D Systems, and PKR-FADD fusion proteins (deriving from PCR 9 and 10) were detected using FADD-specific polyclonal rabbit IgG antibodies from Upstate Biotechnology. Cells were cultured for two days either with or without doxycyline, and the proteins extracted from the cells and analyzed by Western blot following the manufacturers' protocol.

Figure 13:
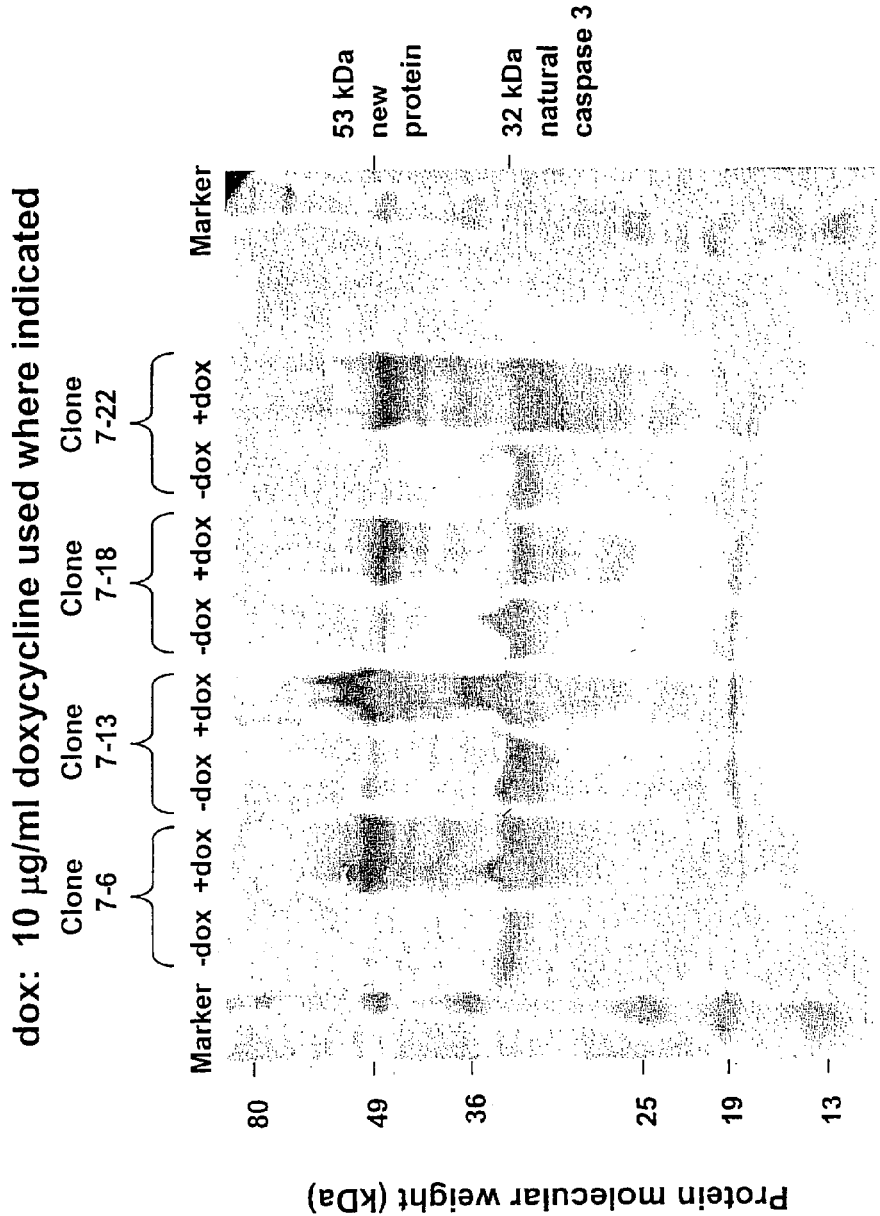
FIG. 13 is a Western blot analysis. Doxycycline induces cells transfected with PCR-7-containing vectors to express the corresponding dsRNA-activated caspase. Clonal populations of transfected cells were isolated by limiting dilutions. Cells are cultured with either 10 µg/ml doxycyline or no doxycline for two days, and then Western blots are used to probe the cell extracts with anti-caspase-3 antibodies. The 32-kDa natural (pro)caspase 3 is visible in all the cells, either with or without doxycycline. For each cell clone shown, doxycycline up-regulates the expression of the transfected dsRNA-activated caspase, which has approximately the predicted size and contains caspase-3 epitopes recognized by the antibodies.

The Western blot in FIG. 13 illustrates that doxycycline induced cells transfected with the PCR-7-containing vector to express the corresponding dsRNA-activated caspase. Cells were cultured with either 10 µg/ml doxycycline or no doxycycline for two days, and the Western blots were used to probe the cell extracts with anti-caspase-3 antibodies. The 32-kDa natural (pro)caspase 3 was visible in all the cells, either with or without doxycycline. For each cell clone shown, doxycycline up-regulates expression of the dsRNA-activated caspase, which has approximately the predicted size and contains caspase-3 epitopes recognized by the antibodies.

Figure 14:
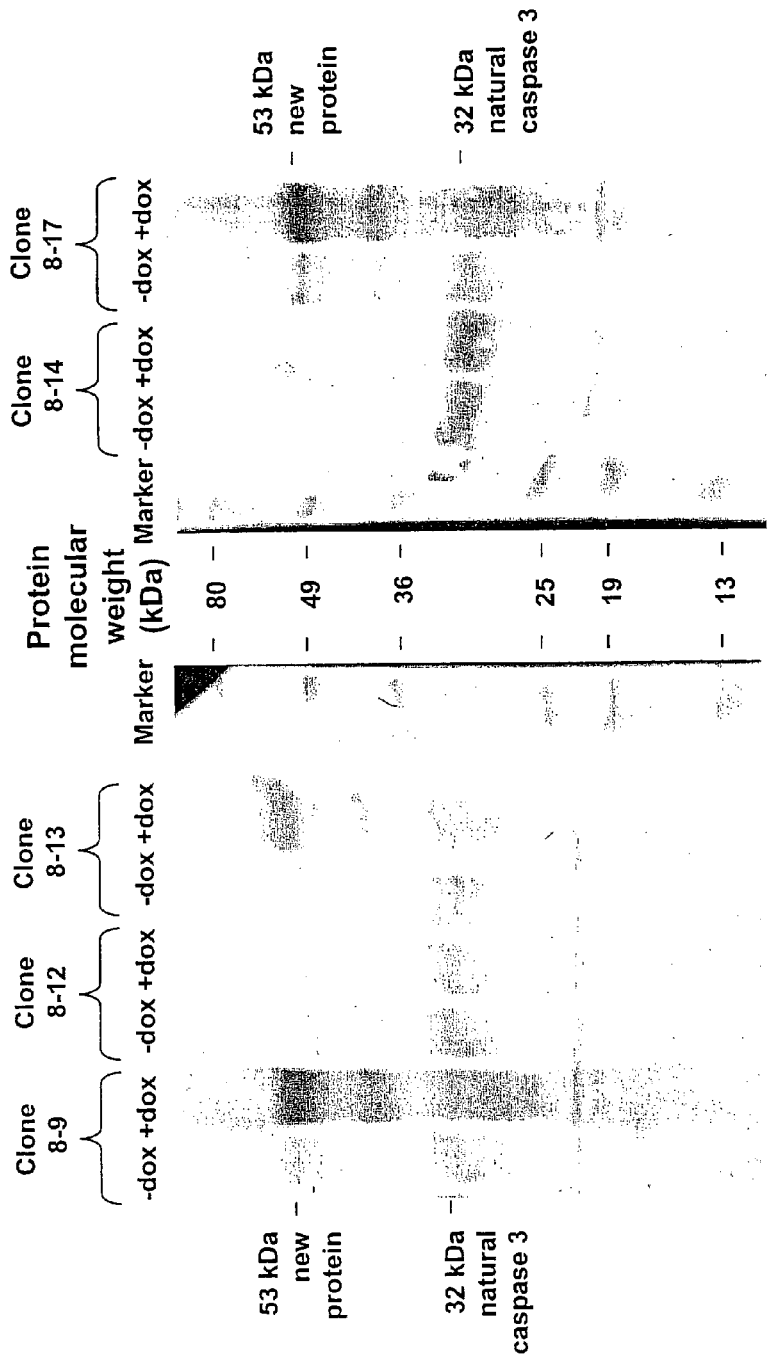
FIG. 14 are Western blot analyses. Doxycycline induces cells transfected with PCR-8-containing vectors to express the corresponding dsRNA-activated caspase. Clonal populations of transfected cells were isolated by limiting dilutions. The cells were cultured with either 10 µg/ml doxycyline or no doxycline for two days, and then Western blots were used to probe the cell extracts with anti-caspase-3 antibodies. The 32-kDa natural (pro)caspase 3 is visible in all the cells, either with or without doxycycline. For cell clones 8-9, 8-13, and 8-17, doxycycline up-regulates the expression of the transfected dsRNA-activated caspase, which has approximately the predicted size and contains caspase-3 epitopes recognized by the antibodies.

The Western blot in FIG. 14 illustrates that doxycycline induces cells transfected with the PCR-8-containing vector to express the corresponding dsRNA-activated caspase. Cells were cultured with either 10 µg/ml doxycycline or no doxycycline for two days, and then Western blots were used to probe the cell extracts with anti-caspase-3 antibodies. The 32-kDa natural (pro)caspase 3 is visible in all the cells, either with or without doxycycline. For cell clones 8-9, 8-13, and 8-17, doxycycline up-regulates expression of the dsRNA-activated caspase, which has approximately the predicted size and contains caspase-3 epitopes recognized by the antibodies.

Figure 15:
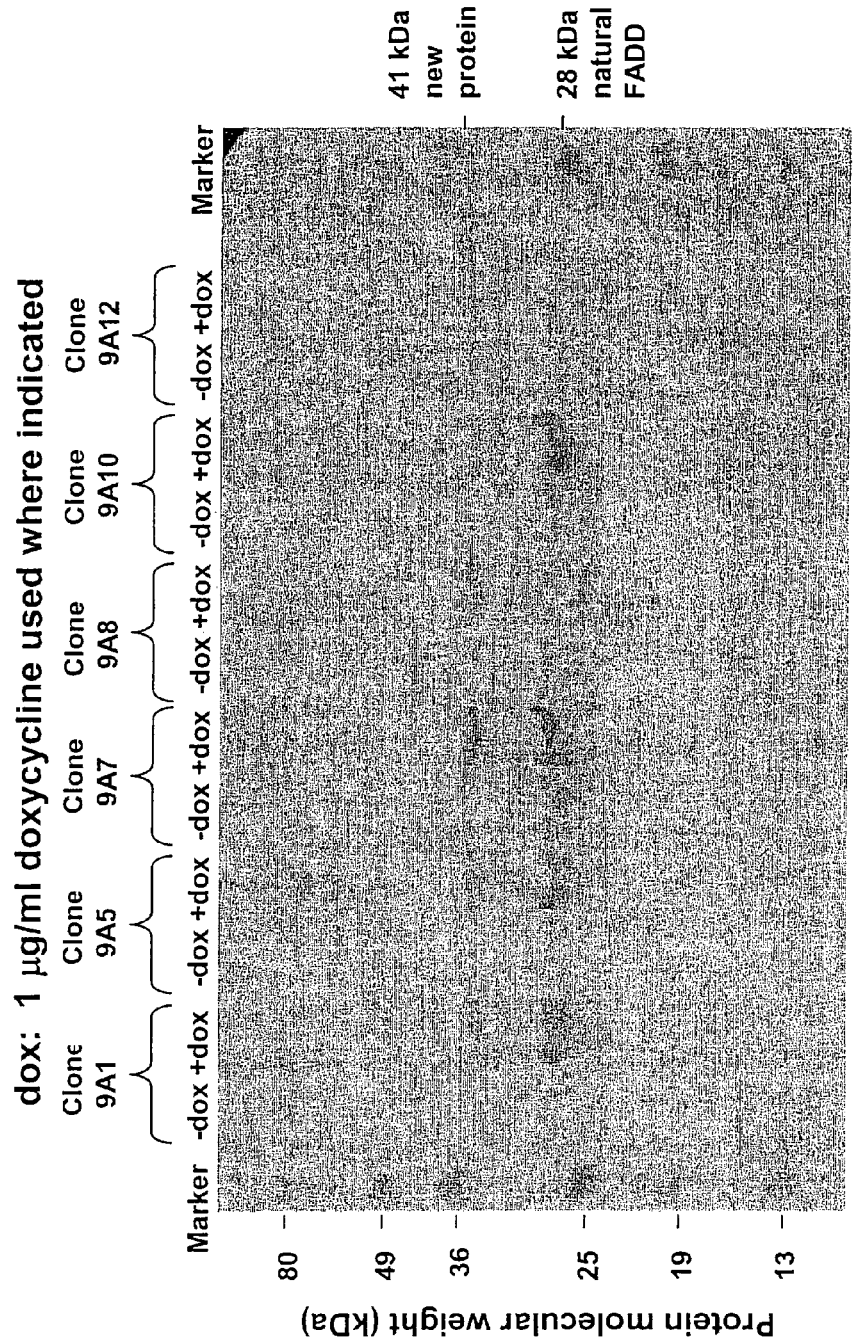
FIG. 15 is a Western blot analysis. Doxycycline induces cells transfected with PCR-9-containing vectors to express the corresponding dsRNA-activated caspase activator. Clonal populations of transfected cells were isolated by limiting dilutions. The cells were cultured with either 1 µg/ml doxycyline or no doxycline for two days, and then Western blots were used to probe the cell extracts with anti-FADD antibodies. The 28-kDa natural FADD is visible in all the cells, either with or without doxycycline. For each cell clone shown, doxycycline upregulates expression of the dsRNA-activated caspase activator, which has approximately the predicted size and contains FADD epitopes recognized by the antibodies.

The Western blot in FIG. 15 illustrates that doxycycline induces cells transfected with the PCR-9-containing vector to express the corresponding dsRNA-activated caspase activator. Cells were cultured with either 1 µg/ml doxycycline or no doxycycline for two days, and then Western blots were used to probe the cell extracts with anti-FADD antibodies. The 28-kDa natural FADD is visible in all the cells, either with or without doxycycline. For each cell clone shown, doxycycline up-regulates expression of the dsRNA-activated caspase activator, which has approximately the predicted size and contains FADD epitopes recognized by the antibodies.

Figure 16:
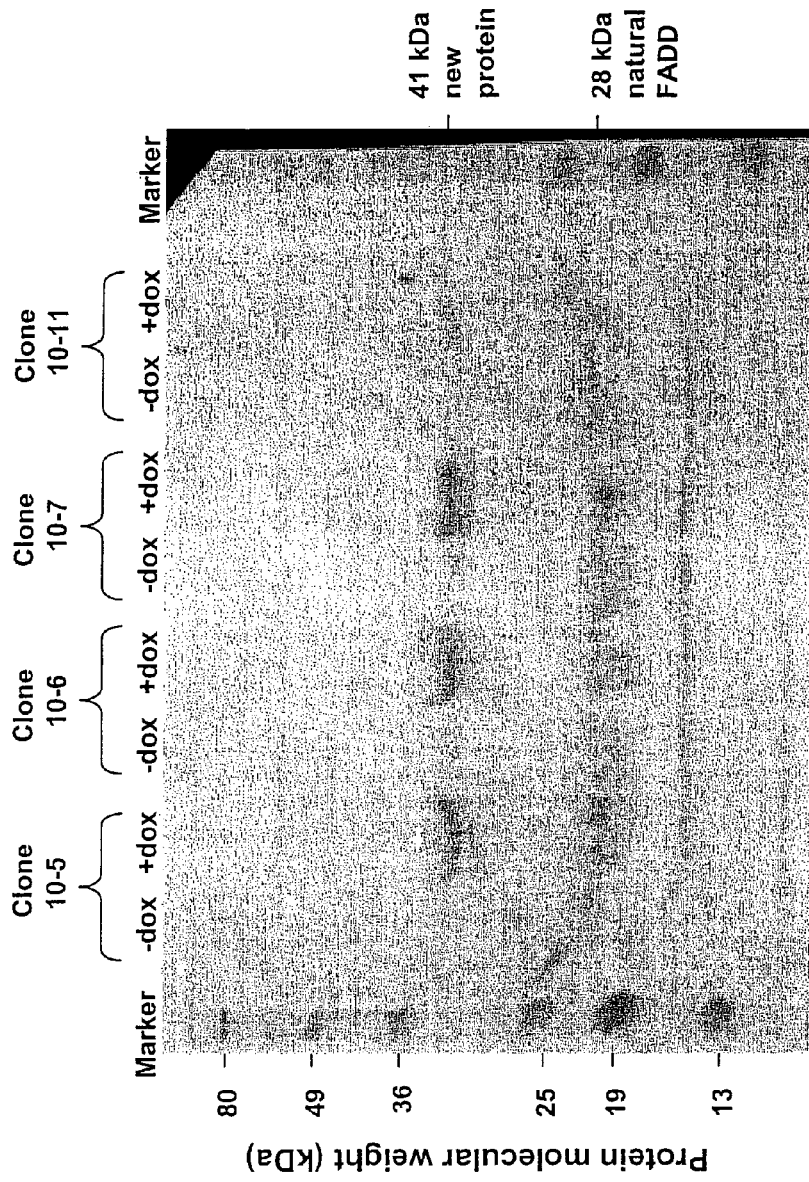
FIG. 16 is a Western blot analysis. Doxycycline induces cells transfected with PCR-10-containing vectors to express the corresponding dsRNA-activated caspase activator. Clonal populations of transfected cells were isolated by limiting dilutions. Cells were cultured with either 10 µg/ml doxycyline or no doxycline for two days, and then Western blots were used to probe the cell extracts with anti-FADD antibodies. The 28-kDa natural FADD is visible in all the cells, either with or without doxycycline. For each cell clone shown, doxycycline up-regulates expression of the dsRNA-activated caspase activator, which has approximately the predicted size and contains FADD epitopes recognized by the antibodies.

The Western blot in FIG. 16 illustrates that doxycycline induces cells transfected with the PCR-10-containing vector to express the corresponding dsRNA-activated caspase activator. Cells are cultured with either 10 µg/ml doxycycline or no doxycycline for two days, and then Western blots are used to probe the cell extracts with anti-FADD antibodies. The 28-kDa natural FADD is visible in all the cells, either with or without doxycycline. For each cell clone shown, doxycycline upregulates expression of the dsRNA-activated caspase activator, which has approximately the predicted size and contains FADD epitopes recognized by the antibodies.

Doxycycline Concentration Dependent Expression in Transfected Cells

Figure 17:
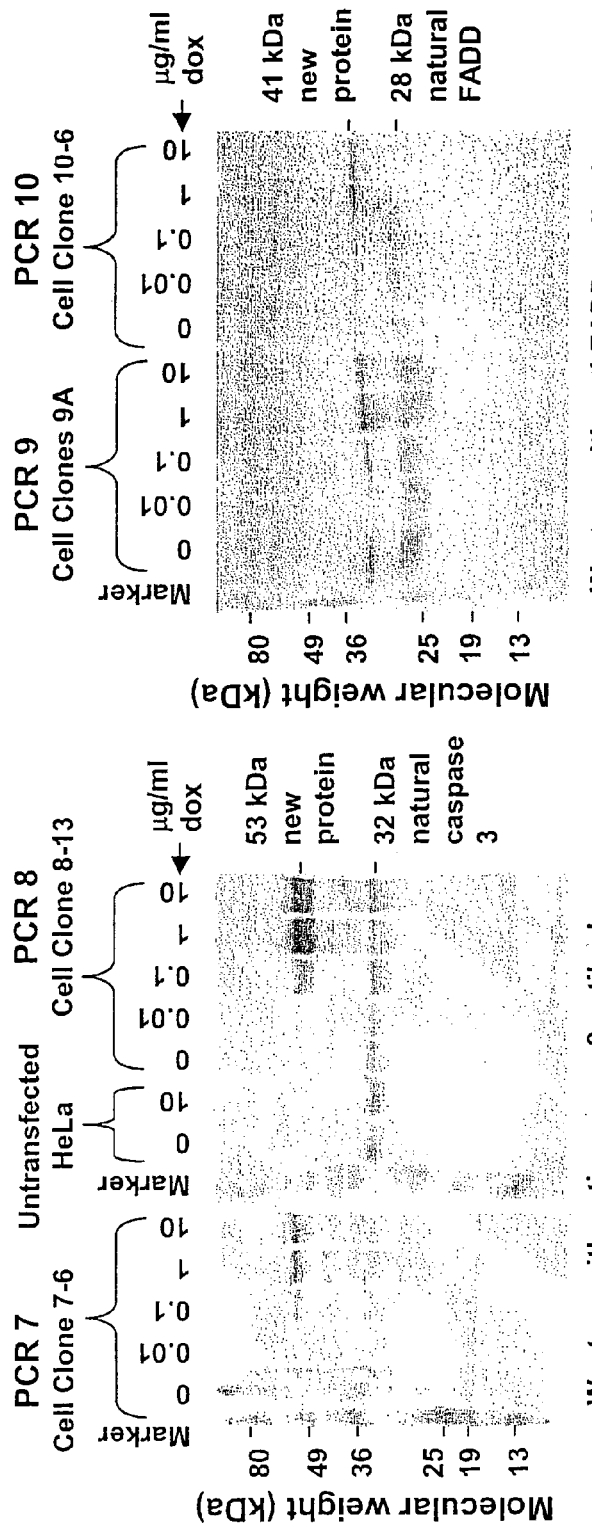
FIG. 17 are Western blot analyses. The concentration of doxycycline controls the level of dsRNA-activated caspase (or caspase activator) expression in transfected cells. Cell clone 7-6 contains PCR 7, clone 8-13 contains PCR 8, clone 10-6 contains PCR 10, and 9A is a pool of clones that contain PCR 9 but are not separated into individual clonal populations by limiting dilution. Untransfected HeLa cells were used as a control. Cells were cultured with 0, 0.01, 0.1, 1, or 10 µg/ml doxycyline for two days, and then Western blots were used to probe the cell extracts with anti-caspase-3 or anti-FADD antibodies. Increasing the doxycycline concentration generally increases the expression level of the dsRNA-activated caspase (or caspase activator) relative to natural caspase 3 or FADD.

The Western blot in FIG. 17 demonstrates that the doxycycline concentration controls the level of dsRNA-activated caspase (or caspase activator) expression in transfected cells. Cell clone 7-6 contains PCR 7, clone 8-13 contains PCR 8, clone 10-6 contains PCR 10, and 9A is a pool of clones that contain PCR 9 but have not been separated into individual clonal populations by limiting dilution. Untransfected HeLa cells were used as a control. Cells were cultured with 0, 0.01, 0.1, 1, or 10 µg/ml doxycycline for two days, and then Western blots were used to probe the cell extracts with anti-caspase-3 or anti-FADD antibodies. Increasing the doxycycline concentration generally increases the expression level of the dsRNA-activated caspase (or caspase activator) relative to natural caspase 3 or FADD.

Toxicity Assays

The toxicity of the transfected genes was assayed as follows. Cells were added to 96-well plates at an initial density of $5\times10^4$ cells/ml and with 100 µl of medium per well. Different expression levels of the transfected genes were induced by adding 0, 0.01, 0.1, 1, or 10 µg/ml doxycycline. The cell numbers were estimated after three days using Promega Cell-Titer 96® AQueous One Solution, which is bioreduced by live cells into a colored formazan product. The manufacturer's recommended protocol was followed. After subtracting the background absorbance found in wells with medium but no cells, the absorbance at 492 nm is approximately linear with the number of live cells. All assays were performed in quadruplicate to reduce statistical variations.

Figure 18:
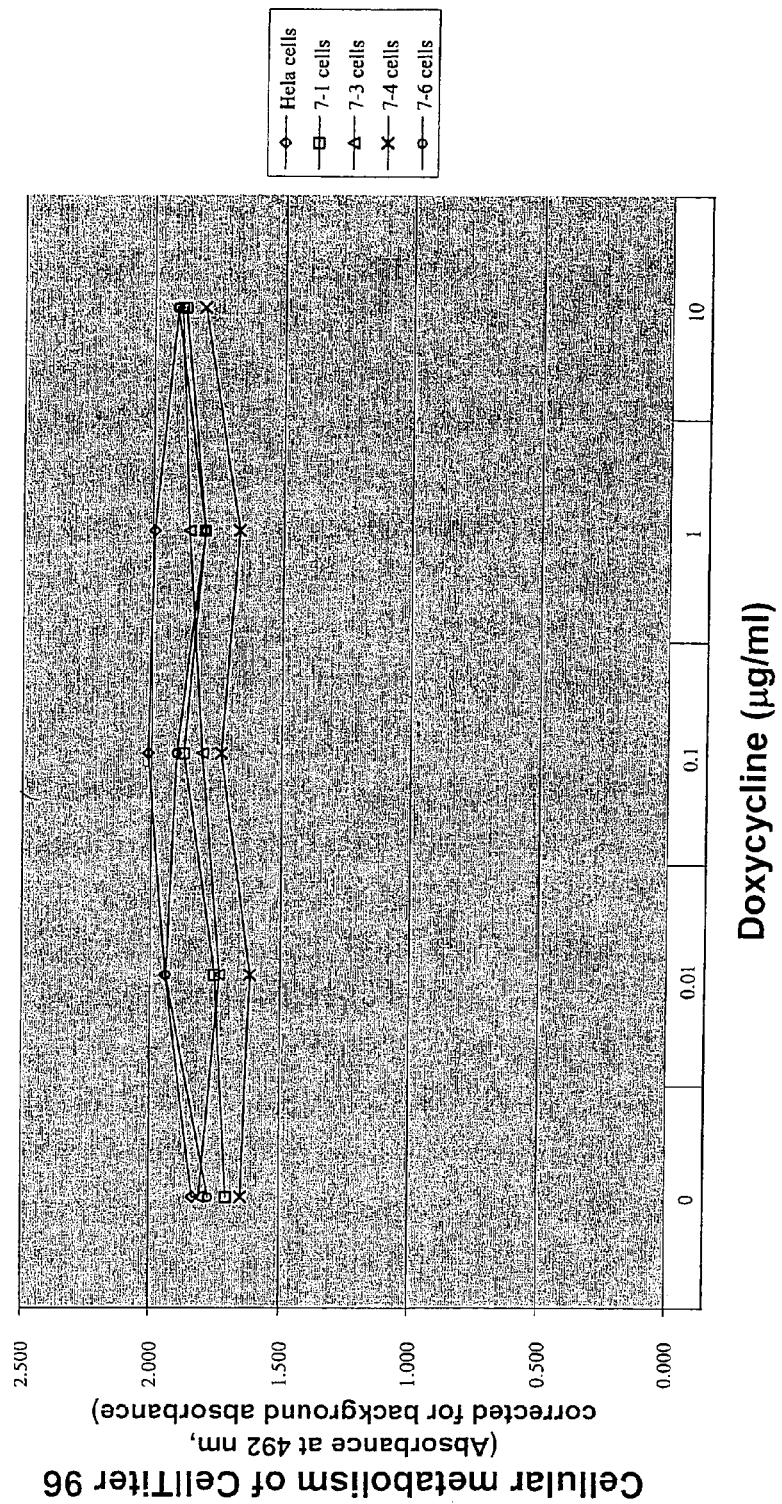
FIG. 18 is a graph charting the toxicity of dsRNA-activated caspase (PCR 7) levels induced by different concentrations of doxycycline assayed. Cells were added to 96-well plates at an initial density of $5 \times 10^4$ cells/ml, and different expression levels of the transfected genes were induced by adding 0, 0.01, 0.1, 1, or 10 µg/ml doxycyline. The cell numbers were estimated after three days using CellTiter 96® (Promega), which is metabolized by live cells. After subtracting the background absorbance without cells, the absorbance at 492 nm was approximately linear with the number of live cells. All assays were performed in quadruplicate to reduce statistical variations. At all doxycycline concentrations, the metabolism of cell clones 7-1, 7-3, 7-4, and 7-6 was approximately the same as that of untransfected HeLa cells, indicating little or no toxicity.

FIG. 18 illustrates the toxicity of dsRNA-activated caspase (PCR 7) levels induced by different concentrations of doxycycline. At all doxycycline concentrations, the metabolism of cell clones 7-1, 7-4, and 7-6 was approximately the same as that of untransfected HeLa cells, indicating little or no toxicity.

Figure 19:
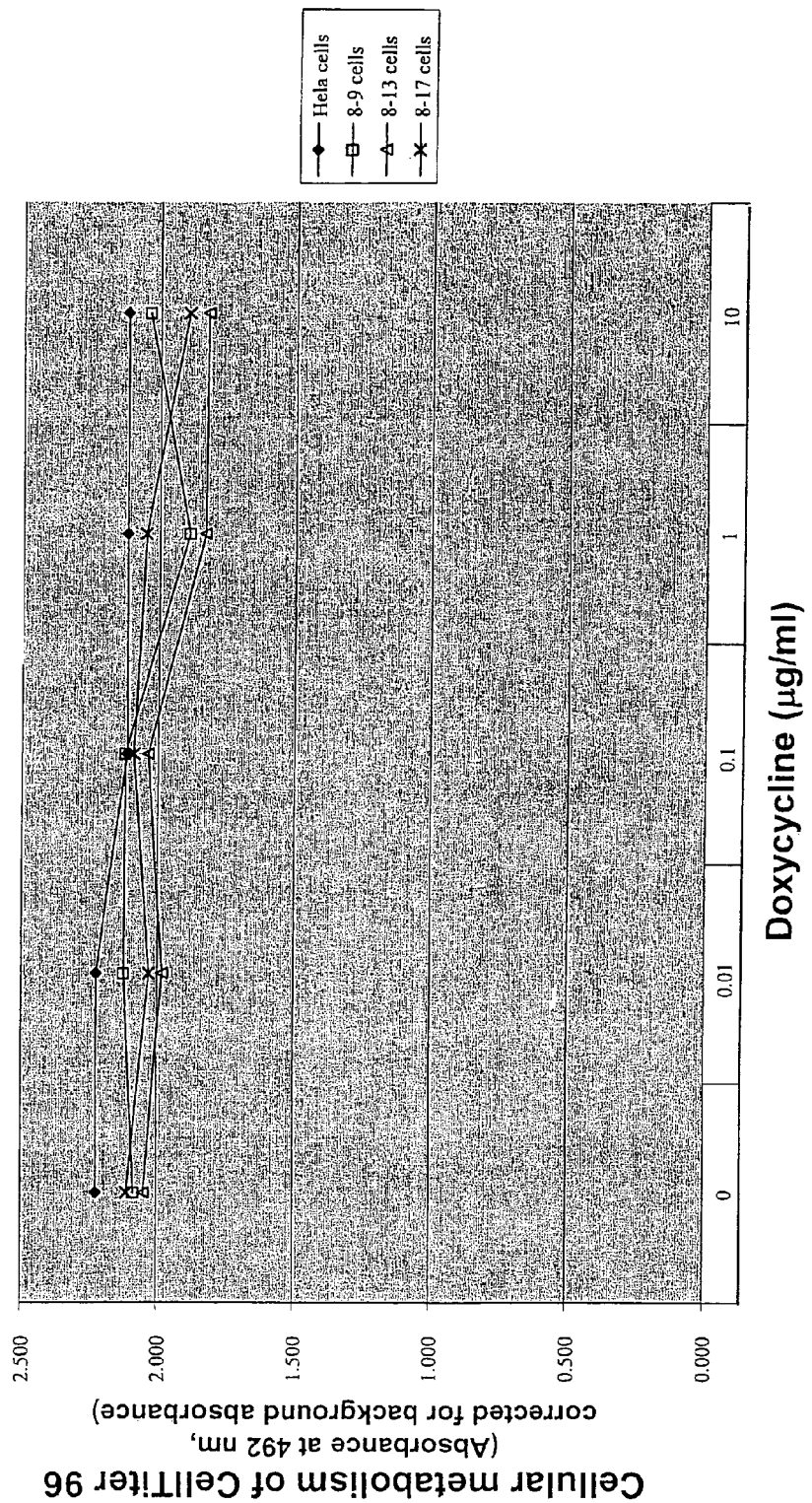
FIG. 19 is a graph charting the toxicity of dsRNA-activated caspase (PCR 8) levels induced by different concentrations of doxycycline assayed. Cells were added to 96-well plates at an initial density of $5 \times 10^4$ cells/ml, and different expression levels of the transfected genes were induced by adding 0, 0.01, 0.1, 1, or 10 µg/ml doxycyline. The cell numbers were estimated after three days using CellTiter 96® (Promega), which is metabolized by live cells. After subtracting the background absorbance without cells, the absorbance at 492 nm was approximately linear with the number of live cells. All assays were performed in quadruplicate to reduce statistical variations. At all doxycycline concentrations, the metabolism of cell clones 8-9, 8-13, and 8-17 is approximately the same as that of untransfected HeLa cells, indicating little or no toxicity.

FIG. 19 illustrates the toxicity of dsRNA-activated caspase (PCR 8) levels induced by different concentrations of doxycycline. At all doxycycline concentrations, the metabolism of cell clones 8-9, 8-13, and 8-17 was approximately the same as that of untransfected HeLa cells, indicating little or no toxicity.

Figure 20:
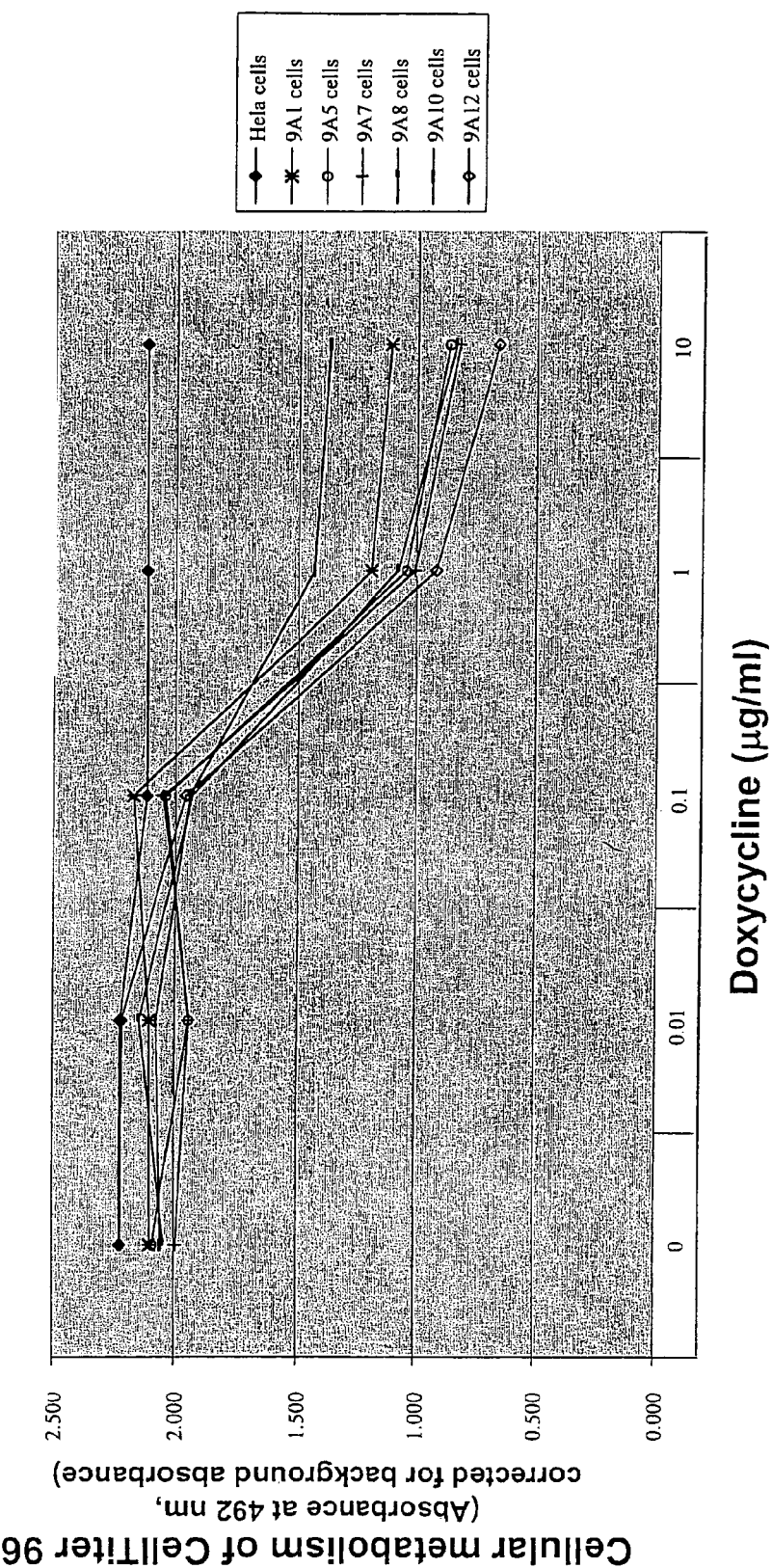
FIG. 20 is a graph charting the toxicity of dsRNA-activated caspase activator (PCR 9) levels induced by different concentrations of doxycycline assayed. Cells were added to 96-well plates at an initial density of $5 \times 10^4$ cells/ml, and different expression levels of the transfected genes were induced by adding 0, 0.01, 0.1, 1, or 10 µg/ml doxycyline. The cell numbers were estimated after three days using CellTiter 96® (Promega), which is metabolized by live cells. After subtracting the background absorbance without cells, the absorbance at 492 nm was approximately linear with the number of live cells. All assays were performed in quadruplicate to reduce statistical variations.

FIG. 20 illustrates the toxicity of dsRNA-activated caspase activator (PCR 9) levels induced by different concentrations of doxycycline. There appears to be some toxicity at high expression levels, thus this dsRNA-activated caspase activator could be used against pathogens at lower levels.

Figure 21:
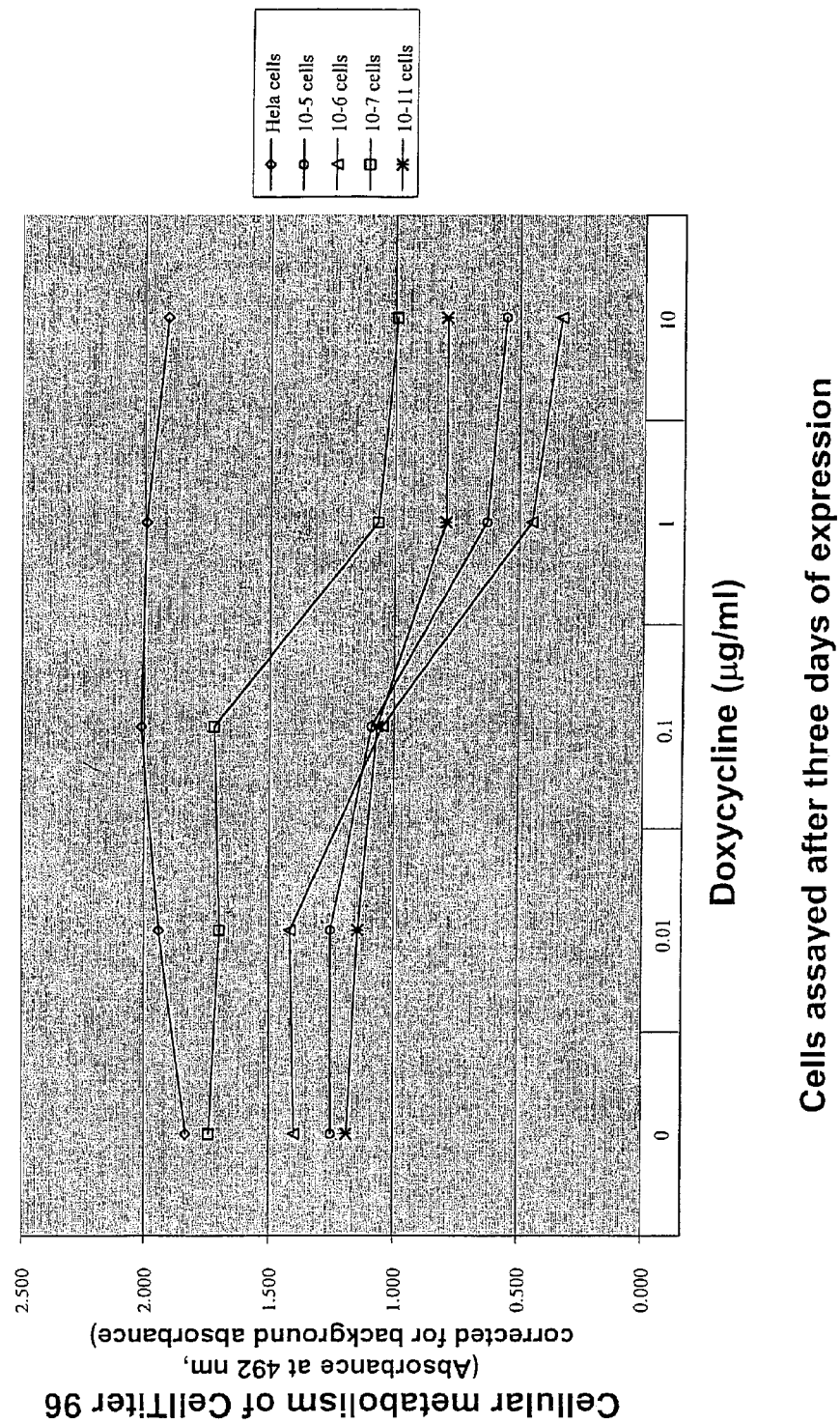
FIG. 21 is a graph charting the toxicity of dsRNA-activated caspase activator (PCR 10) levels induced by different concentrations of doxycycline assayed. Cells were added to 96-well plates at an initial density of $5\times10^4$ cells/ml, and different expression levels of the transfected genes were induced by adding 0, 0.01, 0.1, 1, or 10 μg/ml doxycyline. The cell numbers were estimated after three days using CellTiter 96® (Promega), which is metabolized by live cells. After subtracting the background absorbance without cells, the absorbance at 492 nm was approximately linear with the number of live cells. All assays were performed in quadruplicate to reduce statistical variations.

FIG. 21 illustrates the toxicity of dsRNA-activated caspase activator (PCR 10) levels induced by different concentrations of doxycycline. There appears to be some toxicity at high expression levels, thus this dsRNA-activated caspase activator could be used against pathogens at lower levels.

dsRNA-dependent Apoptosis

Cells were tested with poly(I)•poly(C) dsRNA to determine if apoptosis was induced as expected. Cells were cultured either with or without 10 µg/ml doxycycline for two days. Then the dsRNA was transfected into the cells at a concentration of approximately 7.5 µg/ml using the LIPOFECTIN® and PLUS reagents from Invitrogen and following Invitrogen's recommended protocol for transfecting HeLa cells. Control cells were transfected using the same protocol but without any dsRNA. Cells that had previously been cultured with doxycycline remained in doxycycline, and cells that had not previously been cultured in doxycycline were not treated with doxycycline. Approximately 20 hours after the dsRNA transfections, the cells were photographed using a CCD camera attached to a 400× inverted phase-contrast microscope. Healthy cells tend to spread out, whereas apoptotic cells round up and appear to have bright granulated interiors.

Figure 22:
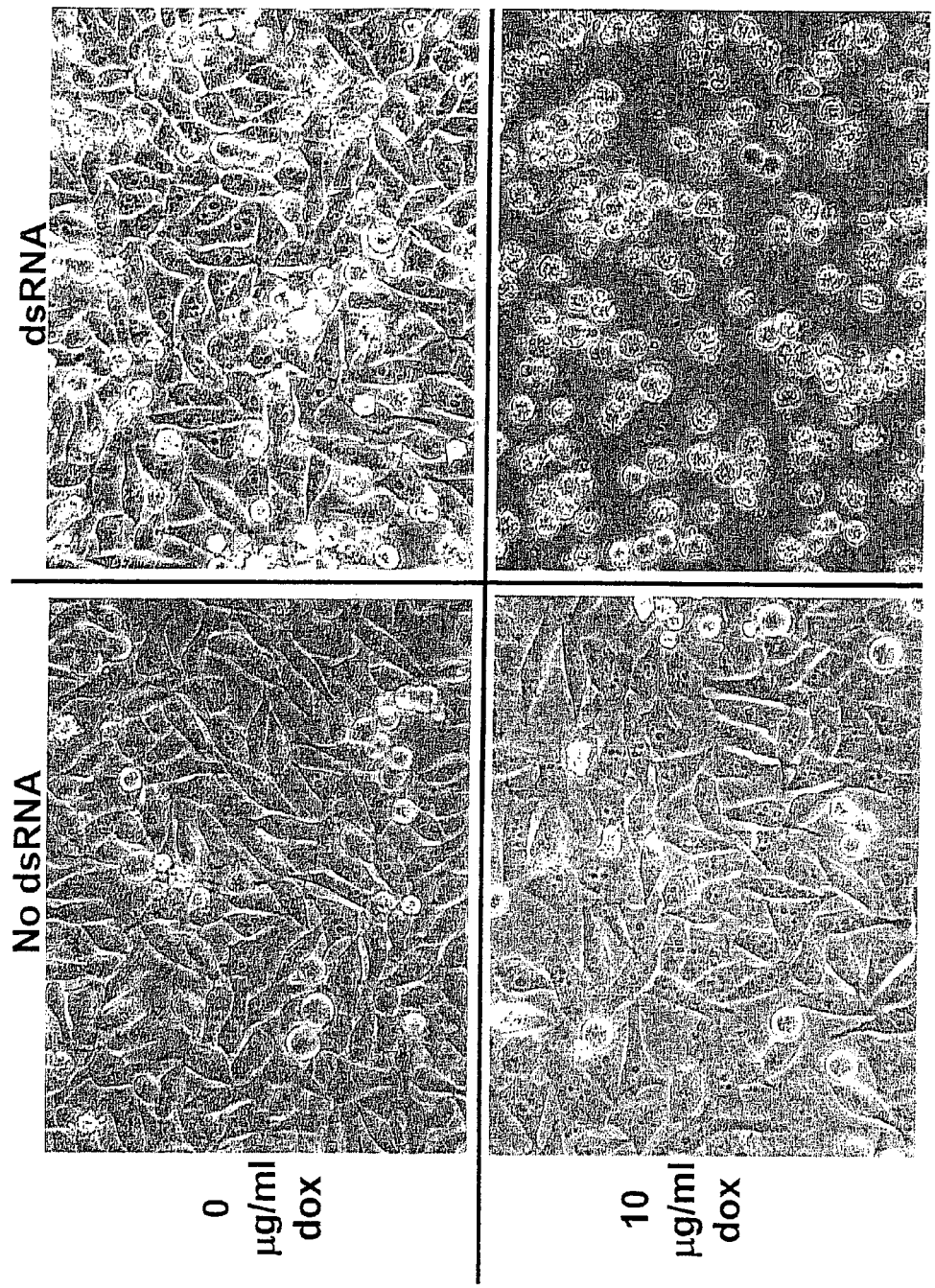
FIG. 22 are photographs demonstrating dsRNA-activated caspase activity of cell clone 8-13. Cells were cultured either with or without 10 μg/ml doxycycline for two days, and then treated with the Invitrogen transfection reagents LIPOFECTIN® and PLUS reagent either alone or with poly(I)•poly(C) synthetic dsRNA approximately 20 hours prior to photographing. Healthy cells tend to spread out, whereas apoptotic cells round up and appear to have bright granulated interiors. Cells without dsRNA appear healthy, regardless of doxycycline treatment (top left and bottom left photographs). Cells without doxycyline but with dsRNA appear generally healthy but include some apoptotic cells (top, right photograph), possibly due to the low-level expression of the dsRNA-activated caspase even in the absence of doxycycline. Cells with both doxycycline and dsRNA exhibit widespread apoptosis as expected (bottom, right photograph).

The photographs in FIG. 22 demonstrate the dsRNA-activated caspase in cell clone 8-13. Cells without dsRNA appear healthy, regardless of doxycycline treatment. Cells without doxycyline but with dsRNA appear generally healthy but include some apoptotic cells, possibly due to the low-level expression of the dsRNA-activated caspase even in the absence of doxycycline. Cells with both doxycycline and dsRNA exhibit widespread apoptosis as expected.

Figure 23:
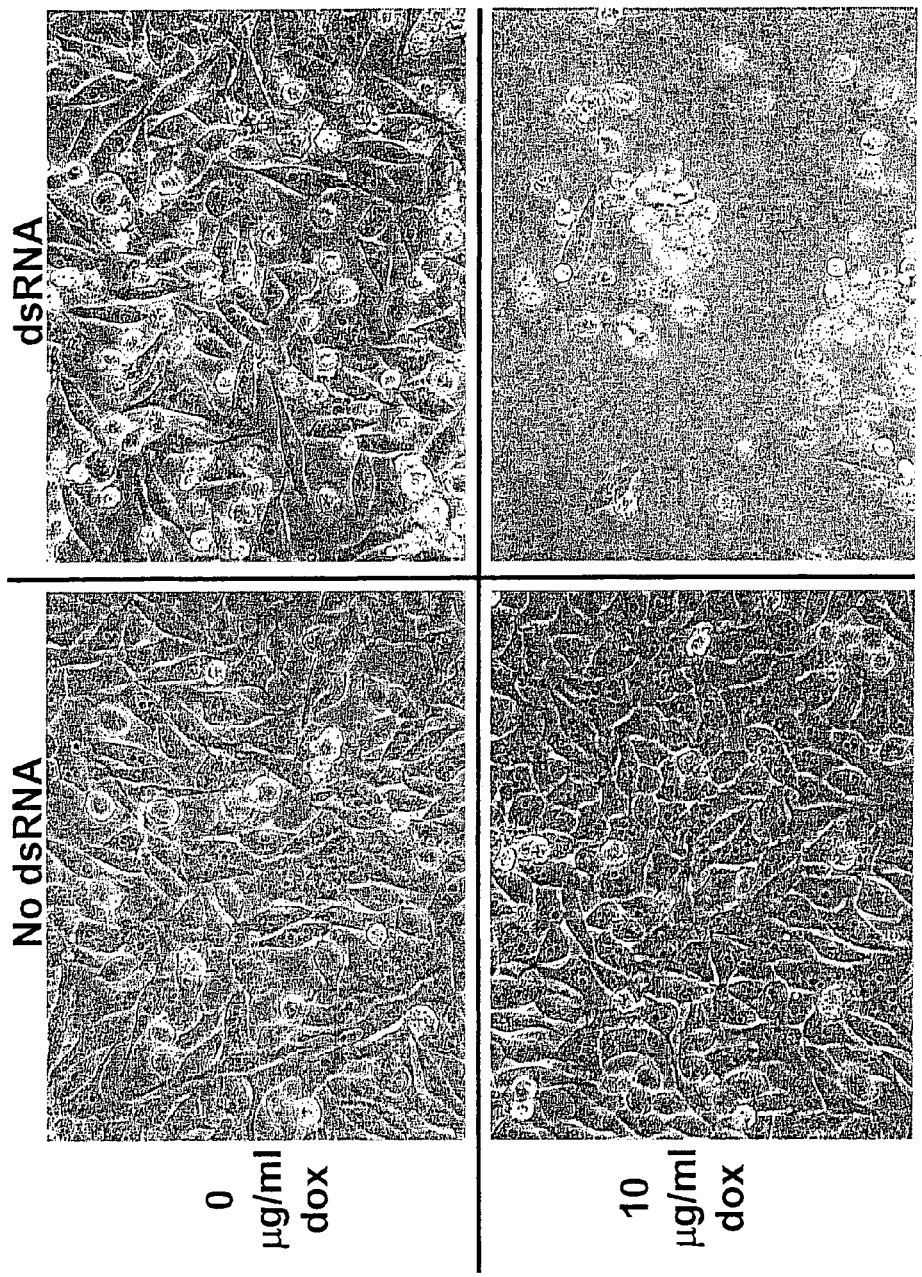
FIG. 23 are photographs demonstrating dsRNA-activated caspase activity of cell clone 8-9. Cells were cultured either with or without 10 μg/ml doxycycline for two days, and then treated with the Invitrogen transfection reagents LIPOFECTIN® and PLUS reagent either alone or with poly(I)•poly(C) synthetic dsRNA approximately 20 hours prior to photographing. Healthy cells tend to spread out, whereas apoptotic cells round up and appear to have bright granulated interiors. Cells without dsRNA appear healthy, regardless of doxycycline treatment (top left and bottom left photographs). Cells without doxycyline but with dsRNA appear generally healthy but include some apoptotic cells (top, right photograph), possibly due to the low-level expression of the dsRNA-activated caspase even in the absence of doxycycline. Cells with both doxycycline and dsRNA exhibit widespread apoptosis as expected (bottom, right photograph).

The photographs in FIG. 23 demonstrate the dsRNA-activated caspase in cell clone 8-9. Cells without dsRNA appear healthy, regardless of doxycycline treatment. Cells without doxycyline but with dsRNA appear generally healthy but include some apoptotic cells, possibly due to the low-level expression of the dsRNA-activated caspase even in the absence of doxycycline. Cells with both doxycycline and dsRNA exhibit widespread apoptosis as expected; the apparently healthy cells that remain may not have received any of the dsRNA.

Figure 24:
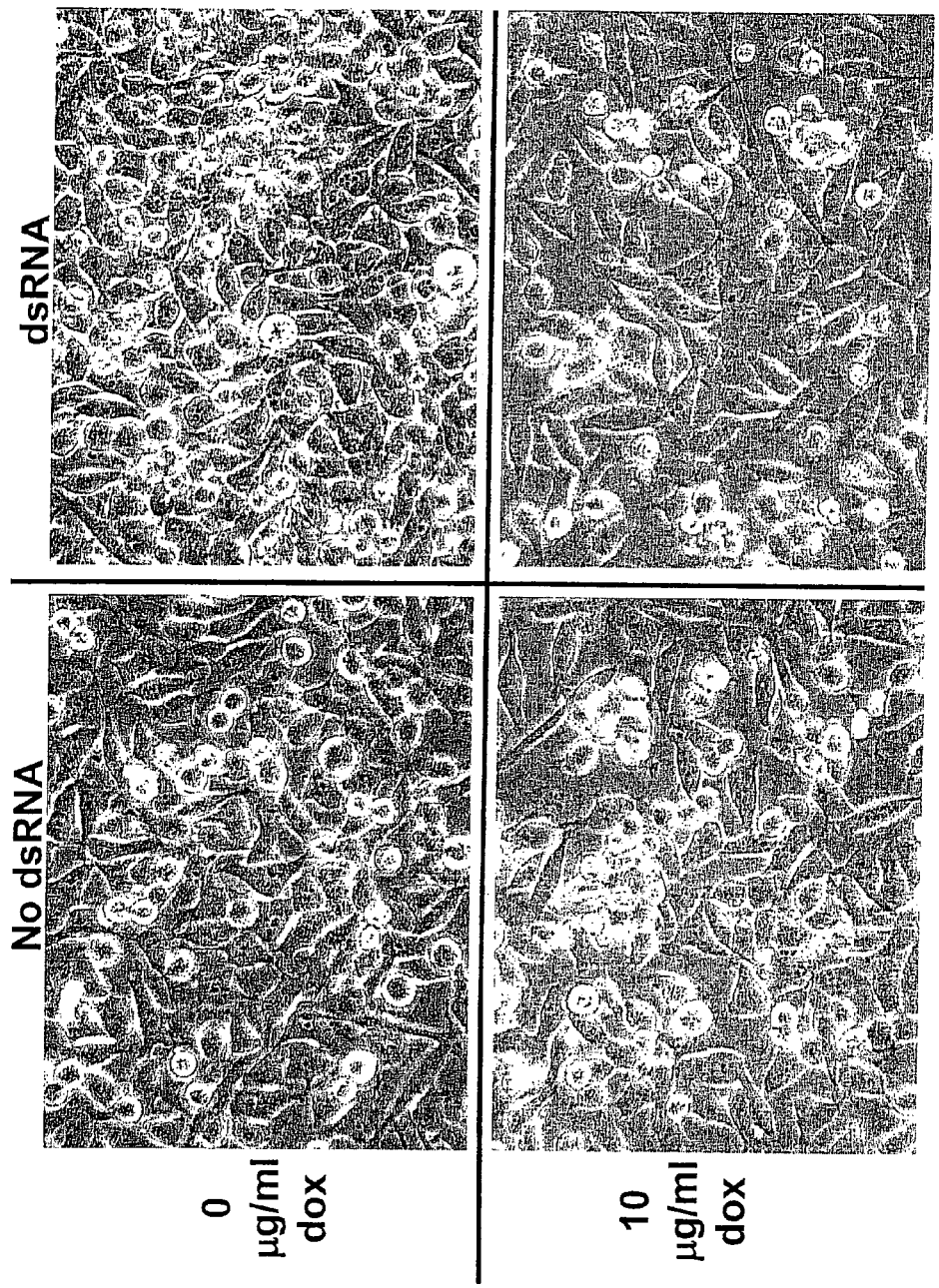
FIG. 24 are photographs demonstrating HeLa cells not transfected with a dsRNA-activated caspase construct (control cells). Cells were cultured either with or without 10 μg/ml doxycycline for two days, and then treated with the Invitrogen transfection reagents LIPOFECTIN® and PLUS reagent either alone or with poly(I)•poly(C) synthetic dsRNA approximately 20 hours prior to photographing. Healthy cells tend to spread out, whereas apoptotic cells round up and appear to have bright granulated interiors. Cells either with or without doxycycline and either with dsRNA (top right and bottom right photographs) or without dsRNA (top left and bottom left photographs) appear generally healthy, with a limited number of round or apoptotic cells visible in each of the four cases. The widespread apoptosis that was visible in clones 8-9 and 8-13 treated with both doxycycline and dsRNA does not occur with the untransfected HeLa cells.

The photographs in FIG. 24 illustrate untransfected HeLa cells used as a control for the dsRNA-activated caspase transfection experiments described supra. Cells either with or without doxycycline and either with or without dsRNA appeared generally healthy, with a limited number of round or apoptotic cells visible in each of the four cases. While there were some variations among the four populations of cells that may or may not be statistically significant, the widespread apoptosis that was visible in clones 8-9 and 8-13 treated with both doxycycline and dsRNA does not occur with the untransfected HeLa cells.

Example 2

Materials: Interferon-Inducible Defense Genes

Plasmids encoding human Hdj-1 (NCBI Accession #X62421) and human Hsp70 (#M11717 M15432) were provided by R. I. Morimoto, Northwestern University. A plasmid encoding human Hsp90 (#M16660) was provided by R. D. Mosser, Biotechnology Research Institute, National Research Council of Canada. The vector pISRE-Luc was obtained from Stratagene. The mammalian expression vector pCMV/Bsd and cloning vector pCR®2.1-TOPO were obtained from Invitrogen. PCR primers, LIPOFECTIN® reagent, and PLUS reagent were obtained from Gibco BRL/Life Technologies/Invitrogen. The H1-HeLa human cell line (CRL-1958) was obtained from ATCC. Human interferon-alpha is from Sigma.

Synthesis of Interferon-Inducible Defense Genes

Figure 26:
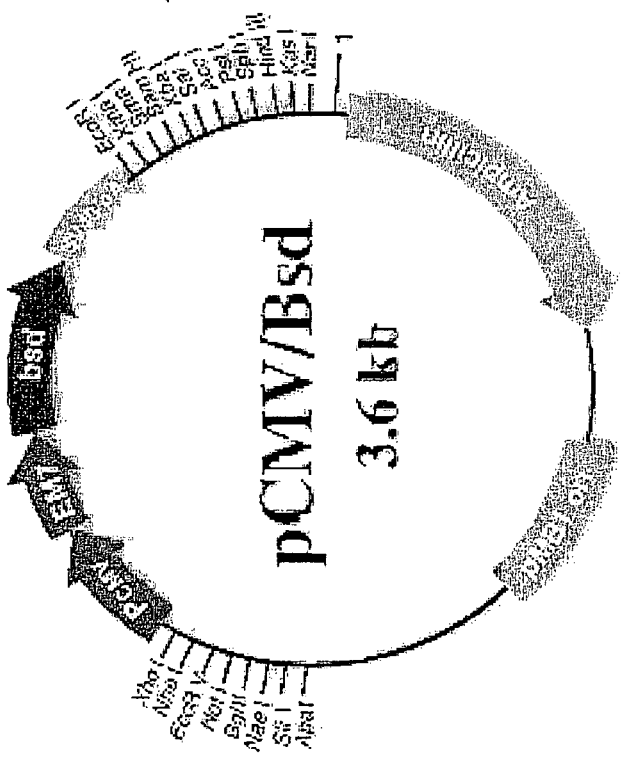
FIG. 26 is a diagram of an interferon-inducible vector created by adding an interferon-inducible promoter and poly-A sequence to the Invitrogen pCMV/Bsd blasticidin-resistance vector. A multiple cloning sequence between the new interferon-inducible promoter and poly-A sequence permits one to add any gene, such as genes for heat shock proteins Hdj-1, Hsp70, Hsp90, luciferase (as a control), or other genes with anti-pathogen effects.

FIG. 26 illustrates how an interferon-inducible vector was created by adding an interferon-inducible promoter and poly-A sequence to the Invitrogen pCMV/Bsd blasticidin-resistance vector. A multiple cloning sequence between the new interferon-inducible promoter and poly-A sequence permits one to add any gene, such as genes for heat shock proteins Hdj-1, Hsp70, Hsp90, luciferase (as a control), or other genes with anti-pathogen effects.

Figure 27:
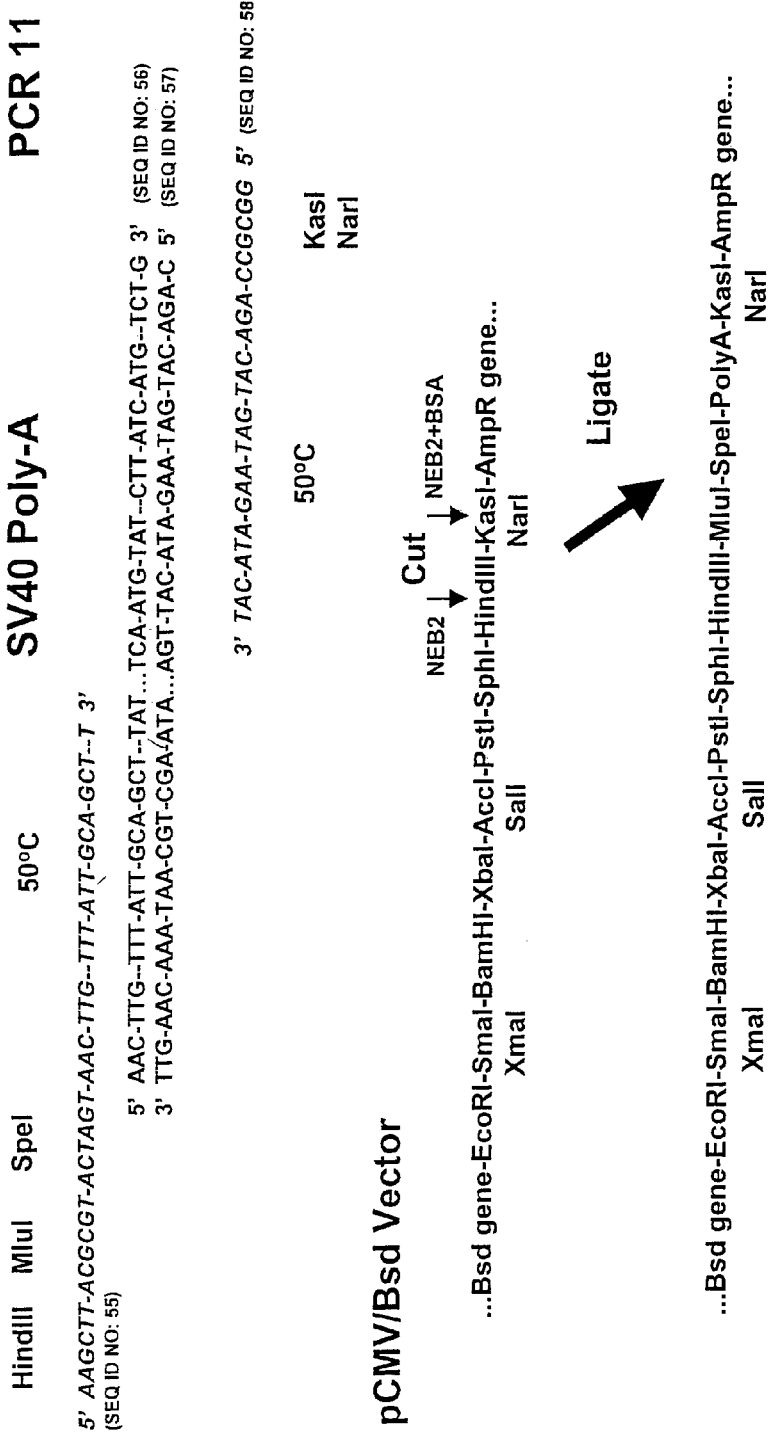
FIG. 27 is an outline of a PCR strategy used to produce the SV40 poly-A sequence copied from pCMV/Bsd via PCR with the illustrated primers (PCR product 11). PCR product 11 is then inserted into pCMV/Bsd as shown to create a second poly-A sequence in the vector.

Using the strategy shown in FIG. 27, the SV40 poly-A sequence was copied from pCMV/Bsd via PCR 11 with the illustrated primers. The product of PCR 11 was gel purified and inserted into the Invitrogen pCR®2.1-TOPO vector following the manufacturer's protocol. The inserts were sequenced on both strands by the Nucleic Acid/Protein Research Core Facility at the Children's Hospital of Philadelphia. The pCR®2.1-TOPO vector containing PCR product 11 was digested by Hind III and Kas I restriction enzymes, and the fragment corresponding to PCR product 11 was gel purified. The pCMV/Bsd vector, shown schematically in FIG. 27, was also digested by Hind III and Kas I, and the larger resulting fragment was gel purified. The digested PCR product 11 was ligated into the digested vector to create modified pCMV/Bsd. The inserted region of the new vector was sequenced on both strands by the Nucleic Acid/Protein Research Core Facility at the Children's Hospital of Philadelphia.

Figure 28:
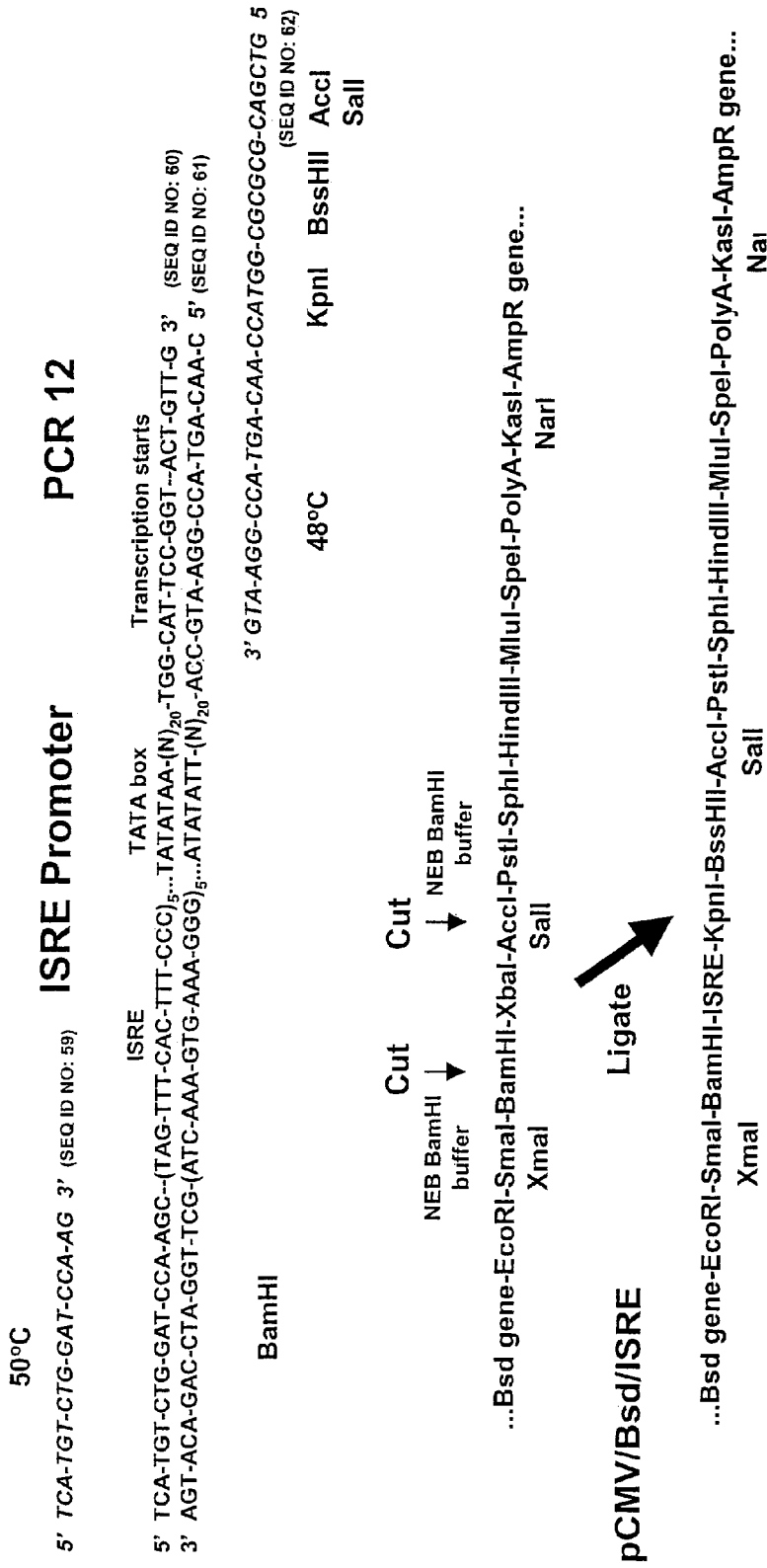
FIG. 28 is an outline of a PCR strategy used to produce PCR product 12. An interferon-inducible promoter containing multiple interferon-stimulated response elements (ISREs) is cloned from the Stratagene vector pISRE-Luc using the PCR primers shown in the figure. PCR product 12 is inserted into the modified pCMV/Bsd containing the second poly-A sequence, resulting in a general-purpose interferon-inducible vector, pCMV/Bsd/ISRE. Any desired gene can be inserted into this new interferon-inducible vector.

Using the strategy shown in FIG. 28, an interferon-inducible promoter containing multiple interferon-stimulated response elements (ISREs) was cloned from the Stratagene vector pISRE-Luc via PCR 12 with the illustrated primers. The product of PCR 12 was gel purified and inserted into the Invitrogen pCR®2.1-TOPO vector following the manufacturer's protocol. The inserts were sequenced on both strands by the Nucleic Acid/Protein Research Core Facility at the Children's Hospital of Philadelphia. The pCR®2.1-TOPO vector containing PCR product 12 was digested by BamH I and Sal I restriction enzymes, and the fragment corresponding to PCR product 12 was gel purified. The modified pCMV/Bsd vector, shown schematically in FIG. 28, was also digested by BamH I and Sal I, and the larger resulting fragment was gel purified. Then the digested PCR product 12 was ligated into the digested vector to create pCMV/Bsd/ISRE, a general-purpose interferon-inducible mammalian expression vector. The inserted region of the new vector was sequenced on both strands by the Nucleic Acid/Protein Research Core Facility at the Children's Hospital of Philadelphia. Any desired gene can be inserted into this new interferon-inducible vector, transfected into mammalian cells, and induced by interferon.

Synthesis of Interferon-Inducible Defense Genes: Hdj-1

Figure 29:
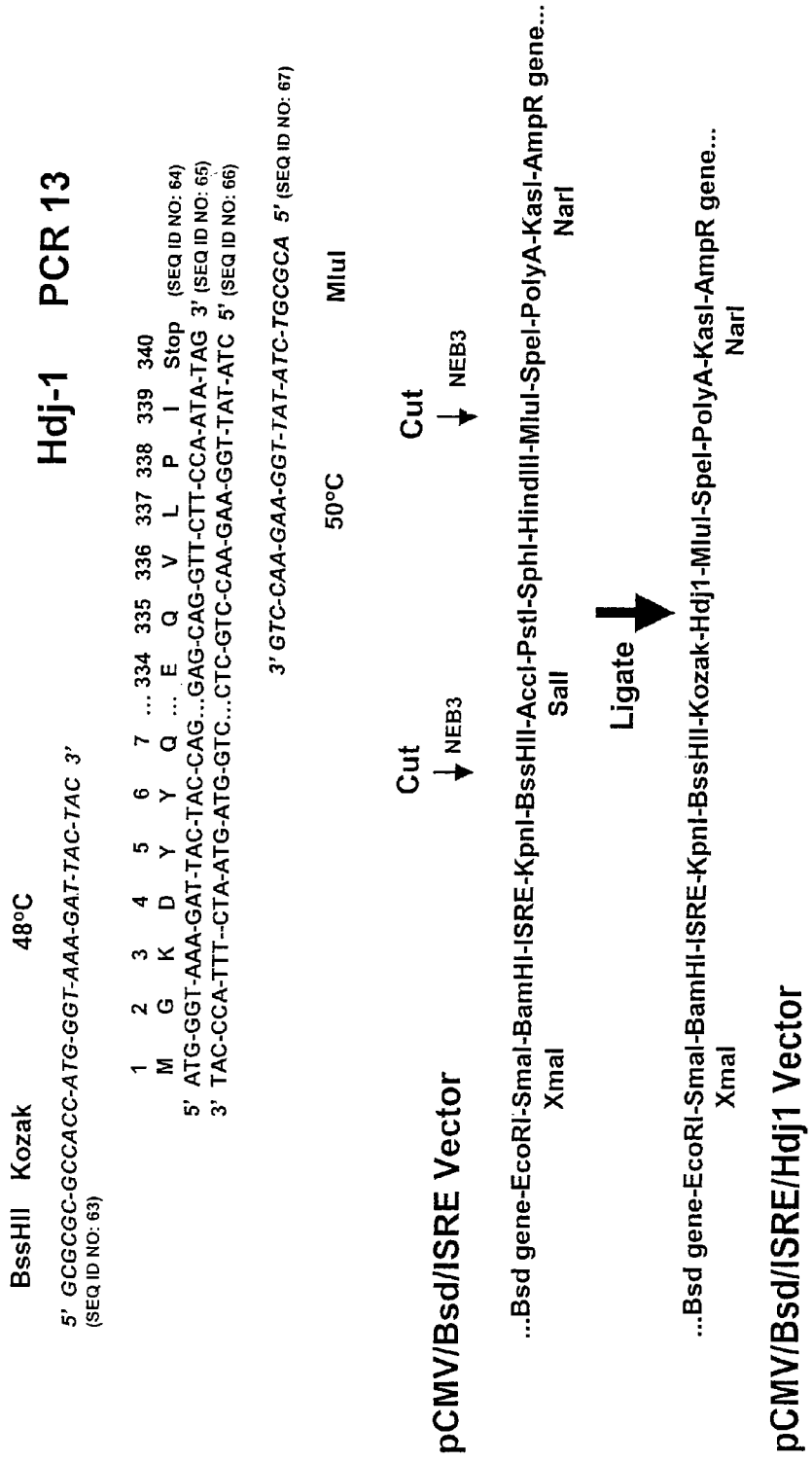
FIG. 29 is an outline of a PCR strategy used to produce PCR product 13. The gene for heat shock protein Hdj-1 (NCBI Accession # X62421) is cloned in PCR 13, and the PCR primers are used to add a Kozak sequence as well as BssH II and Mlu I restriction enzyme sites. PCR product 13 containing Hdj-1 is inserted into the vector from FIG. 28, creating an interferon-inducible Hdj-1 expression vector.

Using the strategy shown in FIG. 29, the gene for heat shock protein Hdj-1 is cloned from the provided plasmid in PCR 13 with the illustrated primers. The PCR primers are used to add a Kozak sequence as well as BssH II and Mlu I restriction enzyme sites. The product of PCR 13 is gel purified and inserted into the Invitrogen pCR®2.1-TOPO vector following the manufacturer's protocol. The inserts are sequenced on both strands by the Nucleic Acid/Protein Research Core Facility at the Children's Hospital of Philadelphia. Site-directed mutagenesis is used to correct the encoded amino acids to the published sequence. The pCR®2.1-TOPO vector containing the corrected PCR product 13 is digested by BssH II and Mlu I restriction enzymes, and the fragment corresponding to PCR product 13 is gel purified. The pCMV/Bsd/ISRE vector, shown schematically in FIG. 29, is also digested by BssH II and Mlu I, and the larger resulting fragment is gel purified. Then the digested PCR product 13 is ligated into the digested vector to create an interferon-inducible Hdj-1 expression vector. The inserted region of the new vector is sequenced on both strands by the Nucleic Acid/Protein Research Core Facility at the Children's Hospital of Philadelphia.

Synthesis of Interferon-Inducible Defense Gene: Hsp70

Figure 30:
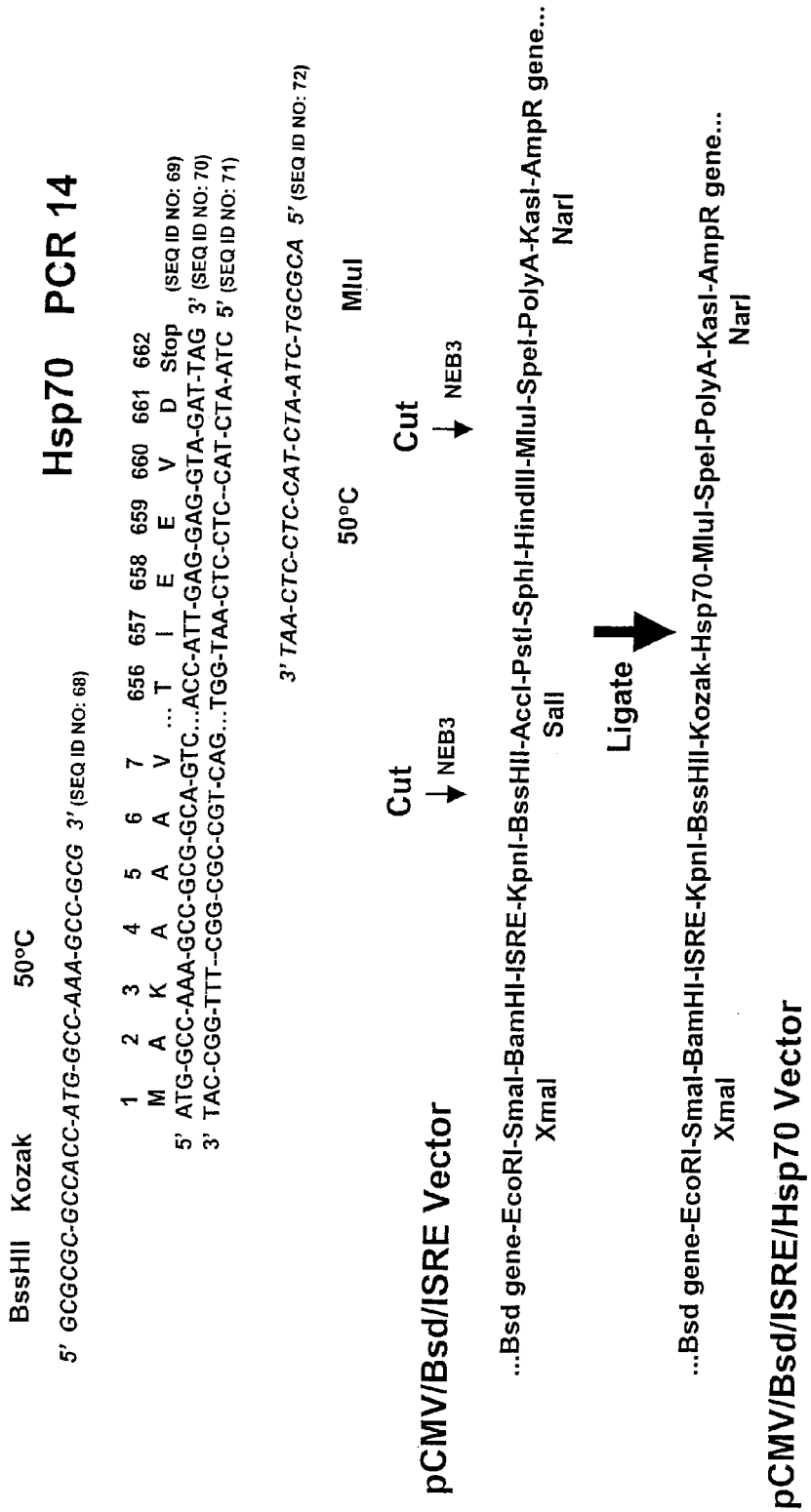
FIG. 30 is an outline of a PCR strategy used to produce PCR product 14. The gene for heat shock protein Hsp70 (NCBI Accession # M11717 M15432) is cloned in PCR 14, and the PCR primers are used to add a Kozak sequence as well as BssH II and Mlu I restriction enzyme sites. PCR product 14 containing Hsp70 is inserted into the vector from FIG. 28, creating an interferon-inducible Hsp70 expression vector.

Using the strategy shown in FIG. 30, the gene for heat shock protein Hsp70 is cloned from the provided plasmid in PCR 14 with the illustrated primers. The PCR primers are used to add a Kozak sequence as well as BssH II and Mlu I restriction enzyme sites. The product of PCR 14 is gel purified and inserted into the Invitrogen pCR®2.1-TOPO vector following the manufacturer's protocol. The inserts are sequenced on both strands by the Nucleic Acid/Protein Research Core Facility at the Children's Hospital of Philadelphia. Site-directed mutagenesis is used to correct the encoded amino acids to the published sequence. The pCR®2.1-TOPO vector containing the corrected PCR product 14 is digested by BssH II and Mlu I restriction enzymes, and the fragment corresponding to PCR product 14 is gel purified. The pCMV/Bsd/ISRE vector, shown schematically in FIG. 30, is also digested by BssH II and Mlu I, and the larger resulting fragment is gel purified. Then the digested PCR product 14 is ligated into the digested vector to create an interferon-inducible Hsp70 expression vector. The inserted region of the new vector is sequenced on both strands by the Nucleic Acid/Protein Research Core Facility at the Children's Hospital of Philadelphia.

Synthesis of Interferon-Inducible Defense Gene: Hsp90

Figure 31:
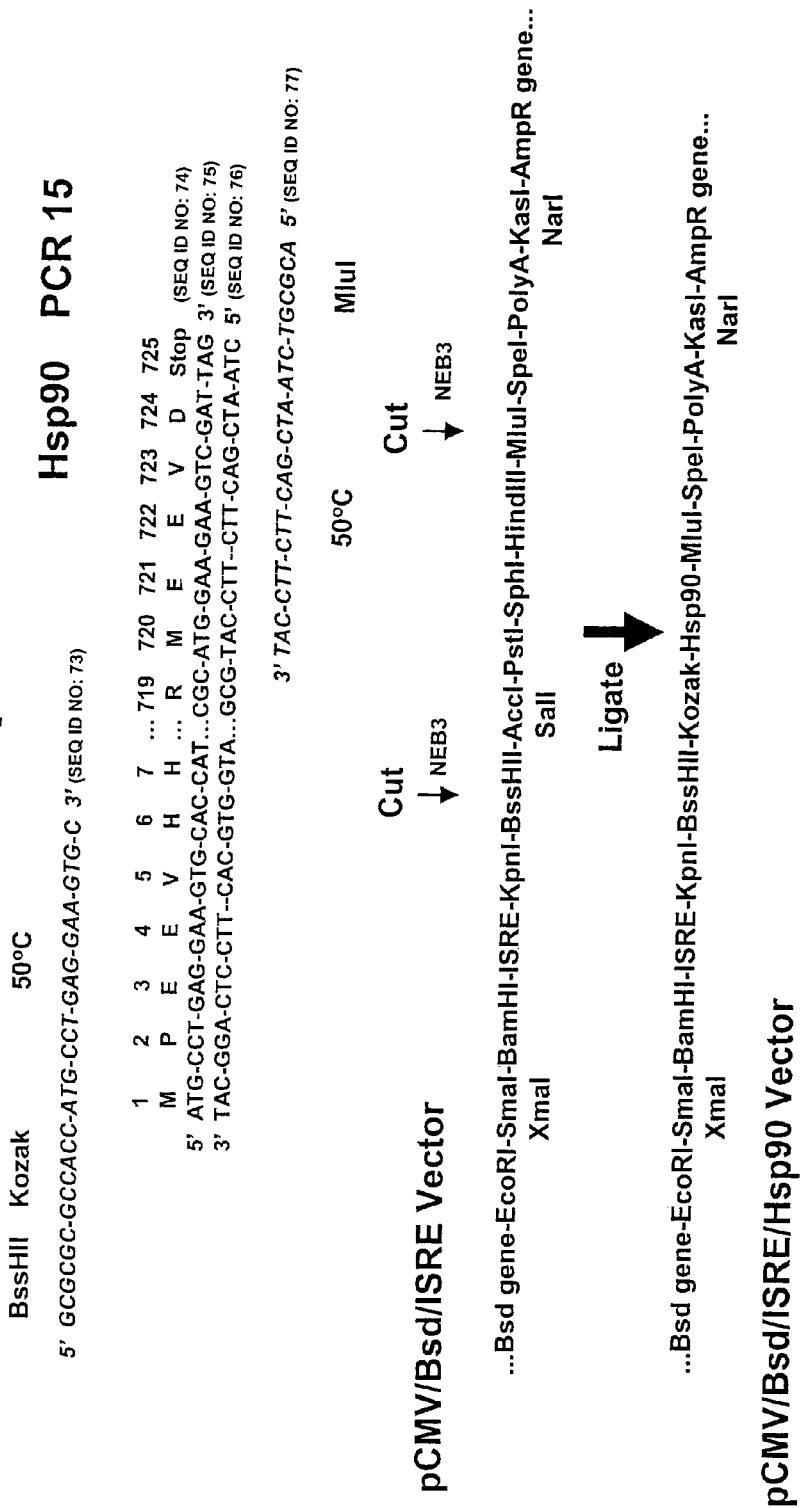
FIG. 31 is an outline of a PCR strategy used to produce PCR product 15. The gene for heat shock Hsp90 (NCBI Accession # M16660) is cloned in PCR 15, and the PCR primers are used to add a Kozak sequence as well as BssH II and Mlu I restriction enzyme sites. PCR product 15 containing Hsp90 is inserted into the vector from FIG. 28, creating an interferon-inducible Hsp90 expression vector.

Using the strategy shown in FIG. 31, the gene for heat shock protein Hsp90 is cloned from the provided plasmid in PCR 15 with the illustrated primers. The PCR primers are used to add a Kozak sequence as well as BssH II and Mlu I restriction enzyme sites. The product of PCR 15 is gel purified and inserted into the Invitrogen pCR®2.1-TOPO vector following the manufacturer's protocol. The inserts are sequenced on both strands by the Nucleic Acid/Protein Research Core Facility at the Children's Hospital of Philadelphia. Site-directed mutagenesis is used to correct the encoded amino acids to the published sequence. The pCR®2.1-TOPO vector containing the corrected PCR product 15 is digested by BssH II and Mlu I restriction enzymes, and the fragment corresponding to PCR product 15 is gel purified. The pCMV/Bsd/ISRE vector, shown schematically in FIG. 31, is also digested by BssH II and Mlu I, and the larger resulting fragment is gel purified. Then the digested PCR product 15 is ligated into the digested vector to create an interferon-inducible Hsp90 expression vector. The inserted region of the new vector is sequenced on both strands by the Nucleic Acid/Protein Research Core Facility at the Children's Hospital of Philadelphia.

Synthesis of Interferon-Inducible Defense Gene: Control Gene

Figure 32:
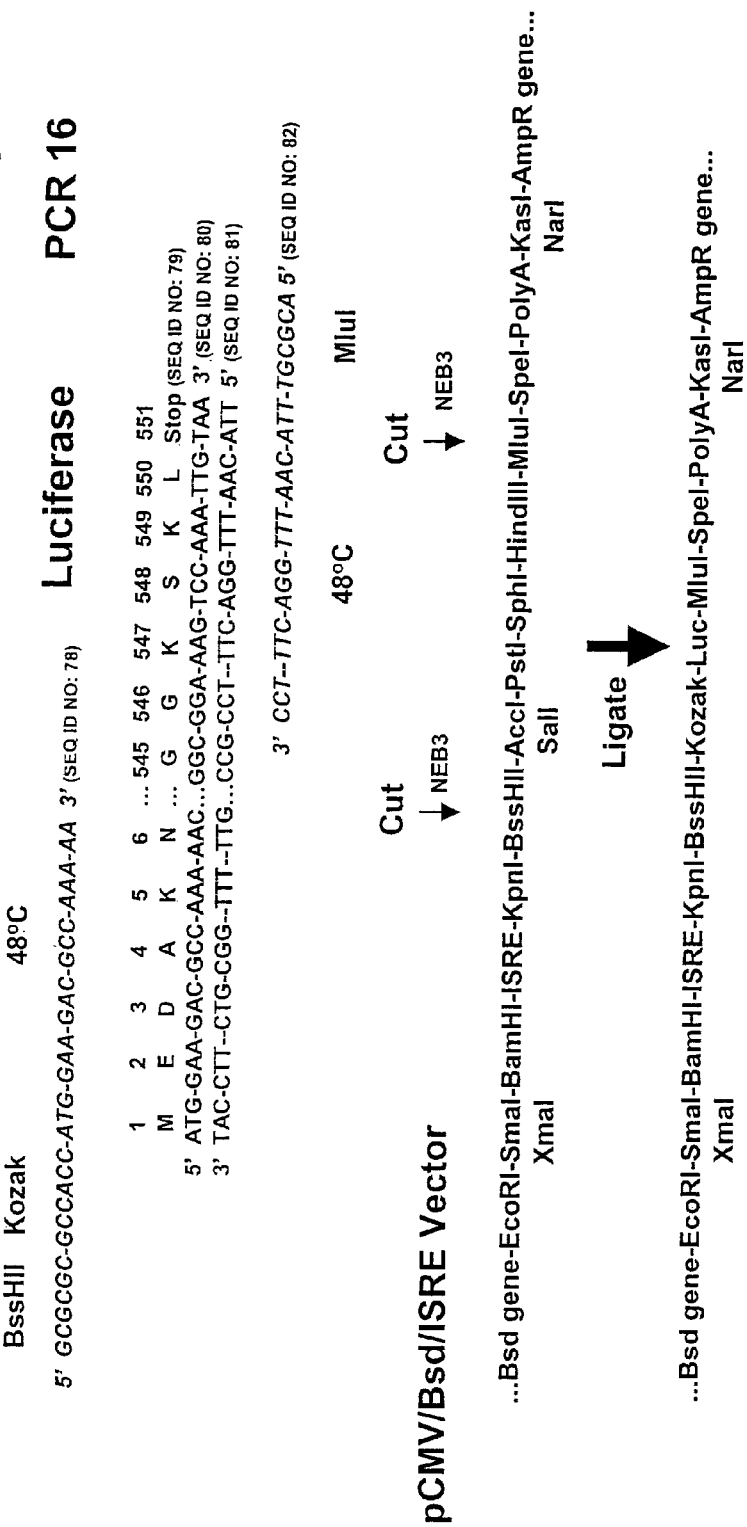
FIG. 32 is an outline of a PCR strategy used to produce PCR product 16. The luciferase gene is cloned from the Stratagene vector pISRE-Luc in PCR 16, and the PCR primers are used to add a Kozak sequence as well as BssH II and Mlu I restriction enzyme sites. PCR product 16 containing the luciferase gene is inserted into the vector from FIG. 28, creating an interferon-inducible luciferase expression vector.

Using the strategy shown in FIG. 32, the gene for luciferase was cloned from pISRE-Luc in PCR 16 with the illustrated primers. The PCR primers were used to add a Kozak sequence as well as BssH II and Mlu I restriction enzyme sites. The product of PCR 16 was gel purified and inserted into the Invitrogen pCR®2.1-TOPO vector following the manufacturer's protocol. The inserts were sequenced on both strands by the Nucleic Acid/Protein Research Core Facility at the Children's Hospital of Philadelphia. The pCR®2.1-TOPO vector containing PCR product 16 was digested by BssH II and Mlu I restriction enzymes, and the fragment corresponding to PCR product 16 was gel purified. The pCMV/Bsd/ISRE vector, shown schematically in FIG. 32, was also digested by BssH II and Mlu I, and the larger resulting fragment is gel purified. Then the digested PCR product 16 was ligated into the digested vector to create an interferon-inducible luciferase expression vector. The inserted region of the new vector was sequenced on both strands by the Nucleic Acid/Protein Research Core Facility at the Children's Hospital of Philadelphia.

DNA Gel Electrophoresis Analyses of Interferon-Inducible Defense Genes

Figure 33:
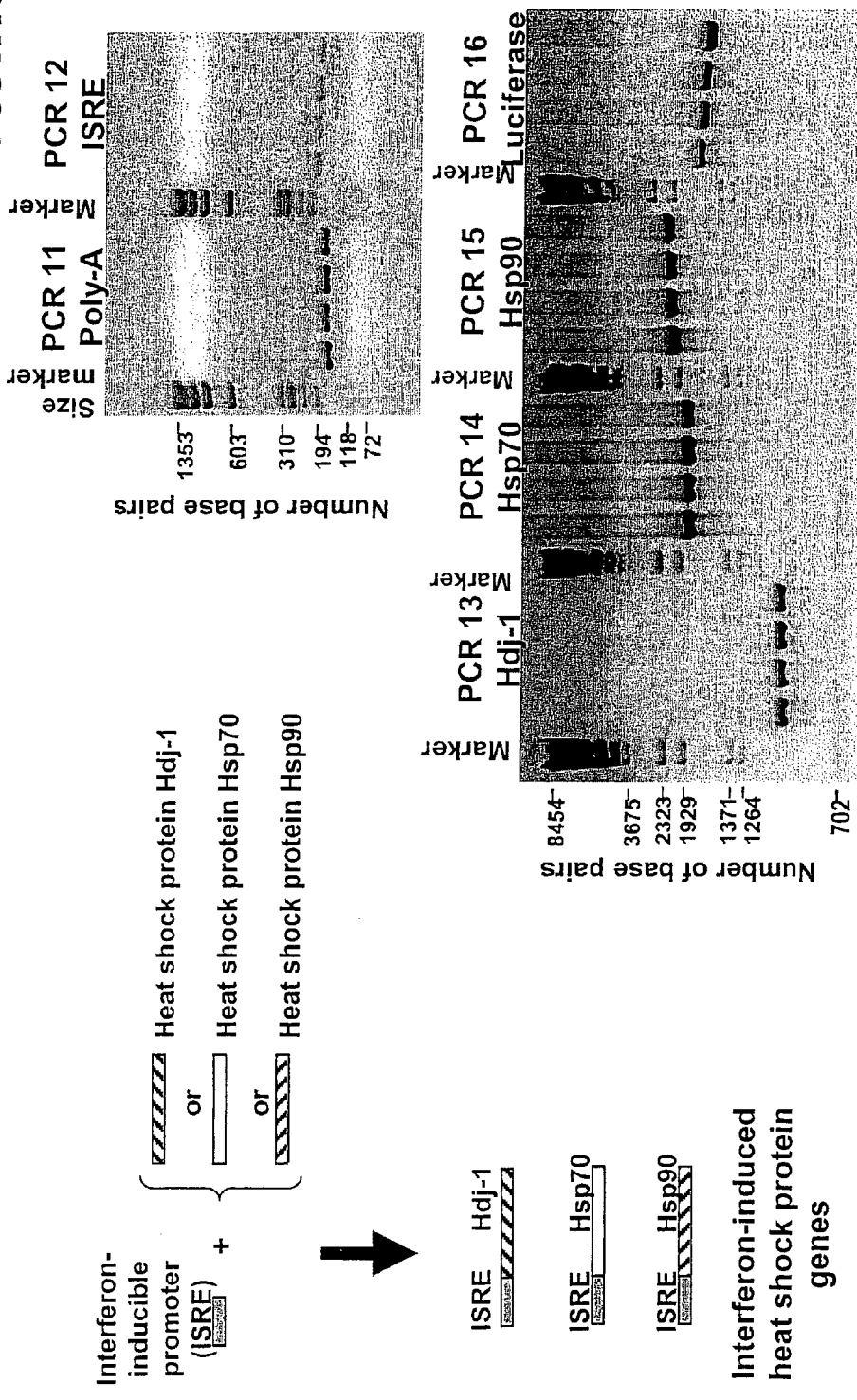
FIG. 33 is a diagram of interferon-induced heat shock proteins and photographs of PCR products 11 through PCR 16 electrophoresed on an agarose gel. PCR 11 is the poly-A sequence, PCR 12 is the ISRE-containing interferon-inducible promoter, PCR 13 is Hdj-1, PCR 14 is Hsp70, PCR 15 is Hsp90, and PCR16 is luciferase.

The DNA electrophoresis gel photographs in FIG. 33 show the products of PCR 11 through PCR 16. PCR 11 is the poly-A sequence, PCR 12 is the ISRE-containing interferon-inducible promoter, PCR 13 is Hdj-1, PCR 14 is Hsp70, PCR 15 is Hsp90, and PCR16 is luciferase.

Figure 34:
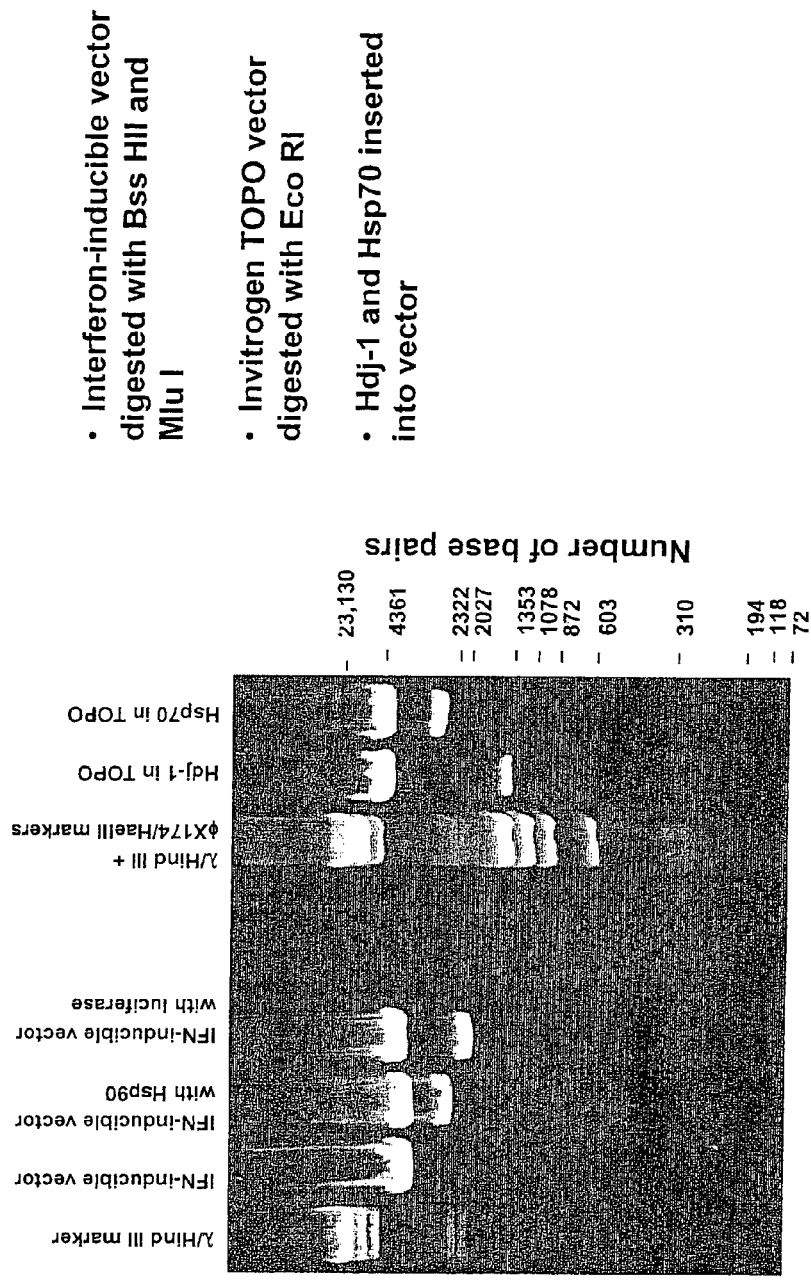
FIG. 34 is a photograph of a DNA electrophoresis agarose gel of the inteferon-inducible vectors and genes. Lane 1 is a DNA size marker. Lane 2 is the completed interferon-inducible vector pCMV/Bsd/ISRE without an inserted gene. Lane 3 is the same vector with Hsp90 inserted, and Lane 4 is the vector with luciferase inserted. The vector in these lanes has been digested with the restriction enzymes Bss HII and Mlu I for analysis. Lane 5 is a DNA size marker. Lanes 6 and 7 are the Hdj-1 and Hsp70 genes inserted into the Invitrogen TOPO vector, respectively, digested with Eco RI for analysis. Using the methods illustrated in FIGS. 29 and 30, the Hdj-1 and Hsp70 genes are inserted into pCMV/Bsd/ISRE.
Figure 36:
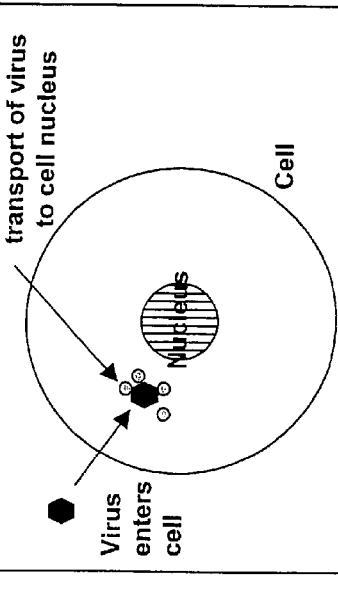
FIG. 36 is a diagram of other anti-pathogen effectors that can be added to cells, and induced by interferon, dsRNA, LPS, apoptosis signals, or other pathogen detection methods, or alternatively, the anti-pathogen effectors can be constitutively present or active. For example, interferon can induce a gene for bacterial RNase III or one of its eukaryotic homolog dsRNases, which degrade viral dsRNA while leaving cellular RNA relatively intact. Or, one or more endosome inhibitors can be used to inhibit the uncoating of a virus in the endosome. Examples of endosome inhibitors include, but are not limited to, vacuolar $H^+$-ATPase inhibitors (such as the human papillomavirus 16 E5 protein, a defective ATPase subunit, or bafilomycin A1) or vesicular trafficking inhibitors (such as the *Salmonella* SpiC protein). Alternatively, expression of a nuclear localization signal (NLS) inhibitor can be induced by interferon in order to prevent transport of pathogens or pathogen components with NLSs into the nucleus. The NLS inhibitor can be a truncated version of importin-alpha that binds to an NLS but is not transported into the nucleus, or it can be any other NLS-binding protein that is not transported into the nucleus. Proteins with an NLS, or other decoy proteins that bind to importin-alpha, can be overexpressed in the presence of interferon as another method of inhibiting pathogen NLSs.

The DNA electrophoresis gel photograph in FIG. 34 illustrates the inteferon-inducible vectors and genes. The second lane of the gel is the completed interferon-inducible vector pCMV/Bsd/ISRE without an inserted gene. Lane 3 is the same vector with Hsp90 inserted, and Lane 4 is the vector with luciferase inserted. The vector in these lanes has been digested with the restriction enzymes BssH II and Mlu I for ease of analysis. The rightmost two lanes are the Hdj-1 and Hsp70 genes inserted into the Invitrogen pCR®2.1-TOPO vector, digested with EcoR I for ease of analysis. Using the methods described in FIGS. 29 and 30, the Hdj-1 and Hsp70 genes are inserted into pCMV/Bsd/ISRE.

Cell Transfections with Interferon-Inducible Defense Genes

H1-HeLa cells are maintained using standard tissue culture practices, humidified incubators at 37° C. and 5% $CO_2$, and DMEM culture medium containing 10% fetal bovine serum, 100 μM nonessential amino acids, 1 mM sodium pyruvate, 4 mM L-glutamine, 100 units/ml penicillin G, 100 μg/ml streptomycin, and 250 ng/ml amphotericin B.

The interferon-inducible expression vectors for Hdj-1, Hsp70, Hsp90, and luciferase are linearized and transfected into the H1-HeLa cells. The transfections use LIPOFECTIN® and PLUS reagents from Invitrogen and follow Invitrogen's recommended protocol for HeLa cells. One day after the transfection, blasticidin is added to the cell culture medium to kill any cells that have not been stably transfected with the vectors, and the cells are permanently kept in blasticidin as a precaution against the possibility that the cells might lose the transfected genes.

The pools of blasticidin-resistant cells that result from each transfection are presumably genetically heterogeneous, with different cells having different copy numbers of the inserted vector or having the vector inserted into different regions of the cellular genome. Therefore, genetically homogeneous clonal cell populations are isolated. Limiting dilutions of the pools of transfected cells are used to deposit approximately 1 cell per well into 96-well plates, and the cells are allowed to multiply. Wells that appear to have received more than one initial cell are disregarded.

Protein Expression of Interferon-Inducible Defense Genes in Transfected Cells

Western blots are used to analyze the cell clones. Cells are cultured for one day either with or without human interferon-alpha, and then proteins are extracted from the cells and analyzed by Western blot with antibodies specific for human Hdj-1, Hsp70, or Hsp90. Cells induced with interferon express more of the heat shock protein with which they were transfected than cells that have not been induced or control untransfected H1-HeLa cells.

Example 3 dsRNA-activated Caspase Protects H1-HeLa Cells from Rhinovirus

Materials and Methods

H1-HeLa cells (ATCC CRL-1958) were chosen because of their particular susceptibility to rhinovirus. Cells were maintained using standard tissue culture practices, humidified incubators at 37° C. and 5% $CO_2$, and DMEM culture medium containing 10% tetracycline-free fetal bovine serum, 100 μM nonessential amino acids, 1 mM sodium pyruvate, 4 mM L-glutamine, 100 units/ml penicillin G, 100 μg/ml streptomycin, and 250 ng/ml amphotericin B. The vector pTetOn encodes the rtTA regulatory protein necessary for the proper functioning of tetracycline or doxycycline-inducible promoters; it was obtained from BD Bioscences Clontech and prepared and linearized following the manufacturer's directions.

H1-HeLa cells were co-transfected with 5 µg each of linearized pTetOn and the linearized pTRE2hyg-derived vector that contained PCR 8. The transfections used LIPOFECTIN® and PLUS reagents from Invitrogen and follow Invitrogen's recommended protocol for HeLa cells. One day after the transfection, 600 µg/ml G418 and 400 µg/ml hygromycin were added to the cell culture medium to kill any cells that had not been stably transfected with the vectors, and the cells were subsequently kept in 800 µg/ml G418 and 400 µg/ml hygromycin as a precaution against the possibility that the cells might lose the transfected genes. The resulting transfected cells were designated 8S or 8 simultaneous.

Results and Discussion

Figure 37:
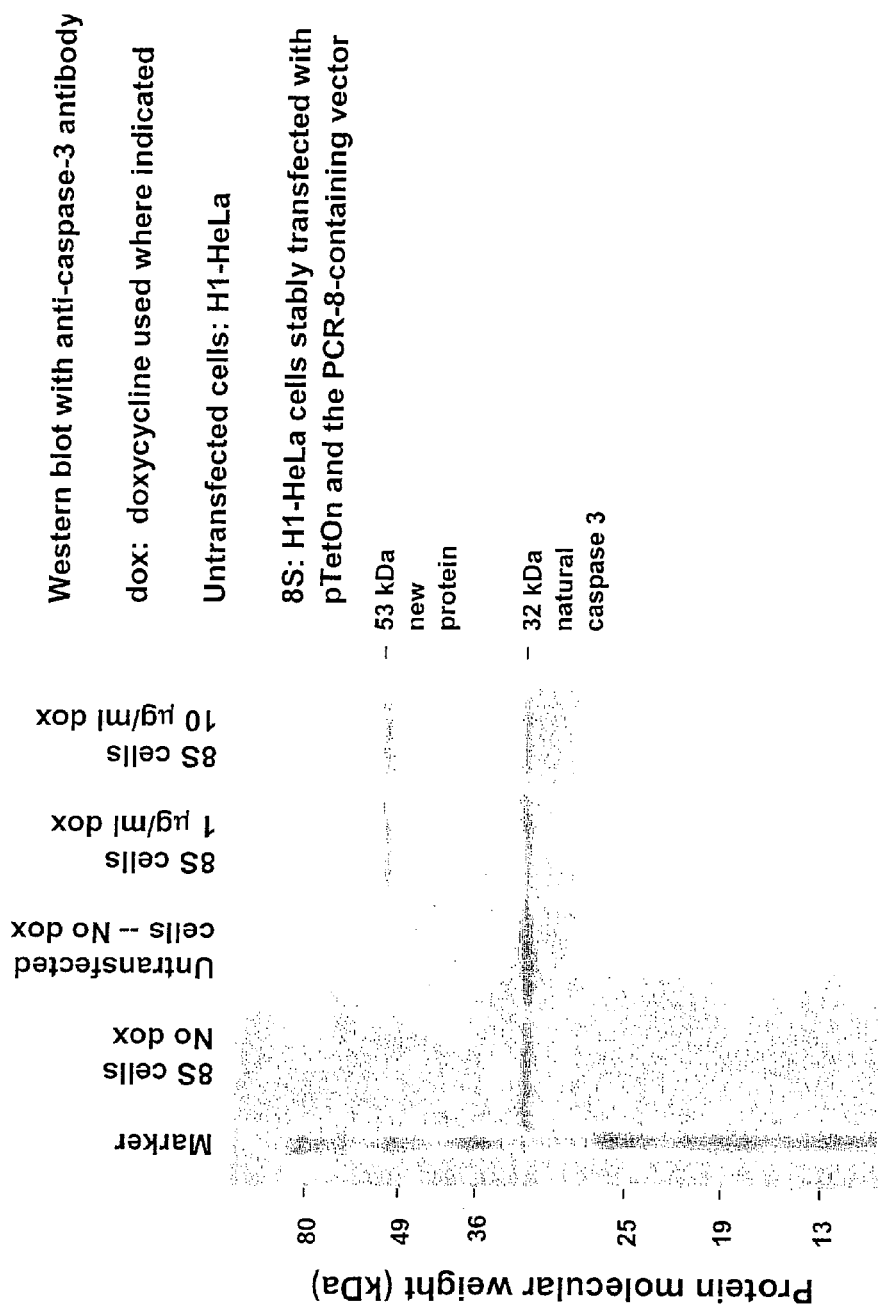
FIG. 37 is a Western blot analysis. Doxycycline induces 8S cells to express the dsRNA-activated caspase. Untransfected H1-HeLa cells were cultured without doxycycline for two days, and 8S cells were cultured with 0, 1, or 10 µg/ml doxycycline for two days. Western blots were then used to probe the cell extracts with anti-caspase-3 antibodies. The 32-kDa natural (pro)caspase 3 was visible in all the cells, regardless of transfection or doxycycline. For 8S cells, 1 or 10 µg/ml doxycycline upregulated expression of the dsRNA-activated caspase, which has approximately the predicted size (FIG. 37, labeled 53 kDa new protein) and contains caspase-3 epitopes recognized by the antibodies.

The Western blot in FIG. 37 demonstrates that doxycycline induced 8S cells to express the dsRNA-activated caspase. Untransfected H1-HeLa cells were cultured without doxycycline for two days, and 8S cells were cultured with 0, 1, or 10 µg/ml doxycycline for two days. Western blots were then used to probe the cell extracts with anti-caspase-3 antibodies. The 32-kDa natural (pro)caspase 3 was visible in all the cells, regardless of transfection or doxycycline. For 8S cells, 1 or 10 µg/ml doxycycline upregulated expression of the dsRNA-activated caspase, which has approximately the predicted size (FIG. 37, labeled as 53 kDa new protein) and contains caspase-3 epitopes recognized by the antibodies.

Figure 38:
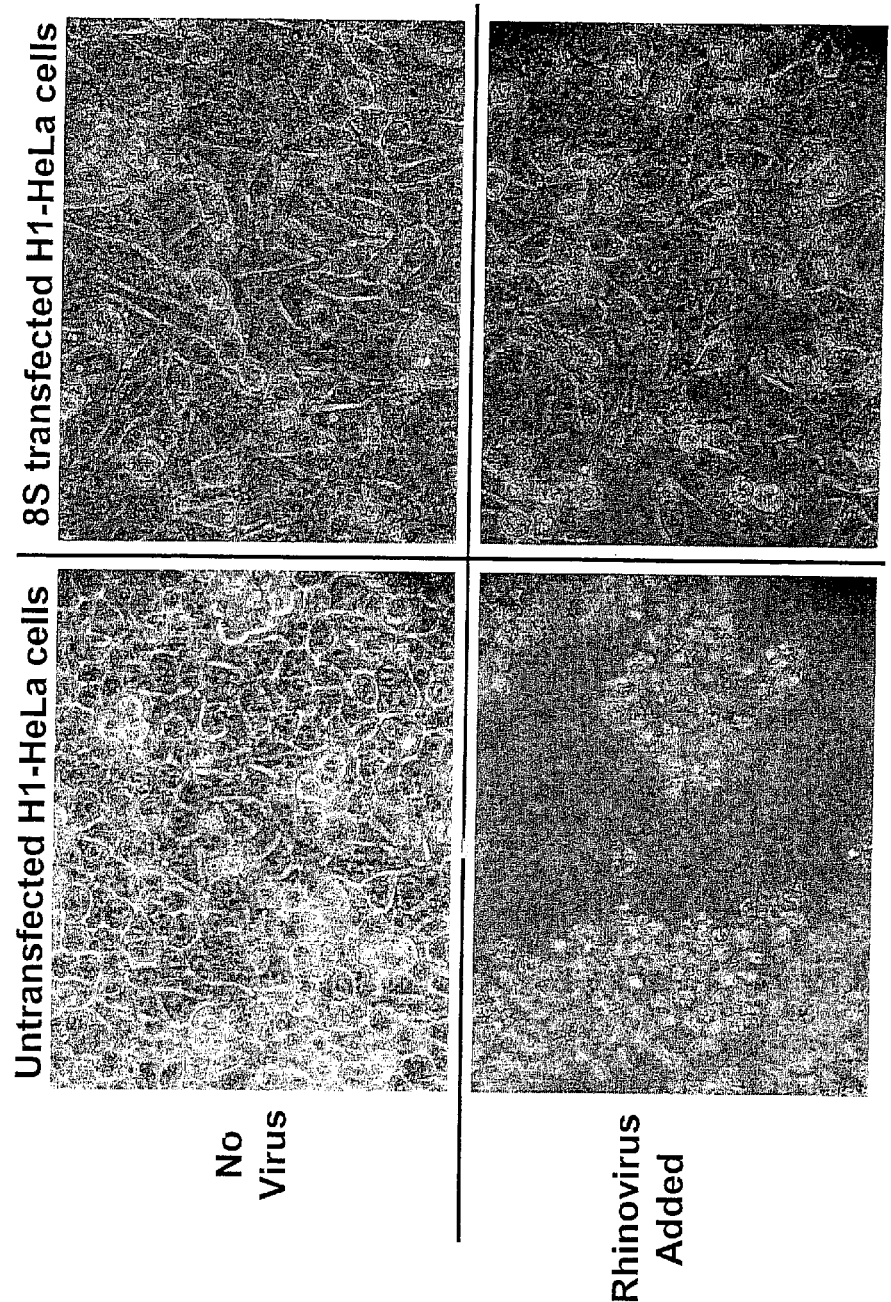
FIG. 38 are photographs demonstrating the effectiveness of dsRNA-activated caspase against virus. Control untransfected H1-HeLa cells without doxycycline and 8S H1-HeLa cells induced with 10 µg/ml doxycycline were grown in 25-cm$^2$ tissue culture flasks. Cells were infected with human rhinovirus 14 (American Type Culture Collection (ATCC) number VR-284) (FIG. 38, lower left and right panels). After 7 days of incubation at 33° C., all untransfected cell populations exposed to rhinovirus were dead and detached from their flasks' surfaces (FIG. 38, lower left panel). In contrast, transfected 8S H1-HeLa cells that have been exposed to rhinovirus were alive, attached, and confluent, and they show no signs of infection (FIG. 38, lower right panel). Both untransfected and transfected cells not exposed to rhinovirus were also confluent and healthy (FIG. 38, upper left and right panels, respectively).

To demonstrate the effectiveness of the dsRNA-activated caspase against virus, cells were infected with human rhinovirus 14 (ATCC VR-284), as shown in FIG. 38. The stock rhinovirus concentration was determined via limiting dilutions and plaque assays on untransfected H1-HeLa cells. Control untransfected H1-HeLa cells without doxycycline and 8S H1-HeLa cells induced with 10 µg/ml doxycycline were grown in 25-cm² tissue culture flasks. Approximately 300 plaque-forming units (pfu) of virus were added to flasks of untransfected and transfected cells, while other flasks were left uninfected as controls. After 7 days of incubation at 33° C., all untransfected cell populations exposed to rhinovirus were completely dead and detached from their flasks' surfaces (FIG. 38, lower left panel). In contrast, transfected 8S H1-HeLa cells that have been exposed to rhinovirus were alive, attached, and confluent, and they show no signs of infection (FIG. 38, lower right panel). Both untransfected and transfected cells not exposed to rhinovirus were also confluent and healthy (FIG. 38, upper left and right panels, respectively). Thus the dsRNA-activated caspase successfully protects HeLa cells against viral infection and has little or no toxicity. Differences in cell density among the various flasks were due to differences in the initial cell seeding densities and therefore are not related to the dsRNA-activated caspase.

Example 4 dsRNA-activated Caspases in Human Embyonic Kidney 293 Cells

Materials and Methods

The 293 TetOn™ cell line (BD Biosciences Clontech) contained the rtTA regulatory protein necessary for the proper functioning of the tetracycline or doxycycline-inducible promoters. Cells were maintained using standard tissue culture practices, humidified incubators at 37° C. and 5% $CO_2$, and DMEM culture medium containing 10% tetracycline-free fetal bovine serum, 100 µM nonessential amino acids, 1 mM sodium pyruvate, 4 mM L-glutamine, 100 units/ml penicillin G, 100 µg/ml streptomycin, 250 ng/ml amphotericin B, and 100 µg/ml G418.

The linearized pTRE2hyg-derived vectors with inserted PCR 7, 8, 9, or 10 were transfected into the 293 Tet-On™ cells. The transfections used LIPOFECTIN® and PLUS reagents from Invitrogen and followed Invitrogen's recommended protocol for HeLa cells. One day after the transfection, 100 µg/ml hygromycin was added to the cell culture medium to kill any cells that had not been stably transfected with the vectors, and the cells were subsequently kept in 100 µg/ml G418 and 200 µg/ml hygromycin as a precaution against the possibility that the cells might lose the transfected genes.

The pools of hygromycin-resistant cells that result from each transfection were presumably genetically heterogeneous, with different cells having different copy numbers of the inserted vector or having the vector inserted into different regions of the cellular genome. Therefore, genetically homogeneous clonal cell populations were isolated. Limiting dilutions of the pools of transfected cells were used to deposit approximately 1 cell per well into 96-well plates, and the cells were allowed to multiply. Wells that appeared to have received more than one initial cell were disregarded. The resulting clonal cell populations were designated 293 7-x, 8-x, 9-x, or 10-x; the first number after the cell line name indicates which PCR product was transfected into the cells, and the x is replaced with the cell clone number. For example, cell line 293 7-3 indicates PCR product 7, cell clone 3.

Western blots were used to analyze the cell clones. PKR-caspase 3 fusion proteins (deriving from PCR 7 and 8) were detected using caspase-3-specific polyclonal goat IgG antibodies from R&D Systems, and PKR-FADD fusion proteins (deriving from PCR 9 and 10) were detected using FADD-specific polyclonal rabbit IgG antibodies from Upstate Biotechnology. Cells were cultured for two days either with or without doxycycline, and then proteins were extracted from the cells and analyzed by Western blot following the manufacturers' protocols.

Results and Discussion

Figure 39:
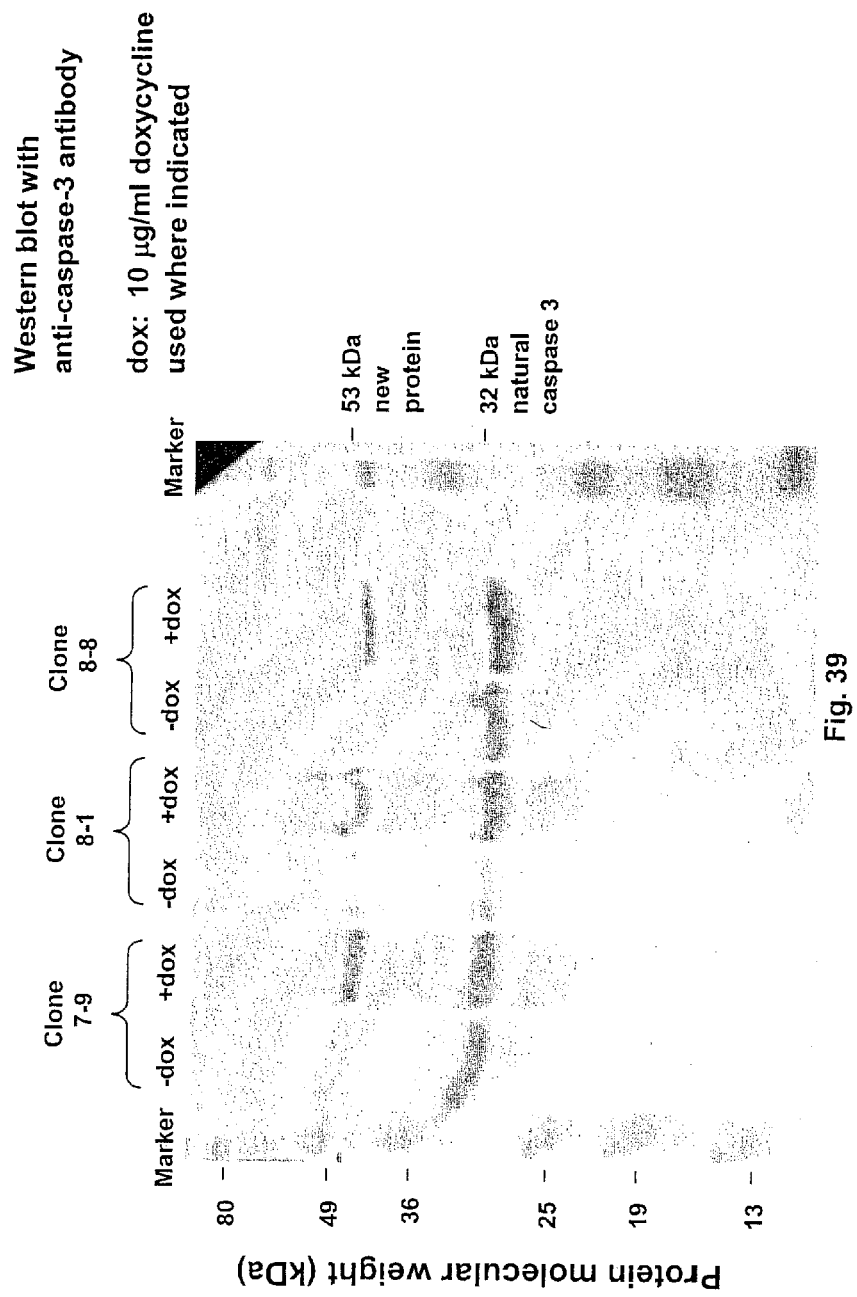
FIG. 39 is a Western blot analysis. Doxycycline induces 293 cells transfected with the PCR-7- or PCR-8-containing vectors to express the corresponding dsRNA-activated caspase. Cells were cultured with either 10 µg/ml doxycycline or no doxycycline for two days, and then Western blots were used to probe the cell extracts with anti-caspase-3 antibodies. The 32-kDa natural (pro)caspase 3 was visible in all the cells, either with or without doxycycline. For each cell clone shown, doxycycline upregulated expression of the dsRNA-activated caspase, which has approximately the predicted size (FIG. 39, labeled as 53 kDa new protein) and contains caspase-3 epitopes recognized by the antibodies.

The Western blot in FIG. 39 demonstrates that doxycycline induces 293 cells transfected with the PCR-7- or PCR-8-containing vectors to express the corresponding dsRNA-activated caspase. Cells were cultured with either 10 µg/ml doxycycline or no doxycycline for two days, and then Western blots were used to probe the cell extracts with anti-caspase-3 antibodies. The 32-kDa natural (pro)caspase 3 was visible in all the cells, either with or without doxycycline. For each cell clone shown, doxycycline upregulated expression of the dsRNA-activated caspase, which has approximately the predicted size (FIG. 39, labeled as 53 kDa new protein) and contains caspase-3 epitopes recognized by the antibodies.

Figure 40:
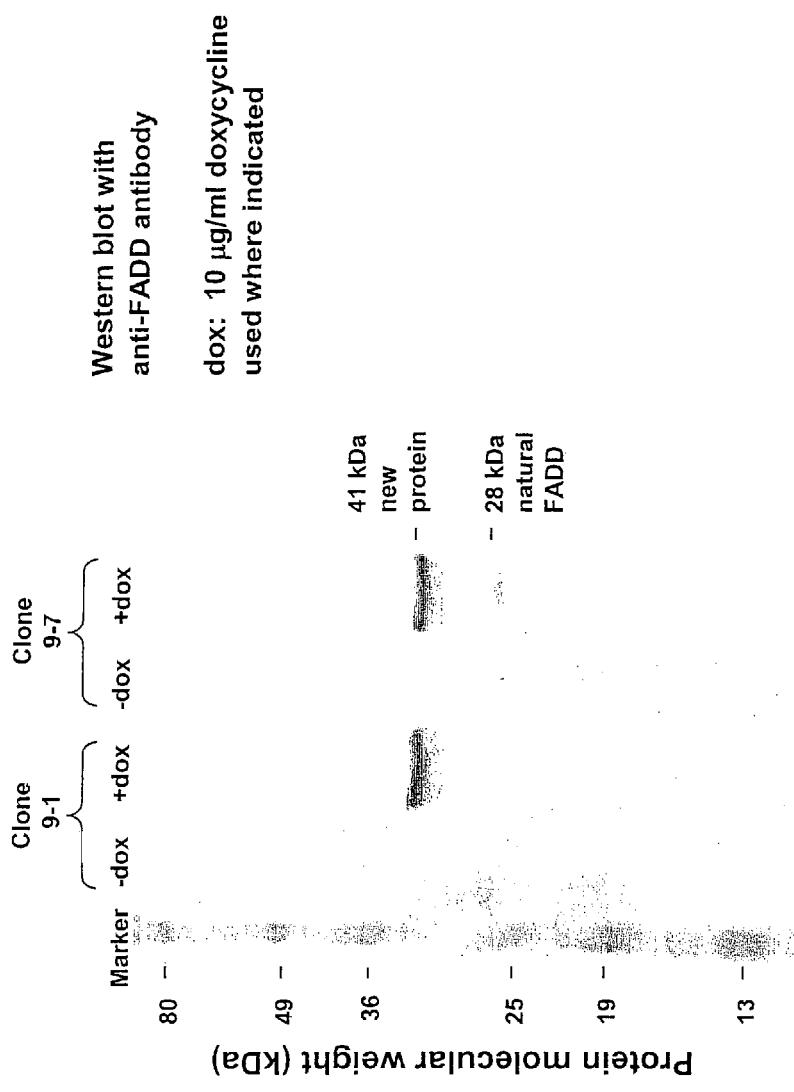
FIG. 40 is a Western blot analysis. Doxycycline induces 293 cells transfected with the PCR-9-containing vector to express the corresponding dsRNA-activated caspase activator. Cells were cultured with either 10 µg/ml doxycycline or no doxycycline for two days, and then Western blots were used to probe the cell extracts with anti-FADD antibodies. The 28-kDa natural FADD was visible in all the cells, either with or without doxycycline. For each cell clone shown, doxycycline upregulated expression of the dsRNA-activated caspase activator, which has approximately the predicted size (FIG. 40, labeled as 41 kDa new protein) and contains FADD epitopes recognized by the antibodies.

The Western blot in FIG. 40 demonstrates that doxycycline induced 293 cells transfected with the PCR-9-containing vector to express the corresponding dsRNA-activated caspase activator. Cells were cultured with either 10 µg/ml doxycycline or no doxycycline for two days, and then Western blots were used to probe the cell extracts with anti-FADD antibodies. The 28-kDa natural FADD was visible in all the cells, either with or without doxycycline. For each cell clone shown, doxycycline upregulated expression of the dsRNA-activated caspase activator, which has approximately the predicted size (FIG. 40, labeled as 41 kDa new protein) and contains FADD epitopes recognized by the antibodies.

Figure 41:
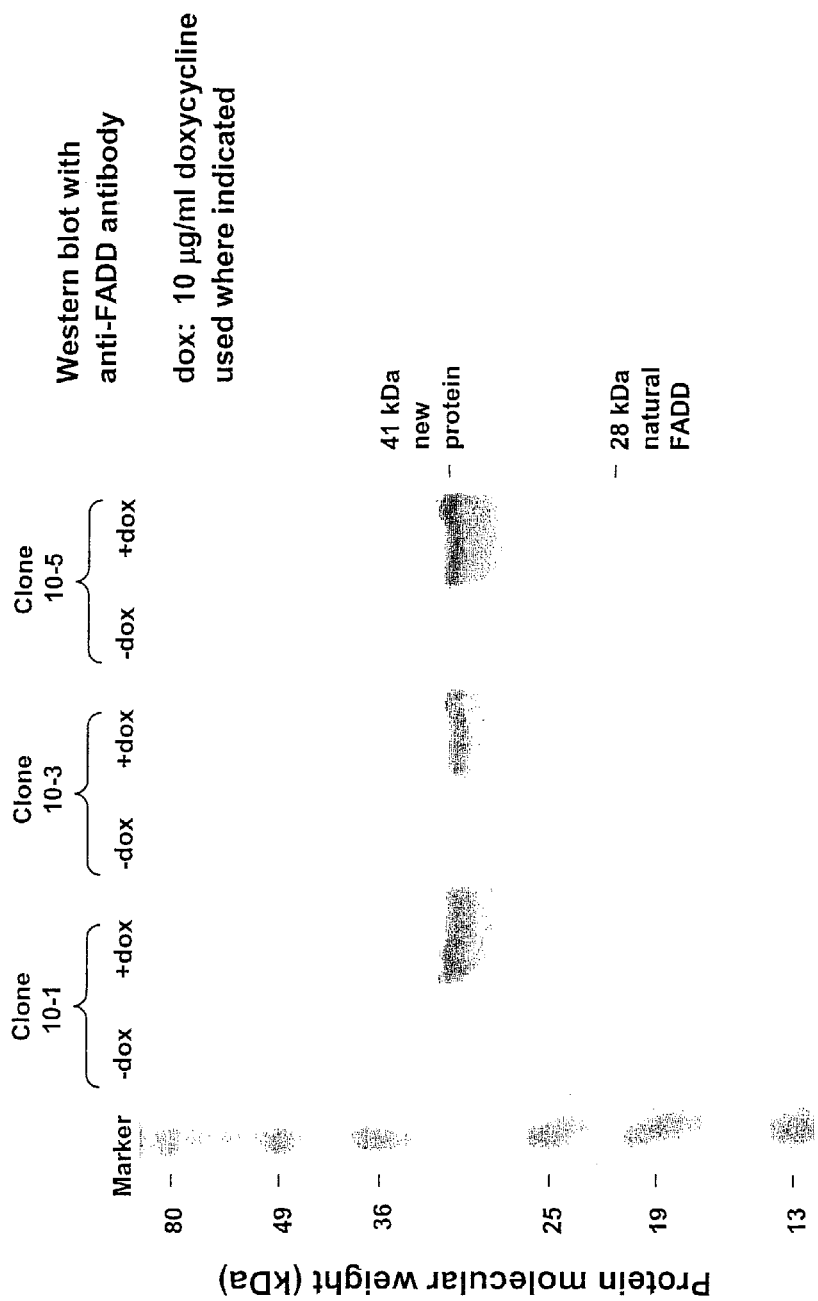
FIG. 41 is a Western blot analysis. Doxycycline induces 293 cells transfected with the PCR-10-containing vector to express the corresponding dsRNA-activated caspase activator. Cells were cultured with either 10 µg/ml doxycycline or no doxycycline for two days, and then Western blots were used to probe the cell extracts with anti-FADD antibodies. The 28-kDa natural FADD was visible in all the cells, either with or without doxycycline. For each cell clone shown, doxycycline upregulated expression of the dsRNA-activated caspase activator, which has approximately the predicted size (FIG. 41, labeled as 41 kDa new protein) and contains FADD epitopes recognized by the antibodies.

The Western blot in FIG. 41 demonstrates that doxycycline induced 293 cells transfected with the PCR-10-containing vector to express the corresponding dsRNA-activated caspase activator. Cells were cultured with either 10 μg/ml doxycycline or no doxycycline for two days, and then Western blots were used to probe the cell extracts with anti-FADD antibodies. The 28-kDa natural FADD was visible in all the cells, either with or without doxycycline. For each cell clone shown, doxycycline upregulated expression of the dsRNA-activated caspase activator, which has approximately the predicted size (FIG. 41, labeled as 41 kDa new protein) and contains FADD epitopes recognized by the antibodies.

This demonstrates that 293 cells can be induced to express PCR 7, 8, 9, or 10 for two days and illustrates that the corresponding proteins have limited or no toxicity to uninfected cells.

Example 5

Other Pathogen-activated Apoptosis Treatments

Materials and Methods

A plasmid encoding human procaspase 3 (NCBI Accession #U26943) was provided by D. M. Spencer, Baylor College of Medicine. A plasmid encoding human protein kinase R (#U50648) was from E. F. Meurs, Institut Pasteur. A plasmid encoding human RNase L (#CAA52920) was provided by R. Silverman, Cleveland Clinic Foundation. A plasmid encoding human Apaf-1 (#NM_013229, NM_001160) was donated by Y. Shi, Princeton University. A plasmid encoding human BPI (#NM_001725) was provided by L. J. Beamer, University of Missouri-Columbia. The mammalian expression vector pTRE2hyg, 293 Tet-On™ human cell line, doxycycline, and tetracycline-free fetal bovine serum were obtained from BD Biosciences Clontech. The pCR®2.1-TOPO vector was supplied by Invitrogen. PCR primers, Lipofectamine™ 2000 reagent, LIPOFECTIN® reagent, and PLUS reagent were obtained from Gibco BRL/Life Technologies/Invitrogen. Polyclonal goat IgG antibodies specific for human caspase 3 come from R&D Systems. Polyclonal rabbit antibodies specific for human BPI were from Cell Sciences, Inc. Antibodies specific for human Apaf-1 were from Exalpha Biologicals (polyclonal rabbit IgG) and Santa Cruz Biotechnology (polyclonal goat IgG). Secondary anti-goat and anti-rabbit antibodies were from Santa Cruz Biotechnology and Zymed.

Results and Discussion

Figure 42:
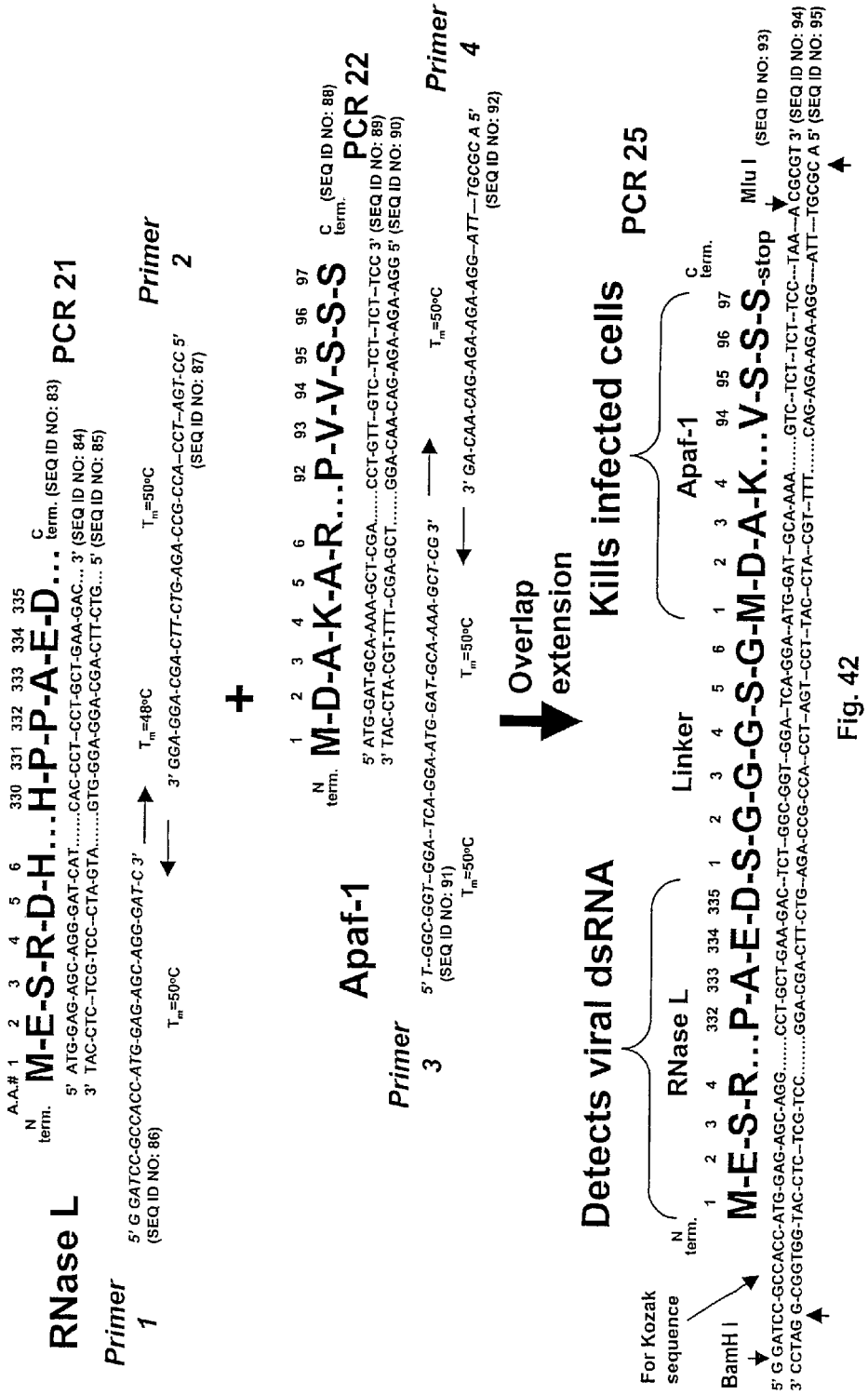
FIG. 42 is a diagram of the synthesis strategy for PCR product 25, which encodes a novel pathogen-activated caspase activator. 2',5'-oligoadenylate is produced within cells in response to pathogen components such as dsRNA. The 2',5'-oligoadenylate-binding domain from RNase L (amino acids 1-335) was fused in frame with a short flexible polypeptide linker (amino acid sequence S-G-G-G-S-G (SEQ ID NO: 1)) and amino acids 1-97 of Apaf-1, which included the caspase recruitment domain (CARD) that binds to procaspase 9. A Kozak sequence and stop codon were included, as shown. BamH I and Mlu I restriction sites were included at the ends for ease of insertion into the pTRE2hyg vector. PCR 21 used the indicated 5' and 3' PCR primers to copy the region encoding amino acids 1-335 of RNase L from the provided plasmid. PCR 22 used the indicated 5' and 3' PCR primers to copy the region encoding amino acids 1-97 of Apaf-1 from the provided plasmid. PCR 25 used the gel-purified products of PCR 21 and 22, 5' primer from PCR 21, and 3' primer from PCR 22 to create the desired product via splicing by overlap extension (C. W. Dieffenbach and G. S. Dveksler (eds.), *PCR Primer: A Laboratory Manual,* 1995, Cold Spring Harbor Laboratory Press, Plainview, N.Y.).

FIG. 42 illustrates the synthesis strategy for PCR product 25, which encodes a novel pathogen-activated caspase activator. 2',5'-oligoadenylate is produced within cells in response to pathogen components such as dsRNA. The 2',5'-oligoadenylate-binding domain from RNase L (amino acids 1-335) was fused in frame with a short flexible polypeptide linker (amino acid sequence S-G-G-G-S-G (SEQ ID NO: 1)) and amino acids 1-97 of Apaf-1, which included the caspase recruitment domain (CARD) that binds to procaspase 9. A Kozak sequence and stop codon were included as shown. BamH I and Mlu I restriction sites were included at the ends for ease of insertion into the pTRE2hyg vector. PCR 21 used the indicated 5' and 3' PCR primers to copy the region encoding amino acids 1-335 of RNase L from the provided plasmid. PCR 22 used the indicated 5' and 3' PCR primers to copy the region encoding amino acids 1-97 of Apaf-1 from the provided plasmid. PCR 25 used the gel-purified products of PCR 21 and 22, 5' primer from PCR 21, and 3' primer from PCR 22 to create the desired product via splicing by overlap extension (C. W. Dieffenbach and G. S. Dveksler (eds.), *PCR Primer: A Laboratory Manual*, (1995), Cold Spring Harbor Laboratory Press, Plainview, N.Y.).

Figure 43:
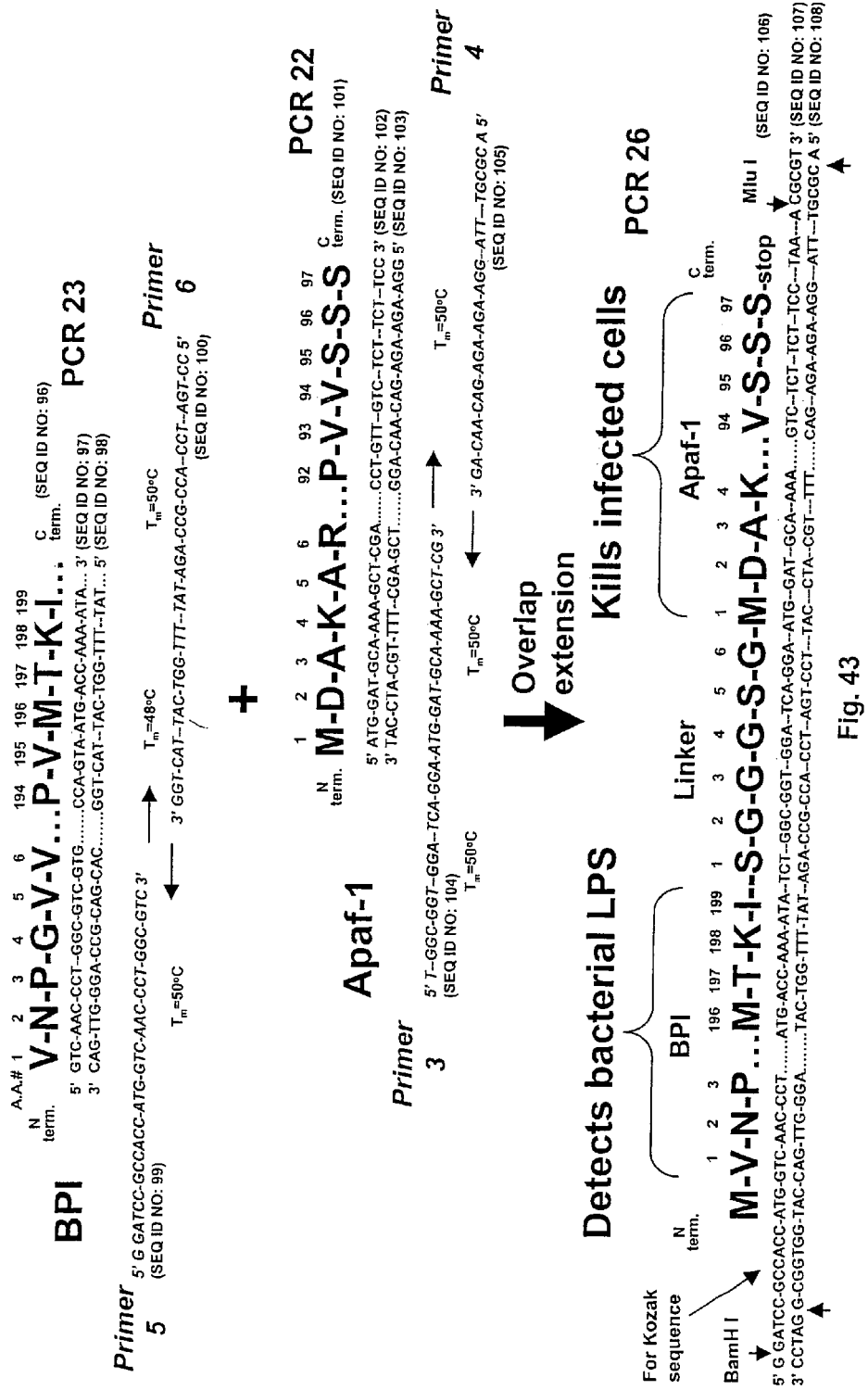
FIG. 43 is a diagram of the synthesis strategy for PCR product 26, which encodes a novel pathogen-activated caspase activator. Lipopolysaccharide (LPS) is a component of pathogens such as bacteria. The LPS-binding domain from BPI (amino acids 1-199) was fused in frame with a short flexible polypeptide linker (amino acid sequence S-G-G-G-S-G (SEQ ID NO: 1)) and amino acids 1-97 of Apaf-1, which included the caspase recruitment domain (CARD) that binds to procaspase 9. A Kozak sequence and stop codon were included, as shown. BamH I and Mlu I restriction sites were included at the ends for ease of insertion into the pTRE2hyg vector. PCR 23 used the indicated 5' and 3' PCR primers to copy the region encoding amino acids 1-199 of BPI from the provided plasmid. PCR 22 used the indicated 5' and 3' PCR primers to copy the region encoding amino acids 1-97 of Apaf-1 from the provided plasmid. PCR 26 used the gel-purified products of PCR 22 and 23, 5' primer from PCR 23, and 3' primer from PCR 22 to create the desired product via splicing by overlap extension.

FIG. 43 illustrates the synthesis strategy for PCR product 26, which encodes a novel pathogen-activated caspase activator. Lipopolysaccharide (LPS) is a component of pathogens such as bacteria. The LPS-binding domain from BPI (amino acids 1-199) was fused in frame with a short flexible polypeptide linker (amino acid sequence S-G-G-G-S-G (SEQ ID NO: 1)) and amino acids 1-97 of Apaf-1, which included the caspase recruitment domain (CARD) that binds to procaspase 9. A Kozak sequence and stop codon were included as shown. BamH I and Mlu I restriction sites were included at the ends for ease of insertion into the pTRE2hyg vector. PCR 23 used the indicated 5' and 3' PCR primers to copy the region encoding amino acids 1-199 of BPI from the provided plasmid. PCR 22 used the indicated 5' and 3' PCR primers to copy the region encoding amino acids 1-97 of Apaf-1 from the provided plasmid. PCR 26 used the gel-purified products of PCR 22 and 23, 5' primer from PCR 23, and 3' primer from PCR 22 to create the desired product via splicing by overlap extension.

Figure 44:
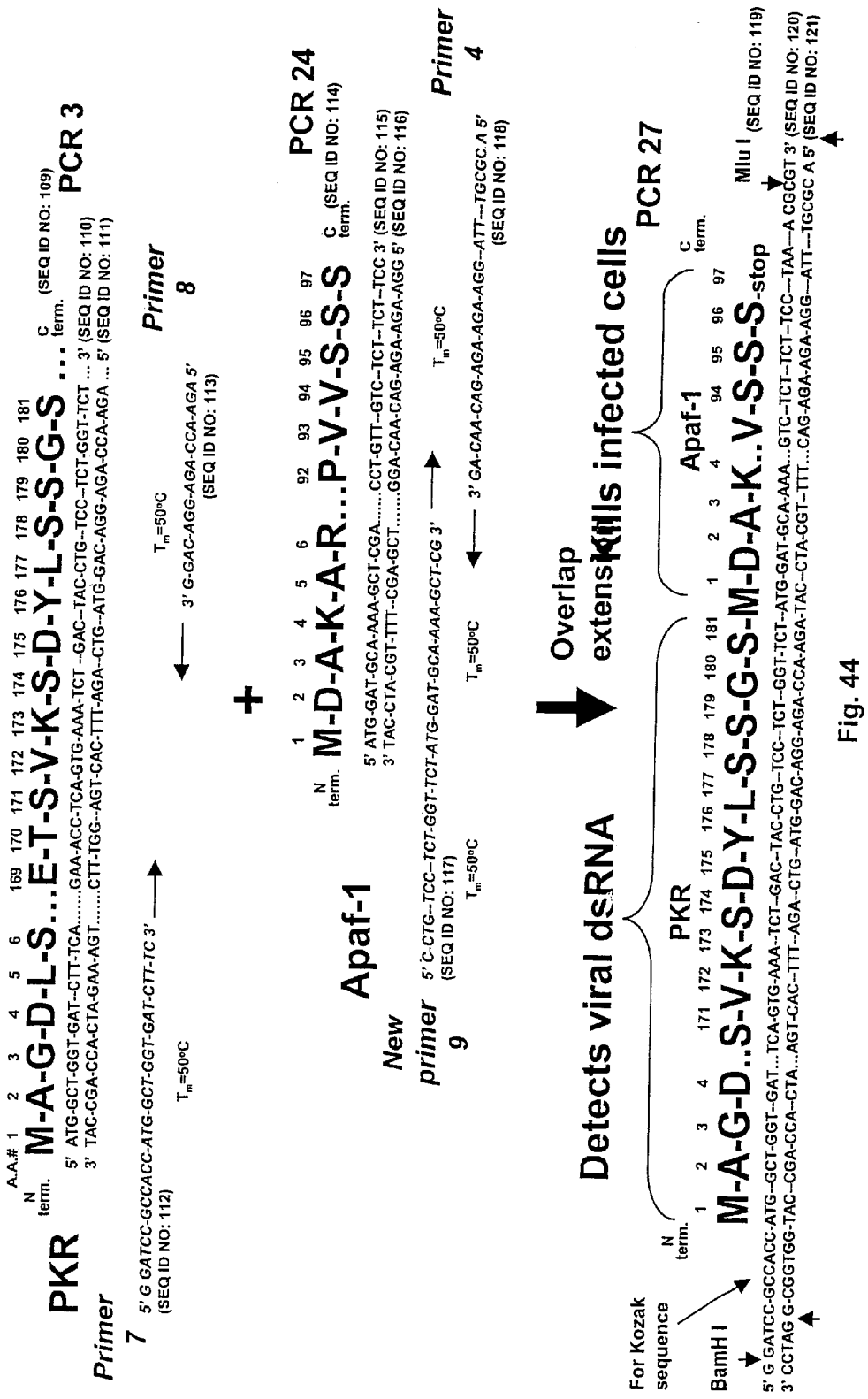
FIG. 44 is a diagram of the synthesis strategy for PCR product 27, which encodes a novel dsRNA-activated caspase activator. The dsRNA-binding domain from PKR (amino acids 1-174) and part of the natural linker region from PKR (amino acids 175-181) were fused in frame with amino acids 1-97 of Apaf-1, which included the caspase recruitment domain (CARD) that binds to procaspase 9. When two or more copies of the protein encoded by PCR 27 are crosslinked by dsRNA, they will crosslink and activate endogenous (pro) caspase 9. A Kozak sequence and stop codon were included, as shown. BamH I and Mlu I restriction sites were included at the ends for ease of insertion into the pTRE2hyg vector. PCR 3 used the indicated 5' and 3' PCR primers to copy the region encoding amino acids 1-181 of PKR from the provided plasmid. PCR 24 used the indicated 5' and 3' PCR primers to copy the region encoding amino acids 1-97 of Apaf-1 from the provided plasmid. PCR 27 used the gel-purified products of PCR 3 and 24, 5' primer from PCR 3, and 3' primer from PCR 24 to create the desired product via splicing by overlap extension.

FIG. 44 illustrates the synthesis strategy for PCR product 27, which encodes a novel dsRNA-activated caspase activator. The dsRNA-binding domain from PKR (amino acids 1-174) and part of the natural linker region from PKR (amino acids 175-181) were fused in frame with amino acids 1-97 of Apaf-1, which included the caspase recruitment domain (CARD) that binds to procaspase 9. When two or more copies of the protein encoded by PCR 27 are crosslinked by dsRNA, they will crosslink and activate endogenous (pro)caspase 9. A Kozak sequence and stop codon were included as shown. BamH I and Mlu I restriction sites were included at the ends for ease of insertion into the pTRE2hyg vector. PCR 3 used the indicated 5' and 3' PCR primers to copy the region encoding amino acids 1-181 of PKR from the provided plasmid. PCR 24 used the indicated 5' and 3' PCR primers to copy the region encoding amino acids 1-97 of Apaf-1 from the provided plasmid. PCR 27 used the gel-purified products of PCR 3 and 24, 5' primer from PCR 3, and 3' primer from PCR 24 to create the desired product via splicing by overlap extension.

Figure 45:
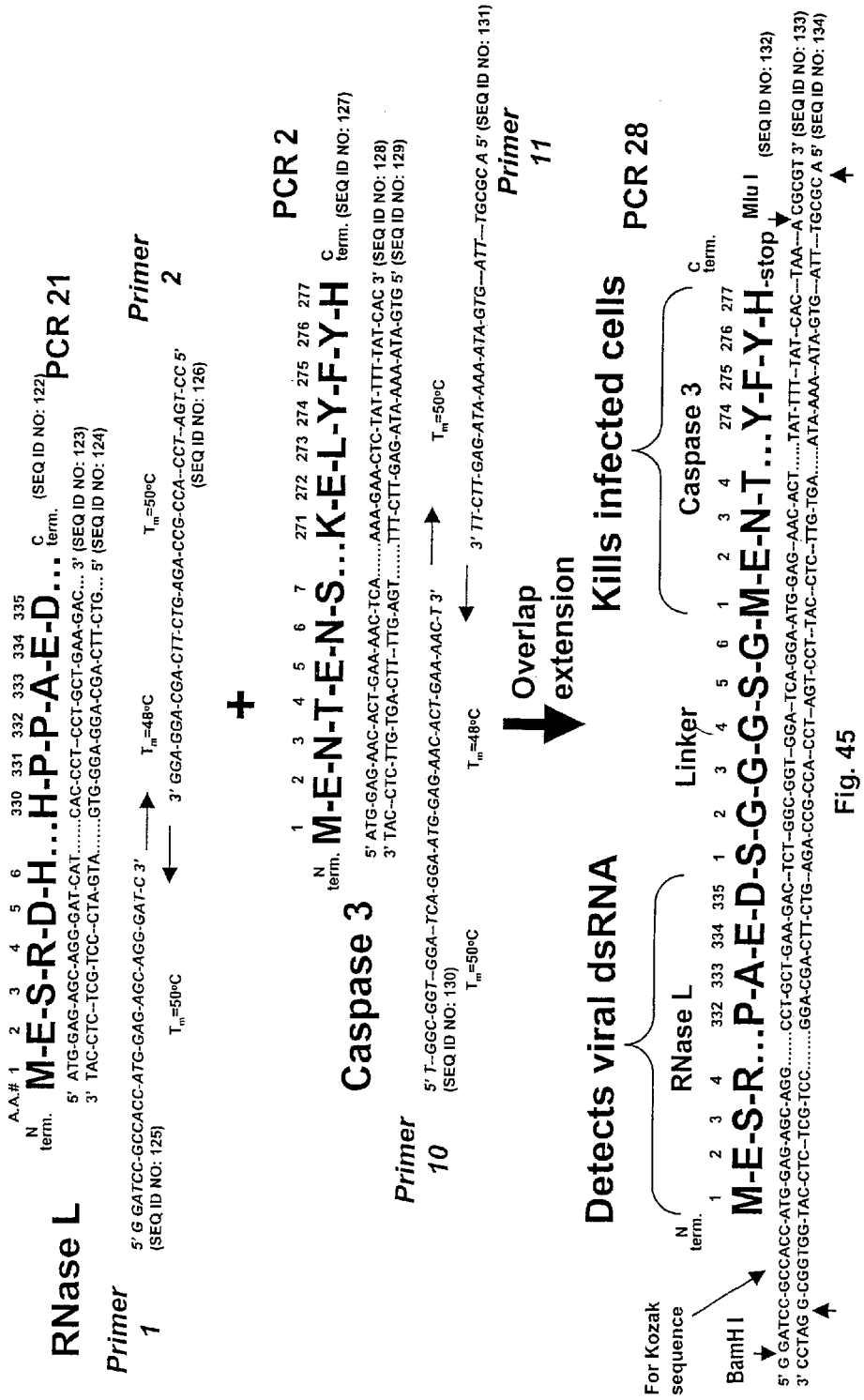
FIG. 45 is a diagram of the synthesis strategy for PCR product 28, which encodes a novel pathogen-activated caspase. 2',5'-oligoadenylate is produced within cells in response to pathogen components such as dsRNA. The 2',5'-oligoadenylate-binding domain from RNase L (amino acids 1-335) was fused in frame with a short flexible polypeptide linker (amino acid sequence S-G-G-G-S-G (SEQ ID NO: 1)) and full-length caspase 3. A Kozak sequence and stop codon were included, as shown. BamH I and Mlu I restriction sites were included at the ends for ease of insertion into the pTRE2hyg vector. PCR 21 used the indicated 5' and 3' PCR primers to copy the region encoding amino acids 1-335 of RNase L from the provided plasmid. PCR 2 used the indicated 5' and 3' PCR primers to copy the coding sequence of caspase 3 from the provided plasmid. PCR 28 used the gel-purified products of PCR 21 and 2, 5' primer from PCR 21, and 3' primer from PCR 2 to create the desired product via splicing by overlap extension.

FIG. 45 illustrates the synthesis strategy for PCR product 28, which encodes a novel pathogen-activated caspase. 2',5'-oligoadenylate is produced within cells in response to pathogen components such as dsRNA. The 2',5'-oligoadenylate-binding domain from RNase L (amino acids 1-335) was fused in frame with a short flexible polypeptide linker (amino acid sequence S-G-G-G-S-G (SEQ ID NO: 1)) and full-length caspase 3. A Kozak sequence and stop codon were included as shown. BamH I and Mlu I restriction sites were included at the ends for ease of insertion into the pTRE2hyg vector. PCR 21 used the indicated 5' and 3' PCR primers to copy the region encoding amino acids 1-335 of RNase L from the provided plasmid. PCR 2 used the indicated 5' and 3' PCR primers to copy the coding sequence of caspase 3 from the provided plasmid. PCR 28 used the gel-purified products of PCR 21 and 2, 5' primer from PCR 21, and 3' primer from PCR 2 to create the desired product via splicing by overlap extension.

Figure 46:
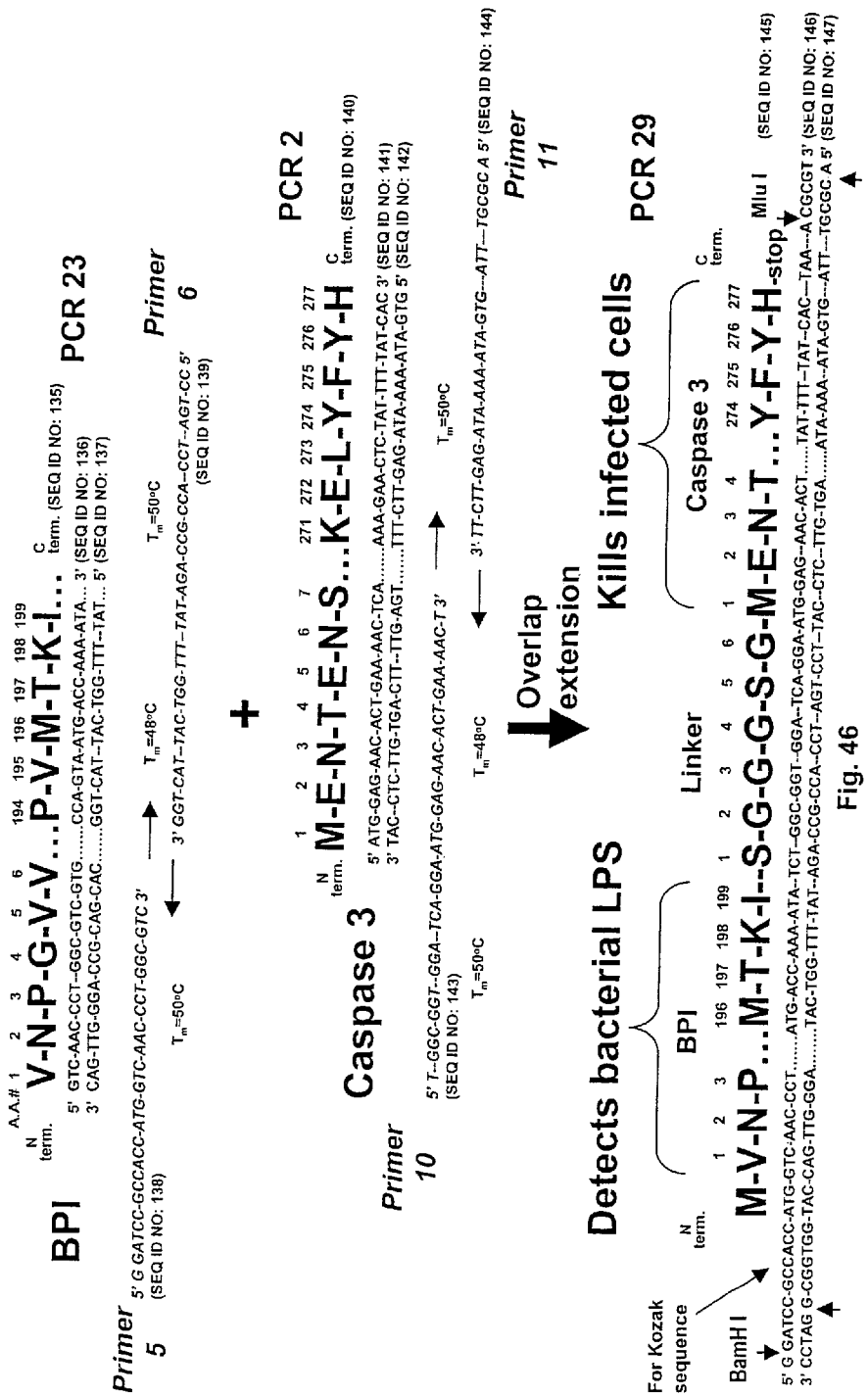
FIG. 46 is a diagram of the synthesis strategy for PCR product 29, which encodes a novel pathogen-activated caspase. Lipopolysaccharide (LPS) is a component of pathogens such as bacteria. The LPS-binding domain from BPI (amino acids 1-199) was fused in frame with a short flexible polypeptide linker (amino acid sequence S-G-G-G-S-G (SEQ ID NO: 1)) and full-length caspase 3. A Kozak sequence and stop codon were included, as shown. BamH I and Mlu I restriction sites were included at the ends for ease of insertion into the pTRE2hyg vector. PCR 23 used the indicated 5' and 3' PCR primers to copy the region encoding amino acids 1-199 of BPI from the provided plasmid. PCR 2 used the indicated 5' and 3' PCR primers to copy the coding sequence of caspase 3 from the provided plasmid. PCR 29 used the gel-purified products of PCR 23 and 2, 5' primer from PCR 23, and 3' primer from PCR 2 to create the desired product via splicing by overlap extension.

FIG. 46 illustrates the synthesis strategy for PCR product 29, which encodes a novel pathogen-activated caspase. Lipopolysaccharide (LPS) is a component of pathogens such as bacteria. The LPS-binding domain from BPI (amino acids 1-199) was fused in frame with a short flexible polypeptide linker (amino acid sequence S-G-G-G-S-G (SEQ ID NO: 1)) and full-length caspase 3. A Kozak sequence and stop codon were included as shown. BamH I and Mlu I restriction sites were included at the ends for ease of insertion into the pTRE2hyg vector. PCR 23 used the indicated 5' and 3' PCR primers to copy the region encoding amino acids 1-199 of BPI from the provided plasmid. PCR 2 used the indicated 5' and 3'

PCR primers to copy the coding sequence of caspase 3 from the provided plasmid. PCR 29 used the gel-purified products of PCR 23 and 2, 5' primer from PCR 23, and 3' primer from PCR 2 to create the desired product via splicing by overlap extension.

Figure 47:
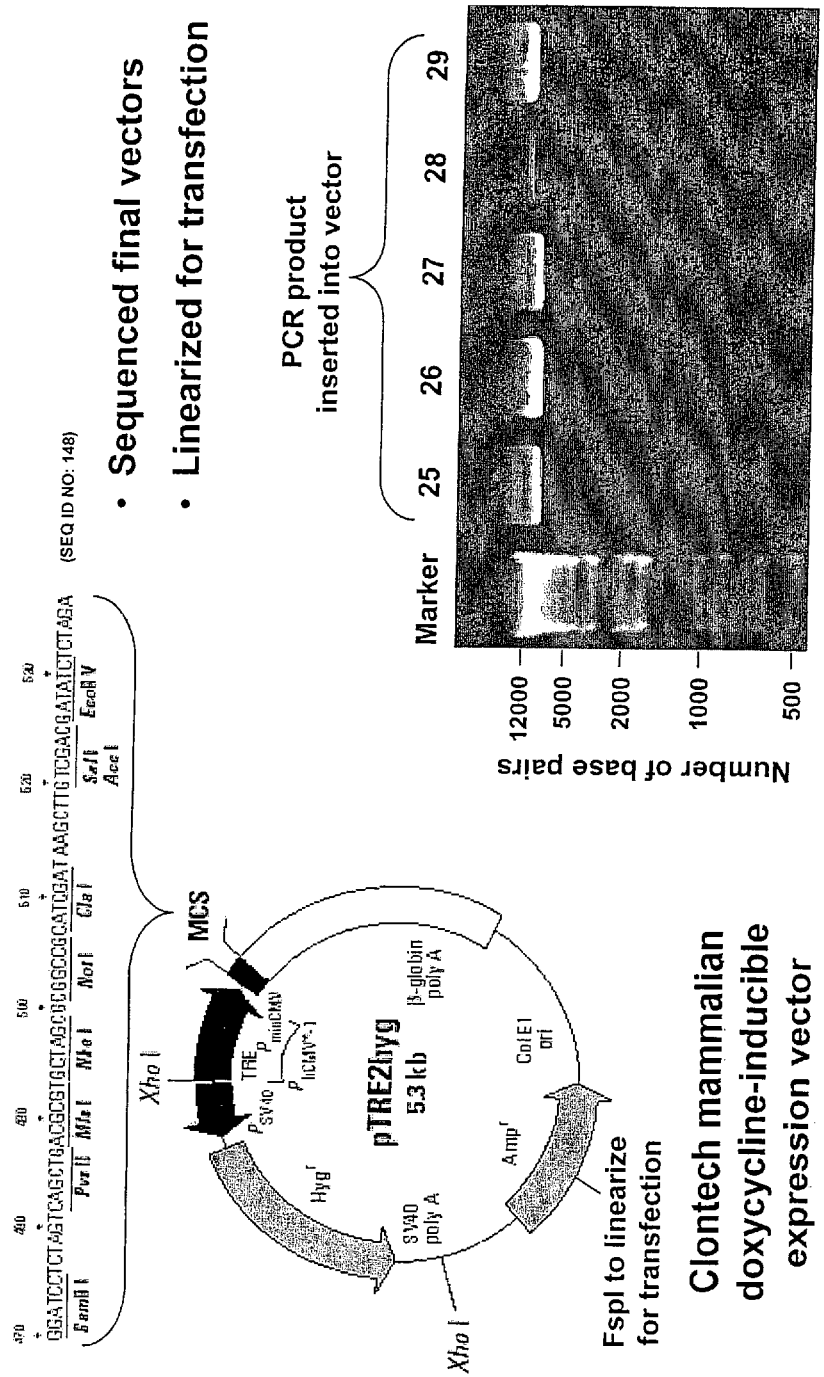
FIG. 47, left panel, is a schematic diagram of a Clontech vector (pTRE2hyg), into which Bam HI and Mlu I restriction enzyme digested PCR products 25, 26, 27, 28, and 29 were ligated into the vector to create expression vectors for PCR 25, 26, 27, 28, and 29. The vectors include a doxycycline or tetracycline-inducible promoter for the inserted gene, as well as a hygromycin resistance gene for selection of transfected cells. All of the vectors with the inserted genes were linearized for transfection using the Fsp I restriction enzyme as shown in the DNA gel electrophoresis photograph in the right panel. DNA size markers are in the left-most lane.
Figure 49:
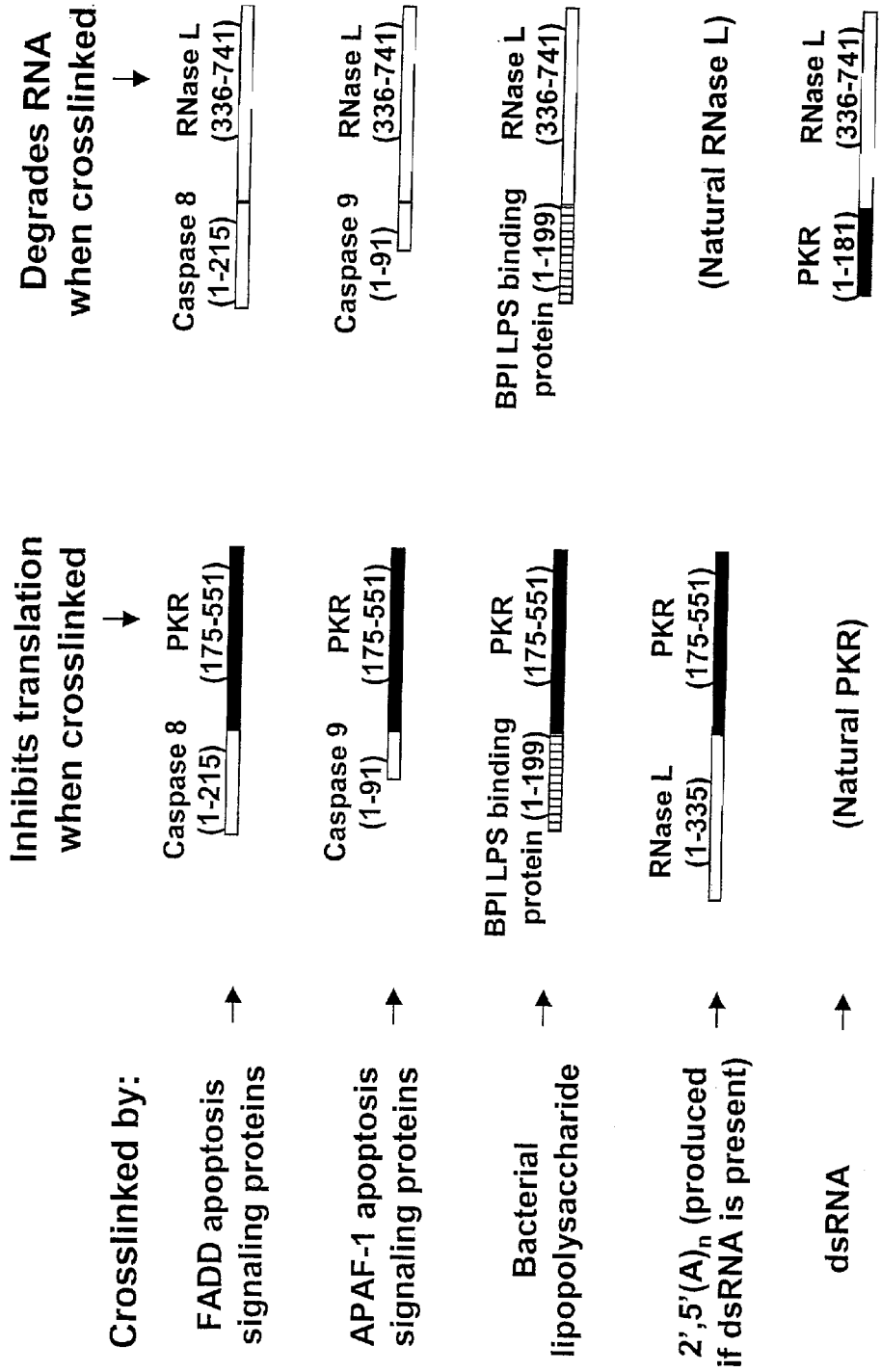
FIG. 49 is an illustration of examples of chimeric proteins.
Figure 50:
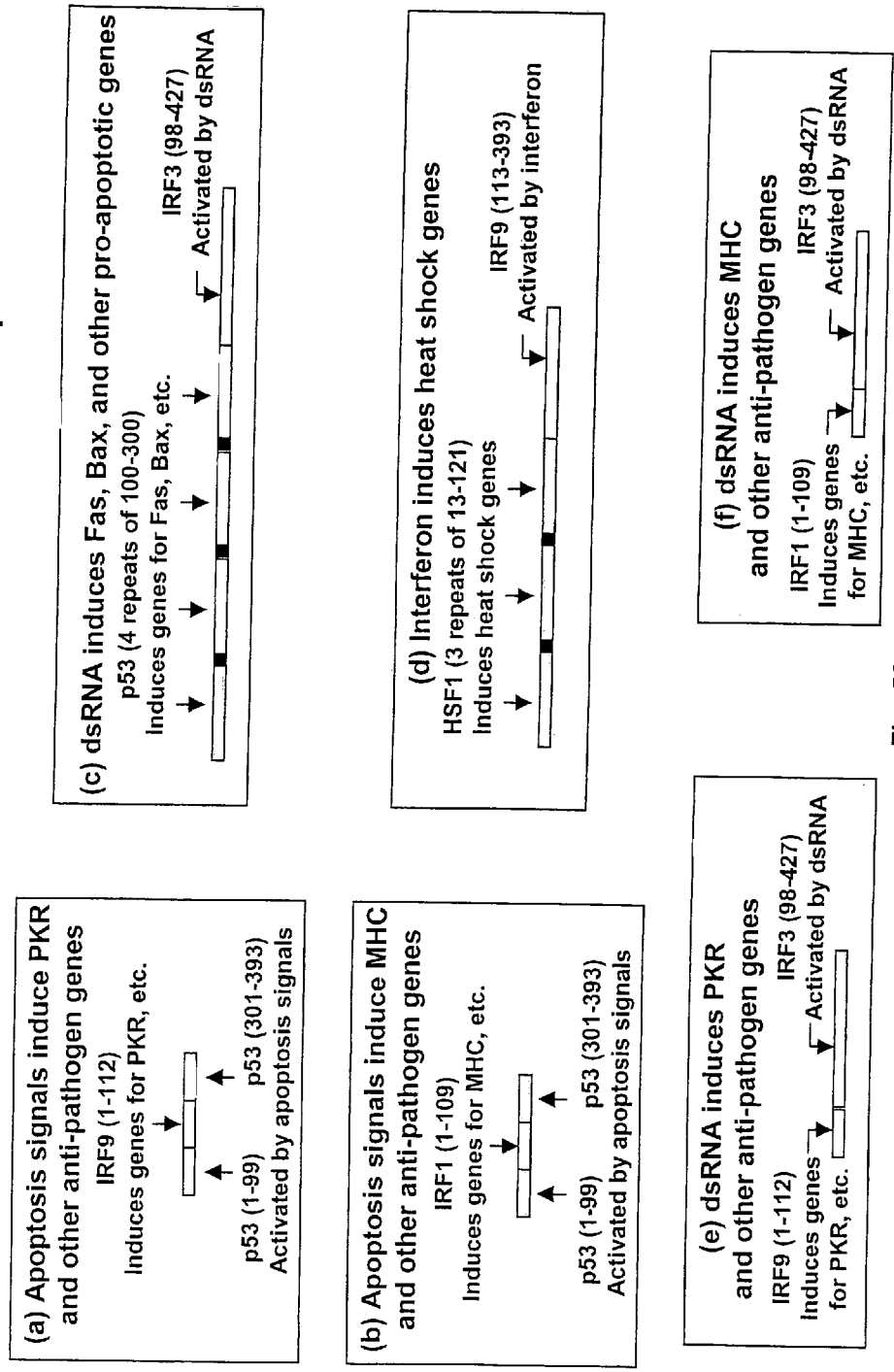
FIGS. 50 (a)-(f) are illustrations of examples of chimeric transcription factors.

PCR products 25, 26, 27, 28, and 29 were gel purified and inserted into the Invitrogen pCR®2.1-TOPO vector following the manufacturer's protocol. The inserts were sequenced on both strands by the Nucleic Acid/Protein Research Core Facility at the Children's Hospital of Philadelphia. The pCR®2.1-TOPO vectors containing PCR products 25 through 29 were digested by BamH I and Mlu I restriction enzymes, and the fragments corresponding to PCR products 25 through 29 were gel purified. The pTRE2hyg vector, shown schematically in FIG. 47, was also digested by BamH I and Mlu I, and the larger resulting fragment was gel purified. Then the digested PCR products 25 through 29 were ligated into the digested vector to create expression vectors for PCR 25, 26, 27, 28, and 29. The vectors include a doxycycline or tetracycline-inducible promoter for the inserted gene, as well as a hygromycin resistance gene for selection of transfected cells. The inserted region of the new vectors was sequenced on both strands by the Nucleic Acid/Protein Research Core Facility at the Children's Hospital of Philadelphia. All of the vectors with the inserted genes were linearized for transfection using the Fsp I restriction enzyme and are shown in the DNA gel electrophoresis photo in FIG. 47.

The 293 Tet-On™ human cell line contains the rtTA regulatory protein necessary for the proper functioning of the tetracycline or doxycycline-inducible promoters. Cells were maintained using standard tissue culture practices, humidified incubators at 37° C. and 5% $CO_2$, and DMEM culture medium containing 10% tetracycline-free fetal bovine serum, 100 μM nonessential amino acids, 1 mM sodium pyruvate, 4 mM L-glutamine, 100 units/ml penicillin G, 100 μg/ml streptomycin, 250 ng/ml amphotericin B, and 100 μg/ml G418.

The linearized pTRE2hyg-derived vectors with inserted PCR 25, 26, 27, 28, or 29 were transfected into the 293 Tet-On™ cells. The transfections use Lipofectamine™ 2000 reagent from Invitrogen and follow Invitrogen's recommended protocol for 293 cells. One day after the transfection, 200 μg/ml hygromycin was added to the cell culture medium to kill any cells that had not been stably transfected with the vectors, and the cells were permanently kept in this concentration of hygromycin as a precaution against the possibility that the cells might lose the transfected genes.

The pools of hygromycin-resistant cells that result from each transfection were presumably genetically heterogeneous, with different cells having different copy numbers of the inserted vector or having the vector inserted into different regions of the cellular genome. Therefore, genetically homogeneous clonal cell populations were isolated. Limiting dilutions of the pools of transfected cells were used to deposit approximately 1 cell per well into 96-well plates, and the cells were allowed to multiply. Wells that appeared to have received more than one initial cell were disregarded. The resulting clonal cell populations were designated 293 25-x, 26-x, 27-x, 28-x, or 29-x; the first number after the cell line name indicates which PCR product from FIGS. 42-46 was transfected into the cells, and the x is replaced with the cell clone number. For example, cell line 293 25-3 indicates PCR product 25, cell clone 3.

Western blots were used to analyze the cell clones. Antibodies listed above in the Materials and Methods section were used to detect fusion proteins containing regions of caspase 3, Apaf-1, and/or BPI. Cells were cultured for two days either with or without doxycycline, and then proteins were extracted from the cells and analyzed by Western blot following the manufacturers' protocols.

Example 6

Anti-pathogen Treatments that Involve Heat Shock Proteins, Import Inhibitors, or dsRNase Plasmids encoding human importin α1 (NCBI Accession #NM_002266), importin α4 (#NM_002267), and importin α6 (#NM_002269) were provided by B. R. Cullen, Duke University. A plasmid encoding *Escherichia coli* (*E. coli*) RNase III (#NP_417062, NC_000913) was from A. W. Nicholson, Wayne State University. A plasmid encoding the human papillomavirus 16 (HPV-16) E5 protein (#W5WLHS) was provided by D. J. McCance, University of Rochester. A plasmid encoding the *Salmonella enterica* SpiC protein (#U51927) was donated by E. A. Groisman, Washington University in St. Louis. Rat $IgG_1$ monoclonal antibodies specific for the hemagglutinin (HA) epitope were provided by Roche. Monoclonal mouse antibodies specific for human Hdj-1 (also known as Hsp40) and human Hsp70 were from Stressgen. Rat antibodies specific for human Hsp90 were provided by Calbiochem. Secondary anti-mouse and anti-rat antibodies were from Santa Cruz Biotechnology and Zymed.

Figure 52:
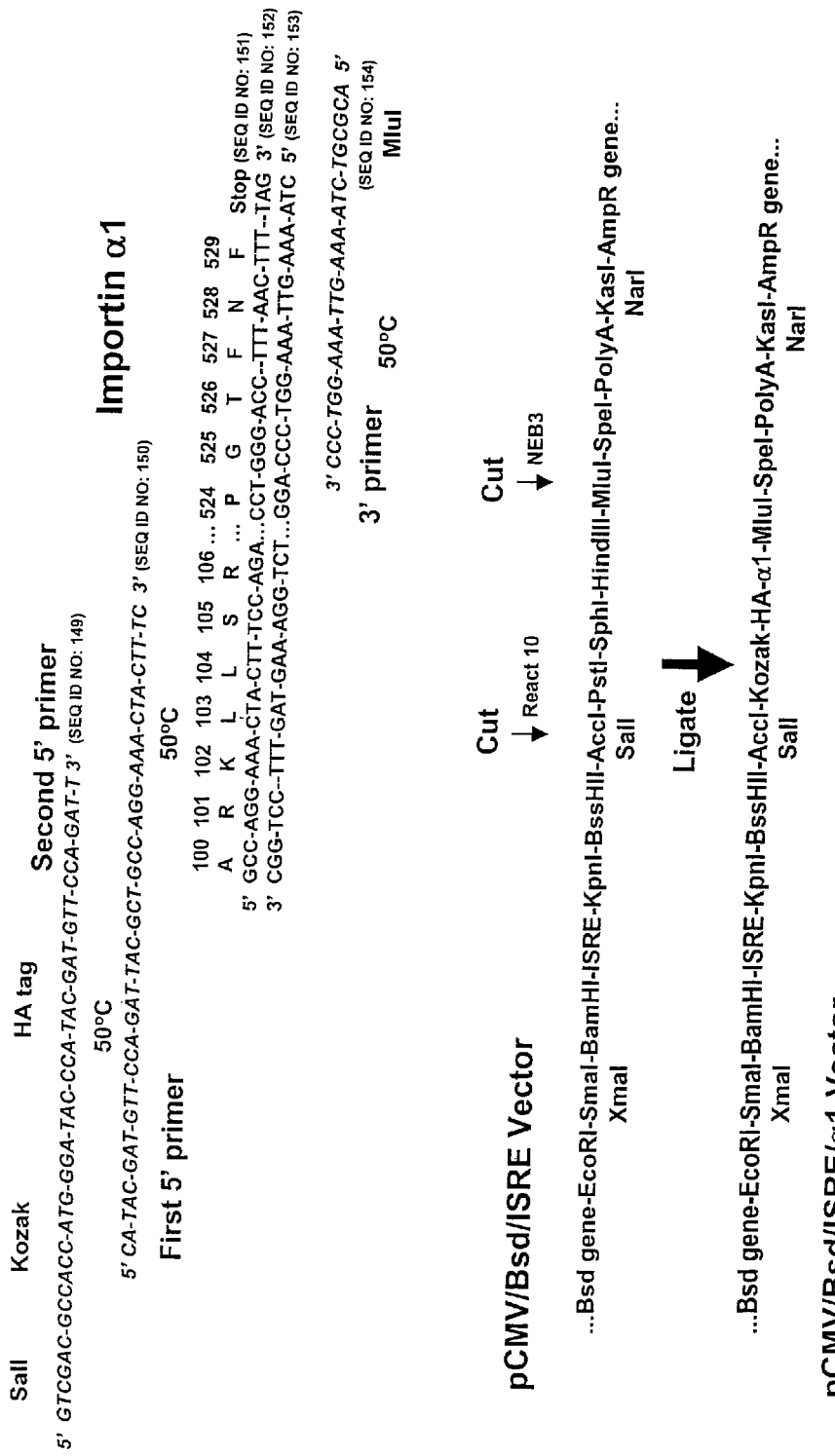
FIG. 52 demonstrates the synthesis strategy for a truncated importin α1 gene and its insertion into the pCMV/Bsd/ISRE vector to produce the new vector pCMV/Bsd/ISRE/α1. It encodes a truncated version of importin α1 that lacks the importin-β-binding domain.

FIG. 52 illustrates the synthesis strategy for a truncated importin α1 gene and its insertion into the pCMV/Bsd/ISRE vector described supra to produce the new vector pCMV/Bsd/ISRE/α1. The region encoding amino acids 100-529 of importin α1 was cloned from the provided plasmid using PCR with the illustrated 3' PCR primer and the first 5' primer. The resulting PCR product was gel purified and used in a subsequent PCR with the same 3' primer and the second 5' primer. This final PCR product includes Sal I and Mlu I restriction sites for ease of insertion into a vector, a Kozak sequence and stop codon for translation, and an HA epitope for detection via immunoassays. It encodes a truncated version of importin α1 that lacks the importin-β-binding domain. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Sal I and Mlu I restriction enzymes, and the fragment corresponding to the PCR product was gel purified. The pCMV/Bsd/ISRE vector was also digested by Sal I and Mlu I, and the larger resulting fragment was gel purified. Then the digested PCR product was ligated into the digested vector to create the expression vector pCMV/Bsd/ISRE/α1.

Figure 53:
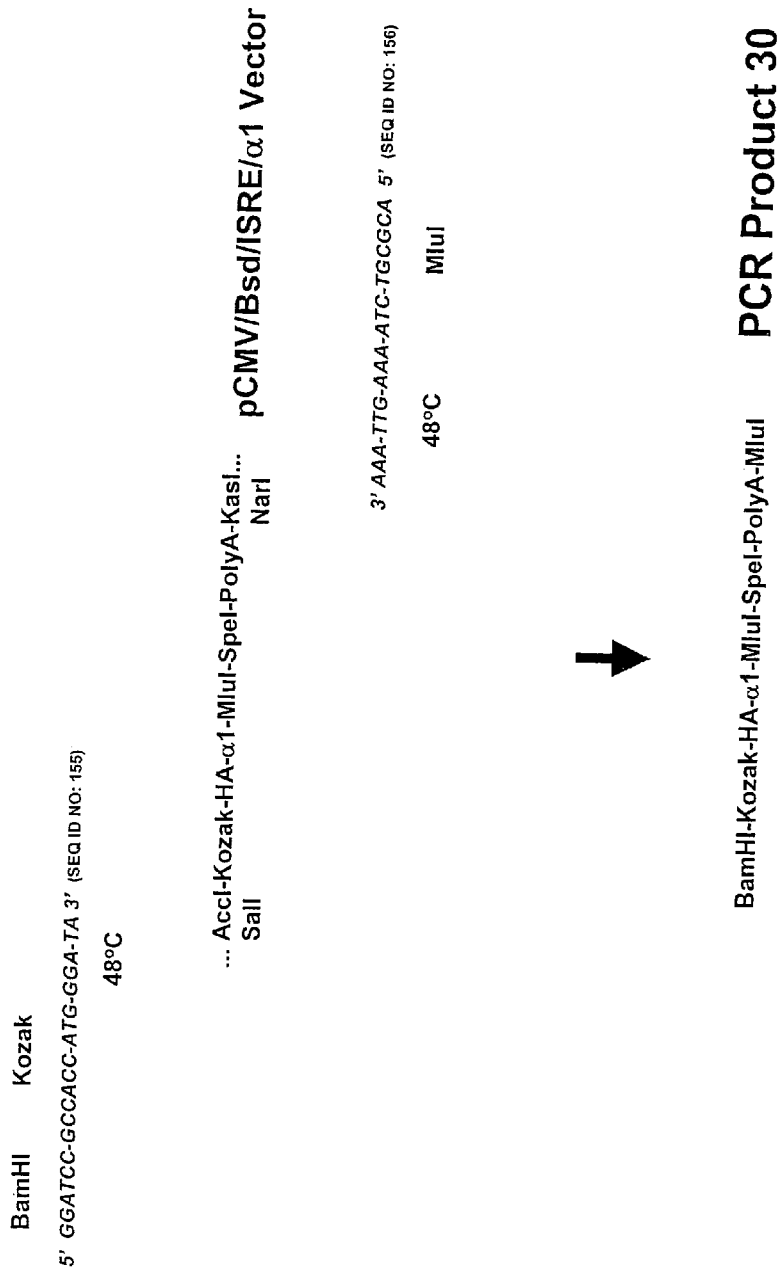
FIG. 53 is a schematic for the production of PCR product 30. It encodes a truncated form of importin α1 that lacks the importin-β-binding domain but includes an HA epitope.

FIG. 53 is a schematic for the production of PCR product 30. PCR was carried out using the illustrated PCR primers and the vector pCMV/Bsd/ISRE/α1. The resulting PCR product 30 has Bam HI and Mlu I restriction sites for ease of insertion into the pTRE2hyg vector. It encodes a truncated form of importin α1 that lacks the importin-β-binding domain but includes an HA epitope.

Figure 54:
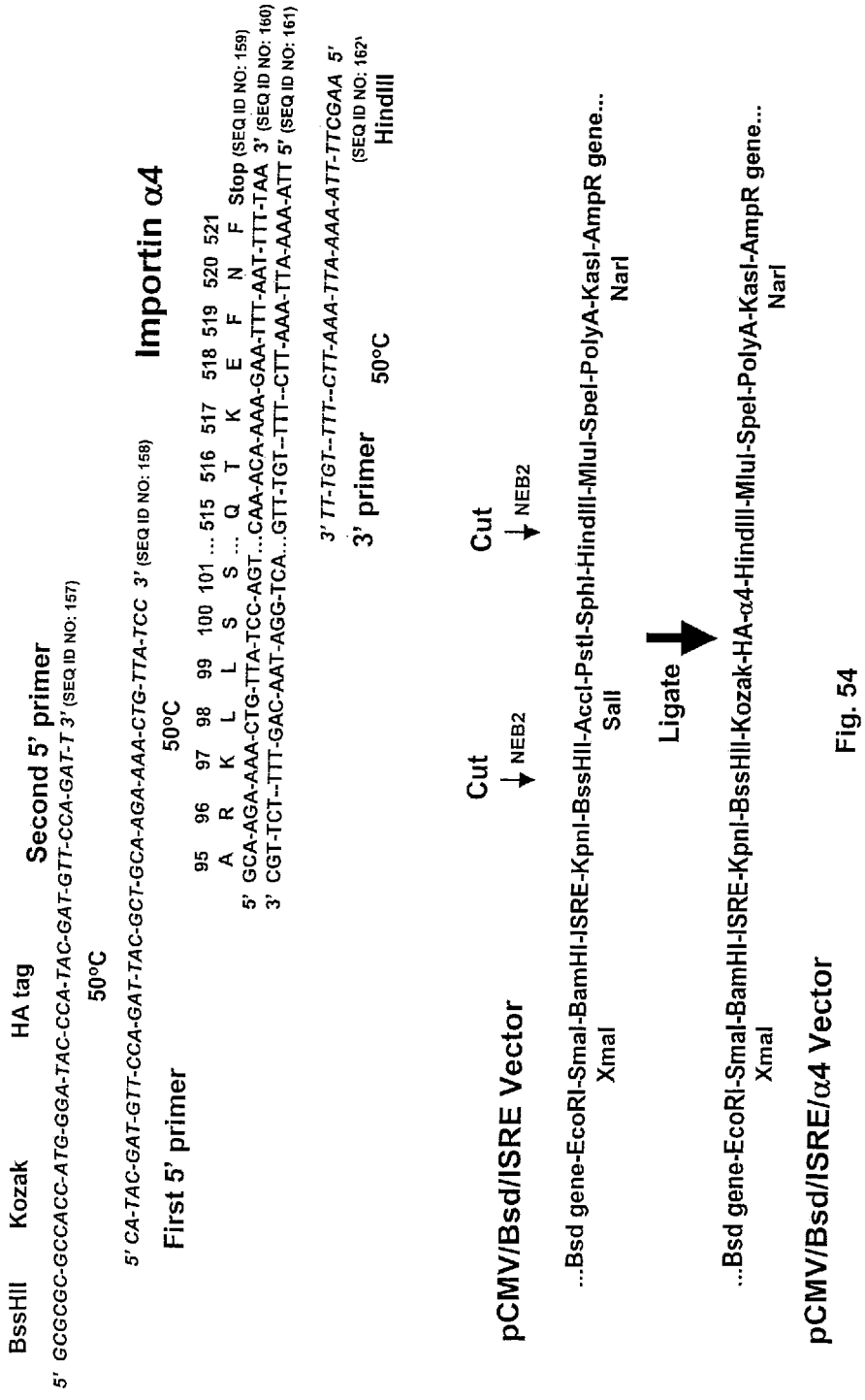
FIG. 54 illustrates the synthesis strategy for a truncated importin α4 gene and its insertion into the pCMV/Bsd/ISRE vector to produce the new vector pCMV/Bsd/ISRE/α4. It encodes a truncated version of importin α4 that lacks the importin-β-binding domain.

FIG. 54 illustrates the synthesis strategy for a truncated importin α4 gene and its insertion into the pCMV/Bsd/ISRE vector described supra to produce the new vector pCMV/Bsd/ISRE/α4. The region encoding amino acids 95-521 of importin α4 was cloned from the provided plasmid using PCR with the illustrated 3' PCR primer and the first 5' primer. The resulting PCR product was gel purified and used in a subsequent PCR with the same 3' primer and the second 5' primer. This final PCR product includes Bss HII and Hind III restriction sites for ease of insertion into a vector, a Kozak sequence and stop codon for translation, and an HA epitope for detection via immunoassays. It encodes a truncated version of importin α4 that lacks the importin-β-binding domain. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Bss HII and Hind III restriction enzymes, and the fragment corresponding to the PCR product was gel purified. The pCMV/Bsd/ISRE vector was also digested by Bss HII and Hind III, and the larger resulting fragment was gel purified. Then the digested PCR product was ligated into the digested vector to create the expression vector pCMV/Bsd/ISRE/α4.

FIG. 55 is a schematic for the production of PCR product 31. PCR was carried out using the illustrated PCR primers and the vector pCMV/Bsd/ISRE/α4. The resulting PCR product 31 has Mlu I and Not I restriction sites for ease of insertion into the pTRE2hyg vector. It encodes a truncated form of importin α4 that lacks the importin-β-binding domain but includes an HA epitope.

Figure 56:
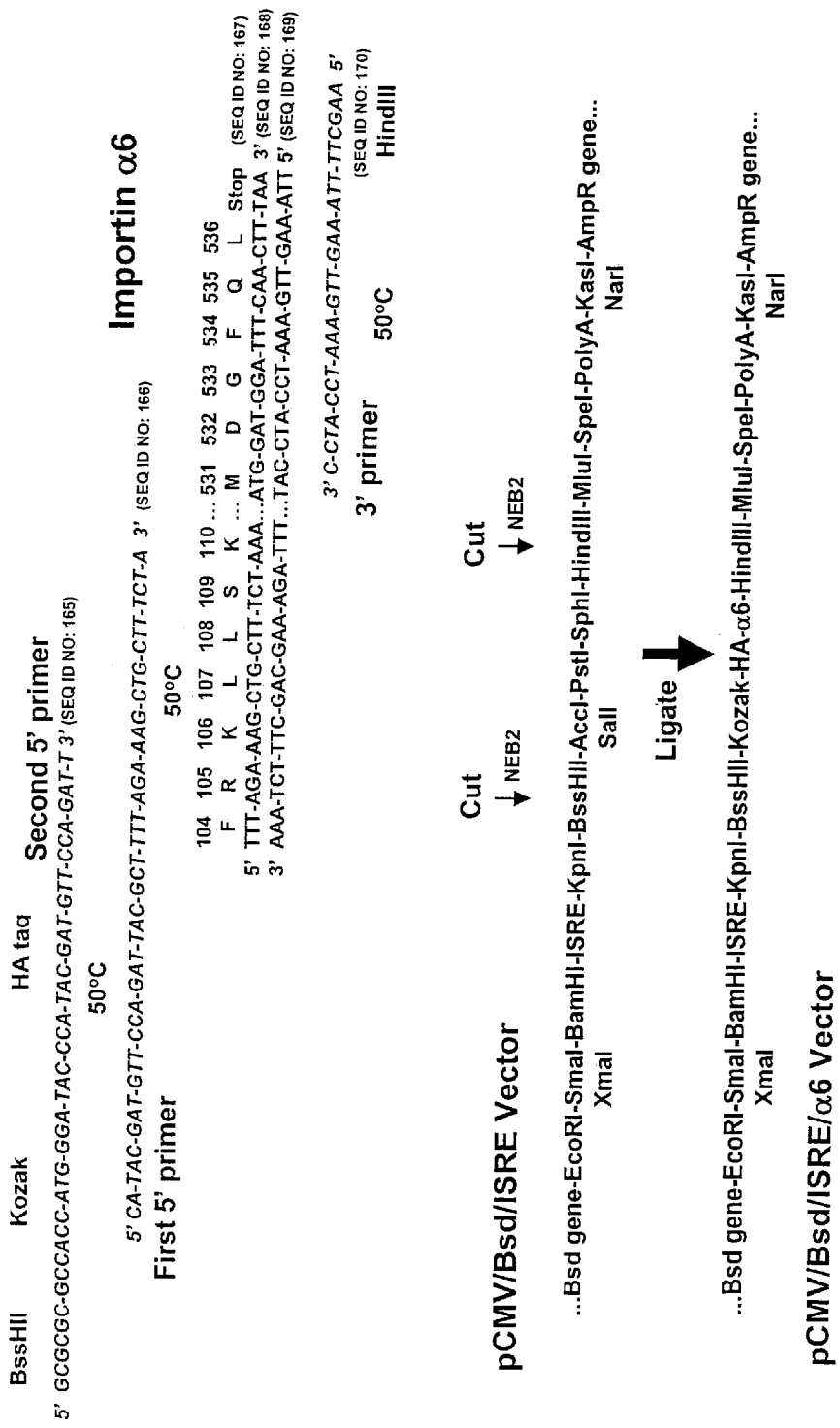
FIG. 56 illustrates the synthesis strategy for a truncated importin α6 gene and its insertion into the pCMV/Bsd/ISRE vector to produce the new vector pCMV/Bsd/ISRE/α6. It encodes a truncated version of importin α6 that lacks the importin-α-binding domain.

FIG. 56 illustrates the synthesis strategy for a truncated importin α6 gene and its insertion into the pCMV/Bsd/ISRE vector described supra to produce the new vector pCMV/Bsd/ISRE/α6. The region encoding amino acids 104-536 of importin α1 was cloned from the provided plasmid using PCR with the illustrated 3' PCR primer and the first 5' primer. The resulting PCR product was gel purified and used in a subsequent PCR with the same 3' primer and the second 5' primer. This final PCR product includes Bss HII and Hind III restriction sites for ease of insertion into a vector, a Kozak sequence and stop codon for translation, and an HA epitope for detection via immunoassays. It encodes a truncated version of importin α6 that lacks the importin-β-binding domain. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Bss HII and Hind III restriction enzymes, and the fragment corresponding to the PCR product was gel purified. The pCMV/Bsd/ISRE vector was also digested by Bss HII and Hind III, and the larger resulting fragment was gel purified. Then the digested PCR product was ligated into the digested vector to create the expression vector pCMV/Bsd/ISRE/α6.

FIG. 57 is a schematic for the production of PCR product 32. PCR was carried out using the illustrated PCR primers and the vector pCMV/Bsd/ISRE/α6. The resulting PCR product 32 has Bam HI and Mlu I restriction sites for ease of insertion into the pTRE2hyg vector. It encodes a truncated form of importin α6 that lacks the importin-β-binding domain but includes an HA epitope.

FIG. 58 illustrates the creation of a gene encoding E. coli RNase III with an HA epitope, and its subsequent insertion into the pCMV/Bsd/ISRE vector described supra to produce the new vector pCMV/Bsd/ISRE/RNase III. The region encoding full-length RNase III was cloned from the provided plasmid using PCR with the illustrated 3' PCR primer and the first 5' primer. The resulting PCR product was gel purified and used in a subsequent PCR with the same 3' primer and the second 5' primer. This final PCR product includes Sal I and Mlu I restriction sites for ease of insertion into a vector, a Kozak sequence and stop codon for translation, and an HA epitope for detection via immunoassays. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Sal I and Mlu I restriction enzymes, and the fragment corresponding to the PCR product was gel purified. The pCMV/Bsd/ISRE vector was also digested by Sal I and Mlu I, and the larger resulting fragment was gel purified. Then the digested PCR product was ligated into the digested vector to create the expression vector pCMV/Bsd/ISRE/RNase III.

Figure 59:
FIG. 59 is a schematic for the production of PCR product 33. PCR was carried out using the illustrated PCR primers and the vector pCMV/Bsd/ISRE/RNase III. It encodes E. coli RNase I with an HA epitope.

FIG. 59 is a schematic for the production of PCR product 33. PCR was carried out using the illustrated PCR primers and the vector pCMV/Bsd/ISRE/RNase III. The resulting PCR product 33 has Bam HI and Mlu I restriction sites for ease of insertion into the pTRE2hyg vector. It encodes E. coli RNase III with an HA epitope.

Figure 60:
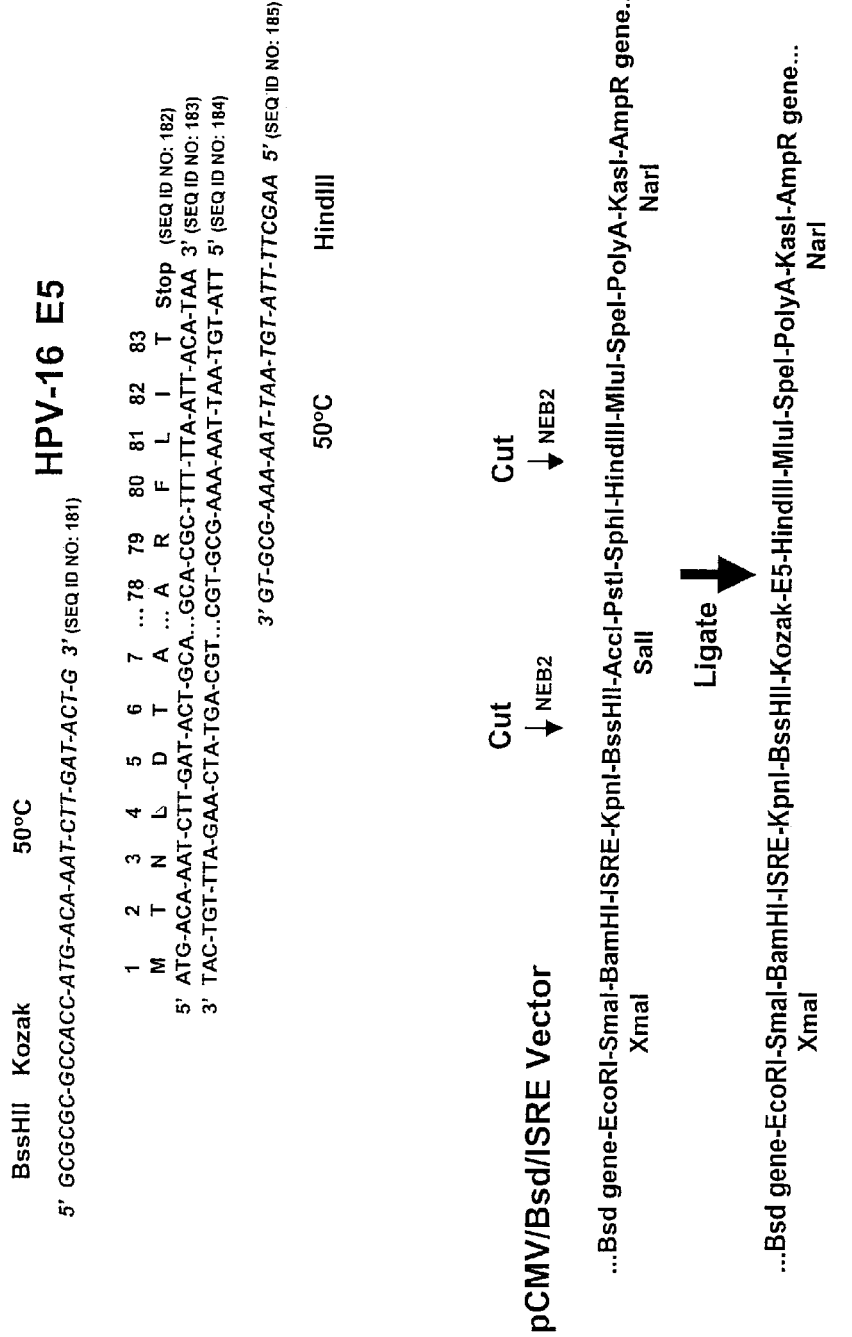
FIG. 60 is a schematic for the insertion of a gene encoding the HPV-16 E5 protein into the pCMV/Bsd/ISRE vector to produce the new vector pCMV/Bsd/ISRE/E5.

FIG. 60 is a schematic for the insertion of a gene encoding the HPV-16 E5 protein into the pCMV/Bsd/ISRE vector described supra to produce the new vector pCMV/Bsd/ISRE/E5. The region encoding full-length RNase III was cloned from the provided plasmid using PCR with the illustrated 5' and 3' PCR primers. The PCR product includes Bss HII and Hind III restriction sites for ease of insertion into a vector, and a Kozak sequence and stop codon for translation. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Bss HII and Hind III restriction enzymes, and the fragment corresponding to the PCR product was gel purified. The pCMV/Bsd/ISRE vector was also digested by Bss HII and Hind III, and the larger resulting fragment was gel purified. Then the digested PCR product was ligated into the digested vector to create the expression vector pCMV/Bsd/ISRE/E5.

Figure 61:
FIG. 61 is a schematic for the production of PCR product 34. PCR was carried out using the illustrated PCR primers and the vector pCMV/Bsd/ISRE/E5. It encodes the HPV-16 E5 protein.

FIG. 61 is a schematic for the production of PCR product 34. PCR was carried out using the illustrated PCR primers and the vector pCMV/Bsd/ISRE/E5. The resulting PCR product 34 has Bam HI and Mlu I restriction sites for ease of insertion into the pTRE2hyg vector. It encodes the HPV-16 E5 protein.

Figure 62:
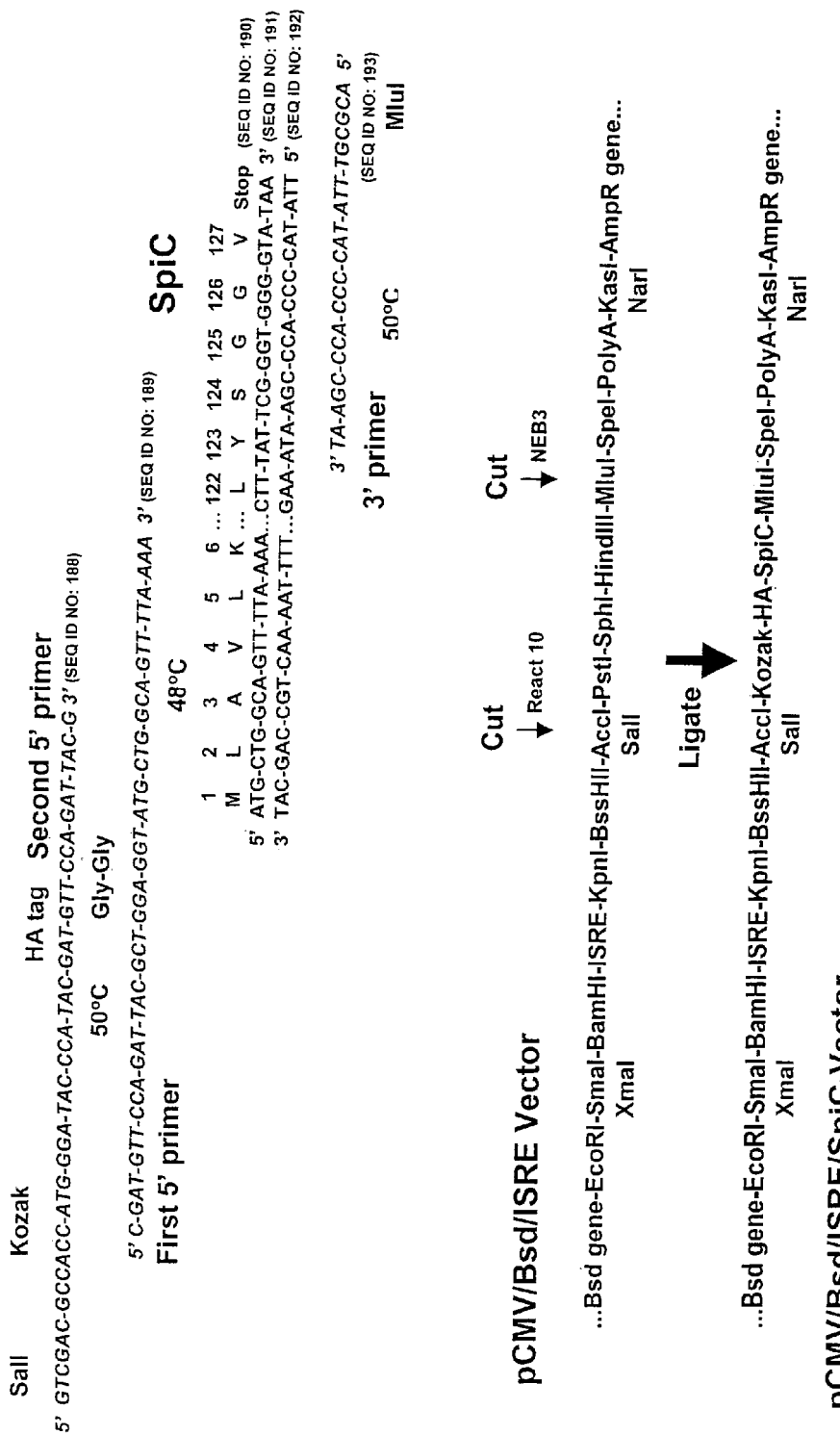
FIG. 62 illustrates the synthesis strategy for a gene encoding the *Salmonella* SpiC protein with an HA epitope, and its subsequent insertion into the pCMV/Bsd/ISRE vector to produce the new vector pCMV/Bsd/ISRE/SpiC.

FIG. 62 illustrates the synthesis strategy for a gene encoding the *Salmonella* SpiC protein with an HA epitope, and its subsequent insertion into the pCMV/Bsd/ISRE vector described supra to produce the new vector pCMV/Bsd/ISRE/SpiC. The region encoding full-length SpiC was cloned from the provided plasmid using PCR with the illustrated 3' PCR primer and the first 5' primer. The resulting PCR product was gel purified and used in a subsequent PCR with the same 3' primer and the second 5' primer. This final PCR product includes Sal I and Mlu I restriction sites for ease of insertion into a vector, a Kozak sequence and stop codon for translation, and an HA epitope for detection via immunoassays. This PCR product was gel purified and inserted into the Invitrogen pCR®2.1-TOPO vector following the manufacturer's protocol. The insert was sequenced on both strands by the Nucleic Acid/Protein Research Core Facility at the Children's Hospital of Philadelphia. The pCR®2.1-TOPO vector containing the PCR insert was digested by Sal I and Mlu I restriction enzymes, and the fragment corresponding to the PCR product was gel purified. The pCMV/Bsd/ISRE vector was also digested by Sal I and Mlu I, and the larger resulting fragment was gel purified. Then the digested PCR product was ligated into the digested vector to create the expression vector pCMV/Bsd/ISRE/SpiC.

FIG. 63 is a schematic for the production of PCR product 35. PCR was carried out using the illustrated PCR primers and the vector pCMV/Bsd/ISRE/SpiC. The resulting PCR product 35 has Bam HI and Mlu I restriction sites for ease of insertion into the pTRE2hyg vector. It encodes the *Salmonella* SpiC protein with an HA epitope.

Figure 64:
FIG. 64 is a schematic for the production of PCR product 36. PCR was carried out using the illustrated PCR primers and the vector pCMV/Bsd/ISRE/Hdj1. The resulting PCR product 36 has Bam HI and Mlu I restriction sites for ease of insertion into the pTRE2hyg vector. It encodes human Hdj-1, also known as Hsp40.

FIG. 64 is a schematic for the production of PCR product 36. PCR was carried out using the illustrated PCR primers and the vector pCMV/Bsd/ISRE/Hdj 1. The resulting PCR product 36 has Bam HI and Mlu I restriction sites for ease of insertion into the pTRE2hyg vector. It encodes human Hdj-1, also known as Hsp40.

Figure 65:
FIG. 65 is a schematic for the production of PCR product 37. The resulting PCR product 37 has Bam HI and Mlu I restriction sites for ease of insertion into the pTRE2hyg vector. It encodes human Hsp70.

FIG. 65 is a schematic for the production of PCR product 37. PCR was carried out using the illustrated PCR primers and the vector pCMV/Bsd/ISRE/Hsp70. The resulting PCR product 37 has Bam HI and Mlu I restriction sites for ease of insertion into the pTRE2hyg vector. It encodes human Hsp70.

Figure 66:
FIG. 66 is a schematic for the production of PCR product 38. It encodes human Hsp90.

FIG. 66 is a schematic for the production of PCR product 38. PCR was carried out using the illustrated PCR primers and the vector pCMV/Bsd/ISRE/Hsp90. The resulting PCR product 38 has Mlu I and Not I restriction sites for ease of insertion into the pTRE2hyg vector. It encodes human Hsp90.

PCR products 30, 31, 32, 33, 34, 35, 36, 37, and 38 were gel purified and inserted into the Invitrogen pCR®2.1-TOPO vector following the manufacturer's protocol. The inserts were sequenced on both strands by the Nucleic Acid/Protein Research Core Facility at the Children's Hospital of Philadelphia.

The pCR®2.1-TOPO vectors containing PCR products 30, 32, 33, 34, 35, 36, and 37 were digested by BamH I and Mlu I restriction enzymes, and the fragments corresponding to the PCR products were gel purified. The pTRE2hyg vector was also digested by BamH I and Mlu I, and the larger resulting fragment was gel purified. Then the digested PCR products were ligated into the digested vector to create expression vectors for PCR 30, 32, 33, 34, 35, 36, and 37.

The pCR®2.1-TOPO vectors containing PCR products 31 and 38 were digested by Mlu I and Not I restriction enzymes, and the fragments corresponding to the PCR products were gel purified. The pTRE2hyg vector was also digested by Mlu I and Not I, and the larger resulting fragment was gel purified. Then the digested PCR products were ligated into the digested vector to create expression vectors for PCR 31 and 38.

Figure 67:
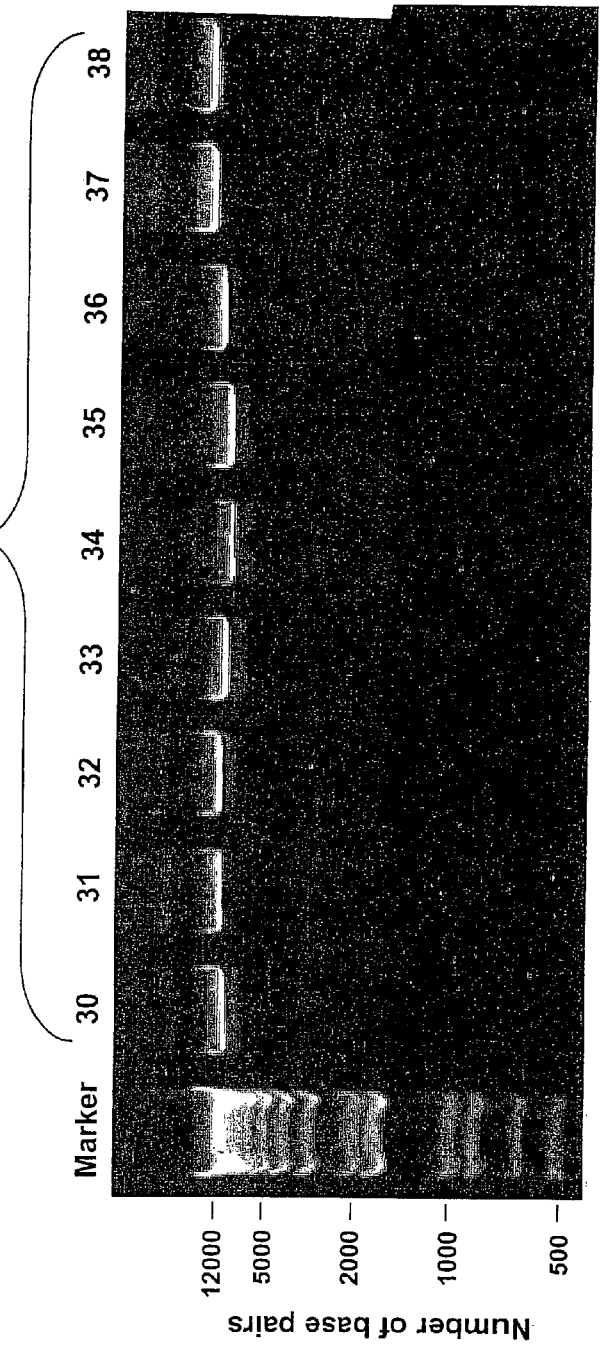
FIG. 67 is a photograph of the linearized vectors with the inserted products PCR 30-38 for transfection after electrophoresis in an agarose gel. The far left lane contains a DNA size marker.

The expression vectors include a doxycycline or tetracycline-inducible promoter for the inserted gene, as well as a hygromycin resistance gene for selection of transfected cells. The inserted region of the new vectors was sequenced on both strands by the Nucleic Acid/Protein Research Core Facility at the Children's Hospital of Philadelphia. All of the vectors with the inserted genes were linearized for transfection using the Fsp I restriction enzyme (except the vector with PCR 37, which was linearized with Apa I) and purified with the Zymo Research DNA Clean & Concentrator kit. The prepared vectors are shown in the DNA gel electrophoresis photo in FIG. 67.

The 293 Tet-On™ human cell line contains the rtTA regulatory protein necessary for the proper functioning of the tetracycline or doxycycline-inducible promoters. Cells were maintained using standard tissue culture practices, humidified incubators at 37° C. and 5% $CO_2$, and DMEM culture medium containing 10% tetracycline-free fetal bovine serum, 100 µM nonessential amino acids, 1 mM sodium pyruvate, 4 mM L-glutamine, 100 units/ml penicillin G, 100 µg/ml streptomycin, 250 ng/ml amphotericin B, and 100 µg/ml G418.

The linearized pTRE2hyg-derived vectors with inserted PCR 30, 31, 32, 33, 34, 35, 36, 37, or 38 were transfected into the 293 Tet-On™ cells. The transfections use Lipofectamine™ 2000 reagent from Invitrogen and follow Invitrogen's recommended protocol for 293 cells. One day after the transfection, 200 µg/ml hygromycin was added to the cell culture medium to kill any cells that have not been stably transfected with the vectors, and the cells were permanently kept in this concentration of hygromycin as a precaution against the possibility that the cells might lose the transfected genes.

The pools of hygromycin-resistant cells that result from each of these transfections were presumably genetically heterogeneous, with different cells having different copy numbers of the inserted vector or having the vector inserted into different regions of the cellular genome. Therefore, genetically homogeneous clonal cell populations were isolated. Limiting dilutions of the pools of transfected cells were used to deposit approximately 1 cell per well into 96-well plates, and the cells were allowed to multiply. Wells that appear to have received more than one initial cell were disregarded. The resulting clonal cell populations were designated 293 30-x, 31-x, 32-x, 33-x, 34-x, 35-x, 36-x, 37-x, or 38-x; the first number indicates which PCR product was transfected into the cells, and the x is replaced with the cell clone number. For example, cell line 293 30-3 indicates PCR product 30, cell clone 3.

H1-HeLa cells were maintained using standard tissue culture practices, humidified incubators at 37° C. and 5% $CO_2$, and DMEM culture medium containing 10% fetal bovine serum, 100 µM nonessential amino acids, 1 mM sodium pyruvate, 4 mM L-glutamine, 100 units/ml penicillin G, 100 µg/ml streptomycin, and 250 ng/ml amphotericin B.

The new expression vectors derived from pCMV/Bsd/ISRE were linearized with the Apa I restriction enzyme, purified with the Zymo Research DNA Clean & Concentrator kit, and transfected into the H1-HeLa cells. The transfections use LIPOFECTIN® and PLUS reagents from Invitrogen and follow Invitrogen's recommended protocol for HeLa cells. One day after the transfection, 4 µg/ml blasticidin was added to the cell culture medium to kill any cells that have not been stably transfected with the vectors, and the cells were permanently kept in blasticidin as a precaution against the possibility that the cells might lose the transfected genes.

The pools of blasticidin-resistant cells that result from each of these transfections were presumably genetically heterogeneous, with different cells having different copy numbers of the inserted vector or having the vector inserted into different regions of the cellular genome. Therefore, genetically homogeneous clonal cell populations were isolated. Limiting dilutions of the pools of transfected cells were used to deposit approximately 1 cell per well into 96-well plates, and the cells were allowed to multiply. Wells that appear to have received more than one initial cell were disregarded.

Example 7

Production and Testing of Anti-pathogen Proteins that can be Transduced into Cells in vitro or in vivo Materials The vector pET100/D-TOPO®, *E. coli* strain BL21(DE) pLysS, Ni-NTA purification kit with anti-Xpress™ antibodies, EKMax™ enterokinase, and EK-Away™ resin are obtained from Invitrogen. The vector pCMV.IRES.AEQ was provided by D. Button, Stanford University, and the vector pEGFP-IRES-puro is from Clontech.

Methods

Figure 68:
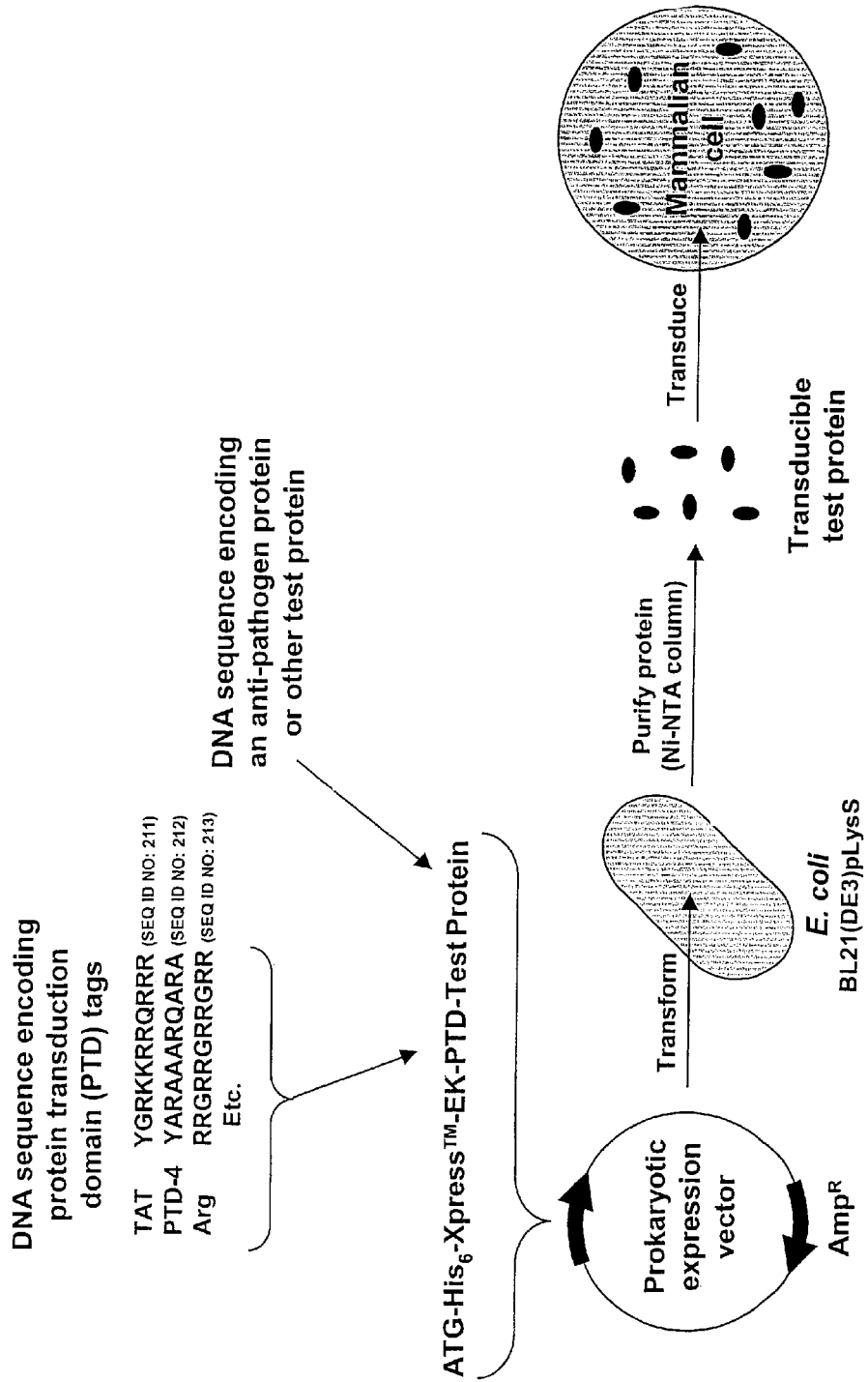
FIG. 68 illustrates schematically how to produce test proteins that contain protein transduction domains or tags.

FIG. 68 illustrates schematically how to produce test proteins that contain protein transduction domains or tags. The tag can have an amino acid sequence such as one of those shown from HIV TAT (S. R. Schwarze, K. A. Hruska, and S. F. Dowdy (2000) *Trends in Cell Biology* 10, 290-295), PTD-4 (A. Ho et al. (2001) *Cancer Research* 61, 474-477), an arginine-rich sequence (P. A. Wender et al. (2000) *Proc. Natl. Acad. Sci.* 97, 13003-13008; J. B. Rothbard et al. (2002) *J. Med. Chem.* 45, 3612-3618), or any other amino acid sequence that facilitates uptake and/or targeting to cells in vitro or in vivo. The encoded test protein can have antipathogen effects or be any other protein or amino acid sequence. The PTD sequence is fused in frame at either end of the test protein or within the test protein. The DNA sequence encoding the fused PTD and test protein is inserted into an expression vector. The illustrated vector is a prokaryotic vector, but an expression vector for yeast, insect cells, mammalian cells, in vitro transcription and translation systems, or other protein expression system can be used. Any suitable prokaryotic expression vector can be used; the example illustrated is the Invitrogen pET100/D-TOPO® vector, which encodes a six-histidine tag for protein purification, Xpress™ epitope for immunoassays, and enterokinase site for cleavage.

The expression vector is transformed into a suitable expression system, as will be understood by one of skill in the art, which in the illustrated example is the *E. coli* strain BL21(DE)pLysS. After approximately 6-24 hours, the tagged expressed protein is harvested from the expression system using the Invitrogen Ni-NTA purification kit and following either the manufacturer's directions or the protocol in M. Becker-Hapak, S. S. McAllister, and S. F. Dowdy (2001) *Methods* 24, 247-256. Protocols for either denatured protein or soluble protein product can be followed. If desired, Invitrogen EKMax™ enterokinase and EK-Away™ resin are used as per the manufacturer's directions to remove the six-histidine and Xpress™ tags and re-purify the protein.

FIG. 69 illustrates PCR primers for producing a DNA sequence encoding aequorin fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and the vector pCMV.IRES.AEQ; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and the vector pCMV.IRES.AEQ; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and the vector pCMV.IRES.AEQ; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and the vector pCMV.IRES.AEQ; the resulting PCR product is gel purified and inserted into the pET100/D-TOPO® vector following the manufacturer's directions. The inserts in pET100/D-TOPO® are sequenced on both strands for sequence confirmation. Transducible aequorin is used to evaluate the relative efficiencies of the protein transduction tags.

FIG. 70 illustrates PCR primers for producing a DNA sequence encoding enhanced green fluorescent protein (EGFP) fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and the vector pEGFP-IRES-puro; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and the vector pEGFP-IRES-puro; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and the vector pEGFP-IRES-puro; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and the vector pEGFP-IRES-puro; the resulting PCR product is gel purified and inserted into the pET100/D-TOPO® vector following the manufacturer's directions. The inserts in pET100/D-TOPO® are sequenced on both strands for sequence confirmation. Transducible EGFP is used to evaluate the relative efficiencies of the protein transduction tags.

FIG. 71 illustrates PCR primers for producing a DNA sequence that includes the coding sequence from PCR product 7 or 8 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 7 or 8 or a vector that contains of one of them; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 7 or 8 or a vector that contains of one of them; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 7 or 8 or a vector that contains of one of them; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 7 or 8 or a vector that contains of one of them; the resulting PCR product is gel purified and inserted into the pET100/D-TOPO® vector following the manufacturer's directions. The inserts in pET100/D-TOPO® are sequenced on both strands for sequence confirmation.

FIG. 72 illustrates PCR primers for producing a DNA sequence that includes the coding sequence from PCR product 9 or 10 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 9 or 10 or a vector that contains of one of them; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 9 or 10 or a vector that contains of one of them; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 9 or 10 or a vector that contains of one of them; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 9 or 10 or a vector that contains of one of them; the resulting PCR product is gel purified and inserted into the pET100/D-TOPO® vector following the manufacturer's directions. The inserts in pET100/D-TOPO® are sequenced on both strands for sequence confirmation.

FIG. 73 illustrates PCR primers for producing a DNA sequence that includes the coding sequence from PCR product 25 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 25 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 25 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 25 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 25 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

Figure 74:
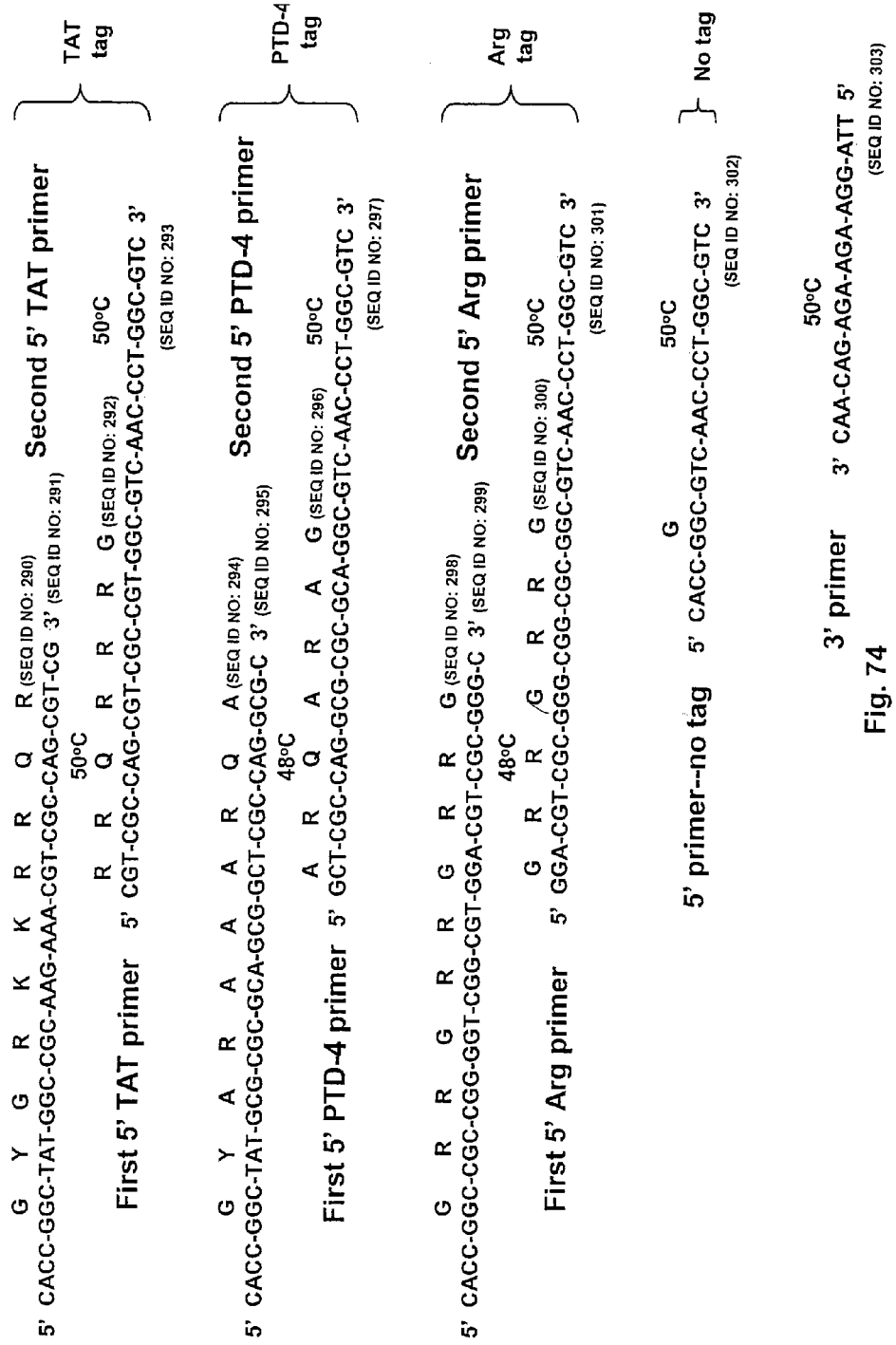
FIG. 74 illustrates PCR primers for producing a DNA sequence that includes the coding sequence from PCR product 26 fused to one of the following protein transduction tags: TAT, PTD-4, an arginine-rich sequence Arg, or no protein transduction tag.

FIG. 74 illustrates PCR primers for producing a DNA sequence that includes the coding sequence from PCR product 26 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 26 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 26 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 26 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 26 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 75 illustrates PCR primers for producing a DNA sequence that includes the coding sequence from PCR product 27 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 27 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 27 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 27 or a vector that contains that PCR product;

the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 27 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 76 illustrates PCR primers for producing a DNA sequence that includes the coding sequence from PCR product 28 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 28 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 28 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 28 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 28 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 77 illustrates PCR primers for producing a DNA sequence that includes the coding sequence from PCR product 29 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 29 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 29 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 29 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 29 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 78 illustrates PCR primers for producing a DNA sequence that includes the coding sequence from PCR product 30 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 30 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 30 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 30 or a vector that contains that PCR product; the resulting PCR product is gel purified and used in a second PCR with the second 5' Arg primer and the 3' primer. This PCR product is gel purified and inserted into the pET100/D-TOPO®; vector following the manufacturer's directions. For no protein transduction tag, a PCR is carried out with the 5' primer for no tag, the 3' primer, and gel-purified PCR product 30 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 79 illustrates PCR primers for producing a DNA sequence that includes the coding sequence from PCR product 31 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 31 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 31 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 31 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 31 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 80 illustrates PCR primers for producing a DNA sequence that includes the coding sequence from PCR product 32 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 32 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 32 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 32 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 32 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 81 illustrates PCR primers for producing a DNA sequence that includes the coding sequence from PCR product 33 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 33 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 33 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 33 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 33 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 82 illustrates PCR primers for producing a DNA sequence that includes the coding sequence from PCR product 34 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 34 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 34 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 34 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 34 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 83 illustrates PCR primers for producing a DNA sequence that includes the coding sequence from PCR product 35 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 35 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 35 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 35 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 35 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 84 illustrates PCR primers for producing a DNA sequence that includes the coding sequence from PCR product 36 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 36 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 36 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 36 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 36 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 85 illustrates PCR primers for producing a DNA sequence that includes the coding sequence from PCR product 37 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 37 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 37 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 37 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 37 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

FIG. 86 illustrates PCR primers for producing a DNA sequence that includes the coding sequence from PCR product 38 fused to one of the following protein transduction tags: TAT, PTD-4, an arginine-rich sequence Arg, or no protein transduction tag. Glycine residues are included at the ends of the protein transduction tags to permit rotation or flexing of the resulting amino acid sequence at those points. For a TAT tag, a first PCR is carried out with the first 5' TAT primer, the 3' primer, and gel-purified PCR product 38 or a vector that contains that PCR product; the resulting PCR product is gel purified and used in a second PCR with the second 5' TAT primer and the 3' primer. This PCR product is gel purified and inserted into the pET100/D-TOPO® vector following the manufacturer's directions. For a PTD-4 tag, a first PCR is carried out with the first 5' PTD-4 primer, the 3' primer, and gel-purified PCR product 38 or a vector that contains that PCR product; the resulting PCR product is gel purified and used in a second PCR with the second 5' PTD-4 primer and the 3' primer. This PCR product is gel purified and inserted into the pET100/D-TOPO® vector following the manufacturer's directions. For an Arg tag, a first PCR is carried out with the first 5' Arg primer, the 3' primer, and gel-purified PCR product 38 or a vector that contains that PCR product; the resulting PCR product is gel purified and used in a second PCR with the second 5' Arg primer and the 3' primer. This PCR product is gel purified and inserted into the pET100/D-TOPO® vector following the manufacturer's directions. For no protein transduction tag, a PCR is carried out with the 5' primer for no tag, the 3' primer, and gel-purified PCR product 38 or a vector that contains that PCR product; the resulting PCR product is gel purified and inserted into the pET100/D-TOPO® vector following the manufacturer's directions. The inserts in pET100/D-TOPO® are sequenced on both strands for sequence confirmation.

The relevant teachings of all the references, patents and patent applications cited herein are incorporated herein by reference in their entirety.

While this invention has been particularly described with references to preferred embodiments thereof, it will be understood by those skilled in the art that various changes in form and details may be made therein without departing from the scope of the invention encompassed by the appended claims.

What is claimed is:

1. A chimeric molecule having at least one pathogen-detection domain and at least one effector domain, said chimeric molecule being one that is non-naturally-occurring in a cell, wherein said pathogen-detection domain comprises a double-stranded RNA binding domain and said effector domain comprises an apoptosis mediator domain isolated from Apaf-1.

2. The chimeric molecule of claim 1, wherein the double-stranded RNA binding domain is isolated from a protein selected from the group consisting of: protein kinase R, Vaccinia virus E3L protein, E. coli RNase III, S. cerevisiae RNT1p, ADAR1 and 2',5'-oligoadenylate synthetase.

3. The chimeric molecule of claim 2, wherein the double-stranded RNA binding domain is isolated from protein kinase R.

4. An agent having at least one double-stranded RNA-interacting molecular structure and at least one apoptosis-effector mediating molecular structure, said agent being one that is non-naturally-occurring in a cell, wherein said one apoptosis-effector mediating molecular structure comprises an apoptosis mediator domain isolated from Apaf-1.

5. The agent of claim 4, wherein the double-stranded RNA-interacting molecular structure is isolated from a protein selected from the group consisting of: protein kinase R, Vaccinia virus E3L protein, E. coli RNase III, S. cerevisiae RNT1p, ADAR1 and 2',5'-oligoadenylate synthetase.

6. The agent of claim 5, wherein the double-stranded RNA-interacting molecular structure is isolated from protein kinase R.

* * * * *